(12) United States Patent
Meldrum et al.

(10) Patent No.: US 11,767,316 B2
(45) Date of Patent: Sep. 26, 2023

(54) NON-FUSED THIOPHENE DERIVATIVES AND THEIR USES

(71) Applicant: ENYO PHARMA, Lyons (FR)

(72) Inventors: Eric Meldrum, Riehen (CH); Benoît De Chassey, Lyons (FR); Peter Machin, London (GB); Karine Fabienne Malagu, Cambridge (GB); Paul Colin Michael Winship, Cambridge (GB); Jean-Laurent Paparin, Vendemian (FR); Mark Chambers, Saffron Walden (GB); Jamie David Knight, Saffron Walden (GB); Roberta Lanaro, Saffron Walden (GB)

(73) Assignee: ENYO PHARMA, Lyons (FR)

( * ) Notice: Subject to any disclaimer, the term of this patent is extended or adjusted under 35 U.S.C. 154(b) by 0 days.

(21) Appl. No.: 16/967,744

(22) PCT Filed: Feb. 8, 2019

(86) PCT No.: PCT/EP2019/053081
§ 371 (c)(1),
(2) Date: Aug. 6, 2020

(87) PCT Pub. No.: WO2019/154956
PCT Pub. Date: Aug. 15, 2019

(65) Prior Publication Data
US 2021/0040059 A1 Feb. 11, 2021

(30) Foreign Application Priority Data
Feb. 8, 2018 (EP) ..................... 18305134

(51) Int. Cl.
*C07D 413/12* (2006.01)
*A61P 31/12* (2006.01)
*A61P 35/00* (2006.01)
*C07D 333/38* (2006.01)
*C07D 409/04* (2006.01)
*C07D 409/12* (2006.01)
*A61P 3/08* (2006.01)
*C07D 333/04* (2006.01)

(52) U.S. Cl.
CPC .............. *C07D 413/12* (2013.01); *A61P 3/08* (2018.01); *A61P 31/12* (2018.01); *A61P 35/00* (2018.01); *C07D 333/04* (2013.01); *C07D 333/38* (2013.01); *C07D 409/04* (2013.01); *C07D 409/12* (2013.01)

(58) Field of Classification Search
None
See application file for complete search history.

(56) References Cited

U.S. PATENT DOCUMENTS

| | | |
|---|---|---|
| 2019/0352275 A1 | 11/2019 | Meldrum et al. |
| 2020/0361924 A1 | 11/2020 | Meldrum et al. |
| 2020/0369655 A1 | 11/2020 | Meldrum et al. |
| 2020/0369682 A1 | 11/2020 | Meldrum et al. |
| 2021/0038566 A1 | 2/2021 | Meldrum et al. |

FOREIGN PATENT DOCUMENTS

| | | | |
|---|---|---|---|
| WO | WO 2010/025295 | 3/2010 | |
| WO | WO 2010/027875 | 3/2010 | |
| WO | WO 2011/097607 | 8/2011 | |
| WO | WO 2014/001554 | * 1/2014 | ........... C07D 495/04 |
| WO | WO 2019/154949 | 8/2019 | |
| WO | WO 2019/154950 | 8/2019 | |
| WO | WO 2019/154953 | 8/2019 | |

OTHER PUBLICATIONS

CAS RN 940541-60-6 (entered into STN Jul. 1, 2007) (Year: 2007).*
CAS RN 1082130-81-1 (entered into STN Dec. 9, 2008) (Year: 2008).*
CAS RN 1082130-93-5 (Year: 2008).*
CAS RN 1082191-75-0 (entered into STN Dec. 9, 2008) (Year: 2008).*
Written Opinion in International Application No. PCT/EP2019/053081, dated Mar. 21, 2019, pp. 1-5.
CAS Registry No. 2113439-04-4; STN Entry Date Aug. 14, 2017; 3-Thiophenecarboxylic acid, 4-(5,6,7,8-tetrahydro-2-naphthalenyl)-2-[[[6-(trifluoromethyl)imidazo[1,2-a]pyridin-3-yl]carbonyl]amino]-, methyl ester, pp. 1-3.
CAS Registry No. 1787618-72-7; STN Entry Date Jun. 24, 2015; 3-Thiophenecarboxylic acid, 4-(5,6,7,8-tetrahydro-2-naphthalenyl)-2-[(4-thiazolylcarbonyl)amino]-, methyl ester, pp. 1-3.
CAS Registry No. 1219196-95-8; STN Entry Date Apr. 15, 2010; 3-Thiophenecarboxylic acid, 2-[(3,4-dimethylbenzoyl)amino]-4-(5,6,7,8-tetrahydro-2-napthalenyl)-, ethyl ester, pp. 1-3.
CAS Registry No. 1219166-79-6; STN Entry Date Apr. 15, 2010; 3-Thiophenecarboxylic acid, 2-[(2,2-dimethyl-1-oxopropyl)amino]-4-(5,6,7,8-tetrahydro-2-naphthalenyl)-, ethyl ester, pp. 1-3.
CAS Registry No. 1082191-72-7; STN Entry Date Dec. 9, 2008; 3-Thiophenecarboxylic acid, 2-[(cyclohexylcarbonyl)amino]-4-(5,6,7,8-tetrahydro-2-naphthalenyl), pp. 1-3.
CAS Registry No. 1082191-69-2; STN Entry Date Dec. 9, 2008; 3-Thiophenecarboxylic acid, 2-[(2,2-dimethyl-1-oxopropyl)amino]-4-(5,6,7,8-tetrahydro-2-naphthalenyl), pp. 1-3.
CAS Registry No. 1082155-72-3; STN Entry Date Dec. 9, 2008; 3-Thiophenecarboxylic acid, 4-(5,6,7,8-tetrahydro-2-naphthalenyl)-2-[(2-thienylcarbonyl)amino], pp. 1-3.
CAS Registry No. 1082130-89-9; STN Entry Date Dec. 9, 2008; 3-Thiophenecarboxylic acid, 2-[[(tetrahydro-2-furanyl)carbonyl]amino]-4-(5,6,7,8-tetrahydro-2-naphthalenyl), pp. 1-3.

(Continued)

*Primary Examiner* — Craig D Ricci
(74) *Attorney, Agent, or Firm* — SALIWANCHIK, LLOYD & EISENSCHENK

(57) ABSTRACT

The present invention relates to a new class of non-fused thiophene derivatives and their uses for treating diseases such as infection, cancer, metabolic diseases, cardiovascular diseases, iron storage disorders and inflammatory disorders.

9 Claims, 1 Drawing Sheet

Specification includes a Sequence Listing.

(56) References Cited

OTHER PUBLICATIONS

CAS Registry No. 565174-04-1; STN Entry Date Aug. 12, 2003; 3-Thiophenecarboxylic acid, 2-[(2-bromobenzoyl)amino]-4-(1,2-dihydro-5-acenaphthylenyl)-, ethyl ester, pp. 1-3.

CAS Registry No. 554426-41-4; STN Entry Date Jul. 25, 2003; 3-Thiophenecarboxylic acid, 4-(1,2-dihydro-5-acenaphthylenyl)-2-[(3-methylbenzoyl)amino]-, ethyl ester, pp. 1-3.

Examination Report No. 2, Australian Application No. 2019219123, dated Jul. 15, 2022, pp. 1-10.

CAS Registry No. 1082141-88-5; STN Entry Date Dec. 9, 2008; 3-Thiophenecarboxylic acid, 2-[(3-pyridinylcarbonyl)amino]-4-(5,6,7,8-tetrahydro-2-naphthalenyl), p. 1.

CAS Registry No. 1082130-93-5; STN Entry Date Dec. 9, 2008; 3-Thiophenecarboxylic acid, 2-[(4-pyridinylcarbonyl)amino]-4-(5,6,7,8-tetrahydro-2-naphthalenyl), p. 1.

CAS Registry No. 1082141-84-1; STN Entry Date Dec. 9, 2008; 3-Thiophenecarboxylic acid, 2-[(2-furanylcarbonyl)amino]-4-(5,6,7,8-tetrahydro-2-naphthalenyl), p. 1.

CAS Registry No. 940715-94-6; 3-Thiophenecarboxylic acid, 2-[[3-(2-ethoxyphenyl)-1-oxo-2-propen-1-yl]amino]-4-(5,6,7,8-tetrahydro-2-naphthalenyl)-, methyl ester (ACI); retrieved Mar. 28, 2023, pp. 1-3.

CAS Registry No. 940722-52-1; 3-Thiophenecarboxylic acid, 2-[(2-benzofuranylcarbonyl)amino]-4-(5,6,7,8-tetrahydro-2-naphthalenyl)-, methyl ester (ACI); retrieved Mar. 28, 2023, pp. 1-3.

CAS Registry No. 1215839-89-6; 3-Thiophenecarboxylic acid, 2-[(1-oxopentyl)amino]-4-(5,6,7,8-tetrahydro-2-naphthalenyl)-, ethyl ester (ACI); retrieved Mar. 28, 2023, pp. 1-3.

CAS Registry No. 940731-79-3; 3-Thiophenecarboxylic acid, 2-[[6-(1,3-dihydro-1,3-dioxo-2H-isoindol-2-yl)-1-oxohexyl]amino]-4-(5,6,7,8-tetrahydro-2-naphthalenyl)-, methyl ester (ACI); retrieved Mar. 28, 2023, pp. 1-3.

CAS Registry No. 1082141-80-7; 3-Thiophenecarboxylic acid, 2-[(cyclopropylcarbonyl)amino]-4-(5,6,7,8-tetrahydro-2-naphthalenyl)- (ACI); retrieved Mar. 28, 2023, pp. 1-3.

CAS Registry No. 1216606-70-0; 3-Thiophenecarboxylic acid, 2-[(4-bromobenzoyl)amino]-4-(5,6,7,8-tetrahydro-2-naphthalenyl)-, ethyl ester (ACI); retrieved Mar. 28, 2023, pp. 1-3.

\* cited by examiner

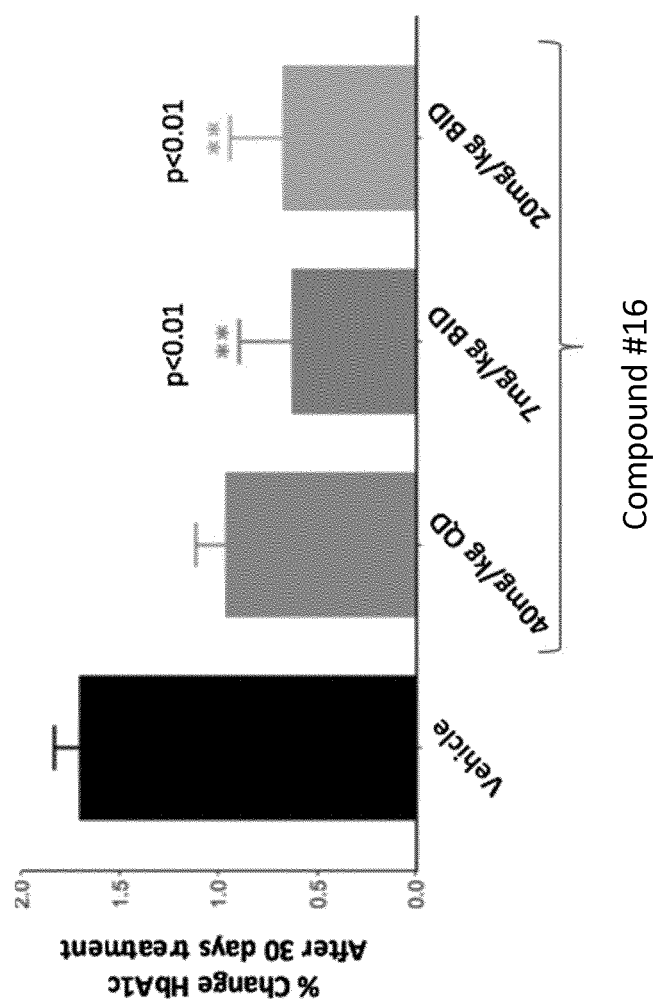

SEQUENCE LISTING

<160> NUMBER OF SEQ ID NOS: 4

<210> SEQ ID NO 1
<211> LENGTH: 35
<212> TYPE: DNA
<213> ORGANISM: artificial
<220> FEATURE:
<223> OTHER INFORMATION: NFKB-NLUC-F

<400> SEQUENCE: 1
ggctctatgg gtcgacggcc taactggccg gtacc            35

<210> SEQ ID NO 2
<211> LENGTH: 37
<212> TYPE: DNA
<213> ORGANISM: artificial
<220> FEATURE:
<223> OTHER INFORMATION: NFKB-NLUC-R

<400> SEQUENCE: 2
agcttagtac tgtcgacgat cagcggaaga gcgccca          37

<210> SEQ ID NO 3
<211> LENGTH: 25
<212> TYPE: DNA
<213> ORGANISM: artificial
<220> FEATURE:
<223> OTHER INFORMATION: AAVS1-T2A-1

<400> SEQUENCE: 3
caccgggggc cactagggac aggat                       25

<210> SEQ ID NO 4
<211> LENGTH: 25
<212> TYPE: DNA
<213> ORGANISM: artificial
<220> FEATURE:
<223> OTHER INFORMATION: AAVS1-T2A-2

<400> SEQUENCE: 4
aaacatcctg tccctagtgg ccccc                       25

NON-FUSED THIOPHENE DERIVATIVES AND THEIR USES

CROSS-REFERENCE TO RELATED APPLICATION

This application is the U.S. national stage application of International Patent Application No. PCT/EP2019/053081, filed Feb. 8, 2019.

The Sequence Listing for this application is labeled "Seq-List.txt" which was created on Jun. 29, 2020 and is 1 KB. The entire content of the sequence listing is incorporated herein by reference in its entirety.

FIELD OF THE INVENTION

The present invention relates to the field of medicine, in particular non-fused thiophene derivatives and their uses for treating diseases such as infection, cancer, metabolic diseases, cardiovascular diseases, iron storage disorders and inflammatory disorders.

BACKGROUND OF THE INVENTION

Viruses are small infectious agents that replicates only inside living cells of other organisms. They can infect all types of life forms, from animals and plants to microorganisms, including bacteria and archaea. Among them, more than 400 species of virus are known to be responsible of diseases in humans, many of them leading to serious pathologies and eventually death. In particular, HIV was classified at the sixth leading cause of death worldwide in 2012 with 1.5 million deaths per year (WHO, Fact sheet No 310, 2014). Seasonal influenza viruses are responsible of flu that affects approximately 20% of the world population and causes 250,000 to 500,000 deaths per year (WHO, Fact sheet No 211, 2014). Among other examples, Hepatitis B and C are responsible altogether for about 1.4 million of death each year and human Papillomaviruses are responsible of cervix cancer, the second most common women cancer worldwide, leading to 270,000 death in 2012 (WHO, Fact sheets, 2016).

Because viruses use vital metabolic pathways within host cells to replicate, they are difficult to eliminate without using drugs that cause toxic effects to host cells in general. The most effective medical approaches to viral diseases are vaccinations to provide immunity to infection, and antiviral drugs that selectively interfere with viral replication. Vaccines are very effective on stable viruses for a preventive use. However, vaccines are of limited use in treating a patient who has already been infected. They are also difficult to successfully deploy against rapidly mutating viruses, such as influenza (the vaccine for which is updated every year) and HIV. Antiviral drugs may be particularly useful in these cases.

Antiviral drugs are a class of medication used specifically for treating viral infections. Antiviral drugs do not destroy their target pathogens, instead they inhibit their development. Antiviral drugs may target any stage of the viral life cycle: attachment to a host cell, release of viral genes and possibly enzymes into the host cell, replication of viral components using host-cell machinery, assembly of viral components into complete viral particles, and release of viral particles to infect new host cells. The most common antiviral drugs are nucleoside analogues that block viruses' replication. Most antiviral drugs are used for specific viral infections, while broad-spectrum antiviral drugs are effective against a wide range of viruses.

Soon after the development of antiviral drugs, resistance appeared. Antiviral drug resistance can be defined as a decreased susceptibility to a drug through either a minimally effective, or completely ineffective, treatment response to prevent associated illnesses from a particular virus. Antiviral drug resistance remains a major obstacle to antiviral therapy as it has developed to almost all specific and effective antiviral drugs. For example, there are two main groups of antiviral drugs available for treatment and prophylaxis of influenza: M2 inhibitors (amantadine and rimantadine) and neuraminidase inhibitors (oseltamivir and zanamivir). Despite the effectiveness of these drugs in reducing influenza-related morbidity and mortality, the emergence of drug resistance poses a critical limitation on their application and have raised an urgent need for developing new anti-influenza drugs against resistant forms.

Thus, there is nowadays a strong need for the development of new antiviral drugs, and in particular broad-spectrum antiviral drugs. The present invention seeks to meet these and other needs.

SUMMARY OF THE INVENTION

The present invention provides a new compound of formula (I):

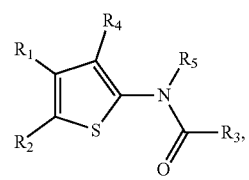

(I)

wherein:
  $R_1$ represents:
    a fused arylcycloalkyl, optionally substituted by at least one radical selected in the group consisting of:
      a halogen,
      a $(C_1-C_6)$alkyl or a $(C_1-C_6)$alkyloxy optionally substituted by at least one halogen, preferably optionally substituted by at least one fluorine, and
      a hydroxy,
      a —CO—$R_6$ or a —$CO_2R_6$ with $R_6$ being a hydrogen or a $(C_1-C_6)$alkyl, and
      an optionally substituted aryl;
  $R_2$ represents:
    a hydrogen,
    a halogen,
    a $(C_1-C_6)$alkyl optionally substituted by at least one halogen, preferably optionally substituted by at least one fluorine,
    an optionally substituted aryl, or
    an optionally substituted cycloalkyl;
  $R_3$ represents:
    a 5-10 membered ring, saturated or unsaturated selected in the group consisting of:
      an aryl optionally fused to a heterocycloalkyl, preferably selected from the group consisting of a dioxole, a morpholine, a dioxane, a tetrahydropyran, and a tetrahydrofuran,
      a heteroaryl,
      a cycloalkyl,
      a heterocycloalkyl, and a 5-10 membered bridged carbocyclyl or heterocyclyl,
said 5-10 membered ring is optionally substituted by at least one radical selected in the group consisting of:
a halogen,
a $(C_1-C_6)$alkyl optionally substituted by at least one halogen, preferably optionally substituted by at least one fluorine, or by an optionally bridged heterocycloalkyl optionally substituted by a $(C_1-C_6)$alkyl,
a —NH—$(C_1-C_6)$alkyl or a —N—$((C_1-C_6)$alkyl$)_2$, optionally substituted by at least one radical selected in the group consisting of a heterocycloalkyl, a cycloalkyl, a hydroxyl, a thiacycloalkyl-1,1dioxide and a $(C_1-C_6)$alkyloxy,
a —NH-heterocycloalkyl, a —NH-cycloalkyl, a —N$((C_1-C_6)$alkyl$)$-heterocycloalkyl, or a —NH$((C_1-C_6)$alkyl$)$-thiacycloalkyl-1,1dioxide optionally substituted by a hydroxyl, a $(C_1-C_6)$alkyl, a $(C_1-C_6)$alkyloxy or a —CO—$R_6$ with $R_6$ being a hydrogen or a $(C_1-C_6)$alkyl,
a hydroxy, a —CN, a —CO—$R_6$ or a —$CO_2R_6$ with $R_6$ being a hydrogen or a $(C_1-C_6)$alkyl,
a $(C_1-C_6)$alkyloxy optionally substituted by at least one radical selected in the group consisting of a halogen, preferably a fluorine, a hydroxy, a $(C_1-C_6)$alkyloxy, a —$NR_7R_8$ with $R_7$ and $R_8$ are independently a hydrogen or a $(C_1-C_6)$alkyl, a —$NHCOR_9$, a —$NHCO_2R_9$, with $R_9$ being a $(C_1-C_6)$alkyl, a —$CO_2R_6$ with $R_6$ being a hydrogen or a $(C_1-C_6)$alkyl, and a heterocycle,
a —$NHCOR_9$, a —$NHCO_2R_9$, or a —$SO_2R_9$, with $R_9$ being a $(C_1-C_6)$alkyl, and
a heterocycloalkyl, a bridged heterocycloalkyl, a heterocycloalkyloxy, a cycloalkyloxy, a thiaheterocycloalkyl-1,1-dioxide or a spiroheterocycloalkyl, optionally substituted by a $(C_1-C_6)$alkyl, a $(C_1-C_6)$alkyloxy, a hydroxy, a ketone, a halogen or a $(C_1-C_6)$alkyl optionally substituted by a $(C_1-C_6)$alkyloxy, or
a $(C_1-C_6)$alkyl or a $(C_2-C_6)$alkenyl, optionally substituted by a 5-10 membered ring as defined above or a —$CO_2R_6$ with $R_6$ being a hydrogen or a $(C_1-C_6)$alkyl;
$R_4$ represents:
a —$CO_2R_{10}$ with $R_{10}$ being a hydrogen or a $(C_1-C_6)$alkyl; or
a 5-10 membered ring, saturated or unsaturated selected in the group consisting of an aryl, a heteroaryl, a cycloalkyl, and a heterocycloalkyl, said 5-10 membered ring is optionally substituted by a hydroxy, a halogen, or a $(C_1-C_6)$alkyl optionally substituted by at least one halogen, preferably optionally substituted by at least one fluorine; and
$R_5$ represents:
a hydrogen, or
a $(C_1-C_6)$alkyl optionally substituted by at least one halogen, preferably optionally substituted by at least one fluorine;
and the stereoisomers, and the pharmaceutical salts thereof.

The present invention further relates to a compound of formula (I) as defined herein, for use for treating a disease selected from the group consisting of an infection, preferably a viral or a bacterial infection, a cancer, a metabolic disease, a cardiovascular disease, an inflammatory disorder, iron storage disease/disorder, aging, and a neurodegenerative disorder.

In a particular embodiment of formula (I), $R_1$ represents:
an optionally substituted fused arylcycloalkyl selected in a group consisting of an indanyl, a 1,2,3,4-tetrahydronaphtalenyl, and a 6,7,8,9-tetrahydro-5H-benzo[7]annulenyl, preferably an indanyl and a 1,2,3,4-tetrahydronaphtalenyl, more preferably a 1,2,3,4-tetrahydronaphtalenyl.

In a very particular embodiment of formula (I), $R_1$ is

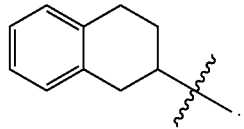

In a further particular embodiment of formula (I), $R_3$ represents:
an aryl optionally fused to a heterocycloalkyl, preferably selected from the group consisting of a dioxole, a morpholine, a dioxane, a tetrahydropyran, and a tetrahydrofuran, or a heteroaryl, said aryl, fused aryl, or heteroaryl is optionally substituted by at least one radical selected in the group consisting of:
a heterocycloalkyl or a bridged heterocycloalkyl, optionally substituted by a $(C_1-C_6)$alkyl, a $(C_1-C_6)$alkyloxy, or a ketone,
a thiaheterocycloalkyl-1,1-dioxide, a heterocycloalkyloxy, or a cycloalkyloxy;
a $(C_1-C_6)$alkyloxy or a $(C_1-C_6)$alkyl optionally substituted by at least one halogen, preferably a fluorine, or a $(C_1-C_6)$alkyloxy,
a halogen, preferably a fluorine or a chlorine,
a —NH—$(C_1-C_6)$alkyl or a —N—$((C_1-C_6)$alkyl$)_2$, optionally substituted by a heterocycloalkyl, a cycloalkyl, a hydroxyl, a thiacycloalkyl-1,1-dioxide or a $(C_1-C_6)$alkyloxy,
a —NH-heterocycloalkyl a —N$((C_1-C_6)$alkyl$)$-heterocycloalkyl, or a —NH$((C_1-C_6)$alkyl$)$-thiacycloalkyl-1,1-dioxide,
a hydroxy,
a —CN,
a $(C_1-C_6)$alkyl substituted by an optionally bridged heterocycloalkyl or an optionally substituted heterocycloalkyl; and
a —$SO_2R_9$, with $R_9$ being a $(C_1-C_6)$alkyl.

In a preferred embodiment, $R_3$ represents:
a phenyl, a pyridinyl or a pyrimidinyl, preferably a phenyl, optionally substituted by at least one radical selected in the group consisting of:
a morpholinyl optionally substituted by at least one methyl,
a —NH-tetrahydropyranyl,
a —NH—$(C_1-C_6)$alkyl or a —N$(CH_3)(C_1-C_6)$alkyl optionally substituted by a tetrahydropyranyl, a cyclohexyl, an optionally bridged morpholinyl optionally substituted by at least one methyl, a thiacycloalkyl-1,1-dioxide, a hydroxy, or a $(C_1-C_6)$alkyloxy,
a azetidinyl optionally substituted by a $(C_1-C_6)$alkyloxy,
a pyrrolidine-2-one, a 6-oxa-3-azabicyclo[3.1.1]heptane, or a 8 oxa-3-azabicyclo[3.2.1]octane, a $(C_1-C_6)$alkyloxy, optionally substituted by at least one halogen, preferably a fluorine, or one $(C_1-C_6)$alkyloxy, a halogen, preferably a fluorine and a chlorine, a hydroxy, a —CN, a —$SO_2$—$CH_3$, a 1,1-dioxo-1,2-thiazolidin, a cyclobutyloxy, or a tetrahydropyranyloxy, a $(C_1-C_6)$alkyl optionally substituted by at least one halogen, preferably optionally substituted by at least one fluorine; and a $(C_1-C_6)$alkyl substituted by a morpholinyl optionally substituted by at least one methyl, a 6-oxa-3-azabicyclo[3.1.1]heptane, a 8 oxa-3-azabicyclo[3.2.1]octane or a tetrahydropyranyl.

In a further particular embodiment of formula (I), $R_2$ represents:

a hydrogen, a halogen, preferably a chlorine, and an optionally substituted $(C_3-C_6)$cycloalkyl, preferably cyclopropyl.

In a preferred embodiment, $R_2$ represents a hydrogen.

In a further particular embodiment of formula (I), $R_4$ represents a —$CO_2R_{10}$ with $R_{10}$ being a hydrogen.

In a preferred embodiment, a compound of formula (I) is selected in the group consisting of compounds of the table A.

Another object of the invention is a compound of formula (I) as defined above for use as a medicine. A further object of the invention is a pharmaceutical composition comprising a compound as defined above, and an acceptable pharmaceutical excipient. In another further particular embodiment, the present invention relates to a compound of the present invention for use in the treatment of a disease selected from the group consisting of an infection, preferably a viral or a bacterial infection, a cancer, a metabolic disease, a cardiovascular disease, an inflammatory disorder, iron storage disease/disorder, aging, and a neurodegenerative disease or disorder.

Preferably, the disease is a viral infection. In a particular embodiment, the viral infection is an infection by a virus selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In a further particular embodiment, the bacterial infection is an infection by a bacterium selected from the group consisting of *Helicobacter pylori, Burkholderia cepacia, Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella parapertussis, Bordetella bronchiseptica, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Campylobacter fetus, Campylobacter jejuni, Campylobacter coli, Borrelia burgdorferi, Vibrio cholerae, Vibrio parahaemolyticus, Listeria monocytogenes, Neisseria gonorrhoeae, Neisseria meningitidis, Kingella denitrificans, Kingella indologenes, Kingella kingae, Kingella oxalis, Legionella pneumophila, Moraxella bovis, Moraxella catarrhalis, Moraxella lacunata, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii, Bacteroides splanchnicus, Clostridium difficile, Clostridium tetani, Mycobacterium species, Corynebacterium ulcerans, Streptococcus agalactiae, Gardnerella vaginitis, Streptococcus pyogenes, Enterococcus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis,* and *Staphylococcus saccharolyticus.*

In a further particular embodiment, the cancer is selected from the group consisting of a breast cancer, a lung cancer, in particular NSCLC, a melanoma, a colorectal cancer, an astrocytoma cancer, a liver cancer, leukemia, in particular acute myeloid leukemia, a gastric cancer, a head and neck cancer, a cervical cancer, a pancreatic cancer, and an ovarian cancer.

In a further particular embodiment, the metabolic disease is selected from the group consisting of Diabetes mellitus, in particular Diabetes mellitus from NEET protein, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, in particular Wolfram syndrome from NEET protein, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In a further particular embodiment, the cardiovascular disease is selected in the group consisting of myocardial injury, Ischemia, Ischemia reperfusion injury and hypertension.

In an additional particular embodiment, the inflammatory disease or disorder is selected from the group consisting of Crohn disease, inflammatory bowel disease, asthma, chronic obstructive pulmonary disease (COPD), systemic lupus erythematosus, cystic fibrosis, psoriasis, infectious arthritis, and multiple sclerosis.

In a further particular embodiment, the iron storage disorder or disease is selected from the group consisting of Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

BRIEF DESCRIPTION OF THE FIGURE

FIG. 1 represents the change of HBA1c in diabetic model mice treated with a compound of the invention (compound #16).

DETAILED DESCRIPTION OF THE INVENTION

Definitions

According to the present invention, the terms below have the following meanings:

The terms mentioned herein with prefixes such as for example $C_1$-$C_3$, $C_1$-$C_6$ or $C_2$-$C_6$ can also be used with lower numbers of carbon atoms such as $C_1$-$C_2$, $C_1$-$C_5$, or $C_2$-$C_5$. If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_6$ is used, it means that the corresponding hydrocarbon chain may comprise from 2 to 6 carbon atoms, especially 2, 3, 4, 5 or 6 carbon atoms.

The term "alkyl" refers to a saturated, linear or branched aliphatic group. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, a propyl, an isopropyl, or a tert-butyl, more preferably a methyl.

The term "alkenyl" refers to an unsaturated, linear or branched aliphatic group comprising at least one carbon-carbon double bound. The term "($C_2$-$C_6$)alkenyl" more specifically means ethenyl, propenyl, isopropenyl, butenyl, isobutenyl, pentenyl, or hexenyl.

The term "alkoxy" or "alkyloxy" corresponds to the alkyl group as above defined bonded to the molecule by an —O— (ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "cycloalkyl" corresponds to a saturated or unsaturated mono-, bi- or tri-cyclic alkyl group comprising between 3 and 20 atoms of carbons. It also includes fused, bridged, or spiro-connected cycloalkyl groups. The term "cycloalkyl" includes for instance cyclopropyl, cyclobutyl, cyclopentyl, and cyclohexyl. The term "cycloalkyl" may also refer to a 5-10 membered bridged carbocyclyl such as bicyclo[2,2,1]heptanyl, bicyclo[2,2,2]octanyl, bicyclo[1.1.1]pentanyl, or adamantyl, preferably bicyclo[2,2,1]heptanyl. In a preferred embodiment, the "cycloalkyl" is a cyclopropyl, cyclobutyl, cyclopentyl or a cyclohexyl.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to 3-dioxolane, benzo[1,3]dioxolyl, azetidinyl, oxetanyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydropyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl, 6-oxa-3-azabicyclo[3,1,1]heptanyl, and 8-oxa-3-azabicyclo[3,1,1]octanyl. In a particular embodiment, it may also refer to spiro-connected heterocycloalkyl groups or spiroheterocycloalkyl groups such as for instance oxetanyl spiro-connected with azetidinyl or piperidinyl. In a preferred embodiment, the heterocycloalkyl group is azetidinyl, oxetanyl, pyranyl, tetrahydrofuranyl, tetrahydropyranyl, morpholinyl, piperidinyl, piperazinyl, and oxetanyl spiro-connected with azetidinyl or piperidinyl.

The term "aryl" corresponds to a mono- or bi-cyclic aromatic hydrocarbons having from 6 to 12 carbon atoms. For instance, the term "aryl" includes phenyl, biphenyl, or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzoisoxazolyl, oxindolyl, benzoxazolinyl, benzothienyl, benzothiazolyl, isatinyl, dihydropyridyl, pyrimidinyl, s-triazinyl, oxazolyl, or thiofuranyl. In a preferred embodiment, the heteroaryl group is a pyridinyl, furanyl, pyrazolyl, pyrazinyl, pyrimidinyl, pyridazinyl, and isoxazolyl.

The terms "fused arylheterocycloalkyl" and "fused arylcycloalkyl" correspond to a bicyclic group in which an aryl as above defined is bounded to the heterocycloalkyl or the cycloalkyl as above defined by at least two carbons. In other terms, the aryl shares a carbon bond with the heterocycloalkyl or the cycloalkyl. A fused arylheterocycloalkyl is for instance a benzodioxole (phenyl fused to a dioxole), an isobenzofurane or a benzomorpholine (phenyl fused to a morpholine. A fused arylcycloalkyl is for instance an indanyl, a 1,2,3,4-tetrahydronaphtalenyl (also called tetralinyl), or a 6,7,8,9-tetrahydro-5H-benzo[7]annulenyl (fused phenyl-$C_7$-cycloalkyl). The term "fused bicycloalkyl" corresponds to a bicyclic group in which a cycloalkyl as above defined is bounded to the cycloalkyl as above defined by at least two carbons. A fused bicycloalkyl is for instance a bicyclo[4.1.0]heptanyl.

The term "halogen" corresponds to a fluorine, chlorine, bromine, or iodine atom, preferably a fluorine, chlorine or bromine.

The expression "substituted by at least" means that the radical is substituted by one or several groups of the list.

The expression "optionally substituted" means, without any otherwise precision, optionally substituted by a hydroxy, a halogen, a ($C_1$-$C_6$)alkyl optionally substituted by at least one halogen, preferably optionally substituted by at least one fluorine, or a ($C_1$-$C_6$)alkoxy optionally substituted by at least one halogen, preferably optionally substituted by at least one fluorine.

The "stereoisomers" are isomeric compounds that have the same molecular formula and sequence of bonded atoms, but differ in the 3D-dimensional orientations of their atoms in space. The stereoisomers include enantiomers, diastereoisomers, Cis-trans and E-Z isomers, conformers, and anomers. In a preferred embodiment of the invention, the stereoisomers include diastereoisomers and enantiomers. The enantiomers compounds may be prepared from the racemate compound using any purification method known by a skilled person, such as LC/MS and chiral HPLC analysis methods and chiral SFC purification methods such as those disclosed in the examples (Example A—Chemistry, Table 1 and Table 3).

The "pharmaceutically salts" include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base includes for instance a salt with methylamine, dimethylamine, trimethylamine, piperidine, morpholine or tris-(2-hydroxyethyl)amine. In a preferred embodiment, the salt is selected from the group consisting of sodium and potassium salt.

As used herein, the terms "treatment", "treat" or "treating" refer to any act intended to ameliorate the health status of patients such as therapy, prevention, prophylaxis and retardation of a disease, in particular an infection, preferably a viral infection. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease, particularly infectious disease. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the active ingredients.

The term "modulator", as used herein, refers to a molecule, a chemical or a substance targeting, added, applied or active to another, to modulate a reaction or to prevent an unwanted change. As used herein, the term "modulator" refers to any molecule or compound having an effect on Fe—S cluster binding by the NEET protein. The "modulator" as used herein may be either a stabiliser or a destabiliser. The term "stabiliser" as used herein refers to any compound, chemical, or substance able to stabilize the Fe—S cluster binding the NEET protein. Particularly, a stabiliser reduces the off-rate of iron (Fe) or slows the release of bound Fe—S. In a preferred embodiment, a compound of the invention as disclosed herein may be a "stabiliser" when it is able to increase the time needed to reach 50% Fe—S cluster bound loss by more than 25%. The term "destabiliser" as used herein refers to any compound, chemical, or substance able to destabilize the Fe—S cluster binding the NEET protein. Particularly, a destabiliser enhances the off-rate of iron (Fe). In a preferred embodiment, a compound of the invention as disclosed herein may be a "destabiliser" when it is able to decrease the time needed to reach 50% Fe—S cluster bound loss by more than 25%. The effect of the modulator can be determined by the protocol detailed in Example B3.

Compounds

The present invention provides new compounds of therapeutic interest.

According to the invention, a compound has the following formula (I):

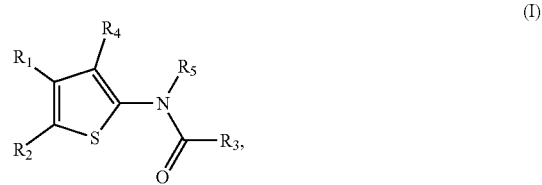

wherein:

$R_1$ represents:
- a 3-10 membered ring, saturated or unsaturated, which is a fused arylcycloalkyl, said 3-10 membered ring is optionally substituted by at least one radical selected in the group consisting of:
  - a halogen,
  - a $(C_1-C_6)$alkyl or a $(C_1-C_6)$alkyloxy optionally substituted by at least one halogen, preferably optionally substituted by at least one fluorine, and
  - a hydroxy,
  - a —CO—$R_6$ or a —$CO_2R_6$ with $R_6$ being a hydrogen or a $(C_1-C_6)$alkyl, and
  - an optionally substituted aryl, $R_2$ represents:
- a hydrogen,
- a halogen,
- a $(C_1-C_6)$alkyl optionally substituted by at least one halogen, preferably optionally substituted by at least one fluorine,
- an optionally substituted aryl, or
- an optionally substituted cycloalkyl;

$R_3$ represents:
- a 5-10 membered ring, saturated or unsaturated selected in the group consisting of:
  - an aryl optionally fused to a heterocycloalkyl, preferably selected from the group consisting of a dioxole, a morpholine, a dioxane, a tetrahydropyran, and a tetrahydrofuran,
  - a heteroaryl,
  - a cycloalkyl,
  - a heterocycloalkyl, and
  - a 5-10 membered bridged carbocyclyl or heterocyclyl, said 5-10 membered ring is optionally substituted by at least one radical selected in the group consisting of:
  - a halogen,
  - a $(C_1-C_6)$alkyl optionally substituted by at least one halogen, preferably optionally substituted by at least one fluorine, or by an optionally bridged heterocycloalkyl optionally substituted by a $(C_1-C_6)$alkyl,
  - a —NH—$(C_1-C_6)$alkyl or a —N—$((C_1-C_6)$alkyl$)_2$, optionally substituted by at least one radical selected in the group consisting of a heterocycloalkyl, a cycloalkyl, a hydroxyl, a thiacycloalkyl-1,1dioxide, and a $(C_1-C_6)$alkyloxy,
  - a —NH-heterocycloalkyl, a —NH-cycloalkyl, a —N($(C_1-C_6)$alkyl)-heterocycloalkyl, or a —NH($(C_1-C_6)$alkyl)-thiacycloalkyl-1,1dioxide, optionally substituted by a hydroxyl, a $(C_1-C_6)$alkyl, a $(C_1-C_6)$alkyloxy or a —CO—$R_6$ with $R_6$ being a hydrogen or a $(C_1-C_6)$alkyl,
  - a hydroxy, a —CN, a —CO—$R_6$ or a —$CO_2R_6$ with $R_6$ being a hydrogen or a $(C_1-C_6)$alkyl,
  - a $(C_1-C_6)$alkyloxy optionally substituted by at least one radical selected in the group consisting of a halogen, preferably a fluorine, a hydroxy, a $(C_1-C_6)$alkyloxy, a —$NR_7R_8$ with $R_7$ and $R_8$ are independently a hydrogen or a $(C_1-C_6)$alkyl, a —$NHCOR_9$, a —$NHCO_2R_9$, with $R_9$ being a $(C_1-C_6)$alkyl, a —$CO_2R_6$ with $R_6$ being a hydrogen or a $(C_1-C_6)$alkyl, and a heterocycle,
  - a —$NHCOR_9$, a —$NHCO_2R_9$, or a —$SO_2R_9$, with $R_9$ being a $(C_1-C_6)$alkyl, and
  - a heterocycloalkyl, a bridged heterocycloalkyl, a heterocycloalkyloxy, a cycloalkyloxy, a thiaheterocycloalkyl-1,1-dioxide or a spiroheterocycloalkyl, optionally substituted by a $(C_1-C_6)$alkyl, a $(C_1-C_6)$alkyloxy, a hydroxy, a ketone, a halogen or a $(C_1-C_6)$alkyl optionally substituted by a $(C_1-C_6)$alkyloxy, or
  - a $(C_1-C_6)$alkyl or a $(C_2-C_6)$alkenyl, optionally substituted by a 5-10 membered ring as defined above or a —$CO_2R_6$ with $R_6$ being a hydrogen or a $(C_1-C_6)$alkyl;

$R_4$ represents:
- a —$CO_2R_{10}$ with $R_{10}$ being a hydrogen or a $(C_1-C_6)$alkyl; or
- a 5-10 membered ring, saturated or unsaturated selected in the group consisting of an aryl, a heteroaryl, a cycloalkyl, and a heterocycloalkyl, said 5-10 membered ring is optionally substituted by a hydroxy, a halogen, or a $(C_1-C_6)$alkyl optionally substituted by at least one halogen, preferably optionally substituted by at least one fluorine; and $R_5$ represents:
- a hydrogen, or
- a $(C_1-C_6)$alkyl optionally substituted by at least one halogen, preferably optionally substituted by at least one fluorine, and the stereoisomers, and the pharmaceutical salts thereof.

In a particular embodiment $R_1$ represents an optionally substituted fused arylcycloalkyl by at least one radical as above defined selected in a group consisting of an optionally substituted indanyl, an optionally substituted 1,2,3,4-tetrahydronaphtalenyl, and an optionally substituted 6,7,8,9-tetrahydro-5H-benzo[7]annulenyl, preferably an optionally substituted indanyl and an optionally substituted 1,2,3,4-tetrahydronaphtalenyl, more preferably an optionally substituted 1,2,3,4-tetrahydronaphtalenyl.

For instance, the optionally substituted fused arylcycloalkyl of $R_1$ can comprise a radical selected in a group consisting of:

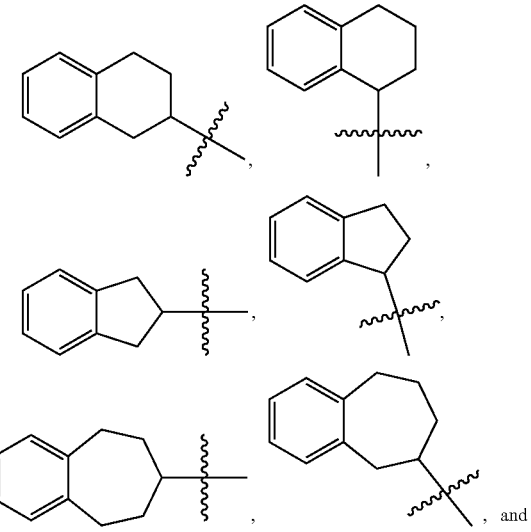

-continued

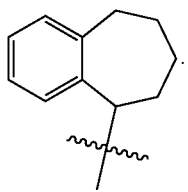

Alternatively, the optionally substituted fused arylcycloalkyl of $R_1$ can comprise a radical selected in a group consisting of:

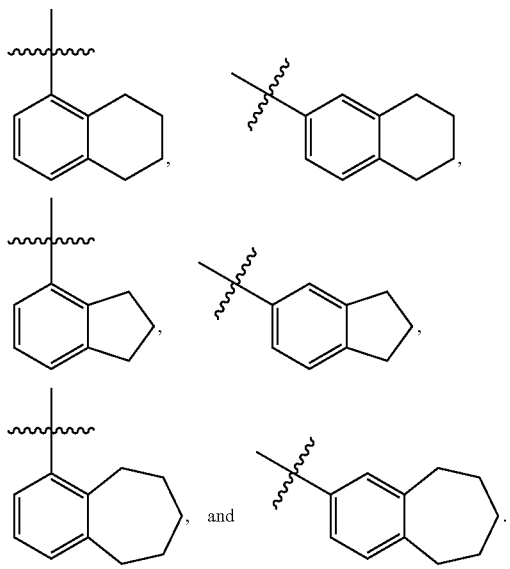

In a particular aspect, $R_1$ is

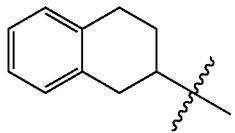 [SMILES: *C1CCc2ccccc2C1]

or a substituted radical thereof.

In a further particular embodiment, $R_2$ represents a hydrogen, a halogen, preferably a chlorine, a bromine or a fluorine, more preferably a chlorine, a $(C_1\text{-}C_6)$alkyl optionally substituted by at least one halogen, preferably optionally substituted by at least one fluorine, preferably a methyl, a difluoromethyl or a trifluoromethyl, an optionally substituted $(C_3\text{-}C_6)$cycloalkyl, preferably cyclopropyl, cyclobutyl, cyclopentyl or cyclohexyl, more preferably cyclopropyl or cyclohexyl, still more preferably a cyclopropyl, or an optionally substituted aryl, preferably a phenyl. In one particular aspect, $R_2$ is a hydrogen. In another particular aspect, $R_2$ is a chlorine. In a further particular aspect, $R_2$ is a cycloalkyl, preferably a cyclopropyl.

In a preferred embodiment, $R_1$ is a fused arylcycloalkyl as above defined and $R_2$ is a hydrogen, a chlorine, or a methyl, more preferably a hydrogen.

According to the present invention, $R_3$ represents:
a 5-10 membered ring, saturated or unsaturated selected in the group consisting of:
  an aryl optionally fused to a heterocycloalkyl, preferably selected from the group consisting of dioxole, a morpholine, a dioxane, a tetrahydropyran, and a tetrahydrofuran,
  a heteroaryl,
  a cycloalkyl,
  a heterocycloalkyl, and
  a 5-10 membered bridged carbocyclyl or heterocyclyl, said 5-10 membered ring is optionally substituted by at least one radical selected in the group consisting of:
    a halogen,
    a $(C_1\text{-}C_6)$alkyl optionally substituted by at least one halogen, preferably optionally substituted by at least one fluorine, or by an optionally bridged heterocycloalkyl optionally substituted by a $(C_1\text{-}C_6)$alkyl,
    a —NH—$(C_1\text{-}C_6)$alkyl or a —N—$((C_1\text{-}C_6)$alkyl$)_2$, optionally substituted by at least one radical selected in the group consisting of a heterocycloalkyl, a cycloalkyl, a hydroxyl, a thiacycloalkyl-1,1dioxide and a $(C_1\text{-}C_6)$alkyloxy,
    a —NH-heterocycloalkyl, a —NH-cycloalkyl, a —N($(C_1\text{-}C_6)$alkyl)-heterocycloalkyl, or a —NH$((C_1\text{-}C_6)$alkyl)-thiacycloalkyl-1,1dioxide, optionally substituted by a hydroxyl, a $(C_1\text{-}C_6)$alkyl, a $(C_1\text{-}C_6)$alkyloxy or a —CO—$R_6$ with $R_6$ being a hydrogen or a $(C_1\text{-}C_6)$alkyl,
    a hydroxy, a —CN, a —CO—$R_6$ or a —$CO_2R_6$ with $R_6$ being a hydrogen or a $(C_1\text{-}C_6)$alkyl,
    a $(C_1\text{-}C_6)$alkyloxy optionally substituted by at least one radical selected in the group consisting of a halogen, preferably a fluorine, a hydroxy, a $(C_1\text{-}C_6)$alkyloxy, a —$NR_7R_8$ with $R_7$ and $R_8$ are independently a hydrogen or a $(C_1\text{-}C_6)$alkyl, a —NH-$COR_9$, a —$NHCO_2R_9$, with $R_9$ being a $(C_1\text{-}C_6)$alkyl, a —$CO_2R_6$ with $R_6$ being a hydrogen or a $(C_1\text{-}C_6)$alkyl, and a heterocycle,
    a —$NHCOR_9$, a —$NHCO_2R_9$, or a —$SO_2R_9$ with $R_9$ being a $(C_1\text{-}C_6)$alkyl, and
    a heterocycloalkyl, a bridged heterocycloalkyl, a heterocycloalkyloxy, a cycloalkyloxy, a thiaheterocycloalkyl-1,1-dioxide or a spiroheterocycloalkyl, optionally substituted by a $(C_1\text{-}C_6)$alkyl, a $(C_1\text{-}C_6)$alkyloxy, a hydroxy, a ketone, a halogen or a $(C_1\text{-}C_6)$alkyl optionally substituted by a $(C_1\text{-}C_6)$alkyloxy, or
  a $(C_1\text{-}C_6)$alkyl or a $(C_2\text{-}C_6)$alkenyl, optionally substituted by a 5-10 membered ring as defined above or a —$CO_2R_6$ with $R_6$ being a hydrogen or a $(C_1\text{-}C_6)$alkyl, and $R_1$, $R_2$, $R_4$, and $R_5$ are such as defined herein.

In a particular embodiment, $R_3$ represents an aryl optionally fused to a dioxole, a morpholine, a dioxane, a tetrahydropyran, or a tetrahydrofuran, or a heteroaryl, said aryl fused aryl, or a heteroaryl is optionally substituted by at least one radical selected in the group consisting of:
  a heterocycloalkyl or a bridged heterocycloalkyl, optionally substituted by a $(C_1\text{-}C_6)$alkyl, a $(C_1\text{-}C_6)$alkyloxy, or a ketone,
  a thiaheterocycloalkyl-1,1-dioxide, a heterocycloalkyloxy, or a cycloalkoxy,
  a $(C_1\text{-}C_6)$alkyloxy or a $(C_1\text{-}C_6)$alkyl, optionally substituted by at least one halogen, preferably a fluorine, or a $(C_1\text{-}C_6)$alkyloxy,
  a halogen, preferably a fluorine or a chlorine, a —NH—$(C_1-C_6)$alkyl or a —N—$((C_1-C_6)$alkyl$)_2$, optionally substituted by a heterocycloalkyl, a cycloalkyl, a hydroxyl, a thiacycloalkyl-1,1-dioxide or a $(C_1-C_6)$alkyloxy, a —NH-heterocycloalkyl, a —N$((C_1-C_6)$alkyl$)$-heterocycloalkyl, or a —NH$((C_1-C_6)$alkyl$)$-thiacycloalkyl-1,1-dioxide, a hydroxy, a —CN, a $(C_1-C_6)$alkyl optionally substituted by an optionally bridged heterocycloalkyl optionally substituted by a $(C_1-C_6)$alkyl, and a —SO$_2$R$_9$, with R$_9$ being a $(C_1-C_6)$alkyl.

In a particular embodiment, R$_3$ represents a phenyl, a pyridinyl or a pyrimidinyl, preferably a phenyl, optionally substituted by at least one radical selected in the group consisting of:

a halogen, preferably a fluorine or a chlorine, a $(C_1-C_6)$alkyl optionally substituted by at least one halogen, preferably a fluorine, or by a $(C_1-C_6)$alkyloxy, a —NH—$(C_1-C_6)$alkyl or a —N—$((C_1-C_6)$alkyl$)_2$, optionally substituted by a heterocycloalkyl, a cycloalkyl, a thiacycloalkyl-1,1-dioxide, a hydroxyl, or a $(C_1-C_6)$alkyloxy, a —NH-heterocycloalkyl, a —NH-cycloalkyl, or a —N$((C_1-C_6)$alkyl$)$-heterocycloalkyl, a or a —NH$((C_1-C_6)$alkyl$)$-thiacycloalkyl-1,1-dioxide, optionally substituted by a hydroxyl, a $(C_1-C_6)$alkyl, a $(C_1-C_6)$alkyloxy or a —CO—R$_6$ with R$_6$ being a hydrogen or a $(C_1-C_6)$alkyl, a hydroxy, a —CN, a —CO—R$_6$ or a —CO$_2$R$_6$ with R$_6$ being a hydrogen or a $(C_1-C_6)$alkyl, a $(C_1-C_6)$alkyloxy optionally substituted by at least one radical selected in the group consisting of a halogen, preferably a fluorine, a hydroxy, a $(C_1-C_6)$alkyloxy, a —NR$_7$R$_8$ with R$_7$ and R$_8$ are independently a hydrogen or a $(C_1-C_6)$alkyl, a —NHCOR$_9$, a —NHCO$_2$R$_9$, with R$_9$ being a $(C_1-C_6)$alkyl, a —CO$_2$R$_6$ with R$_6$ being a hydrogen or a $(C_1-C_6)$alkyl, and a heterocycle, a —NHCOR$_9$, a —NHCO$_2$R$_9$, or a —SO$_2$R$_9$ with R$_9$ being a $(C_1-C_6)$alkyl, and a heterocycloalkyl, a bridged heterocycloalkyl, a heterocycloalkyloxy, a cycloalkoxy, a thiaheterocycloalkyl-1,1-dioxide or a spiroheterocycloalkyl, optionally substituted by a $(C_1-C_6)$alkyloxy, a hydroxy, a halogen, a ketone (C=O), or a $(C_1-C_6)$alkyl optionally substituted by a $(C_1-C_6)$alkyloxy.

In a further particular embodiment, R$_3$ represents a phenyl, a pyridinyl or a pyrimidinyl, preferably a phenyl, optionally substituted by at least one radical selected in the group consisting of:

a morpholinyl optionally substituted by at least one methyl, a 1,1-dioxo-1,2-thiazolidin, a —NH-tetrahydropyranyl, a —NH—$(C_1-C_6)$alkyl or a —N(CH$_3$)$(C_1-C_6)$alkyl) optionally substituted by a tetrahydropyranyl, a cyclohexyl, an optionally bridged morpholinyl optionally substituted by at least one methyl, a thiacycloalkyl-1, 1-dioxide, a hydroxy, or a $(C_1-C_6)$alkyloxy, an azetidinyl optionally substituted by a $(C_1-C_6)$alkyloxy, a pyrrolidin-2-one, a 6-oxa-3-azabicyclo[3.1.1]heptane, or a 8 oxa-3-azabicyclo[3.2.1]octane, a $(C_1-C_6)$alkyloxy, optionally substituted by at least one halogen, preferably a fluorine, or one $(C_1-C_6)$alkyloxy, a halogen, preferably a fluorine and a chlorine, a hydroxy, a —CN, a —SO$_2$—CH$_3$, a cyclobutyloxy, or a tetrahydropyranyloxy, a $(C_1-C_6)$alkyl optionally substituted by at least one halogen, preferably optionally substituted by at least one fluorine and a $(C_1-C_6)$alkyl substituted by a morpholinyl optionally substituted by at least one methyl, a 6-oxa-3-azabicyclo[3.1.1]heptane, a 8 oxa-3-azabicyclo[3.2.1]octane or a tetrahydropyranyl.

In a preferred embodiment, R$_3$ is a phenyl, i.e. an unsubstituted phenyl. In an alternative embodiment, R$_3$ is a pyridinyl or a pyrimidinyl.

In one aspect, R$_3$ is a phenyl, a pyridinyl or a pyrimidinyl, preferably a phenyl, substituted by at least one radical selected in the group consisting of a halogen, preferably a chlorine, a fluorine, or a bromine, a methyl, a difluoromethyl, a trifluoromethyl, a hydroxy, a cyano (—CN), a methoxy, a difluoromethoxy, a trifluoromethoxy, an isopropyloxy, a tertiobutyloxy, a cyclobutyloxy, an ethoxy, propyloxy or butyloxy substituted by a methoxy (—O—(CH$_2$)$_{2-4}$—OCH$_3$) or by a hydroxy (—O—(CH$_2$)$_2$—OH), a —SO$_2$—CH$_3$, and a —NHCOR$_7$ with R$_7$ being a methyl.

In another aspect, R$_3$ is a phenyl, a pyridinyl or a pyrimidinyl, preferably a phenyl, substituted by an optionally bridged heterocycle, preferably an azetidinyl, a morpholinyl, a bridged morpholinyl, a piperidinyl, a piperazinyl, a tetrahydropyranyl, a pyrrolidine-2-one, a 1,1-dioxo-1,2-thiazolidin, or a azetidinyl or piperidinyl spiro-connected with an oxetanyl, more preferably an azetidinyl, a tetrahydropyranyl, a morpholinyl, a 6-oxa-3-azabicyclo[3.1.1]heptane, or a 8 oxa-3-azabicyclo[3.2.1]octane, said heterocycle being optionally substituted by a methoxy, an ethoxy, a hydroxy, a methyl optionally substituted by a methoxy, a halogen, preferably a fluorine. In a very particular aspect, R$_3$ is a phenyl, a pyridinyl or a pyrimidinyl, preferably a phenyl, substituted by an azetidinyl optionally substituted by a methoxy, or an optionally bridged morpholinyl (e.g., linked to the phenyl by the nitrogen) optionally substituted by one or two methyl. In another very particular aspect, R$_3$ is a phenyl, a pyridinyl or a pyrimidinyl, preferably a phenyl, substituted by a bridged heterocycle, preferably, a 6-oxa-3-azabicyclo[3.1.1]heptane, and a 8 oxa-3-azabicyclo[3.2.1] octane.

In a further aspect, R$_3$ is a phenyl, a pyridinyl or a pyrimidinyl, preferably a phenyl, substituted by a $(C_1-C_6)$ alkyl substituted by a heterocycle, preferably a —CH$_2$-morpholinyl.

In a further aspect, R$_3$ is a phenyl, a pyridinyl or a pyrimidinyl, preferably a phenyl, substituted by a —NH—$(C_1-C_6)$alkyl or a —N—$((C_1-C_6)$alkyl$)_2$, optionally substituted by a heterocycloalkyl, a cycloalkyl, a hydroxyl, a thiacycloalkyl-1,1-dioxide, or a $(C_1-C_6)$alkyloxy, preferably a phenyl, a pyridinyl or a pyrimidinyl, preferably a phenyl, substituted by a —NH—CH$_2$-azetidinyl, a —NH—(CH$_2$)$_2$—OCH$_3$, a —NH—(CH$_2$)$_3$—OCH$_3$, a —NH—(CH$_2$)$_4$—OCH$_3$, a —NH—CH$_2$-tetrahydropyranyl, a —N(CH$_3$)—CH$_2$-tetrahydropyranyl, a —NH—(CH$_2$)-cyclohexyl, a —NH—CH(CH$_2$OH)-tetrahydropyranyl, a —NH—CH$_2$-hydroxytetrahydropyranyl, a —NH—(CH$_2$)$_4$—OH, —N(CH$_3$)—(CH$_2$)$_2$—OCH$_3$, a —N(CH$_3$)—CH$_2$-tetrahydropyranyl and NH—CH$_2$-thiacycloalkyl-1,1-dioxide.

In a further aspect, R$_3$ is a phenyl, a pyridinyl or a pyrimidinyl, preferably a phenyl, substituted by a —NH-heterocycloalkyl, a —NH-cycloalkyl, a —N$((C_1-C_6)$alkyl$)$-heterocycloalkyl or —NH$((C_1-C_6)$alkyl$)$-thiacycloalkyl-1, 1dioxide, optionally substituted by a (C$_1$-C$_6$)alkyl, a hydroxyl, a (C$_1$-C$_6$)alkyloxy or a —CO—R$_6$ with R$_6$ being a hydrogen or a (C$_1$-C$_6$)alkyl, preferably a —NH-tetrahydropyranyl, a —NH-tetrahydrofuranyl, a —NH-oxetanyl, a —NH-piperidinyl optionally substituted by a —CO—CH$_3$, a —NH-azetidinyl optionally substituted by a —CO—CH$_3$, a —N(CH$_3$)-azetidinyl optionally substituted by a —CO—CH$_3$, a —N(CH$_3$)-tetrahydropyranyl, and a —NH-cyclohexyl, more preferably a —NH— tetrahydropyranyl.

In a further preferred embodiment, R$_3$ is a phenyl, a pyridinyl or a pyrimidinyl, preferably a phenyl, substituted by a (C$_1$-C$_6$)alkyloxy, preferably a methoxy, an ethoxy, a propoxy, a butoxy, a pentoxy, a difluoromethoxy, a trifluoromethoxy, optionally substituted by a radical selected in the group consisting of a hydroxyl, a methoxy, a —NHCO$_2$R$_9$, with R$_9$ being a methyl, a —NR$_7$R$_8$ with R$_7$ and R$_8$ are a hydrogen, a —CO$_2$R$_6$ with R$_6$ being a methyl, and a heterocycle, preferably a tetrahydropyranyl or a oxetanyl, preferably optionally substituted by a group consisting of a hydroxyl, a methoxy, a tetrahydropyranyl and a oxetanyl. In a further aspect, R$_3$ is a phenyl, a pyridinyl or a pyrimidinyl, preferably a phenyl, substituted by a heterocycloalkyloxy, preferably a tetrahydropyranyloxy or by a cycloalkyloxy, preferably a cyclobutyloxy.

In a further particular aspect, R$_3$ is an aryl fused to a dioxole, preferably a benzo[1,3]dioxole optionally substituted by at least one fluorine, an aryl fused to a morpholine, preferably a benzo[1,3]morpholine optionally substituted by a methyl, an aryl fused to a dioxane, an aryl fused to a tetrahydrofuran optionally substituted by at least one methyl, an aryl fused to a tetrahydropyran. Preferably, the aryl is a phenyl.

In a further particular aspect, R$_3$ is a heteroaryl, preferably a pyridinyl, a pyrimidinyl, a furanyl, a pyrazolyl, or a benzoisoxazolyl, said heteroaryl being optionally substituted by at least one radical as disclosed above, for instance selected in the group consisting of a methoxy, a methyl, and a morpholinyl.

In a particular aspect, R$_3$ is a radical selected in the group consisting of:

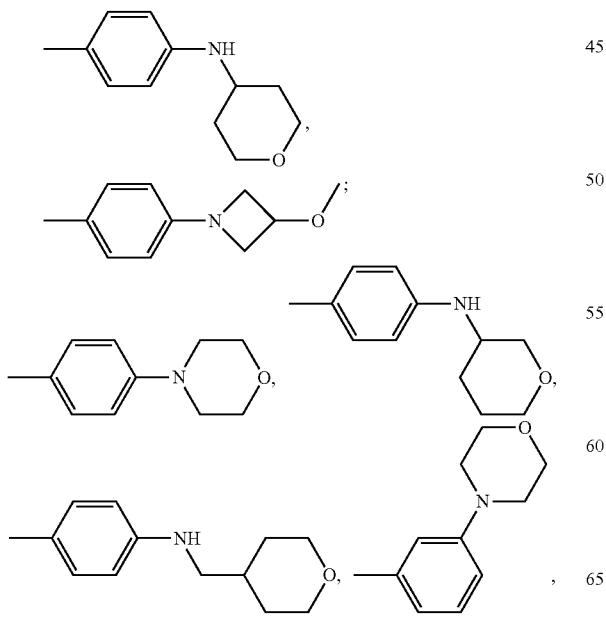

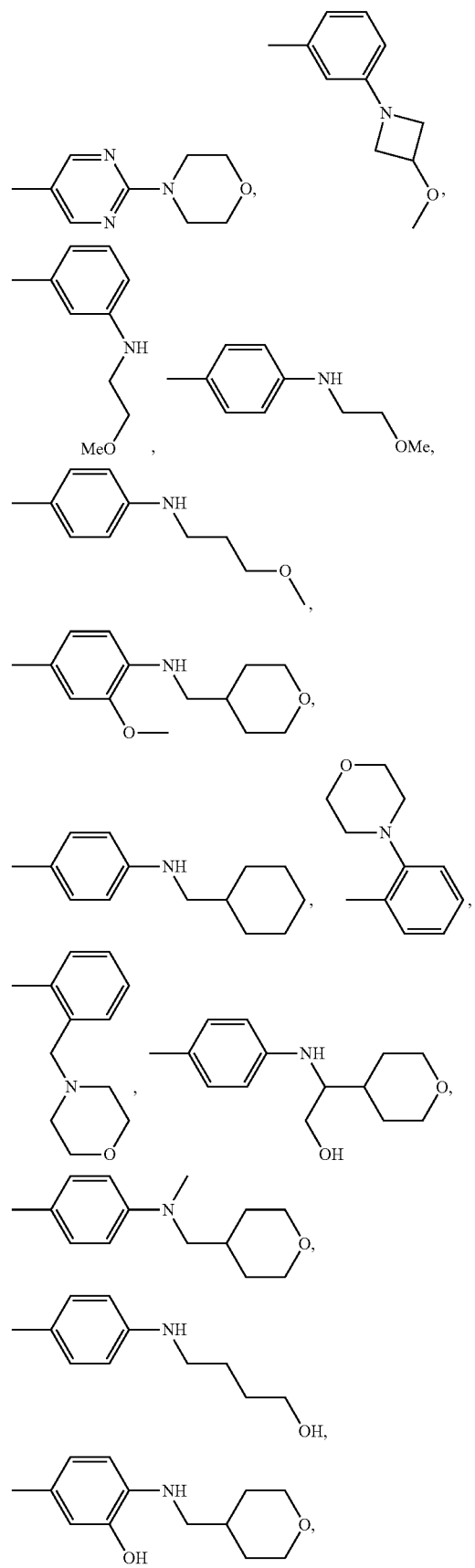

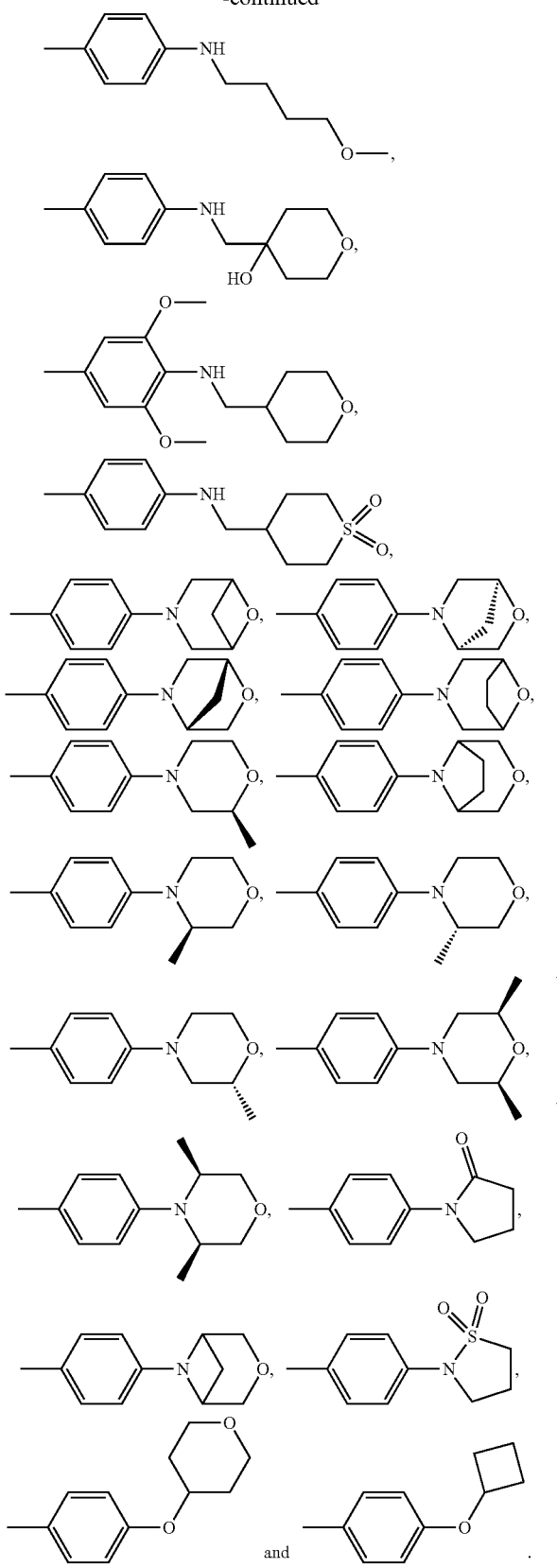
In another particular aspect, $R_3$ is a radical selected in the group consisting of:
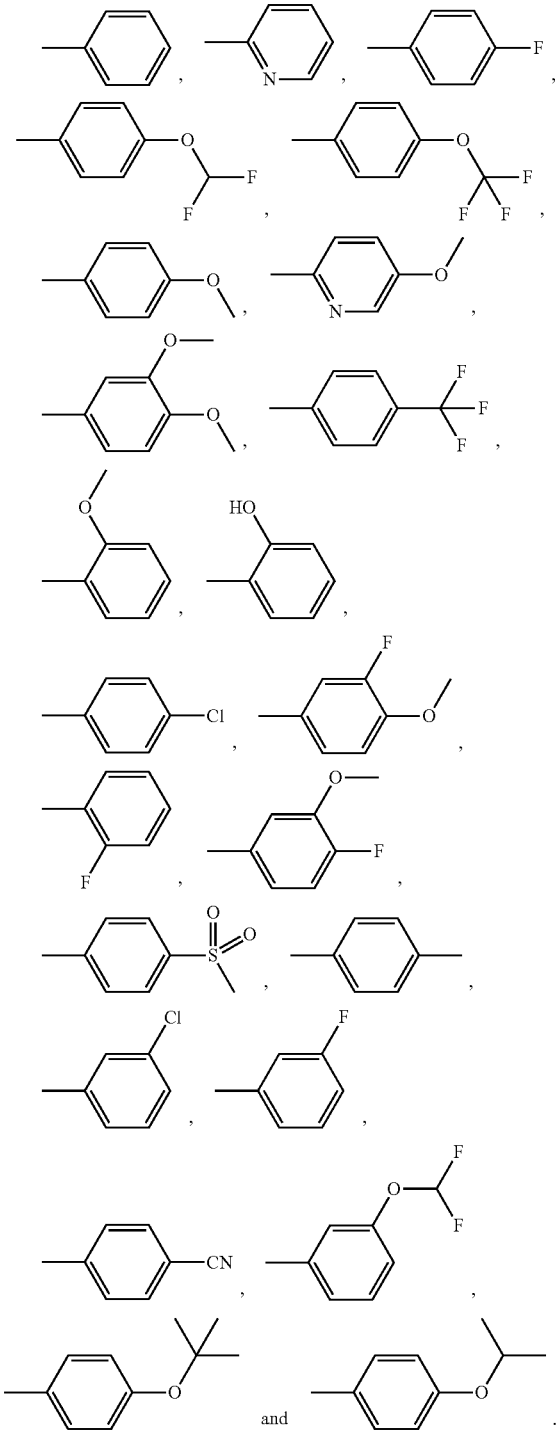
In a further particular aspect, $R_3$ is a radical selected in the group consisting of:

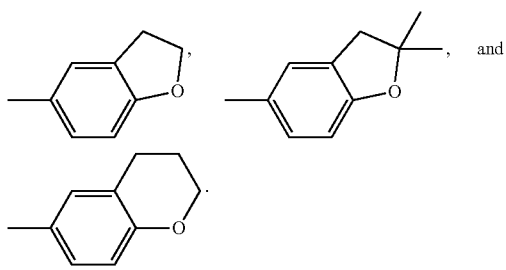

In a further particular aspect, $R_3$ is a cycloalkyl, preferably a cyclohexyl, optionally substituted by a $(C_1-C_6)$alkyl, preferably a methyl, or a halogen, preferably a fluorine. In a further particular aspect, $R_3$ is a bridged cycloalkyl, preferably a bicyclo[1.1.1]pentanyl, optionally substituted by a $(C_1-C_6)$alkyl, preferably a methyl, or a halogen, preferably a fluorine.

In a further particular aspect, $R_3$ is a $(C_1-C_6)$alkyl, preferably a tert-butyl or a methyl substituted by a phenyl (i.e., a benzyl).

In a particular embodiment, $R_4$ represents:
- a —$CO_2R_{10}$ with $R_{10}$ being a hydrogen or a $(C_1-C_6)$alkyl; or
- a 5-10 membered ring, saturated or unsaturated selected in the group consisting of an aryl, a heteroaryl, a cycloalkyl, and a heterocycloalkyl, said 5-10 membered ring is optionally substituted by a hydroxy, a halogen, or a $(C_1-C_6)$alkyl optionally substituted by at least one halogen, preferably optionally substituted by at least one fluorine, and $R_1$, $R_2$, $R_3$, and $R_5$ are such as defined herein are such as defined herein.

In one embodiment, the 5-10 membered ring is selected so as to be an (bio)isostere of a carboxyl group.

In a preferred embodiment, $R_4$ represents a heteroaryl, preferably a tetrazolyl, an aryl optionally substituted by a hydroxy, preferably a phenyl substituted by a hydroxy, or a —$CO_2R_{10}$ with $R_{10}$ being a hydrogen or a $(C_1-C_6)$alkyl, preferably an ethyl. In a more preferred embodiment, $R_4$ represents a —$CO_2R_{10}$ with $R_{10}$ being a hydrogen, i.e. —COOH.

In a particular embodiment, $R_5$ represents a hydrogen.

In a preferred embodiment, the compound according to the present invention is selected in the group consisting of compounds of the table A below:

TABLE A

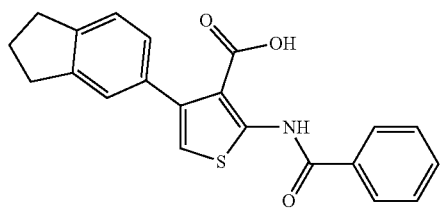 [SMILES: O=C(Nc1scc(-c2ccc3c(c2)CCC3)c1C(=O)O)c1ccccc1]

Compound #3

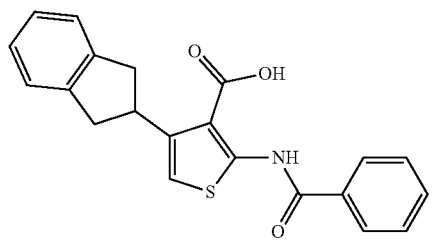 [SMILES: O=C(Nc1scc(C2Cc3ccccc3C2)c1C(=O)O)c1ccccc1]

Compound #7

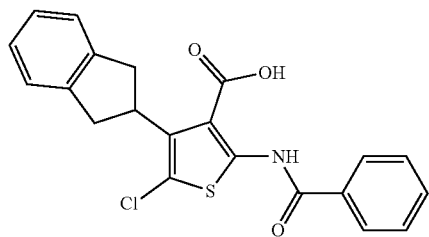 [SMILES: O=C(Nc1sc(Cl)c(C2Cc3ccccc3C2)c1C(=O)O)c1ccccc1]

Compound #8

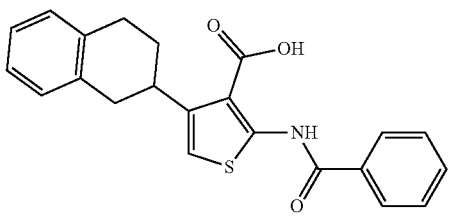

Compound #16

TABLE A-continued
Compound #17
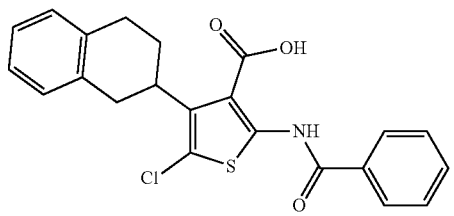 [SMILES: O=C(Nc1sc(Cl)c(C2CCc3ccccc3C2)c1C(=O)O)c1ccccc1]
Compound #19
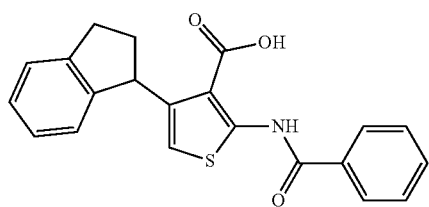 [SMILES: O=C(Nc1scc(C2CCc3ccccc32)c1C(=O)O)c1ccccc1]
Compound #49
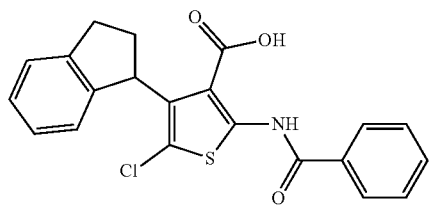 [SMILES: O=C(Nc1sc(Cl)c(C2CCc3ccccc32)c1C(=O)O)c1ccccc1]
Compound #51
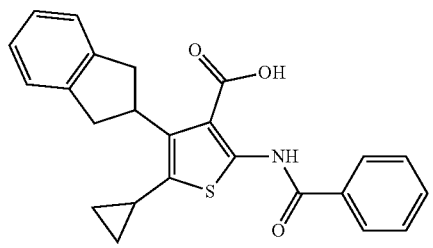 [SMILES: O=C(Nc1sc(C2CC2)c(C2Cc3ccccc3C2)c1C(=O)O)c1ccccc1]
Compound #52
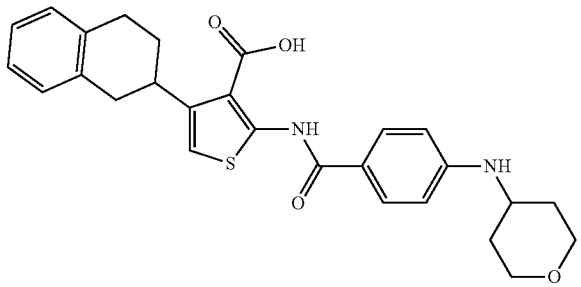 [SMILES: O=C(Nc1scc(C2CCc3ccccc3C2)c1C(=O)O)c1ccc(NC2CCOCC2)cc1]
Compound #53
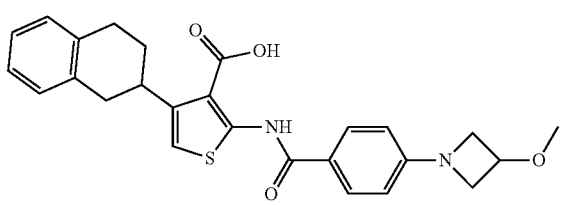 [SMILES: COC1CN(c2ccc(C(=O)Nc3scc(C4CCc5ccccc5C4)c3C(=O)O)cc2)C1]

TABLE A-continued
Compound #55
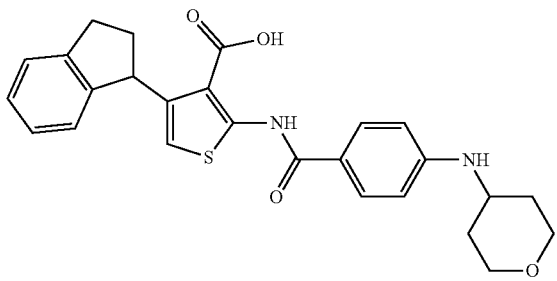 [SMILES: O=C(Nc1scc(C2CCc3ccccc32)c1C(=O)O)c1ccc(NC2CCOCC2)cc1]
Compound #56
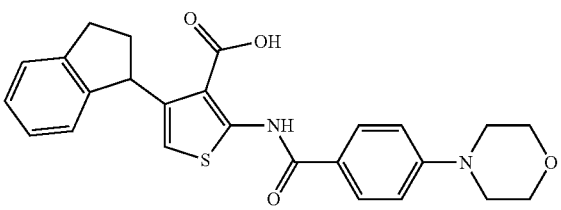 [SMILES: O=C(Nc1scc(C2CCc3ccccc32)c1C(=O)O)c1ccc(N2CCOCC2)cc1]
Compound #57
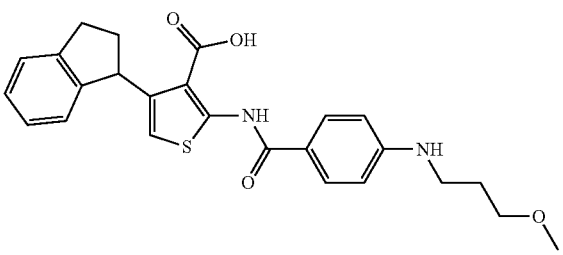 [SMILES: COCCCNc1ccc(C(=O)Nc2scc(C3CCc4ccccc43)c2C(=O)O)cc1]
Compound #58
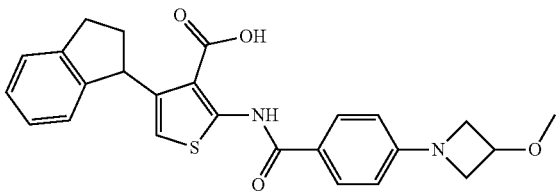 [SMILES: COC1CN(c2ccc(C(=O)Nc3scc(C4CCc5ccccc54)c3C(=O)O)cc2)C1]
Compound #64
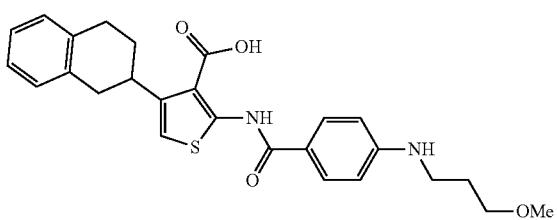 [SMILES: COCCCNc1ccc(C(=O)Nc2scc(C3CCc4ccccc4C3)c2C(=O)O)cc1]
Compound #65
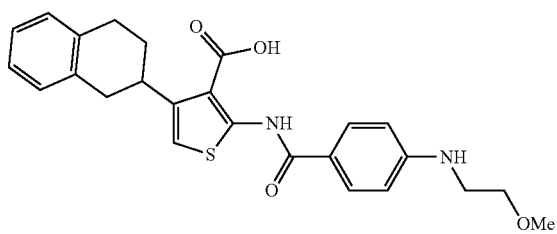

TABLE A-continued
Compound #67
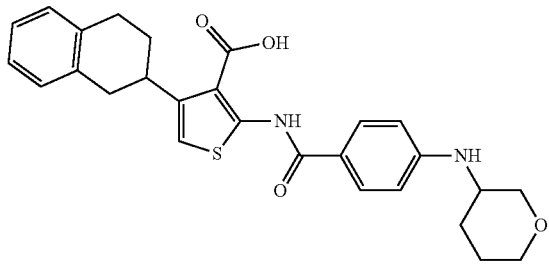 [SMILES: O=C(Nc1scc(C2CCc3ccccc3C2)c1C(=O)O)c1ccc(NC2CCCOC2)cc1]
Compound #68
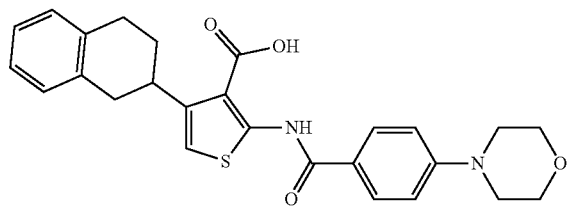
Compound #69
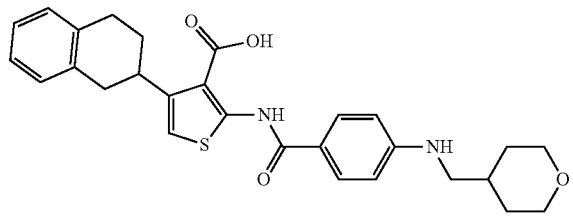 [SMILES: O=C(Nc1scc(C2CCc3ccccc3C2)c1C(=O)O)c1ccc(NCC2CCOCC2)cc1]
Compound #70
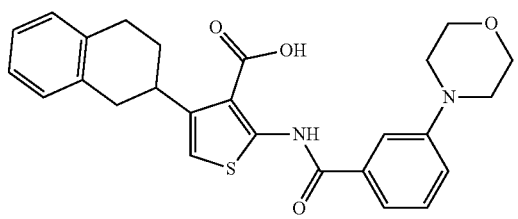
Compound #86
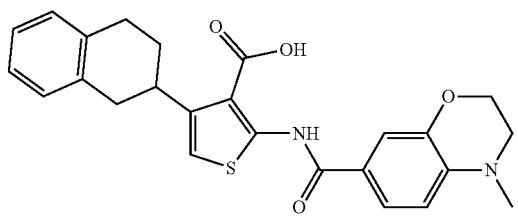 [SMILES: CN1CCOc2cc(C(=O)Nc3scc(C4CCc5ccccc5C4)c3C(=O)O)ccc21]
Compound #89
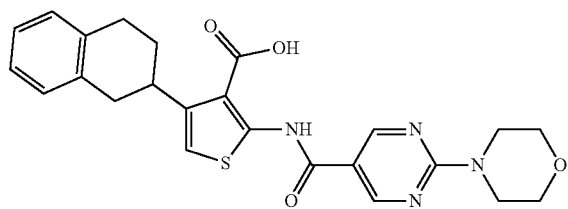 [SMILES: O=C(Nc1scc(C2CCc3ccccc3C2)c1C(=O)O)c1cnc(N2CCOCC2)nc1]

TABLE A-continued
Compound #93
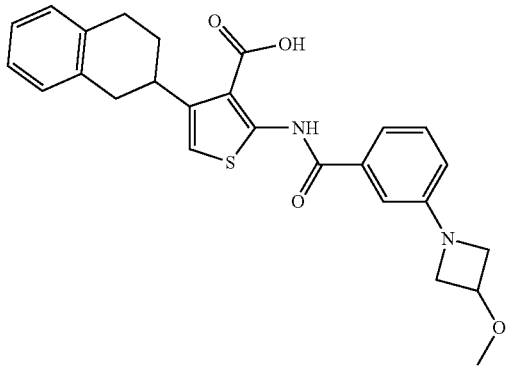 [SMILES: COC1CN(c2cccc(C(=O)Nc3scc(C4CCc5ccccc5C4)c3C(=O)O)c2)C1]
Compound #94
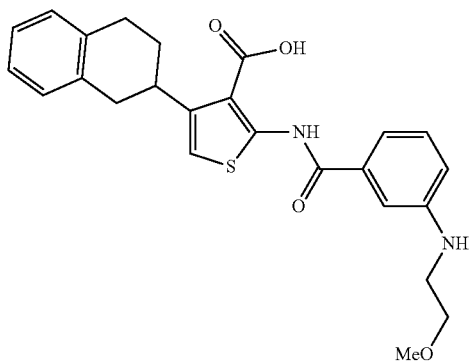 [SMILES: COCCNc1cccc(C(=O)Nc2scc(C3CCc4ccccc4C3)c2C(=O)O)c1]
Compound #101
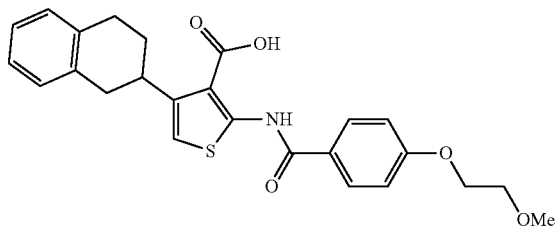 [SMILES: COCCOc1ccc(C(=O)Nc2scc(C3CCc4ccccc4C3)c2C(=O)O)cc1]
Compound #122
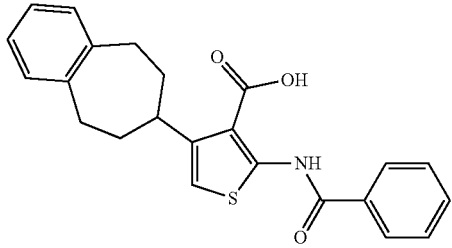 [SMILES: O=C(Nc1scc(C2CCc3ccccc3CC2)c1C(=O)O)c1ccccc1]
Compound #123
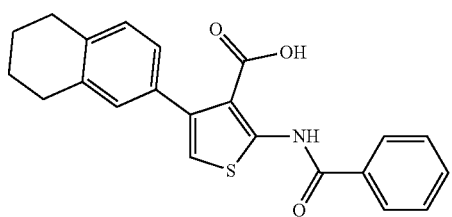 [SMILES: O=C(Nc1scc(-c2ccc3c(c2)CCCC3)c1C(=O)O)c1ccccc1]

TABLE A-continued
Compound #124
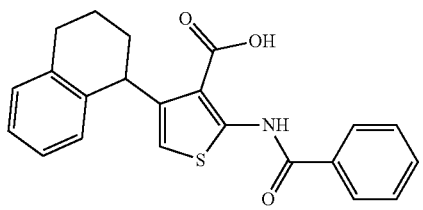 [SMILES: O=C(Nc1scc(C2CCCc3ccccc32)c1C(=O)O)c1ccccc1]
Compound #125
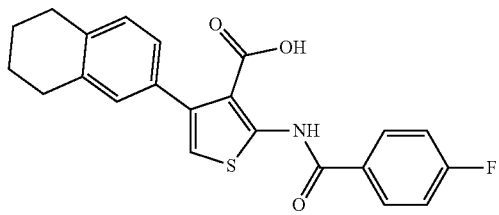 [SMILES: O=C(Nc1scc(-c2ccc3c(c2)CCCC3)c1C(=O)O)c1ccc(F)cc1]
Compound #126
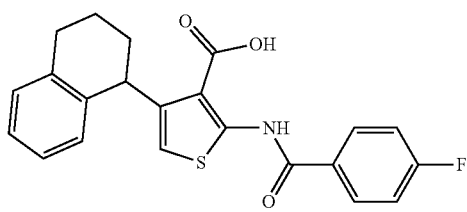 [SMILES: O=C(Nc1scc(C2CCCc3ccccc32)c1C(=O)O)c1ccc(F)cc1]
Compound #127
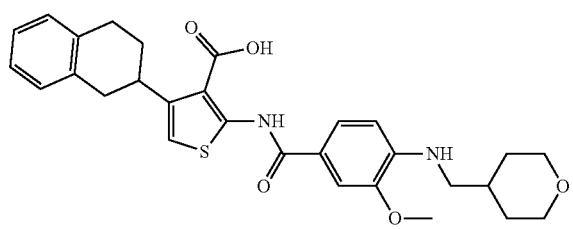 [SMILES: COc1cc(C(=O)Nc2scc(C3CCc4ccccc4C3)c2C(=O)O)ccc1NCC1CCOCC1]
Compound #128
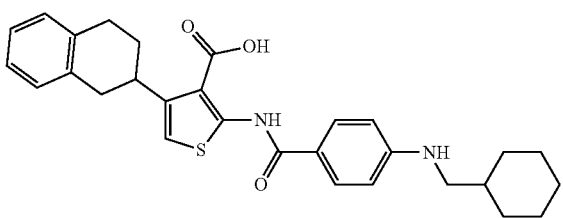 [SMILES: O=C(Nc1scc(C2CCc3ccccc3C2)c1C(=O)O)c1ccc(NCC2CCCCC2)cc1]
Compound #129
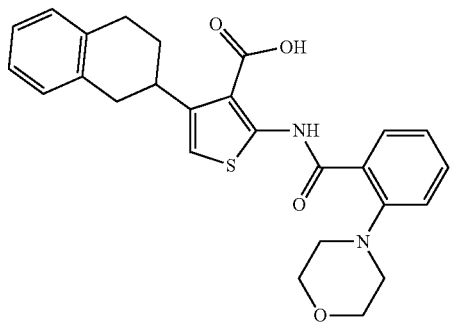 [SMILES: O=C(Nc1scc(C2CCc3ccccc3C2)c1C(=O)O)c1ccccc1N1CCOCC1]

TABLE A-continued
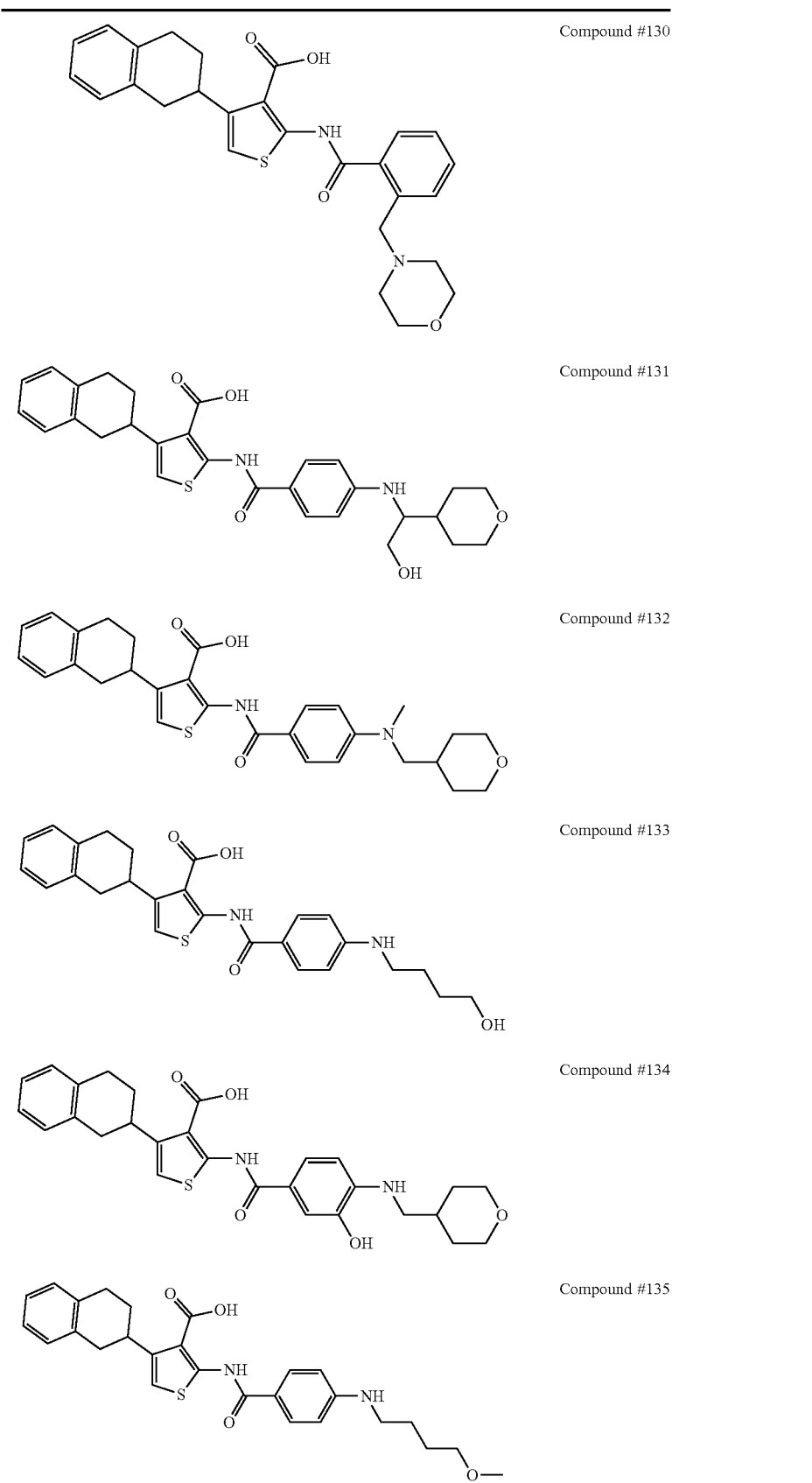
Compound #130
Compound #131
Compound #132
Compound #133
Compound #134
Compound #135

TABLE A-continued
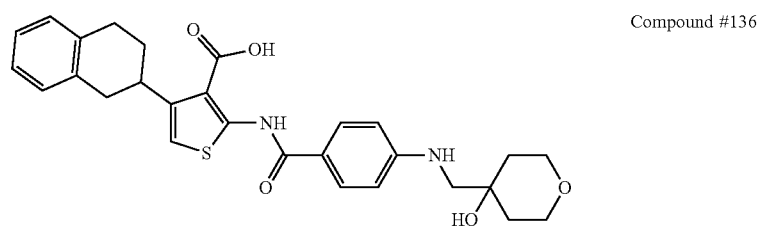 Compound #136
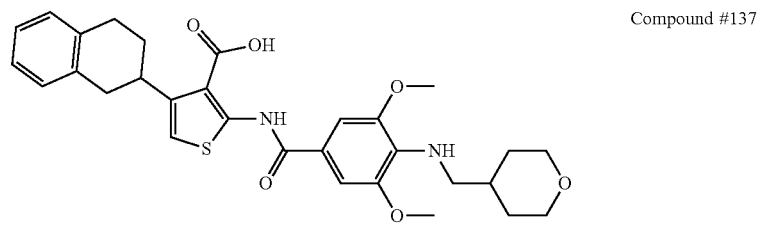 Compound #137
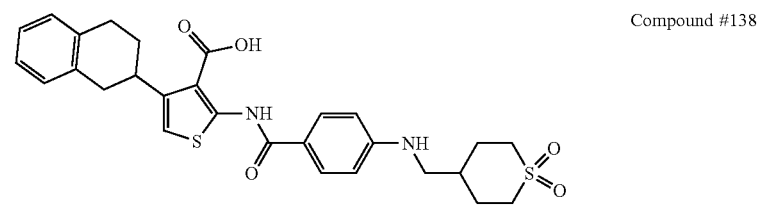 Compound #138
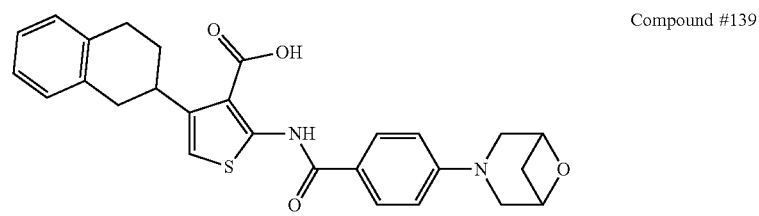 Compound #139
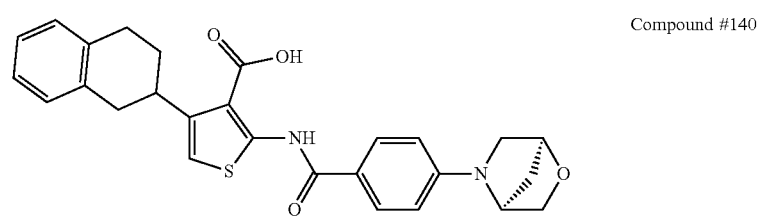 Compound #140
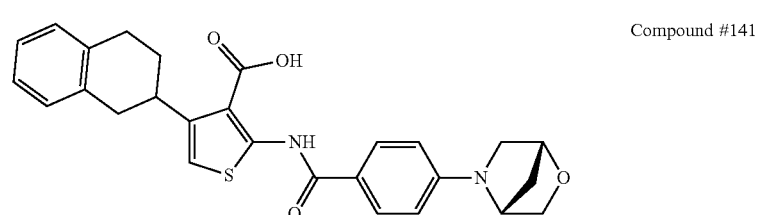 Compound #141
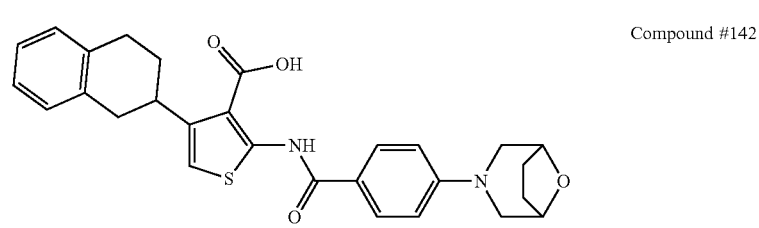 Compound #142

TABLE A-continued
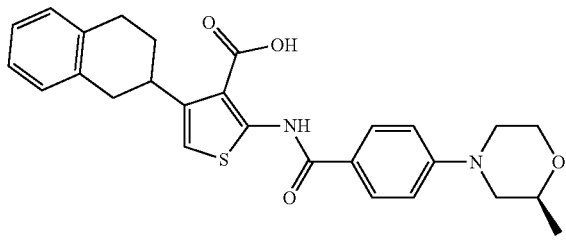 [SMILES: C[C@H]1CN(c2ccc(C(=O)Nc3scc(C4CCc5ccccc5C4)c3C(=O)O)cc2)CCO1]
Compound #143
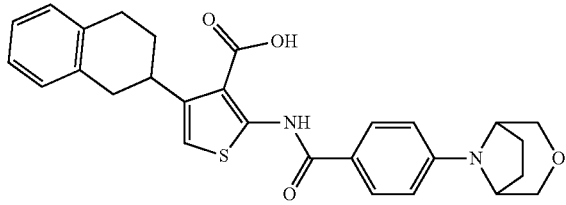 [SMILES: O=C(Nc1scc(C2CCc3ccccc3C2)c1C(=O)O)c1ccc(N2C3CCC2COC3)cc1]
Compound #144
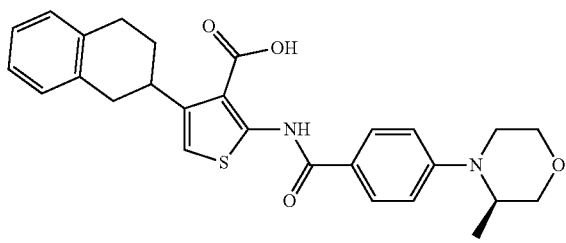
Compound #145
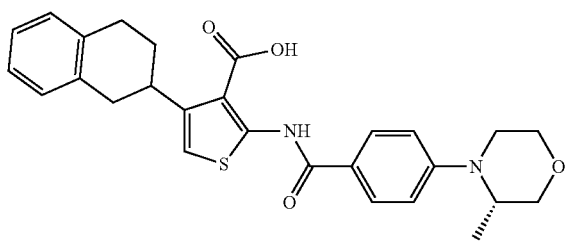 [SMILES: C[C@H]1COCCN1c1ccc(C(=O)Nc2scc(C3CCc4ccccc4C3)c2C(=O)O)cc1]
Compound #146
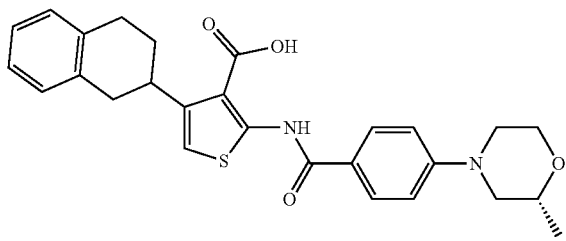
Compound #147
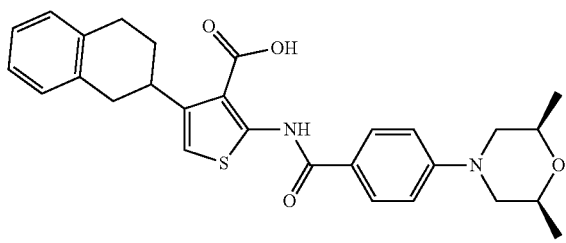 [SMILES: C[C@@H]1CN(c2ccc(C(=O)Nc3scc(C4CCc5ccccc5C4)c3C(=O)O)cc2)C[C@H](C)O1]
Compound #148

TABLE A-continued
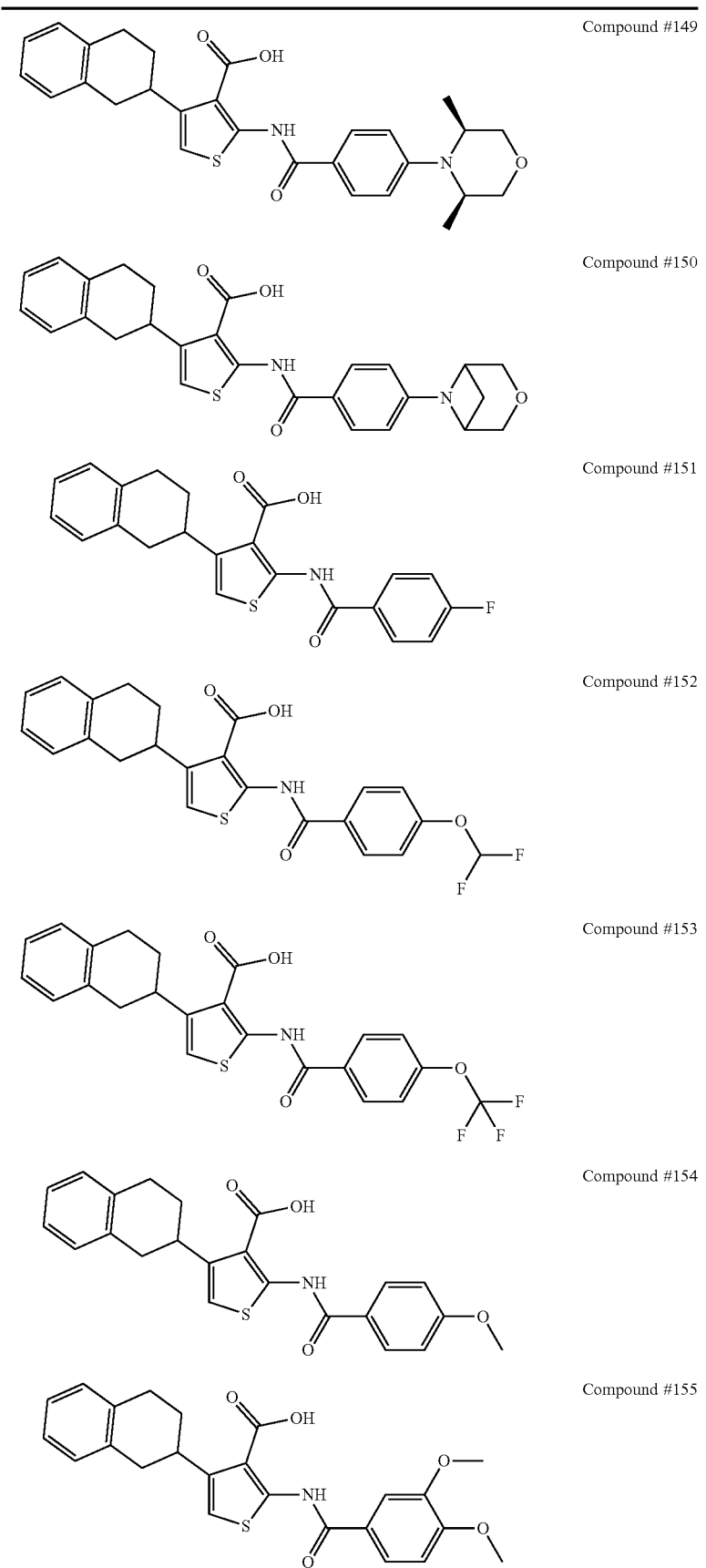
Compound #149
Compound #150
Compound #151
Compound #152
Compound #153
Compound #154
Compound #155

TABLE A-continued
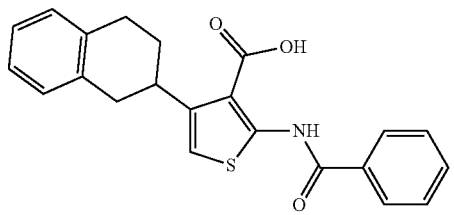 [SMILES: O=C(Nc1scc(C2CCc3ccccc3C2)c1C(=O)O)c1ccccc1] Compound #156
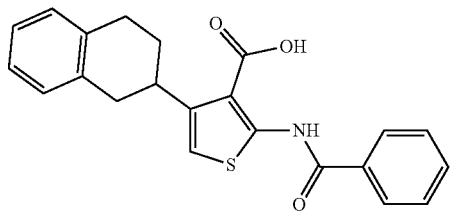 [SMILES: O=C(Nc1scc(C2CCc3ccccc3C2)c1C(=O)O)c1ccccc1] Compound #157
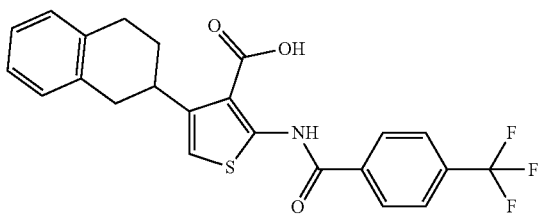 [SMILES: O=C(Nc1scc(C2CCc3ccccc3C2)c1C(=O)O)c1ccc(C(F)(F)F)cc1] Compound #158
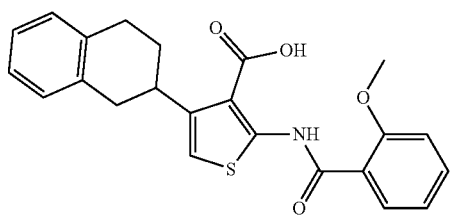 Compound #159
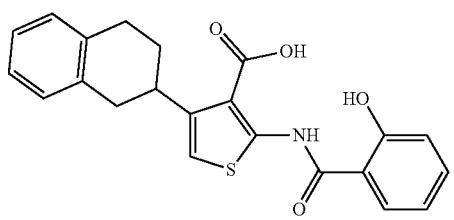 Compound #160
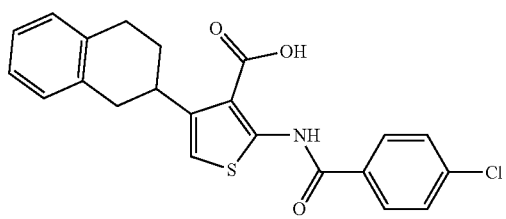 [SMILES: O=C(Nc1scc(C2CCc3ccccc3C2)c1C(=O)O)c1ccc(Cl)cc1] Compound #161
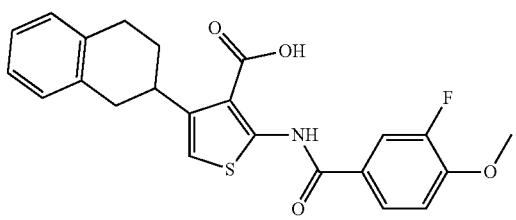 [SMILES: COc1ccc(C(=O)Nc2scc(C3CCc4ccccc4C3)c2C(=O)O)cc1F] Compound #162

TABLE A-continued
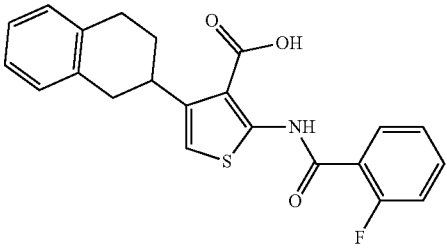 [SMILES: O=C(Nc1scc(C2CCc3ccccc3C2)c1C(=O)O)c1ccccc1F]
Compound #163
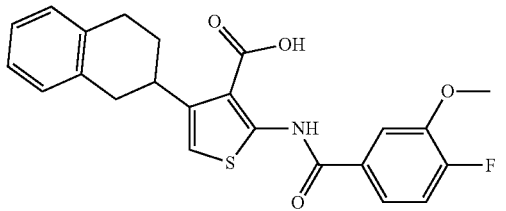 [SMILES: COc1cc(C(=O)Nc2scc(C3CCc4ccccc4C3)c2C(=O)O)ccc1F]
Compound #164
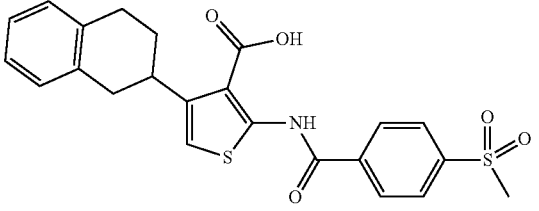 [SMILES: CS(=O)(=O)c1ccc(C(=O)Nc2scc(C3CCc4ccccc4C3)c2C(=O)O)cc1]
Compound #165
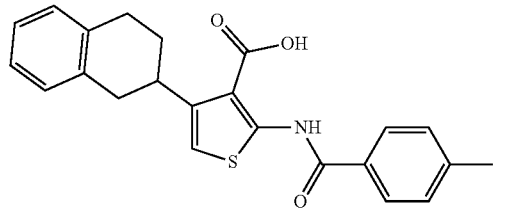 [SMILES: Cc1ccc(C(=O)Nc2scc(C3CCc4ccccc4C3)c2C(=O)O)cc1]
Compound #166
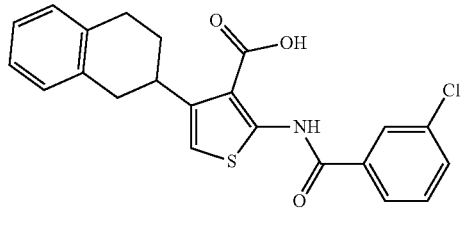 [SMILES: O=C(Nc1scc(C2CCc3ccccc3C2)c1C(=O)O)c1cccc(Cl)c1]
Compound #167
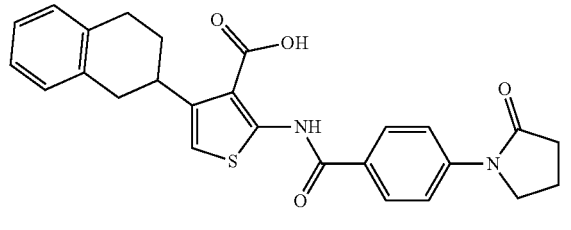 [SMILES: O=C(Nc1scc(C2CCc3ccccc3C2)c1C(=O)O)c1ccc(N2CCCC2=O)cc1]
Compound #168
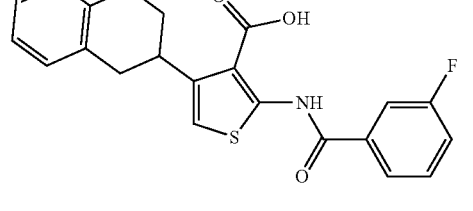
Compound #169

TABLE A-continued
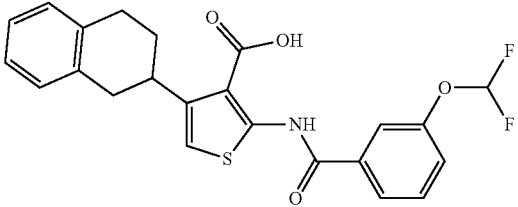 [SMILES: O=C(Nc1scc(C2CCc3ccccc3C2)c1C(=O)O)c1cccc(OC(F)F)c1] Compound #170
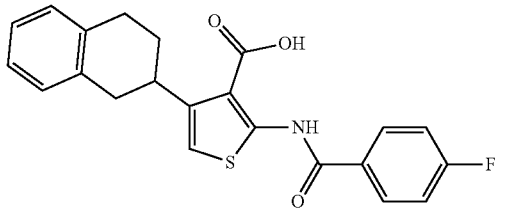 [SMILES: O=C(Nc1scc(C2CCc3ccccc3C2)c1C(=O)O)c1ccc(F)cc1] Compound #171
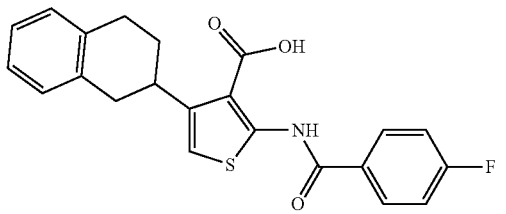 [SMILES: O=C(Nc1scc(C2CCc3ccccc3C2)c1C(=O)O)c1ccc(F)cc1] Compound #172
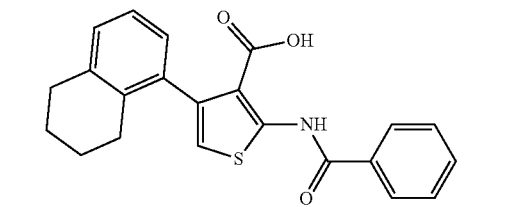 [SMILES: O=C(Nc1scc(-c2cccc3c2CCCC3)c1C(=O)O)c1ccccc1] Compound #194
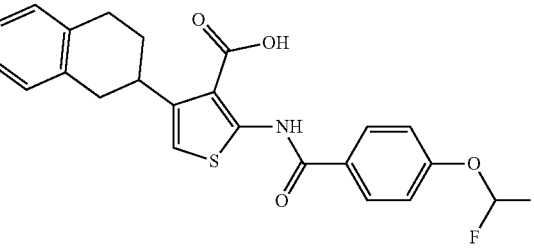 Compound #174
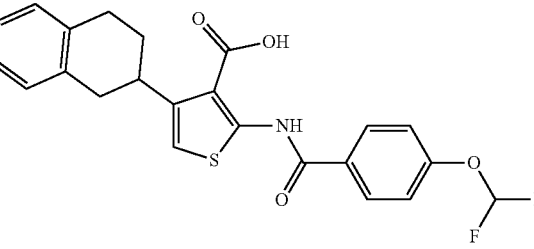 Compound #175
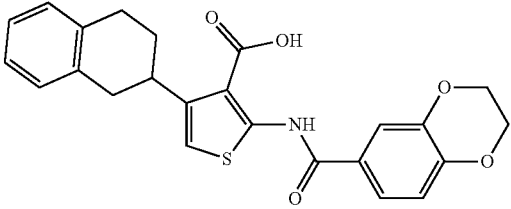 [SMILES: O=C(Nc1scc(C2CCc3ccccc3C2)c1C(=O)O)c1ccc2c(c1)OCCO2] Compound #176

TABLE A-continued
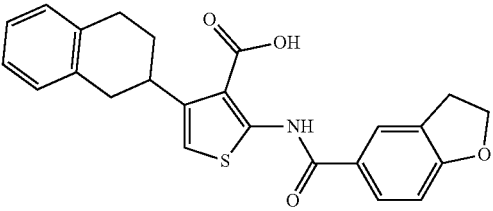 [SMILES: O=C(Nc1scc(C2CCc3ccccc3C2)c1C(=O)O)c1ccc2c(c1)CCO2]
Compound #177
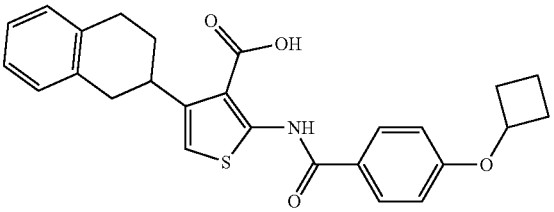 [SMILES: O=C(Nc1scc(C2CCc3ccccc3C2)c1C(=O)O)c1ccc(OC2CCC2)cc1]
Compound #178
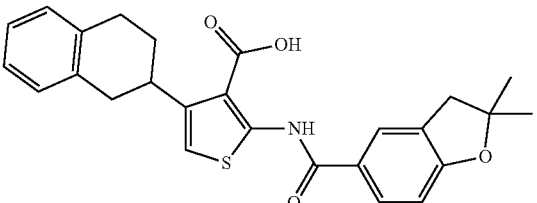
Compound #179
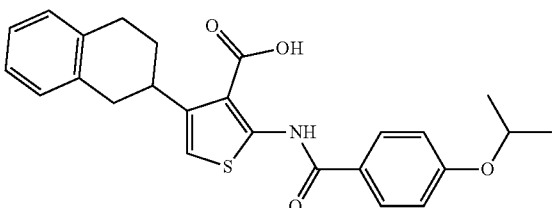
Compound #180
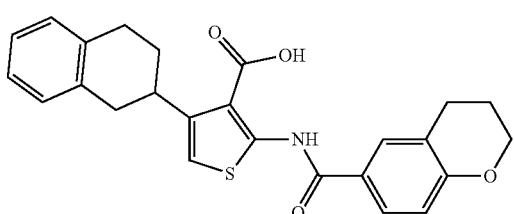
Compound #181
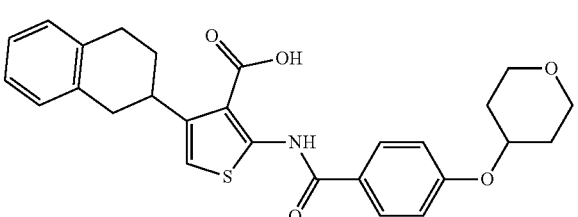
Compound #182
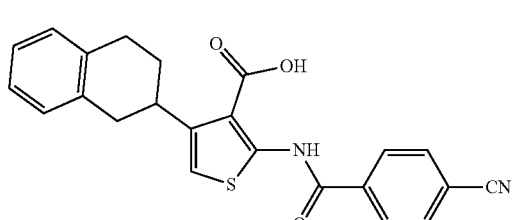
Compound #183

TABLE A-continued
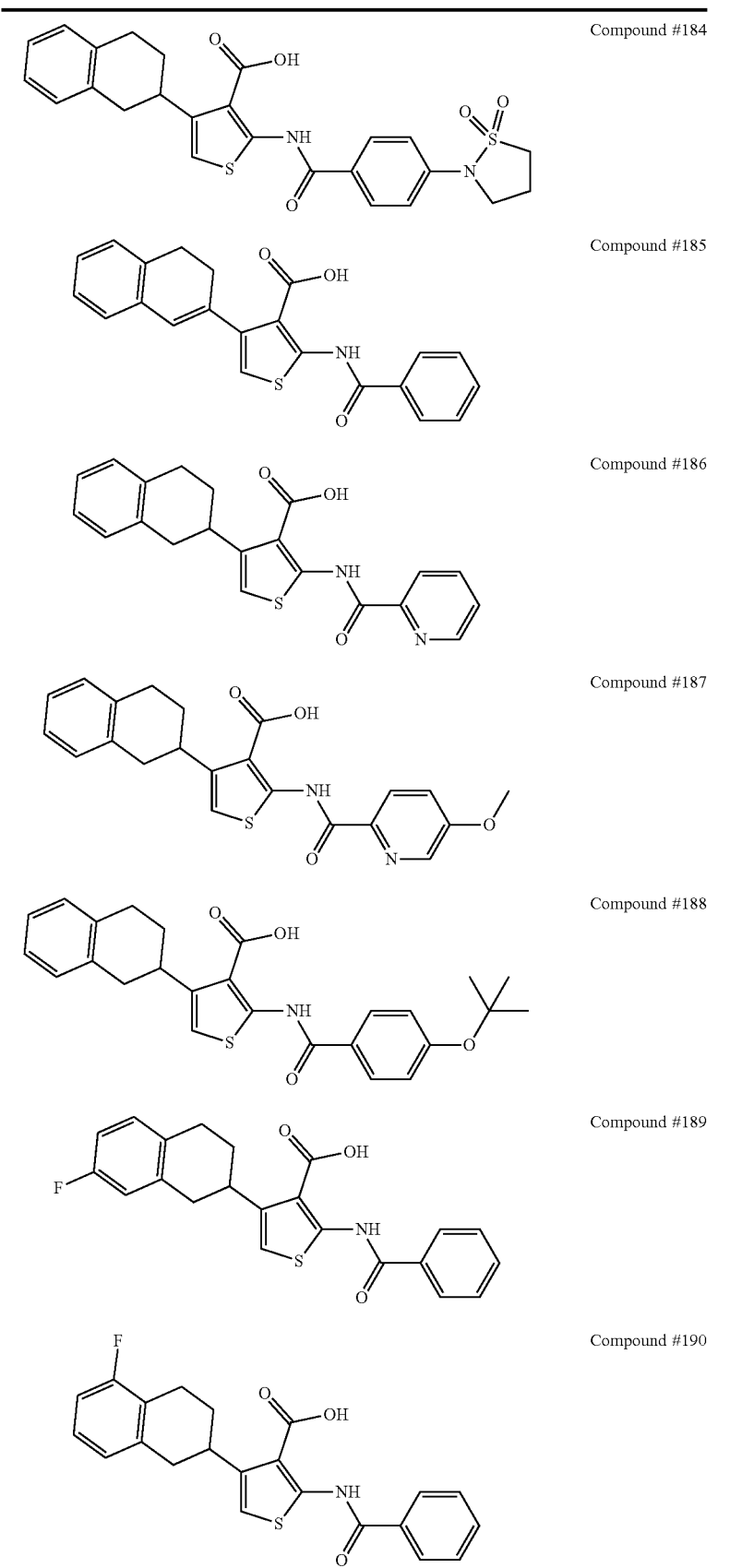
Compound #184
Compound #185
Compound #186
Compound #187
Compound #188
Compound #189
Compound #190

TABLE A-continued

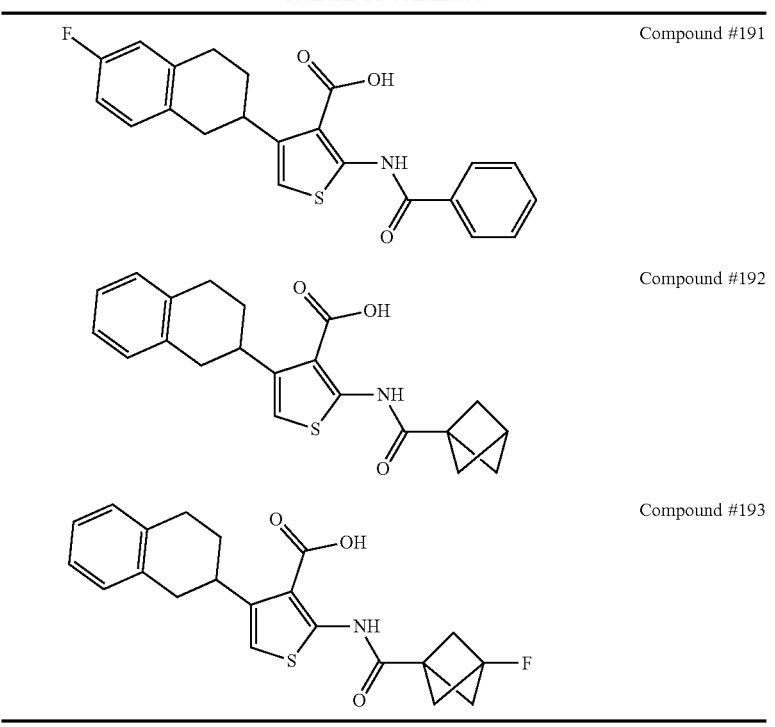

Compound #191

Compound #192

Compound #193

A particular aspect of the present invention relates to any pharmaceutically acceptable salt of the compounds as disclosed above and any enantiomer or diastereoisomer of the compounds as disclosed above.

A more particular aspect relates to any enantiomer of the compounds as disclosed above. These enantiomers can be obtained from the corresponding carboxylate compound which is purified by chiral SFC (in particular the Chiral SFC purification method of table 3) to give a first eluting enantiomer carboxylate compound and a second eluting enantiomer carboxylate compound follow by a step of deprotecting the carboxylate to give the corresponding enantiomer 1 and 2. The first enantiomer carboxylate compound corresponds to the first compound eluted from the chiral SFC. The second enantiomer carboxylate compound corresponds to the second compound eluted from the chiral SFC. After the deprotection step, the first enantiomer carboxylate compound gives a so called "first enantiomer" and the second enantiomer carboxylate compound gives a so called "second enantiomer". These enantiomers can also be obtained from the corresponding racemate which is purified by chiral SFC (in particular the Chiral SFC purification method of table 3) to give a first enantiomer compound and a second enantiomer compound. The first enantiomer compound corresponds to the first compound eluted from the chiral SFC. The second enantiomer compound corresponds to the second compound eluted from the chiral SFC.

More particularly, the present invention relates to the following enantiomers:
- second enantiomer of compound #16: compound #157;
- first enantiomer of compound #151: compound #171; and
- first enantiomer of compound #152: compound #175, and
  - second enantiomer of compound #152: compound #174.

Therapeutic Uses of Compounds

As illustrated by examples, the inventors have demonstrated the therapeutic interest of the new compounds of the invention.

Accordingly, the present invention relates to a pharmaceutical or veterinary composition comprising a new compound according to the invention. Preferably, the pharmaceutical composition further comprises a pharmaceutically or veterinary acceptable carrier or excipient. The present invention relates to the use of a new compound according to the invention as a drug or a medicine. The invention further relates to a method for treating a disease in a subject, wherein a therapeutically effective amount of a new compound according to the invention, is administered to said subject in need thereof. The invention also relates to the use of a new compound according to the invention, for the manufacture of a medicine. The invention also relates to a pharmaceutical composition comprising a new compound according to the invention for use as a drug.

The present invention relates to a new compound according to the invention for use for treating a disease selected from the group consisting of an infection, preferably a viral or a bacterial infection, a cancer, a metabolic disease, a cardiovascular disease, an inflammatory disorder, iron storage disease/disorder, aging and a neurodegenerative disease or disorder. It further relates to the use of a new compound according to the invention, for the manufacture of a medicine for treating a disease selected from the group consisting of an infection, preferably a viral or a bacterial infection, a cancer, a metabolic disease, a cardiovascular disease, an inflammatory disorder, iron storage disease/disorder, aging and a neurodegenerative disease or disorder. It also relates to a pharmaceutical composition comprising a new compound according to the invention for use for treating a disease selected from the group consisting of an infection, preferably a viral or a bacterial infection, a cancer, a metabolic disease, a cardiovascular disease, an inflammatory disorder, iron storage disease/disorder, aging and a neurodegenerative disease or disorder. Finally, it relates to a method for treating a disease selected from the group consisting of an infection, preferably a viral or a bacterial infection, a cancer, a metabolic disease, a cardiovascular disease, an inflammatory disorder, iron storage disease/disorder, aging and a neurodegenerative disease or disorder in a subject in need thereof, wherein a therapeutically effective amount of a new compound according to the invention, is administered to said subject in need thereof.

In addition, the present invention relates to a method for treating an infectious disease, preferably a viral disease, in a subject, wherein a therapeutically effective amount of a compound according to the invention, is administered to said subject suffering of an infectious disease, preferably a viral disease. The present invention relates to the use of the compounds according to the invention as an anti-infectious agent, preferably an antiviral agent. The invention also relates to the use of the compounds according to the invention, for the manufacture of a medicine for the treatment of an infectious disease, preferably a viral infection. The invention relates to a compound according to the invention for use in the treatment of an infectious disease, preferably a viral infection.

The present invention further relates to a method for treating a cancer in a subject, wherein a therapeutically effective amount of a compound according to the invention is administered to said subject suffering of a cancer. The present invention relates to the use of the compounds according to the invention as an antitumor agent. The invention also relates to the use of the compounds according to the invention, for the manufacture of a medicine for the treatment of a cancer. The invention relates to a compound according to the invention for use in the treatment of a cancer.

The present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

The present invention further relates to a method for treating an inflammatory disease or disorder in a subject, wherein a therapeutically effective amount of a compound according to the invention is administered to said subject suffering of an inflammatory disease or disorder. The invention also relates to the use of the compounds according to the invention, for the manufacture of a medicine for the treatment of an inflammatory disease or disorder. The invention relates to a compound according to the invention for use in the treatment of an inflammatory disease or disorder.

The present invention also relates to a phytosanitary composition comprising a compound according to the invention. It also relates to the use of a compound according to the invention as a phytosanitary agent. Thereby, the compound according to the invention. It further relates to a method for treating a plant against infection, especially infection by a virus, comprising contacting the plant with an efficient amount of a compound according to the invention.

The present invention further relates to a method for treating aging or a neurodegenerative disease or disorder in a subject, wherein a therapeutically effective amount of a compound according to the invention is administered to said subject suffering of aging or a neurodegenerative disease or disorder. The invention also relates to the use of a compound according to the invention, for the manufacture of a medicine for the treatment of aging or a neurodegenerative disease or disorder. The invention relates to a compound according to the invention for use in the treatment of aging or a neurodegenerative disease or disorder.

Antiviral Agents

The present invention relates to the use of a compound according to the invention as an antiviral agent. The present invention also relates to a compound of the present invention for use in the treatment of viral infections, the use of a compound of the present invention for the manufacture of a medicine for the treatment of viral infections, and to a method for treating a viral infection in a subject, comprising administering a therapeutically effective amount of a compound according to the invention to the subject.

The present invention also relates to the use of a compound of the present invention as a research tool, especially for studying viral infections. It further relates to a method for blocking viral infection in a cell, a tissue or a subject.

The viral agent can be a DNA virus or a RNA virus. The viral agent can be selected from the group consisting of Alphaviridae, Flaviviridae, Hepadnaviridae, Herpesviridae, Orthomyxoviridae, Papovaviridae, Paramyxoviridae, Picornaviridae, Polyomaviridae, Reoviridae, Retroviridae, Rhabdoviridae, and Tobamoviruses.

In one embodiment, the Alphaviridae is selected from the group consisting of Barmah Forest virus, Middelburg virus, Ndumu virus, Bebaru virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus, Cabassou virus, Everglades virus, Mosso das Pedras virus, Mucambo virus, Parmana virus, Pixuna virus, Rio Negro virus, Trocara virus, Aura virus, Babanki virus, Kyzylagach virus, Ockelbo virus, Whataroa virus, Sleeping disease virus, Samon pancreatic disease virus, Southern elephant seal virus, and Western equine encephalitis virus; preferably selected from the group consisting of Barmah Forest virus, Chikungunya virus, Mayaro virus, O'nyong'nyong virus, Ross River virus, Semliki Forest virus, Sindbis virus, Una virus, Eastern equine encephalitis virus, Tonate virus, Venezuelan equine encephalitis virus and Western equine encephalitis virus.

In one embodiment, the Flaviviridae is selected from the group consisting of dengue virus, Hepatitis C virus, Japanese encephalitis virus, West Nile virus, yellow fever virus, Zika virus, Tick-borne encephalitis virus, Kyasanur forest disease virus, Murray Valley encephalitis virus, and Saint Louis encephalitis virus.

In one embodiment, the Hepadnaviridae is selected from the group consisting of Hepatitis B virus.

In one embodiment, the Herpesviridae is selected from the group consisting of Herpes Simplex virus 1 (HSV-1), Herpes Simplex virus 2 (HSV-2), Varicella zoster virus (VZV), Epstein-Barr virus (EBV), Cytomegalovirus (CMV), Roseolovirus (HHV-6A and 6B), HHV-7 and Kaposi's sarcoma-associated herpesvirus (KSHV).

In one embodiment, the Orthomyxoviridae is selected from the group consisting of Influenza virus A, Influenza virus B, Influenza virus C, Isavirus, Thogotovirus and Quaranjavirus, preferably selected from the group consisting of Influenza virus A and Influenza virus B. In one embodiment, the Influenza virus A is selected from the subtypes consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7.

In one embodiment, the Papovaviridae is selected from the group consisting of Papillomavirus (HPC) and Polyomavirus, especially Simian virus 40, Merkel cell polyomavirus, Trichodysplasia spinulosa polyomavirus, BK polyomavirus, JC polyomavirus and Human polyomavirus 7.

In one embodiment, the Paramyxoviridae is selected from the group consisting of Rubulavirus, Morbillivirus, Pneumovirus, Metapneumovirus, Avulavirus, Ferlavirus, Henipavirus, and Respirovirus. In a particular embodiment, the Paramyxoviridae is the mumps virus, measles virus, human parainfluenza viruses (HPIV), especially HPIV-1, HPIV-2, HPIV-3 or HPIV-4, respiratory syncytial virus (RSV), in particular Human respiratory syncytial virus (HRSV), canine distemper virus, phocine distemper virus, cetacean morbillivirus, Newcastle disease virus, rinderpest virus, Hendra virus and Nipah virus.

In one embodiment, the Picornaviridae is selected from the group consisting of Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Piscevirus, Rhinovirus, Salivirus, Sapelovirus, Senecavirus, Techovirus, and Tremovirus. In a particular embodiment, the Picornaviridae is a Rhinovirus, for instance a Rhinovirus A, Rhinovirus B or Rhinovirus C.

In one embodiment, the Retroviridae is selected from the group consisting of Alpharetrovirus; especially Avian leukosis virus and Rous sarcoma virus; Betaretrovirus, especially Mouse mammary tumour virus; Gammaretrovirus, especially Murine leukemia virus and Feline leukemia virus; Deltaretrovirus, especially Bovine leukemia virus and Human T-lymphotropic virus; Epsilonretrovirus, especially Walleye dermal sarcoma virus; Lentivirus, especially Human immunodeficiency virus 1 and Simian, Feline immunodeficiency viruses; Spumavirus, especially Simian foamy virus.

In one embodiment, the Rhabdoviridae is selected from the group consisting of vesiculovirus, especially vesicular stomatitis virus, lyssavirus, rabies virus, Ephemerovirus, novirhabdovirus, cytorhabdovirus and nucleorhabdovirus.

In one preferred embodiment, the viral agent according to the invention is selected from the group consisting in Herpesviridae such as Varicella zoster virus (VZV), Epstein-Barr (EB) virus, Herpes simplex virus of type 1 (HSV-1), Kaposis sarcoma herpesvirus (KSHV), murine γ-HV68 virus (γ-MHV68), or human cytomegalovirus (HCMV); Hepadnaviridae such as Hepatitis virus B (HBV); Papovaviridae such as Human papillomavirus type 16 (HPV16); Parvoviridae such as Human parvovirus B19; Polyomaviridae such as Simian virus 40; Retroviridae such has Human immunodeficiency virus 1 (HIV-1), or Simian immunodeficiency virus type 1 (SIV 1); Orthomyxoviridae such as Influenza A virus; Flaviviridae such as Dengue virus, or Hepatitis C virus; Picornaviridae such as Poliovirus, Coxsakievirus B3 (CVB3), or Coxsakievirus B4 (CVB4); Reoviridae such as Rotavirus; Alphaviridae such as Sindbis virus; Tobamoviruses such as Tabacco mosaic virus; Rhabdoviridae such as vesicular stomatitis virus. More preferably, the viral agent according to the invention is an influenza virus. Still preferably, the viral agent according to the invention is an influenza virus A or B, even more preferably an influenza virus A.

In another preferred embodiment, the viral agent according to the invention presents an antiviral resistance to classic antiviral drugs. The terms "antiviral resistance", "antiviral agent resistance" or "antiviral drug resistance", as used herein, are equivalent and refer to the ability of viruses to resist the effects of an antiviral agent previously used to treat them. Antiviral resistance can be defined by a decreased susceptibility to a drug through either a minimally effective, or completely ineffective, treatment response to prevent associated illnesses from a particular virus.

In one embodiment, the compound of the invention can be used in combination with another antiviral drug, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

Antibacterial Agents

The present invention relates to the use of a compound according to the invention as an antibacterial agent. The present invention also relates to a compound of the present invention for use in the treatment of bacterial infections, the use of a compound of the present invention for the manufacture of a medicine for the treatment of bacterial infections, and to a method for treating a bacterial infection in a subject, comprising administering a therapeutically effective amount of a compound according to the invention to the subject.

The bacterium can be gram-negative and gram-positive bacteria, preferably an infectious bacterium. Such gram-positive bacteria include, but are not limited to, *Pasteurella* species, Staphylococci species, and *Streptococcus* species.

Specific examples of bacteria include but are not limited to, *Helicobacter pylori, Burkholderia cepacia, Pseudomonas aeruginosa, Pseudomonas fluorescens, Pseudomonas acidovorans, Pseudomonas alcaligenes, Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella parapertussis, Bordetella bronchiseptica, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Campylobacter fetus, Campylobacter jejuni, Campylobacter coli, Borrelia burgdorferi, Vibrio cholerae, Vibrio parahaemolyticus, Listeria monocytogenes, Neisseria gonorrhoeae, Neisseria meningitidis, Kingella denitrificans, Kingella indologenes, Kingella kingae, Kingella oralis, Legionella pneumophila, Moraxella bovis, Moraxella catarrhalis, Moraxella lacunata, Gardnerella vaginalis, Bacteroides fragilis, Bacteroides distasonis, Bacteroides vulgatus, Bacteroides ovalus, Bacteroides thetaiotaomicron, Bacteroides uniformis, Bacteroides eggerthii, Bacteroides splanchnicus,*

*Clostridium difficile, Clostridium tetani, Mycobacterium species, Corynebacterium ulcerans, Streptococcus agalactiae, Gardnerella vaginitis, Streptococcus pyogenes, Enterococcus faecalis, Enterococcus faecium, Fusobacterium nucleatum, Porphyromonas gingivalis, Vibrio vulnificus, Clostridium botulinum, Corynebacterium diptheriae, Staphylococcus aureus, Staphylococcus epidermidis, Staphylococcus saprophyticus, Staphylococcus intermedius, Staphylococcus hyicus, Staphylococcus haemolyticus, Staphylococcus hominis,* or *Staphylococcus* saccharolyticus.

In a particular embodiment, the bacterium is a *Mycobacterium*, for instance *Mycobacterium* species is selected from the group consisting of *M. africanum, M. bovis, M. bovis* BCG, *M. canetti, M. caprae, M. microti, M. mungi, M. orygis, M. pinnipedii, M. suricattae, M. tuberculosis, M. avium, M. avium paratuberculosis, M. avium silvaticum, M. avium* "hominissuis", *M. colombiense, M. indicus pranii, M. asiaticum, M. gordonae, M. gastri* and *M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. bohemicum, M. botniense, M. branderi, M. celatum, M. chimaera, M. conspicuum, M. cookie, M. doricum, M. farcinogenes, M. haemophilum, M. heckeshornense, M. intracellular, M. lacus, M. leprae, M. lepraemurium, M. lepromatosis, M. liflandii, M. malmoense, M. marinum, M. monacense, M. montefiorense, M. murale, M. nebraskense, M. saskatchewanense, M. scrofulaceum, M. shimoidei, M. szulgai, M. tusciae, M. xenopi, M. yongonense, M. intermedium, M. abscessus, M. chelonae, M. bolletii, M. fortuitum, M. fortuitum* subsp. *Acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodie, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense,* and *M. tokaiense,* preferably *Mycobacterium tuberculosis, Mycobacterium leprae,* or *Mycobacterium ulcerans.*

In another preferred embodiment, the bacterium according to the invention presents a resistance to classic antibacterial drugs. The terms "antibacterial resistance", "antibacterial agent resistance" or "antibacterial drug resistance", as used herein, are equivalent and refer to the ability of bacteria to resist the effects of an antibacterial agent previously used to treat them. Antibacterial resistance can be defined by a decreased susceptibility to a drug through either a minimally effective, or completely ineffective, treatment response to prevent associated illnesses from a particular bacterium.

In one embodiment, the compound of the invention can be used in combination with another antibacterial drug.

NEET Proteins Modulators

Compounds of the present invention are able to modulate NEET proteins. In particular, the compounds can be a NEET protein stabiliser. Alternatively, the compounds can be a NEET protein destabiliser.

The NEET protein family includes three class of proteins encoded by the CISD1, CISD2 and CISD3 genes.

CISD1 gene encodes the protein mitoNEET. It was previously called C10orf70 or ZCD1 or MDS029. The gene encoding the protein is described in databases GeneCards GCID GC10P058269; HGNC: 30880; Entrez Gene: 55847; and UniGene: Hs.370102. The protein is described in UniProtKB under: Q9NZ45. Amino acid and nucleotide reference sequences of mitoNEET are disclosed in GenPept and Genbank under NP_060934.1 and NM_018464.4, respectively.

CISD2 gene encodes the protein NAF-1 (nutrient-deprivation autophagy factor-1). It was previously called WFS2 or ZCD2 and is also called Miner1, ERIS (endoplasmic reticulum intermembrane small protein) and mitoNEET related 1. The gene encoding the protein is described in databases GeneCards GCID GC04P102868; HGNC: 24212; Entrez Gene: 493856; and UniGene: Hs.444955. and Hs.745013. The protein is described in UniProtKB under: Q8N5K1. Amino acid and nucleotide reference sequences of NAF-1 are disclosed in GenPept and Genbank under NP_001008389.1 and NM_001008388.4, respectively.

CISD3 gene encodes the protein Miner2. It is also called mitoNEET-Related protein 2 or mitochondrial matrix-localized mitochondrial inner NEET protein (MiNT). The gene encoding the protein is described in databases GeneCards GCID GC17P038730; HGNC: 27578; Entrez Gene: 284106; and UniGene: Hs.713595. The protein is described in UniProtKB under ID P0C7P0. Amino acid and nucleotide reference sequences of Miner2 are disclosed in GenPept and Genbank under NP 001129970.1 and NM 001136498.1, respectively. NEET proteins are important for human health and disease. For instance, they are involved in oncology (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895), especially apoptosis and autophagy; in metabolic disorders and diseases (Tamir et al, 2015, Biochim Biophys Acta, 1853, 1294-1315; Takahashi et al, Journal of Pharmacology and experimental therapeutics, 2015, 352, 338-345); cardiovascular diseases (Du et al, 2015, Cell Biol Int, 39, 816-823; Habener et al, 2016, PLoS One, 11, e0156054); inflammatory diseases and disorders (Taminelli et al, 2008, Biochem Biophys Res Commun, 365, 856-862); iron storage disorders (REF); aging (Chen et al, 2009, Genes Dev, 23, 1183-1194) and neurodegenerative diseases or disorders (He et al, 2016, Sci Rep, 6, 35205). Studies demonstrated a role for mitoNEET and NAF-1 in the regulation of cellular iron, calcium and ROS homeostasis, and a key role for NEET proteins in critical processes, such as cancer cell proliferation and tumor growth, lipid and glucose homeostasis in obesity and diabetes, control of autophagy, longevity in mice, and senescence in plants (Tamir et al, 2015, Biochim Biophys Acta, 1853, 1294-1315). Abnormal regulation of NEET proteins was consequently found to result in multiple health conditions. For instance, missplicing of NAF-1 causes Wolfram syndrome 2. NAF-1 is also functionally linked to the regulation of autophagy in cancer and aging.

Cancers

The compounds of the present invention are able to kill tumor cells. In addition, the compounds of the present invention are also able to modulate NEET proteins (Holt et al, 2016, J Cell Sci, 129, 155-165; Bai et al, 2015, Proc Natl Acad Sci USA, 112, 3698-3703; Tamir et al, 2014, Proc Natl Acad Sci USA, 111, 5177-5182; Sohn et al, 2013, Proc Natl Acad Sci USA, 110, 14676-14681; Darash-Yahana et al, 2016, Proc Natl Acad Sci USA, 113, 10890-10895). NEET proteins are involved in the regulation of apoptosis/autophagy in cancer biology. Accordingly, the present invention relates to the use of a compound of the present invention as an antitumor agent. The present invention also relates to a compound of the present invention for use for treating a cancer, the use of a compound of the present invention for the manufacture of a medicine for treating a cancer, and to a method for treating a cancer in a subject, comprising administering an effective amount of a compound of the present invention to the subject.

In one aspect, the cancer can be a solid tumor or a hematopoietic cancer. For instance, the cancer can be selected from the group consisting of bone cancer, gastrointestinal cancer, liver cancer, pancreatic cancer, gastric cancer, colorectal cancer, esophageal cancer, or oro-pharyngeal cancer, laryngeal cancer, salivary gland carcinoma, thyroid cancer, lung cancer, cancer of the head or neck, skin cancer, squamous cell cancer, melanoma, uterine cancer, cervical cancer, endometrial carcinoma, vulvar cancer, ovarian cancer, breast cancer, prostate cancer, cancer of the endocrine system, sarcoma of soft tissue, bladder cancer, kidney cancer, glioblastoma and various types of cancers of the central nervous system, lymphoma and leukemia. In a preferred embodiment, the cancer is a breast cancer, in particular a triple-negative breast cancer, prostate cancer and ovarian cancer. In one particular embodiment, the cancer is a breast cancer.

Optionally, the compound of the present invention used for treating cancer is a modulator of mitoNEET and/or NAF-1. In one aspect, the compound is a modulator of mitoNEET. In another aspect, the compound is a modulator of NAF-1. In a further aspect, the compound is a modulator of mitoNEET and NAF-1.

In this aspect, the compound of the present invention can be combined with radiotherapy, immunotherapy, hormonotherapy, or chemotherapy, all well-known by the person skilled in the field.

Metabolic Disorders and Diseases

NEET proteins are involved in metabolic disorders and diseases (Tamir et al., 2015, Biochim Biophys Acta, 1853, 1294-1315). Accordingly, the present invention further relates to a method for treating a metabolic disorder or disease in a subject, wherein a therapeutically effective amount of a compound according to the invention is administered to said subject suffering of a metabolic disorder or disease. The invention also relates to the use of the compounds according to the invention, for the manufacture of a medicine for the treatment of a metabolic disorder or disease. The invention relates to a compound according to the invention for use in the treatment of a metabolic disorder or disease.

The metabolic disorders and diseases can be selected in the group consisting of diabetes mellitus, insulin resistance, insulin deficiency, hepatic steatosis, nonalcoholic fatty liver disease, Nonalcoholic steatohepatitis (NASH), glucose intolerance, obesity, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In one aspect, the metabolic disease or disorder can be selected from the group consisting of diabetes, in particular diabetes type I or diabetes type II, atherosclerosis, obesity, diabetic neuropathies, lysosomal storage diseases, severe insulin resistance, hyperinsulinemia, hyperlipidemia, Rabson-Mendenhall syndrome, leprechaunism, lipoatrophic diabetes, acute and chronic renal insufficiency, end-stage chronic renal failure, glomerulonephritis, interstitial nephritis, pyelonephritis, glomerulosclerosis, and lipoatrophic diabetes, hepatic steatosis, nonalcoholic fatty liver disease, Nonalcoholic steatohepatitis (NASH), glucose intolerance, lipodystrophy, coronary heart disease, diabetic retinopathy, diabetic neuropathy, diabetic nephropathy, hypoglycemia, hyperglycemia, beta cell dysfunction or hyperinsulinaemia, Wolfram syndrome, Polycystic ovary syndrome, pyruvate dehydrogenase deficiency, Albright hereditary osteodystrophy, cystinosis, fructose intolerance, Walker-Warburg syndrome, hypobetalipoproteinemia, Alström syndrome, and cirrhosis.

In another aspect, the metabolic disease or disorder can be selected from the group consisting of activator deficiency/GM2 gangliosidosis, alpha-mannosidosis, aspartylglucoaminuria, cholesteryl ester storage disease, chronic hexosaminidase A deficiency, cystinosis, Danon disease, Fabry disease, Farber disease, fucosidosis, galactosialidosis, Gaucher Disease (Types I, II and III), GM1 Ganliosidosis, including infantile, late infantile/juvenile and adult/chronic), Hunter syndrome (MPS II), Mucolipidosis II, Infantile Free Sialic Acid Storage Disease (ISSD), Juvenile Hexosaminidase A Deficiency, Krabbe disease, Lysosomal acid lipase deficiency, Metachromatic Leukodystrophy, Hurler syndrome, Scheie syndrome, Hurler-Scheie syndrome, Sanfilippo syndrome, Morquio Type A and B, Maroteaux-Lamy, Sly syndrome, mucolipidosis, multiple sulfate deficiency, Niemann-Pick disease, Neuronal ceroid lipofuscinoses, CLN6 disease, Jansky-Bielschowsky disease, pycnodysostosis, Sandhoff disease, Schindler disease, and Tay-Sachs or Wolman disease.

In a preferred embodiment, metabolic disorders and diseases can be selected in the group consisting of diabetes mellitus, insulin resistance, obesity and Wolfram syndrome.

Optionally, the compound of the present invention used for treating metabolic diseases or disorders is a modulator of mitoNEET, NAF-1 and/or MiNT. In particular, it can be a modulator of a combination of NEET proteins, such as mitoNEET and NAF-1, mitoNEET and MiNT, NAF-1 and MiNT or mitoNEET, NAF-1 and MiNT. Alternatively, it can be a modulator of mitoNEET, NAF-1 or MiNT.

The compound of the present invention can be combined with other drugs known for their uses in the treatment of metabolic diseases or disorders.

Cardiovascular Diseases

NEET proteins have been disclosed to be involved in cardiovascular diseases and disorders (Du et al, 2015, Cell Biol Int, 39, 816-823; Habener et al, 2016, PLoS One, 11, e0156054; Tamir et al, 2015, Biochim Biophys Acta, 1853, 1294-1315). Therefore, the present invention further relates to a method for treating a cardiovascular disease in a subject, wherein a therapeutically effective amount of a compound according to the invention is administered to said subject suffering of a cardiovascular disease. The invention also relates to the use of the compounds according to the invention, for the manufacture of a medicine for the treatment of a cardiovascular disease. The invention relates to a compound according to the invention for use in the treatment of a cardiovascular disease.

In one aspect, the cardiovascular disease is selected from the group consisting of myocardial injury, Ischemia, Ischemia reperfusion injury and hypertension. In one embodiment, the cardiovascular disease is myocardial injury.

Optionally, the compound of the present invention used for treating a cardiovascular disease is a modulator of mitoNEET and/or NAF-1. In one aspect, the compound is a modulator of mitoNEET. In another aspect, the compound is a modulator of NAF-1. In a further aspect, the compound is a modulator of mitoNEET and NAF-1.

The compound of the present invention can be combined with other drugs known for their uses in the treatment of cardiovascular diseases or disorders.

Inflammatory Diseases

NEET proteins have been disclosed to be involved in inflammation (Tamir et al, 2015, Biochim Biophys Acta, 1853, 1294-1315).

In one aspect, the inflammatory disease or disorder can be selected from the group consisting of Crohn disease, inflammatory bowel disease, asthma, chronic obtrusive pulmonary disease (COPD), systemic lupus erythematosus, cystic fibrosis, psoriasis, infectious arthritis, and multiple sclerosis.

Optionally, the compound of the present invention used for treating inflammatory diseases or disorders is a modulator of nitoNEET.

In one particular embodiment, the inflammatory disease or disorder is cystic fibrosis (Taminelli et al, 2008, Biochem Biophys Res Commun, 365, 856-862). Optionally, the compound of the present invention used for treating cystic fibrosis is a modulator of mitoNEET.

The compound of the present invention can be combined with other drugs known for their uses in the treatment of inflammatory diseases or disorders.

Iron Storage Disorders

NEET proteins are involved in iron homeostasis. The compounds of the present invention are able to modulate the NEET protein binding to iron, for instance by stabilizing and destabilizing this binding.

Accordingly, the present invention relates to a compound of the present invention for use for treating an iron storage disorder, the use of a compound of the present invention for the manufacture of a medicine for treating an iron storage disorder, and to a method for treating an iron storage disorder in a subject, comprising administering an effective amount of a compound of the present invention to the subject.

The iron storage disorder or disease can be associated to an iron deficiency or to an iron overload.

The iron storage disorders or diseases include, but are not limited thereto, Ferroportin Deficiency, Hereditary Hemochromatosis, including Hereditary Hemochromatosis due to HFE mutations and Hereditary Hemochromatosis due to transferrin receptor 2 mutations, Juvenile Hemochromatosis, including Juvenile Hemochromatosis due to hepcidin mutations and Juvenile Hemochromatosis due to hemojuvelin mutations, Iron Overload, including African Iron Overload, Iron Overload secondary to atransferrinemia and Iron Overload secondary to aceruloplasminemia, Thalassemia, Myelodysplastic Syndromes, Congenital Dyserythropoietic Anemias, Sickle Cell Disease and other Hemoglobinopathies, Red Cell Enzyme Deficiencies and Multiple Blood Transfusions.

Aging and Neurodegenerative Diseases

It is known that NEET proteins are involved in aging (Chen et al, 2009, Genes Dev, 23, 1183-1194) and in neurodegenerative diseases and disorders (He et al, 2016, Sci Rep, 6, 35205). Therefore, a compound of the present invention can be used for the treatment of aging or a neurodegenerative disease or disorder. Accordingly, the present invention relates to a method for treating aging or a neurodegenerative disease or disorder in a subject, wherein a therapeutically effective amount of a compound according to the invention is administered to said subject suffering of aging or a neurodegenerative disease or disorder. The invention also relates to the use of a compound according to the invention for the manufacture of a medicine for the treatment of aging or a neurodegenerative disease or disorder. The invention relates to a compound according to the invention for use in the treatment of aging or a neurodegenerative disease or disorder.

In one embodiment, the compound of the present invention used for treating aging or treating or preventing aging damage. Optionally, the compound of the present invention used for treating aging is a modulator of NAF-1.

In another embodiment, the compound of the present invention used for treating a neurodegenerative disease or disorder. The neurodegenerative disease can be selected from the group consisting of Adrenal Leukodystrophy, Alexander's disease, Alper's disease, Alzheimer's disease, Amyotrophic lateral sclerosis, ataxia telangiectasia, Batten disease, bovine spongiform encephalopathy, Canavan disease, cerebral palsy, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes dorsalis and toxic encephalopathy. Preferably, the neurodegenerative disease or disorder can be selected from the group consisting of multiple sclerosis, Alzheimer's disease, Parkinson's disease and amyotrophic lateral sclerosis.

The neurodegenerative disease or disorder also includes central nervous system (CNS) injury.

Optionally, the compound of the present invention used for treating a neurodegenerative disease or disorder is a modulator of mitoNEET.

The compound of the present invention can be combined with other drugs known for their uses in the treatment of neurodegenerative diseases or disorders.

Pharmaceutical Composition

The present invention also relates to a pharmaceutical composition comprising a compound of the present invention. The composition further comprises at least one pharmaceutically acceptable carrier or excipient.

In a particular embodiment, the pharmaceutical composition according to the invention further comprises at least another active ingredient, preferably selected from the group consisting in an antiviral agent, an anti-cancerous agent, an antibiotic, or a molecule aimed to treat metabolic diseases, cardiovascular diseases, inflammatory diseases, aging, muscle diseases, neurodegenerative diseases or iron storage disorders. Preferably, the other active ingredient is an antiviral agent. More preferably, the other active ingredient is an antiviral agent against an influenza virus, preferably an influenza A virus.

In a particular embodiment, the pharmaceutical composition according to the invention further comprises an antiviral agent, for instance and non-exhaustively, an agent selected from the group consisting of neuraminidase inhibitors, M2 inhibitors, RNA polymerase inhibitors, interferons (immune system modulators interferon alpha-2a and PEGylated interferon alpha-2a (Pegasys) and interferon alpha-2b (ViraferonPeg ou Introna)), antiviral vaccine, antigenic polypeptides or neutralizing antibodies directed to a viral antigenic polypeptide.

The invention also concerns the pharmaceutical composition of the invention for use in the treatment of a disease. The invention also relates to the use of a pharmaceutical composition according to the invention for the manufacture of a medicine for treating a disease in a subject. The invention further relates to a method for treating a disease in a subject, wherein a therapeutically effective amount of a pharmaceutical composition according to the invention is administered to said subject suffering from said disease.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human subject according to the invention may be a human at the prenatal stage, a newborn, a child, an infant, an adolescent or an adult.

In a preferred embodiment, the subject has been diagnosed with a disease. Preferably, the subject has been diagnosed with a disease selected from the group consisting in viral infections, bacterial infections, cancers, metabolic diseases or disorders, cardiovascular diseases or disorders, inflammatory diseases or disorders, iron storage disorders, aging and neurodegenerative diseases or disorders. Diagnostic methods of these diseases are well known by the man skilled in the art.

The compound according to the invention or the pharmaceutical composition according to the invention may be administered by any conventional route of administration. In particular, the compound or the pharmaceutical composition of the invention can be administered by a topical, enteral, oral, parenteral, intranasal, intravenous, intra-arterial, intramuscular, intratumoral, subcutaneous or intraocular administration and the like.

In particular, the compound according to the invention or the pharmaceutical composition according to the invention can be formulated for a topical, enteral, oral, parenteral, intranasal, intravenous, intra-arterial, intramuscular, intratumoral, subcutaneous or intraocular administration and the like.

Preferably, the compound according to the invention or the pharmaceutical composition according to the invention is administered by enteral or parenteral route of administration. When administered parenterally, the compound according to the invention or the pharmaceutical composition according to the invention is preferably administered by intravenous route of administration. When administered enterally, the compound according to the invention or the pharmaceutical composition according to the invention is preferably administered by oral route of administration.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Preferably, the treatment with the compound according to the invention or the pharmaceutical composition according to the invention start no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease persists.

The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

Kit and Use of a Kit

The present invention also relates to the combined use of a compound of the present invention with at least another active ingredient, preferably selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat neurodegenerative diseases, inflammatory diseases, autoimmune diseases, liver diseases, aging, muscle diseases, or metabolic diseases for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases.

The present invention also relates to a product comprising a compound of the present invention, and another active ingredient, as a combined preparation for simultaneous, separate or sequential use, in particular for use for the treatment of a disease selected from the group consisting of cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is selected from the group consisting in an antiviral agent, an anti-cancerous agent, an anti-apoptotic agent, an anti-autophagy agent, an autophagy inducing agent, an antibiotic, an antiparasitic agent, an antifungal agent, or a molecule aimed to treat cancer, infectious diseases, in particular viral diseases, metabolic diseases or disorders, cardiovascular diseases or disorders, inflammatory diseases, iron storage disorders, aging, and neurodegenerative diseases. Preferably, the other active ingredient is an antiviral.

Further aspects and advantages of the present invention will be described in the following examples, which should be regarded as illustrative and not limiting.

EXAMPLES

Example A—Chemistry

Abbreviations

Aq Aqueous
br s Broad singlet
$CDCl_3$ Deuterated chloroform
d Doublet
DAD Diode Array Detector
DCM Dichloromethane (methylene chloride)
dd Doublet of doublets
ddd Doublet of doublets of doublets
DIPEA N,N-Diisopropylethylamine
DMF N,N-Dimethylformamide
DMSO Dimethyl sulfoxide
dq Doublet of quartets
dt Doublet of triplets
EtOAc Ethyl acetate
$Et_2O$ Diethyl ether
EtOH Ethanol
g Gram(s)
h Hour(s)
HATU O-(7-Azabenzotriazol-1-yl)-N,N,N',N'-tetramethyluronium hexafluorophosphate
HCl Hydrochloric acid
HPLC High-pressure liquid chromatography
i-PrOH Isopropanol
LC/MS Liquid chromatography/mass spectrometry
LiOH Lithium hydroxide
m Multiplet
M Molar
MeCN Acetonitrile
MeOH Methyl alcohol
$MgSO_4$ Magnesium sulfate
min Minute(s)
mmol Millimole
MHz MegaHertz
MS Mass spectrometry
N Normal
$NaHCO_3$ Sodium bicarbonate
$NH_4Cl$ Ammonium chloride
NMR Nuclear magnetic resonance
p para
PDA Photodiode Array
pH $-log[H^+]$
ppm Parts per million
q Quadruplet
quin Quintuplet
RP-HPLC Reverse-phase high-pressure liquid chromatography
$R_t$ Retention time
RT Room temperature
s Singlet
t Triplet
td Triplet of doublets
TFA Trifluoroacetic acid
tert- Tertiary
THF Tetrahydrofuran General Synthetic Schemes Compounds of the invention may be prepared using the synthetic transformations illustrated in Schemes I-V. Starting materials are commercially available or may be prepared by the procedures described herein, by literature procedures, or by procedures that would be well known to one skilled in the art of organic chemistry. Unless stated, all aqueous solutions are saturated.

Methods for preparing 2-benzamidothiophene-3-carboxylic acid compounds 5 of the invention containing various substitutions on position 4 and 5 of the thiophene and on the benzamides are illustrated in Scheme I. In Scheme I, step a, the 2-aminothiophene-3-carboxylate scaffold 3 can be commercially available or synthesised from commercially available cyanoacetate 2 and acyclic ketones 1 in a 3-component reaction using sulfur and a suitable base. This reaction, called Gewald reaction (as described in *Ber.,* 1966, 99, 94-100), can be carried out using for example one of the procedures described in Example #1, or by methods known to one skilled in the art (for example, *Eur. J. Med. Chem.,* 2016, 123, 31-47) to provide the 2-aminothiophene-3-carboxylate based compounds 3. 2-Aminothiophenes 3 may react with substituted benzoyl chloride as described in Scheme I, step b using conditions such as those described in Example #1, or by methods known to one skilled in the art (for instance, *J. Med. Chem.,* 2013, 56(24), 10118-10131) to give 2-(benzamido)thiophene-3-carboxylate derivatives 4. Acyl chlorides can be commercially available or synthesised as described by methods known to one skilled in the art (for example, *J. Med. Chem.,* 2016, 59(13), 6201-6220). In Scheme I, step c, the ester of 2-(benzamido)thiophene-3-carboxylate derivatives 4 may be hydrolysed to the 2-(benzamido)thiophene-3-carboxylic acids 5 using conditions such as those described in Example #1 or by methods known to one skilled in the art (for example, *J. Med. Chem.,* 2013, 56(24), 10118-10131).

Scheme II

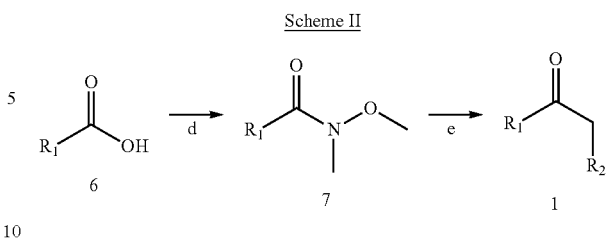

Methods for preparing 2-benzamido-5-chloro-thiophene-3-carboxylic acid compounds 10 of the invention containing various substitutions on position 4 of the thiophene and on the benzamides are illustrated in Scheme III and IV. In Scheme III, step f, the 2-amino-5-chloro-thiophene-3-carboxylate compounds 8 may be synthesised from 2-aminothiophene-3-carboxylate derivatives 3 of commercial availability, or prepared via the Gewald cyclisation described in Scheme I, step a using for example the procedure described in Example #3, or by methods known to one skilled in the art (for example, *Journal of Heterocyclic Chemistry,* 2008, 45, 201-207). 2-Aminothiophenes 8 may react with substituted benzoyl chloride as described in Scheme III, step g using conditions such as those described in Example #1, or by methods known to one skilled in the art (for instance, *J. Med. Chem.,* 2013, 56(24), 10118-10131) to give 2-(benzamido)-5-chloro-thiophene-3-carboxylate derivatives 9. In Scheme III, step h, the ester of 2-(benzamido)-5-chloro-thiophene-3-carboxylate derivatives 9 may be hydrolysed to the 2-(benzamido)-5-chloro-thiophene-3-carboxylic acids 10 using conditions such as those described in Example #1, or by methods known to one skilled in the art (for example, *J. Med. Chem.,* 2013, 56(24), 10118-10131).

Scheme I

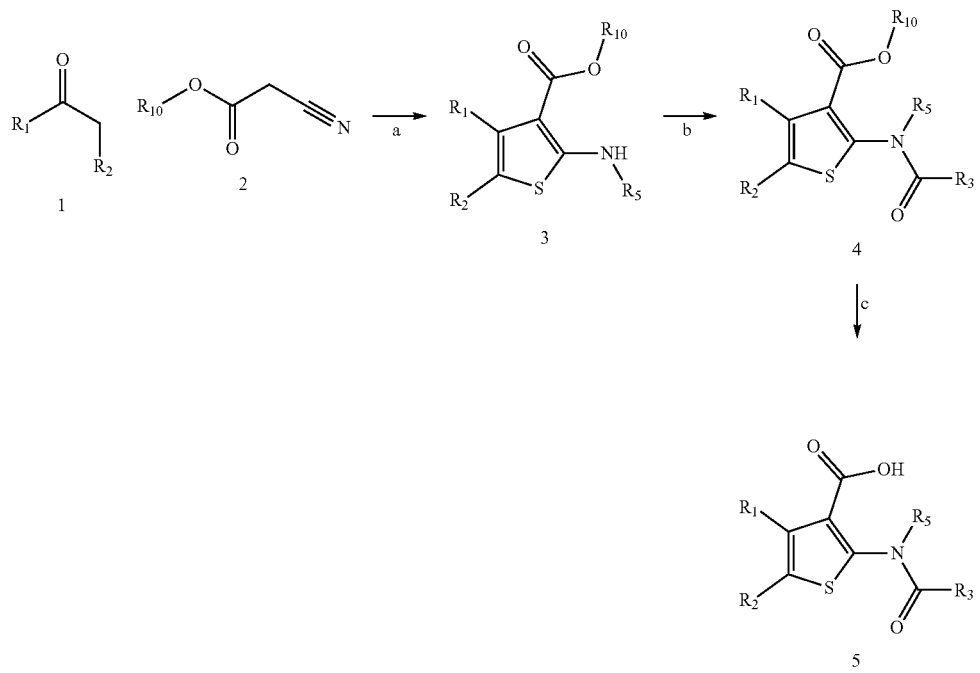

Methods for preparing acyclic ketones 1 used in Scheme 1, step a, are illustrated in Scheme II. In Scheme II, step d, the Weinreb amide 7 may be synthesised from commercially available carboxylic acid 6 using for example one of the procedures described in Preparation #1, or by methods known to one skilled in the art (for example, *Organic Letters,* 2012, 14, 5518-5521). Acyclic ketones 1 may be synthesized from Weinreb amide 7 using conditions such as those described in Preparation #1, or by methods known to one skilled in the art (for example, *Synthesis,* 2018, 50, 4949-4957).

Scheme III

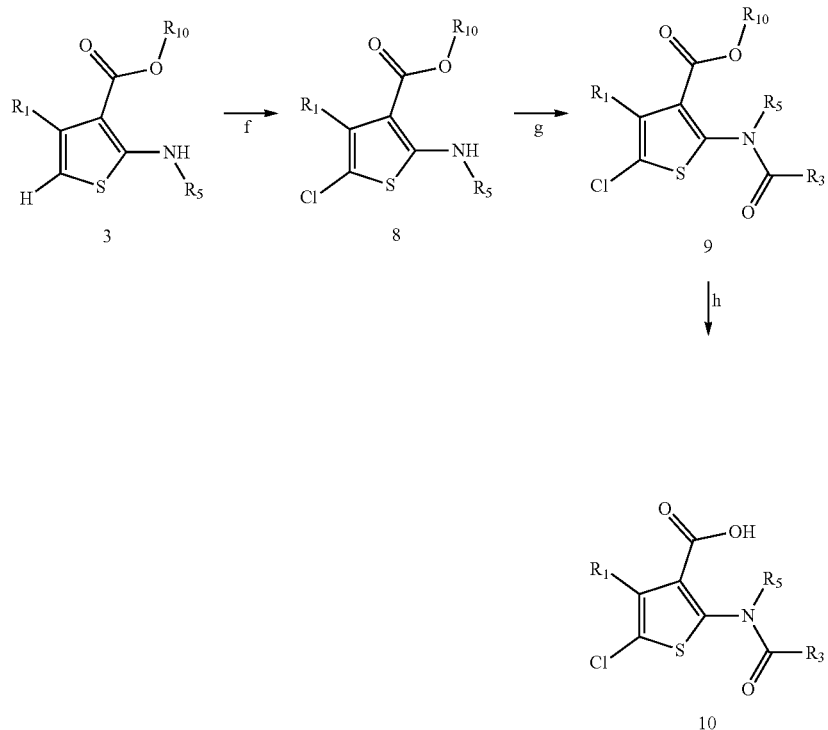

Alternative methods for preparing 2-benzamido-5-chloro-thiophene-3-carboxylic acid compounds 10 of the invention containing various substitutions on position 4 of the thiophene and on the benzamides are illustrated in Scheme IV. In Scheme IV, step i, the 2-(benzamido)-5-chloro-thiophene-3-carboxylate compounds 9 may be synthesised from 2-(benzamido)thiophene-3-carboxylate derivatives 4, prepared as described in Scheme I, step b ($R^1$=H), using conditions such as those described in Example #5.

Scheme IV

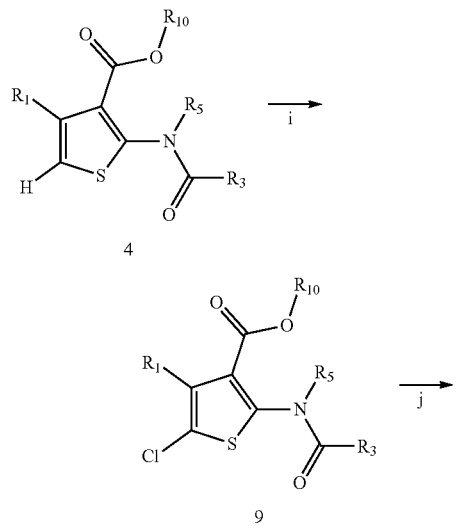

-continued

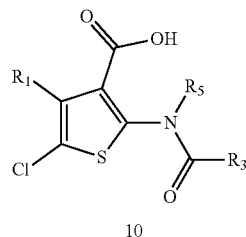

Compounds of general structure 4 may be modified later in the synthesis as described in Scheme V. 2-Aminothiophenes 3 may react with halobenzoyl chloride as described in Scheme V, step b using, for example, similar conditions described in Scheme I, step b. In Scheme V, step k, the 4-halobenzamide 13 may be reacted with an amine as described in Example #9 and Example #72, for example, or by methods known to one skilled in the art (for example, *J. Med. Chem.*, 2016, 59, 3489-3498). In Scheme V, step c, the ester of 2-(4-aminobenzamido)thiophene-3-carboxylate derivatives 14 may be hydrolysed to the 2-(4-aminobenzamido)thiophene-3-carboxylic acids 15 using conditions such as those described in Example #1 or by methods known to one skilled in the art (for example, *J. Med. Chem.*, 2013, 56(24), 10118-10131).

Scheme V

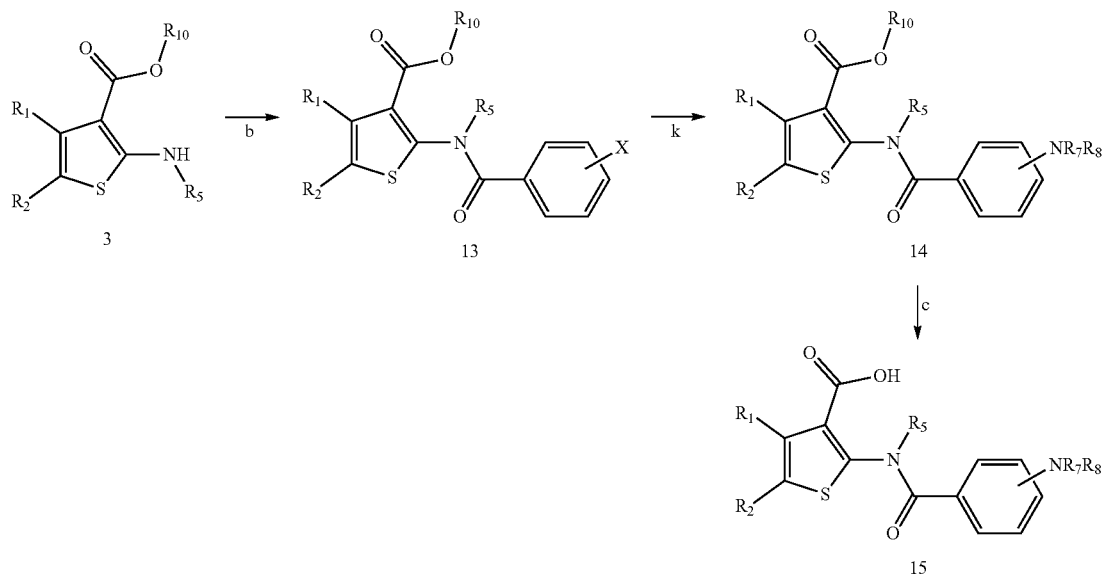

Analytical Methods

All $^1$H NMR data were collected on a Bruker Avance 400 MHz equipped with 5 mm QNP probe or Bruker Avance III 400 MHz, 5 mm BBFO Plus probe instruments and chemical shifts are quoted in parts per million (ppm). LC/MS data is referenced to LC/MS conditions using the method number provided in Table 1. data is referenced to HPLC conditions using the method number provided in Table 1.

TABLE 1

| LC/MS and Chiral SFC analysis methods | |
|---|---|
| Method | Conditions |
| A | LC/MS analysis condition: Column: Acquty UPLC BEH Shield RP18 1.7 μm, 100 × 2.1 mm plus guard cartridge, maintained at 40° C. Mobile phase: MeCN in water (with 10 mM ammonium bicarbonate), from 5% to 95% within 6 min; Flow rate: 0.5 ml/min; Wavelength: 210-400 nm DAD. Waters DAD + Waters SQD2, single quadrapole UPLC-MS |
| B | LC/MS analysis condition: Column: Acquty UPLC HSS C18 1.8 μm, 100 × 2.1 mm plus guard cartridge, maintained at 40° C. Mobile phase: MeCN (0.1% formic acid) in water (0.1% formic acid), from 5% to 95% within 6 min; Flow rate: 0.5 ml/min; Wavelength: 210-400 nm DAD. Waters DAD + Waters SQD2, single quadrapole UPLC-MS |
| C | LC/MS analysis condition: Column: Acquty UPLC HSS C18 1.8 μm, 100 × 2.1 mm plus guard cartridge, maintained at temp. Mobile phase: MeCN (0.1% formic acid) in water (0.1% formic acid), from 5% to 95% within 8 min; Flow rate: 0.4 ml/min; Wavelength: 210-400 nm DAD. Waters DAD + Waters SQD2, single quadrapole UPLC-MS |
| D | LC/MS analysis condition: Column: Acquty UPLC BEH Shield RP18 1.7 μm, 100 × 2.1 mm plus guard cartridge, maintained at temp. Mobile phase: MeCN in water (with 10 mM ammonium bicarbonate), from 5% to 95% within 8 min; Flow rate: 0.4 ml/min; Wavelength: 210-400 nm DAD. Waters DAD + Waters SQD2, single quadrapole UPLC-MS |
| E | LC/MS analysis condition: Column: ACQUITY UPLC BEH C$_{18}$ 1.7 μm, 100 × 2.1 mm, maintained at 40° C. Mobile phase: MeCN (0.1% formic acid) in water (0.1% formic acid), from 5% to 95% within 8 min; Flow rate: 0.4 ml/min; Wavelength: 200-500 nm DAD. Acquity i-Class (quarternary pump/PDA detector) + Quattro Micro Mass Spectrometer |

TABLE 1-continued

| LC/MS and Chiral SFC analysis methods | |
|---|---|
| Method | Conditions |
| F | Chiral SFC analysis condition: Column: LUX Cellulose-3 5 μm, 4.6 × 250 mm, 120 bar, maintained at 40° C. Mobile phase: 35/65 MeOH (0.1% DEA)/CO$_2$ within 5 min; Flow rate: 5.0 ml/min |
| G | Chiral SFC analysis condition: Column: LUX Cellulose-3 5 μm, 4.6 × 250 mm, 120 bar, maintained at 40° C. Mobile phase: 40/60 MeOH (0.1% DEA)/CO$_2$ within 7 min; Flow rate: 5.0 ml/min |
| H | Chiral SFC analysis condition: Column: YMC Amylose-C 5 μm, 4.6 × 250 mm, 120 bar, maintained at 40° C. Mobile phase: 30/70 IPA (0.1% DEA)/CO$_2$; Flow rate: 5.0 ml/min |

Purification Methods

For the general procedures, intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; RP-HPLC purification performed on Agilent Technologies 1260 Infinity purification system and Agilent 6120 series Single Quadrupole Mass Spectrometer (see Table 2 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated NaHCO$_3$, EtOAc/saturated NaHCO$_3$, DCM/10% aqueous HCl, EtOAc/10% aqueous HCl, etc.); distillation (i.e. simple, fractional, Kugelrohr, etc.). Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. *J. Org. Chem.* 1978, 43(14), 2923-2925; Yan, B. "Analysis and Purification Methods in Combinatorial Chemistry" 2003; Harwood, L. M., Moody, C. J. and Percy, J. M. "Experimental Organic Chemistry: Standard and Microscale, 2$^{nd}$ Edition", 1999.

TABLE 2

RP-HPLC purification methods

| Method | Conditions |
|---|---|
| A | RP-HPLC purification condition: Column Waters Xbridge Phenyl 10 μm, 100 × 19 mm. Mobile phase: MeOH in water (0.1% ammonium bicarbonate); Flow rate: 20 ml/min; Wavelength: 210-400 nm DAD. Sample injected in DMSO, 23 min non-linear gradient from 5% to 100% MeOH, centered on a specific focused gradient |
| B | RP-HPLC purification condition: Column XSELECT CSH Prep C18 5 μm, 19 × 250 mm. Mobile phase: MeCN in water (0.1% formic acid); Flow rate: 20 ml/min; Wavelength: 210-260 nm DAD. Sample injected in DMSO (+optional formic acid and water), 22 min non-linear gradient from 10% to 95% MeCN, centered on a specific focused gradient |

Chiral SFC purification is referenced to SFC conditions using the method number provided in Table 3.

TABLE 3

Chiral SFC purification methods

| Method | Conditions |
|---|---|
| A | Chiral SFC purification condition: Column: LUX Cellulose-3 5 μm, 10 × 250 mm, 120 bar, maintained at 40° C. Mobile phase: 35/65 MeOH (0.1% DEA)/CO$_2$; Flow rate: 15 ml/min |

PREPARATIONS AND EXAMPLES

All starting materials are commercially available from Sigma-Aldrich (including Fluka and Discovery CPR) or Acros unless otherwise noted after the chemical name. Reagent/reactant names given are as named on the commercial bottle or as generated by IUPAC conventions or ChemDraw 16.0. None of the specific conditions and reagents noted herein is to be construed as limiting the scope of the invention and are provided for illustrative purposes only.

Example #1.
2-Benzamido-4-indan-5-yl-thiophene-3-carboxylic acid (compound #3)

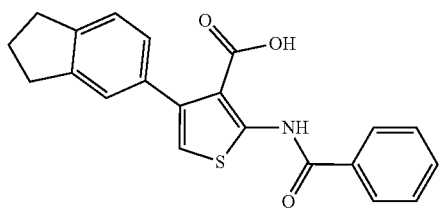 [SMILES: O=C(Nc1scc(-c2ccc3c(c2)CCC3)c1C(=O)O)c1ccccc1]

To a solution of 5-acetylindane (CAS: 4228-10-8, 1.00 g, 6.24 mmol) in ethanol (15 ml) was added ethyl cyanoacetate (CAS: 105-56-6, 0.66 ml, 6.24 mmol), sulfur (CAS: 7704-34-9, 200 mg, 6.24 mmol) and morpholine (CAS: 110-91-8, 1.6 ml, 18.7 mmol). The reaction mixture was heated at 80° C. for 16 hours and then allowed to cool to RT. The volatiles were removed under reduced pressure and the residue was partitioned between EtOAc and brine. The two phases were separated. The organic phase was washed with brine, dried over MgSO$_4$ and the solvent was removed under reduced pressure. Purification by flash chromatography on silica gel (eluting with 0-40% EtOAc in isohexane) afforded ethyl 2-amino-4-(2,3-dihydro-1H-inden-5-yl)thiophene-3-carboxylate as a pale yellow solid (155 mg, yield 9%). To a solution of ethyl 2-amino-4-(2,3-dihydro-1H-inden-5-yl)thiophene-3-carboxylate (155 mg, 0.54 mmol) in DCM (7.0 ml) was added DIPEA (CAS: 7087-68-5, 280 μl, 1.62 mmol) and benzoyl chloride (CAS: 98-88-4, 75 μl, 0.65 mmol). The reaction mixture was stirred at RT for 16 hours. The reaction was diluted with DCM. The organic phase was sequentially washed with 1N aqueous HCl solution and brine, dried over MgSO$_4$ and the solvent was removed under reduced pressure. Purification by flash chromatography on silica gel (eluting with 0-30% EtOAc in isohexane) afforded ethyl 2-benzamido-4-(2,3-dihydro-1H-inden-5-yl)thiophene-3-carboxylate as a white solid (211 mg, yield quant.). Ethyl 2-benzamido-4-(2,3-dihydro-1H-inden-5-yl)thiophene-3-carboxylate (211 mg, 0.54 mmol) was dissolved in THF (3.0 ml), MeOH (3.0 ml) and water (3.0 ml). To the solution was added lithium hydroxide monohydrate (CAS: 1310-66-3, 113 mg, 2.69 mmol). The reaction mixture was heated at 40° C. for 16 hours. The mixture was allowed to cool to RT and partitioned between EtOAc and 1N aqueous HCl solution. The two phases were separated and the organic phase was washed with brine, dried over MgSO$_4$ and the solvent was removed under reduced pressure. Purification by RP-HPLC (Table 2, Method A) afforded 2-benzamido-4-indan-5-yl-thiophene-3-carboxylic acid as an off-white solid (119 mg, yield 61%). $^1$H NMR (DMSO-d$_6$, 400 MHz): δ=13.93 (br s, 1H), 8.01-7.96 (m, 2H), 7.70-7.59 (m, 3H), 7.22-7.09 (m, 4H), 6.77 (s, 1H), 2.88 (t, J=7.3 Hz, 4H), 2.09-2.01 ppm (m, 2H). LC/MS (Table 1, Method A) R$_t$=2.84 min; MS m/z: 364 [M+H]$^+$.

Example #2.
2-Benzamido-4-indan-2-yl-thiophene-3-carboxylic acid (compound #7)

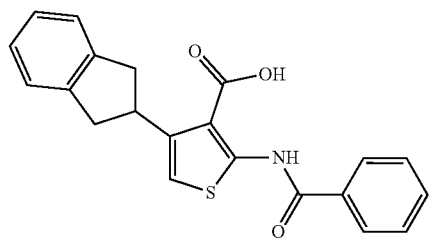 [SMILES: O=C(Nc1scc(C2Cc3ccccc3C2)c1C(=O)O)c1ccccc1]

To a solution of 1-indan-2-yl-ethanone (CAS: 3982-85-3, 1.00 g, 6.24 mmol) in ethanol (15 ml) was added ethyl cyanoacetate (CAS: 105-56-6, 0.66 ml, 6.24 mmol), sulfur (CAS: 7704-34-9, 200 mg, 6.24 mmol) and morpholine (CAS: 110-91-8, 1.6 ml, 18.7 mmol). The reaction mixture was heated at 50° C. for 3 hours and then at 80° C. for 16 hours. The reaction was allowed to cool to RT. The volatiles were removed under reduced pressure and the residue was partitioned between EtOAc and brine. The two phases were separated. The organic phase was washed with brine, dried over MgSO₄ and the solvent was removed under reduced pressure. Purification by flash chromatography on silica gel (eluting with 0-40% EtOAc in isohexane) afforded ethyl 2-amino-4-(2,3-dihydro-1H-inden-2-yl)thiophene-3-carboxylate as a yellow oil (461 mg, yield 24%). To a solution of ethyl 2-amino-4-(2,3-dihydro-1H-inden-2-yl)thiophene-3-carboxylate (300 mg, 1.04 mmol) in DCM (7.0 ml) was added DIPEA (CAS: 7087-68-5, 550 µl, 3.13 mmol) and benzoyl chloride (CAS: 98-88-4, 150 µl, 1.25 mmol). The reaction mixture was stirred at RT for 16 hours. The reaction was diluted with DCM. The organic phase was sequentially washed with 1N aqueous HCl solution and brine, dried over MgSO₄ and the solvent was removed under reduced pressure. Purification by flash chromatography on silica gel (eluting with 0-30% EtOAc in isohexane) afforded ethyl 2-benzamido-4-(2,3-dihydro-M-inden-2-yl)thiophene-3-carboxylate as a yellow oil (375 mg, yield 92%). Ethyl 2-benzamido-4-(2,3-dihydro-1H-inden-2-yl)thiophene-3-carboxylate (375 mg, 0.96 mmol) was dissolved in THF (3.0 ml), MeOH (3.0 ml) and water (3.0 ml). To this solution was added lithium hydroxide monohydrate (CAS: 1310-66-3, 201 mg, 4.79 mmol). The reaction mixture was heated at 40° C. for 16 hours. The mixture was allowed to cool to RT and partitioned between EtOAc and 1N aqueous HCl solution. The two phases were separated and the organic phase was washed with brine, dried over MgSO₄ and the solvent was removed under reduced pressure. Purification by RP-HPLC (Table 2, Method A) afforded 2-benzamido-4-indan-2-yl-thiophene-3-carboxylic acid as a yellow solid (33 mg, yield 10%). ¹H NMR (DMSO-d₆, 400 MHz): δ=13.70 (br s, 1H), 12.66 (br s, 1H), 7.99 (d, J=7.6 Hz, 2H), 7.77-7.67 (m, 3H), 7.32-7.27 (m, 2H), 7.21-7.18 (m, 2H), 6.85 (s, 1H), 4.26 (t, J=7.6 Hz, 1H), 3.37-3.31 (m, 2H, partially obscured by the water peak), 3.03 ppm (dd, J=7.5, 15.7 Hz, 2H). LC/MS (Table 1, Method A) R$_t$=2.86 min; MS m/z: 364 [M+H]⁺.

Example #3. 2-Benzamido-5-chloro-4-indan-2-yl-thiophene-3-carboxylic acid (Compound #8)

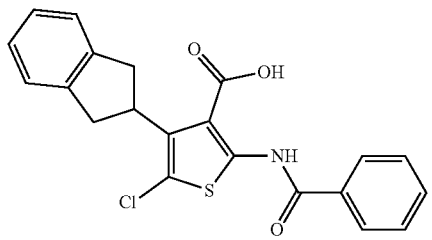 [SMILES: O=C(Nc1sc(Cl)c(C2Cc3ccccc3C2)c1C(=O)O)c1ccccc1]

To a solution of ethyl 2-amino-4-(2,3-dihydro-1H-inden-2-yl)thiophene-3-carboxylate (synthesized according to the procedure described in Example #2, 300 mg, 1.04 mmol) in chloroform (5.0 ml) at −5° C. was added N-chlorosuccinimide (CAS: 128-09-6, 167 mg, 1.25 mmol). The reaction mixture was stirred at −5° C. for 1 hour. The reaction was diluted with DCM and poured into an aqueous sodium thiosulfate solution (5%). The two phases were separated. The organic phase was washed with brine, dried over MgSO₄ and the solvent was removed under reduced pressure. Purification by flash chromatography on silica gel (eluting with 0-20% EtOAc in isohexane) afforded ethyl 2-amino-5-chloro-4-(2,3-dihydro-M-inden-2-yl)thiophene-3-carboxylate as a purple solid (130 mg, yield 39%). To a solution of ethyl 2-amino-5-chloro-4-(2,3-dihydro-1H-inden-2-yl)thiophene-3-carboxylate (130 mg, 0.40 mmol) in DCM (5.0 ml) was added DIPEA (CAS: 7087-68-5, 210 µl, 1.21 mmol) and benzoyl chloride (CAS: 98-88-4, 70 µl, 0.61 mmol). The reaction mixture was stirred at RT for 16 hours. The reaction was diluted with DCM. The organic phase was sequentially washed with 1N aqueous HCl solution and brine, dried over MgSO₄ and the solvent was removed under reduced pressure. Purification by flash chromatography on silica gel (eluting with 0-30% EtOAc in isohexane) afforded ethyl 2-benzamido-5-chloro-4-(2,3-dihydro-1H-inden-2-yl)thiophene-3-carboxylate as a yellow oil (170 mg, yield 99%). Ethyl 2-benzamido-5-chloro-4-(2,3-dihydro-1H-inden-2-yl)thiophene-3-carboxylate (160 mg, 0.38 mmol) was dissolved in THF (3.0 ml), MeOH (3.0 ml) and water (3.0 ml). To the solution was added lithium hydroxide monohydrate (CAS: 1310-66-3, 79 mg, 1.88 mmol). The reaction mixture was heated at 35° C. for 16 hours. The mixture was allowed to cool to RT and partitioned between EtOAc and 1N aqueous HCl solution. The two phases were separated and the organic phase was washed with brine, dried over MgSO₄ and the solvent was removed under reduced pressure. Purification by RP-HPLC (Table 2, Method A) afforded 2-benzamido-5-chloro-4-indan-2-yl-thiophene-3-carboxylic acid as a pale yellow solid (30 mg, yield 20%). ¹H NMR (DMSO-d₆, 400 MHz): δ=13.95 (br s, 1H), 8.01-7.96 (m, 2H), 7.74-7.59 (m, 3H), 7.32-7.19 (m, 4H), 7.06 (br s, 1H), 4.55 (tt, J=9.7, 9.7 Hz, 1H), 3.51 (dd, J=10.4, 15.1 Hz, 2H), 3.10 ppm (dd, J=9.4, 15.2 Hz, 2H). LC/MS (Table 1, Method A) R$_t$=3.06 min; MS m/z: 398 [M+H]⁺.

Example #4. 2-Benzamido-4-tetralin-2-yl-thiophene-3-carboxylic acid (Compound #16)

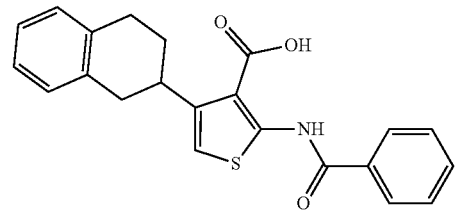 [SMILES: O=C(Nc1scc(C2CCc3ccccc3C2)c1C(=O)O)c1ccccc1]

To a solution of ethyl 2-amino-4-(1,2,3,4-tetrahydronaphthalen-2-yl)thiophene-3-carboxylate (Preparation #1, 1.56 g, 5.18 mmol) in DCM (25 ml) was added DIPEA (CAS: 7087-68-5, 2.7 ml, 15.5 mmol) and benzoyl chloride (CAS: 98-88-4, 0.90 ml, 7.76 mmol). The reaction mixture was stirred at RT for 16 hours. The reaction was diluted with DCM. The organic phase was sequentially washed with 1N aqueous HCl solution and brine, dried over MgSO₄ and the solvent was removed under reduced pressure. Purification by flash chromatography on silica gel (eluting with 0-20% EtOAc in isohexane) afforded ethyl 2-benzamido-4-(1,2,3,4-tetrahydronaphthalen-2-yl)thiophene-3-carboxylate as a white solid (1.10 g, yield 55%). Ethyl 2-benzamido-4-(1,2,3,4-tetrahydronaphthalen-2-yl)thiophene-3-carboxylate (300 mg, 0.74 mmol) was dissolved in THF (3.0 ml), MeOH (3.0 ml) and water (3.0 ml). To the solution was added lithium hydroxide monohydrate (CAS: 1310-66-3, 155 mg, 3.70 mmol). The reaction mixture was heated at 35° C. for 16 hours. The mixture was allowed to cool to RT. The reaction was partitioned between EtOAc and 1N aqueous HCl solution and the two phases were separated. The organic phase was washed with brine, dried over MgSO₄ and the solvent was removed under reduced pressure. Purification by RP-HPLC (Table 2, Method A) afforded 2-benzamido-4-tetralin-2-yl-thiophene-3-carboxylic acid as a white solid (146 mg, yield 52%). ¹H NMR (DMSO-d₆, 400 MHz): δ=13.66 (br s, 1H), 12.63 (s, 1H), 7.99 (d, J=7.2 Hz, 2H), 7.78-7.66 (m, 3H), 7.18-7.12 (m, 4H), 6.87 (s, 1H), 3.71-3.62 (m, 1H), 3.13 (dd, J=3.5, 16.0 Hz, 1H), 2.96-2.77 (m, 3H), 2.22-2.14 (m, 1H), 1.90-1.79 ppm (m, 1H). LC/MS (Table 1, Method A) R$_t$=2.93 min; MS m/z: 378 [M+H]⁺.

Example #5. 2-Benzamido-5-chloro-4-tetralin-2-yl-thiophene-3-carboxylic acid (Compound #17)

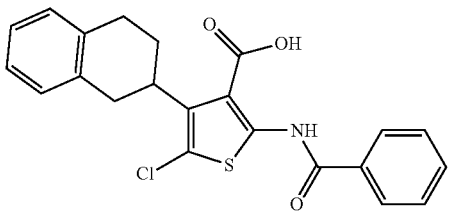 [SMILES: O=C(Nc1sc(Cl)c(C2CCc3ccccc3C2)c1C(=O)O)c1ccccc1]

To a stirred solution of ethyl 2-benzamido-4-(1,2,3,4-tetrahydronaphthalen-2-yl)thiophene-3-carboxylate (prepared as described in Example #4, 300 mg, 0.74 mmol) in chloroform (10.0 ml) was added N-chlorosuccinimide (CAS: 128-09-6, 119 mg, 0.89 mmol). The reaction mixture was stirred at RT for 16 hours. Further N-chlorosuccinimide (197 mg, 1.48 mmol) was added. The reaction was stirred at RT for 96 hours and then it was heated at 60° C. for 24 hours. The reaction mixture was allowed to cool to RT. The reaction was partitioned between DCM and aqueous sodium thiosulfate solution (5%). The two phases were separated. The organic phase was washed with brine, dried over MgSO₄ and the solvent was removed under reduced pressure. Purification by flash chromatography on silica gel (eluting with 0-25% EtOAc in isohexane) afforded ethyl 2-benzamido-5-chloro-4-(1,2,3,4-tetrahydronaphthalen-2-yl)thiophene-3-carboxylate as a yellow oil (325 mg, yield quant.). Ethyl 2-benzamido-5-chloro-4-(1,2,3,4-tetrahydronaphthalen-2-yl)thiophene-3-carboxylate (305 mg, 0.69 mmol) was dissolved in THF (3.0 ml), MeOH (3.0 ml) and water (3.0 ml). To this solution was added lithium hydroxide monohydrate (CAS: 1310-66-3, 145 mg, 3.47 mmol). The reaction mixture was heated at 40° C. for 16 hours. The mixture was allowed to cool to RT and partitioned between EtOAc and 1N aqueous HCl solution. The two phases were separated and the organic phase was washed with brine, dried over MgSO₄ and the solvent was removed under reduced pressure. Purification by RP-HPLC (Table 2, Method A) afforded 2-benzamido-5-chloro-4-tetralin-2-yl-thiophene-3-carboxylic acid as a pale yellow solid (74 mg, yield 26%). ¹H NMR (DMSO-d₆, 400 MHz): δ=14.00 (br s, 1H), 12.48 (s, 1H), 7.95-7.92 (m, 2H), 7.74-7.70 (m, 1H), 7.65 (dd, J=7.4, 7.4 Hz, 2H), 7.15-7.09 (m, 4H), 4.00-3.91 (m, 1H), 3.41-3.33 (m, 1H, partially obscured by the water peak), 2.93-2.81 (m, 3H), 2.50-2.41 (m, 1H), 1.95-1.89 (m, 1H). LC/MS (Table 1, Method A) R$_t$=3.10 min; MS m/z: 412 [M+H]⁺.

Example #6. 2-Benzamido-4-indan-1-yl-thiophene-3-carboxylic acid (Compound #19)

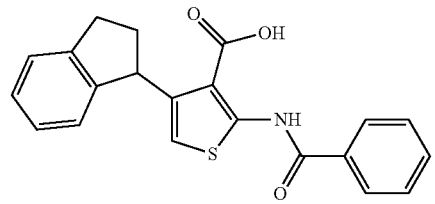 [SMILES: O=C(Nc1scc(C2CCc3ccccc32)c1C(=O)O)c1ccccc1]

The title compound was synthesized according to the procedure described in Example #2 using 1-(2,3-dihydro-1H-inden-1-yl)ethanone (CAS: 703-77-5) as a starting material (off-white solid, yield 6%). ¹H NMR (DMSO-d₆, 400 MHz): δ=12.61 (br s, 1H), 7.95 (d, J=7.1 Hz, 2H), 7.74-7.67 (m, 1H), 7.64 (dd, J=7.3, 7.3 Hz, 2H), 7.29 (d, J=6.6 Hz, 1H), 7.20-7.09 (m, 3H), 6.27 (s, 1H), 5.03 (dd, J=7.2, 7.2 Hz, 1H), 2.98-2.80 (m, 2H), 2.53-2.47 (m, 1H, partially obscured by the DMSO peak), 2.05-1.94 (m, 1H), one exchangeable proton not observed. LC/MS (Table 1, Method A) R$_t$=2.90 min; MS m/z: 364 [M+H]⁺.

Example #7. 2-Benzamido-5-chloro-4-indan-1-yl-thiophene-3-carboxylic acid (Compound #49)

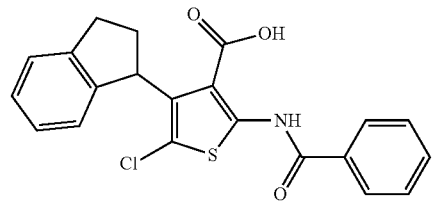 [SMILES: O=C(Nc1sc(Cl)c(C2CCc3ccccc32)c1C(=O)O)c1ccccc1]

The title compound was synthesized according to the procedure described in Example #5 using ethyl 2-benzamido-4-(2,3-dihydro-1H-inden-1-yl)thiophene-3-carboxylateethyl 2-benzamido-4-(2,3-dihydro-1H-inden-1-yl)thiophene-3-carboxylate (prepared as described in Example #6) as a starting material (off-white solid, yield 1%). ¹H NMR (DMSO-d₆, 400 MHz): δ=13.64 (br s, 1H), 7.99 (d, J=7.4 Hz, 2H), 7.78-7.65 (m, 3H), 7.30 (d, J=7.0 Hz, 1H), 7.21-7.09 (m, 3H), 6.90 (br s, 1H), 3.14-2.95 (m, 2H), 2.51-2.29 (m, 2H), one proton obscured by the water peak. LC/MS (Table 1, Method A) R$_t$=3.08 min; MS m/z: 398 [M+H]⁺.

Example #8. 2-Benzamido-5-cyclopropyl-4-indan-2-yl-thiophene-3-carboxylic acid (Compound #51)

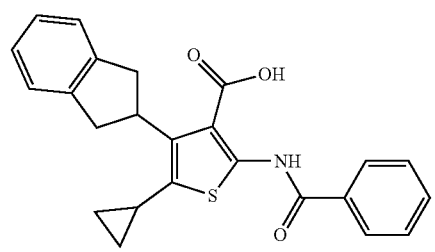 [SMILES: O=C(Nc1sc(C2CC2)c(C2Cc3ccccc3C2)c1C(=O)O)c1ccccc1]

To a solution of ethyl 2-benzamido-4-(2,3-dihydro-1H-inden-2-yl)thiophene-3-carboxylate (prepared as described in Example #2, 500 mg, 1.28 mmol) in chloroform (10.0 ml) was added N-bromosuccinimide (CAS: 128-08-5, 455 mg, 2.55 mmol). The reaction mixture was heated at 60° C. for 1 hour and then allowed to cool to RT. The reaction was diluted with DCM. The organic phase was sequentially washed with 1N aqueous sodium thiosulfate solution and brine, dried over $MgSO_4$ and the solvent was removed under reduced pressure. Purification by flash chromatography on silica gel (eluting with 0-25% EtOAc in isohexane) afforded ethyl 2-benzamido-5-bromo-4-(2,3-dihydro-1H-inden-2-yl)thiophene-3-carboxylate as a pale orange solid (283 mg, 47%). The residue was dissolved in 1,4-dioxane (4.0 ml) and water (1.0 ml) and then potassium cyclopropyltrifluoroborate (CAS: 1065010-87-8, 147 mg, 1.20 mmol) and $Cs_2CO_3$ (CAS: 534-17-8, 392 mg, 1.20 mmol) were added. The mixture was degassed with nitrogen for 5 minutes, before RuPhos Pd G2 (CAS: 1375325-68-0, 93 mg, 0.12 mmol) was added. The reaction mixture was heated at 95° C. for 20 hours. The reaction mixture was allowed to cool to RT, diluted with EtOAc and washed with brine. The organic phase was dried over $MgSO_4$ and the solvent was removed under reduced pressure. Purification by flash chromatography on silica gel (eluting with 0-25% EtOAc in isohexane) afforded ethyl 2-benzamido-5-cyclopropyl-4-(2,3-dihydro-1H-inden-2-yl)thiophene-3-carboxylate as a pale yellow oil (240 mg, yield 92%, purity ~70%). The residue was dissolved in THF (3.0 ml), MeOH (3.0 ml) and water (3.0 ml). To this solution was added lithium hydroxide monohydrate (CAS: 1310-66-3, 117 mg, 2.78 mmol) and the reaction mixture was heated at 40° C. overnight. The mixture was allowed to cool to RT. The reaction was diluted with EtOAc and 1N aqueous HCl solution. The two phases were separated and the organic phase was washed with brine, dried over $MgSO_4$ and the solvent was removed under reduced pressure. Purification by RP-HPLC (Table 2, Method B) afforded 2-benzamido-5-cyclopropyl-4-indan-2-yl-thiophene-3-carboxylic acid as an off-white solid (70 mg, yield 31%). $^1$H NMR (DMSO-$d_6$, 400 MHz): δ=13.56 (br s, 1H), 12.64 (s, 1H), 7.96 (d, J=7.3 Hz, 2H), 7.76-7.64 (m, 3H), 7.31-7.18 (m, 4H), 4.57-4.45 (m, 1H), 3.48 (dd, J=10.5, 15.1 Hz, 2H), 3.24-3.11 (m, 2H), 2.10-2.02 (m, 1H), 1.05-0.98 (m, 2H), 0.77-0.70 (m, 2H). LC/MS (Table 1, Method A) $R_t$=3.12 min; MS m/z: 404 [M+H]$^+$.

Example #9. 2-[[4-(Tetrahydropyran-4-ylamino)benzoyl]amino]-4-tetralin-2-yl-thiophene-3-carboxylic acid (Compound #52)

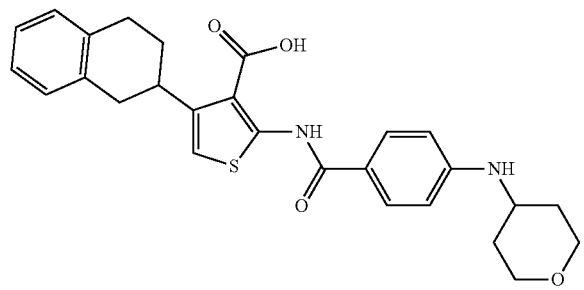 [SMILES: O=C(Nc1scc(C2CCc3ccccc3C2)c1C(=O)O)c1ccc(NC2CCOCC2)cc1]

Ethyl 2-(4-bromobenzamido)-4-(1,2,3,4-tetrahydronaphthalen-2-yl)thiophene-3-carboxylate (Preparation #2, 300 mg, 0.62 mmol), 4-aminotetrahydropyran (CAS: 38041-19-9, 94 mg, 0.93 mmol), RuPhos Pd G2 (CAS: 1375325-68-0, 96 mg, 0.12 mmol) and $Cs_2CO_3$ (CAS: 534-17-8, 303 mg, 0.93 mmol) were suspended in 1,4-dioxane (5.0 ml). The reaction mixture was degassed with nitrogen for 5 minutes. The reaction was heated at 70° C. for 20 hours and then it was allowed to cool to RT. The reaction was diluted with EtOAc and sequentially washed with water and brine. The organic phase was dried over $MgSO_4$ and the solvent was removed under reduced pressure. Purification by flash chromatography on silica gel (eluting with 0-60% EtOAc in isohexane) afforded ethyl 2-(4-((tetrahydro-2H-pyran-4-yl)amino)benzamido)-4-(1,2,3,4-tetrahydronaphthalen-2-yl)thiophene-3-carboxylate as a yellow solid (240 mg, yield 77%). Ethyl 2-(4-((tetrahydro-2H-pyran-4-yl)amino)benzamido)-4-(1,2,3,4-tetrahydronaphthalen-2-yl)thiophene-3-carboxylate (240 mg, 0.48 mmol) was dissolved in THF (3.0 ml), MeOH (3.0 ml) and water (2.4 ml). Lithium hydroxide monohydrate (CAS: 1310-66-3, 100 mg, 2.4 mmol) was added. The reaction mixture was stirred at 40° C. overnight. The mixture was allowed to cool to RT and then diluted with EtOAc. The reaction was sequentially washed with 1N aqueous HCl solution and brine. The organic phase was dried over $MgSO_4$ and the solvent was removed under reduced pressure. Purification by RP-HPLC (Table 2, Method A) afforded 2-[[4-(tetrahydropyran-4-ylamino)benzoyl]amino]-4-tetralin-2-yl-thiophene-3-carboxylic acid as an off-white solid (70 mg, yield 31%). $^1$H NMR (DMSO-$d_6$, 400 MHz): δ=13.71 (br s, 1H), 7.69 (d, J=8.7 Hz, 2H), 7.23 (br s, 1H), 7.12-7.07 (m, 4H), 6.73 (d, J=8.8 Hz, 2H), 6.58 (s, 1H), 6.47 (d, J=7.5 Hz, 1H), 3.92-3.85 (m, 2H), 3.79 (t, J=10.5 Hz, 1H), 3.62-3.53 (m, 1H), 3.44 (dt, J=2.0, 11.5 Hz, 2H), 3.09 (dd, J=4.0, 16.2 Hz, 1H), 2.90-2.67 (m, 3H), 2.14-2.09 (m, 1H), 1.89 (d, J=12.4 Hz, 2H), 1.83-1.70 (m, 1H), 1.47-1.36 (m, 2H). LC/MS (Table 1, Method B) $R_t$=3.76 min; MS m/z: 477 [M+H]$^+$.

Example #10. 2-[[4-(3-Methoxyazetidin-1-yl)benzoyl]amino]-4-tetralin-2-yl-thiophene-3-carboxylic acid (Compound #53)

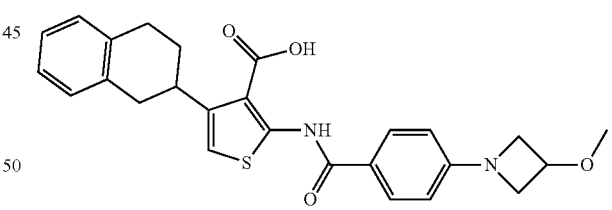

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 3-methoxyazetidine hydrochloride (CAS: 148644-09-1) as starting materials (pale yellow solid, yield 16%). $^1$H NMR (DMSO-$d_6$, 400 MHz): δ=12.86 (br s, 1H), 7.77 (d, J=8.8 Hz, 2H), 7.14-7.09 (m, 4H), 6.70 (s, 1H), 6.56 (d, J=8.9 Hz, 2H), 4.41-4.34 (m, 1H), 4.18-4.14 (m, 2H), 3.77 (dd, J=4.0, 8.9 Hz, 2H), 3.70-3.65 (m, 1H), 3.28 (s, 3H), 3.09 (dd, J=4.4, 16.0 Hz, 1H), 2.91-2.84 (m, 2H), 2.76 (dd, J=11.2, 16.2 Hz, 1H), 2.18-2.09 (m, 1H), 1.84-1.72 (m, 1H), one exchangeable proton not observed. LC/MS (Table 1, Method B) $R_t$=3.86 min; MS m/z: 463 [M+H]$^+$.

Example #11. 4-Indan-1-yl-2-[[4-(tetrahydropyran-4-ylamino)benzoyl]amino]thiophene-3-carboxylic acid (Compound #55)

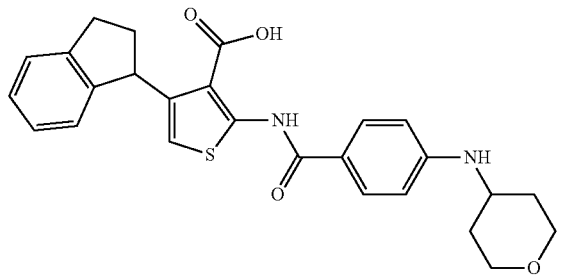 [SMILES: O=C(Nc1scc(C2CCc3ccccc32)c1C(=O)O)c1ccc(NC2CCOCC2)cc1]

To a solution of ethyl 2-amino-4-(2,3-dihydro-1H-inden-1-yl)thiophene-3-carboxylate (prepared as described in Example #6, 2.00 g, 6.96 mmol) in DCM (50.0 ml) was added DIPEA (CAS: 7087-68-5, 1.6 ml, 9.05 mmol) and 4-bromobenzoyl chloride (CAS: 586-75-4, 2.00 g, 9.05 mmol). The reaction mixture was stirred at RT overnight. The resulting mixture was diluted with DCM and the organic phase was sequentially washed with a 2N aqueous HCl solution and brine. The organic phase was dried over MgSO$_4$ and the solvent was removed under reduced pressure. Purification by flash chromatography on silica gel (eluting with 0-30% EtOAc in isohexane) afforded ethyl 2-(4-bromobenzamido)-4-(2,3-dihydro-1H-inden-1-yl)thiophene-3-carboxylate as a yellow solid (2.45 g, yield 74%). The title compound was then synthesized according to the procedure described in Example #9 using ethyl 2-(4-bromobenzamido)-4-(2,3-dihydro-1H-inden-1-yl)thiophene-3-carboxylate and 4-aminotetrahydropyran (CAS: 38041-19-9) as starting materials (off-white solid, yield 29%). $^1$H NMR (DMSO-d$_6$, 400 MHz): δ=13.52 (br s, 1H), 12.42 (s, 1H), 7.68 (d, J=8.8 Hz, 2H), 7.30 (d, J=6.6 Hz, 1H), 7.22-7.10 (m, 3H), 6.76 (d, J=8.9 Hz, 2H), 6.58 (d, J=7.9 Hz, 1H), 6.17 (s, 1H), 5.03 (t, J=7.1 Hz, 1H), 3.89 (td, J=3.3, 11.7 Hz, 2H), 3.65-3.54 (m, 1H), 3.45 (dt, J=1.7, 11.5 Hz, 2H), 2.99-2.82 (m, 2H), 2.50-2.45 (m, 1H, partially obscured by the DMSO peak), 2.05-1.88 (m, 3H), 1.49-1.37 (m, 2H). LC/MS (Table 1, Method B) R$_t$=3.69 min; MS m/z: 463 [M+H]$^+$.

Example #12. 4-Indan-1-yl-2-[(4-morpholinobenzoyl)amino]thiophene-3-carboxylic acid (Compound #56)

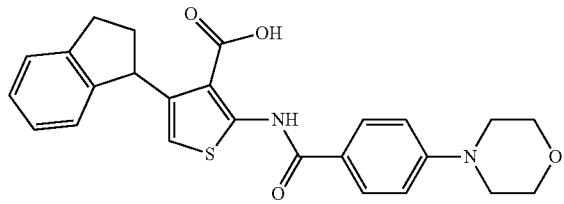 [SMILES: O=C(Nc1scc(C2CCc3ccccc32)c1C(=O)O)c1ccc(N2CCOCC2)cc1]

The title compound was then synthesized according to the procedure described in Example #11 using ethyl 2-amino-4-(2,3-dihydro-1H-inden-1-yl)thiophene-3-carboxylate (prepared as described in Example #6) and morpholine (CAS: 110-91-8) as starting materials (off-white solid, yield 26%). $^1$H NMR (DMSO-d$_6$, 400 MHz): δ=13.49 (br s, 1H), 12.35 (s, 1H), 7.72 (d, J=9.0 Hz, 2H), 7.24-7.03 (m, 6H), 6.13 (s, 1H), 4.94 (t, J=7.3 Hz, 1H), 3.70-3.66 (m, 4H), 3.25-3.18 (m, 1H, partially obscured by the water peak), 2.90-2.73 (m, 2H), 2.47 (s, 4H), 1.97-1.87 (m, 1H). LC/MS (Table 1, Method A) R$_t$=3.03 min; MS m/z: 449 [M+H]$^+$.

Example #13. 4-Indan-1-yl-2-[[4-(3-methoxypropylamino)benzoyl]amino]thiophene-3-carboxylic acid (Compound #57)

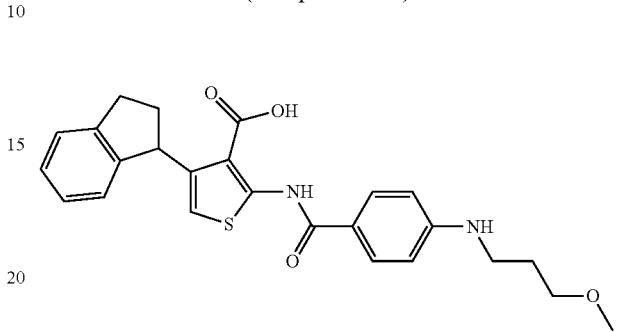

The title compound was then synthesized according to the procedure described in Example #11 using ethyl 2-amino-4-(2,3-dihydro-1H-inden-1-yl)thiophene-3-carboxylate (prepared as described in Example #6) and 3-methoxypropan-1-amine (CAS: 5332-73-0) as starting materials (yellow solid, yield 30%). $^1$H NMR (DMSO-d$_6$, 400 MHz): δ=13.55 (br s, 1H), 12.46 (s, 1H), 7.69 (d, J=8.9 Hz, 2H), 7.30 (d, J=6.7 Hz, 1H), 7.22-7.11 (m, 3H), 6.70 (d, J=8.7 Hz, 2H), 6.64 (t, J=5.0 Hz, 1H), 6.16 (s, 1H), 5.04 (t, J=7.2 Hz, 1H), 3.43 (t, J=6.2 Hz, 2H), 3.27 (s, 3H), 3.18 (q, J=6.1 Hz, 2H), 2.99-2.81 (m, 2H), 2.50-2.46 (m, 1H, partially obscured by the DMSO peak), 2.05-1.95 (m, 1H), 1.85-1.77 (m, 2H). LC/MS (Table 1, Method A) R$_t$=3.07 min; MS m/z: 451 [M+H]$^+$.

Example #14. 4-Indan-1-yl-2-[[4-(3-methoxyazetidin-1-yl)benzoyl]amino]thiophene-3-carboxylic acid (Compound #58)

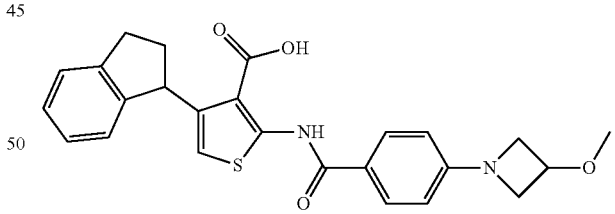

The title compound was then synthesized according to the procedure described in Example #11 using ethyl 2-amino-4-(2,3-dihydro-1H-inden-1-yl)thiophene-3-carboxylate (prepared as described in Example #6) and 3-methoxyazetidine hydrochloride (CAS: 148644-09-1) as starting materials (yellow solid, yield 29%). $^1$H NMR (DMSO-d$_6$, 400 MHz): δ=14.04 (br s, 1H), 7.79 (d, J=8.8 Hz, 2H), 7.32-7.11 (m, 5H), 6.54 (d, J=8.9 Hz, 2H), 6.11 (s, 1H), 5.31 (t, J=7.5 Hz, 1H), 4.40-4.34 (m, 1H), 4.15 (dd, J=6.5, 8.4 Hz, 2H), 3.75 (dd, J=3.8, 8.8 Hz, 2H), 3.28 (s, 3H), 2.98-2.80 (m, 2H), 2.50-2.45 (m, 1H, partially obscured by the DMSO peak), 2.03-1.93 (m, 1H). LC/MS (Table 1, Method B) R$_t$=3.82 min; MS m/z: 449 [M+H]$^+$.

Example #15. 2-[[4-(3-Methoxypropylamino)benzoyl]amino]-4-tetralin-2-yl-thiophene-3-carboxylic acid (Compound #64)

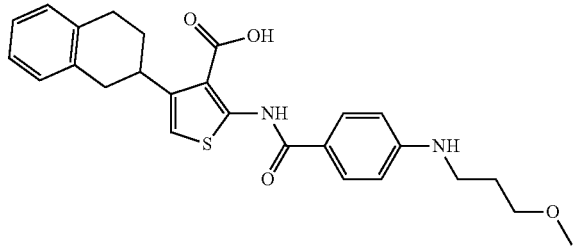 [SMILES: COCCCNc1ccc(C(=O)Nc2scc(C3CCc4ccccc4C3)c2C(=O)O)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 3-methoxypropan-1-amine (CAS: 5332-73-0) as starting materials (pale yellow solid, yield 5%). $^{1}$H NMR (DMSO-$d_6$, 400 MHz): δ=13.45 (br s, 1H), 12.35 (s, 1H), 7.68 (d, J=8.9 Hz, 2H), 7.14-7.09 (m, 4H), 6.73-6.67 (m, 3H), 6.63 (t, J=5.4 Hz, 1H), 3.65-3.56 (m, 1H), 3.43 (t, J=6.2 Hz, 2H), 3.27 (s, 3H), 3.18 (q, J=6.3 Hz, 2H), 3.11-3.04 (m, 1H), 2.91-2.84 (m, 2H), 2.77 (dd, J=11.3, 16.4 Hz, 1H), 2.18-2.09 (m, 1H), 1.85-1.77 (m, 3H). LC/MS (Table 1, Method A) $R_t$=3.09 min; MS m/z: 465 [M+H]$^{+}$.

Example #16. 2-[[4-(2-Methoxyethylamino)benzoyl]amino]-4-tetralin-2-yl-thiophene-3-carboxylic acid (Compound #65)

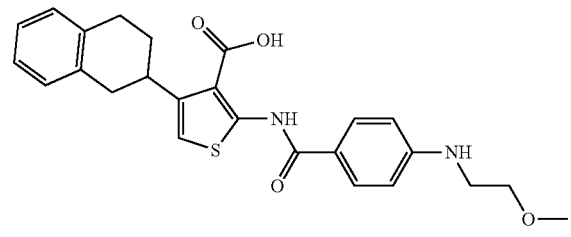 [SMILES: COCCNc1ccc(C(=O)Nc2scc(C3CCc4ccccc4C3)c2C(=O)O)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 2-methoxyethanamine (CAS: 109-85-3) as starting materials (yellow solid, yield 16%). $^{1}$H NMR (DMSO-$d_6$, 400 MHz): δ=13.46 (br s, 1H), 12.44 (s, 1H), 7.68 (d, J=8.6 Hz, 2H), 7.13-7.08 (m, 4H), 6.77-6.71 (m, 3H), 6.65 (t, J=5.6 Hz, 1H), 3.67-3.57 (m, 1H), 3.52 (t, J=5.6 Hz, 2H), 3.33-3.29 (m, 5H, partially obscured by the water peak), 3.08 (dd, J=3.4, 16.5 Hz, 1H), 2.91-2.72 (m, 3H), 2.18-2.09 (m, 1H), 1.85-1.73 (m, 1H). LC/MS (Table 1, Method B) $R_t$=3.76 min; MS m/z: 451 [M+H]$^{+}$.

Example #17. 2-[[4-(Tetrahydropyran-3-ylamino)benzoyl]amino]-4-tetralin-2-yl-thiophene-3-carboxylic acid (Compound #67)

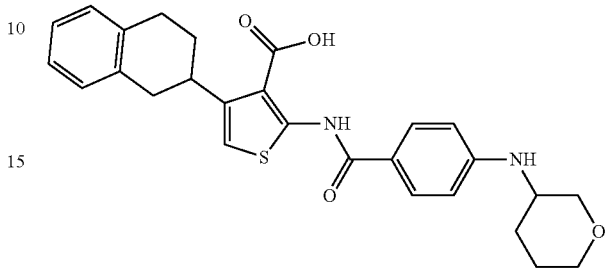

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and tetrahydro-2H-pyran-3-amine hydrochloride (CAS: 120811-32-7) as starting materials (off-white solid, yield 3%). $^{1}$H NMR (DMSO-$d_6$, 400 MHz): δ=13.48 (br s, 1H), 12.61 (br s, 1H), 7.68 (d, J=8.7 Hz, 2H), 7.13-7.09 (m, 4H), 6.77 (d, J=8.9 Hz, 2H), 6.70 (s, 1H), 6.51 (d, J=8.0 Hz, 1H), 3.87 (dd, J=2.7, 11.1 Hz, 1H), 3.75 (td, J=3.9, 10.9 Hz, 1H), 3.64 (dd, J=10.6, 10.6 Hz, 1H), 3.55-3.37 (m, 2H), 3.21-3.04 (m, 2H), 2.91-2.71 (m, 3H), 2.17-2.09 (m, 1H), 2.05-1.96 (m, 1H), 1.84-1.46 (m, 4H). LC/MS (Table 1, Method A) $R_t$=3.09 min; MS m/z: 477 [M+H]$^{+}$.

Example #18. 2-[(4-Morpholinobenzoyl)amino]-4-tetralin-2-yl-thiophene-3-carboxylic acid (Compound #68)

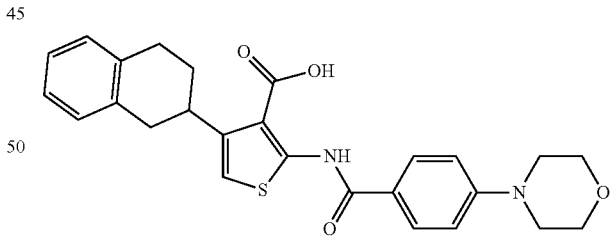

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and morpholine (CAS: 110-91-8) as starting materials (off-white solid, yield 22%). $^{1}$H NMR (DMSO-$d_6$, 400 MHz): δ=13.51 (br s, 1H), 12.42 (s, 1H), 7.81 (d, J=8.8 Hz, 2H), 7.17-7.08 (m, 6H), 6.77 (s, 1H), 3.79-3.74 (m, 4H), 3.66-3.56 (m, 1H), 3.36-3.29 (m, 5H, partially obscured by the water peak), 3.08 (dd, J=3.4, 16.7 Hz, 1H), 2.92-2.73 (m, 2H), 2.18-2.09 (m, 1H), 1.85-1.73 (m, 1H). LC/MS (Table 1, Method B) $R_t$=3.83 min; MS m/z: 463 [M+H]$^{+}$.

Example #19. 2-[[4-(Tetrahydropyran-4-ylmethyl-amino)benzoyl]amino]-4-tetralin-2-yl-thiophene-3-carboxylic acid (Compound #69)

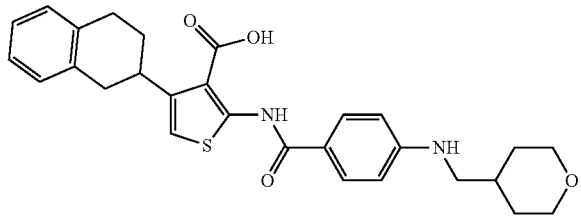 [SMILES: O=C(Nc1scc(C2CCc3ccccc3C2)c1C(=O)O)c1ccc(NCC2CCOCC2)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and tetrahydropyran-4-ylmethanamine (CAS: 130290-79-8) as starting materials (off-white solid, yield 18%). $^1$H NMR (DMSO-d$_6$, 400 MHz): δ=13.51 (br s, 1H), 12.65 (s, 1H), 7.60 (d, J=8.7 Hz, 2H), 7.06-6.99 (m, 4H), 6.66-6.53 (m, 4H), 3.79 (dd, J=2.8, 11.1 Hz, 2H), 3.64-3.56 (m, 1H), 3.21 (t, J=11.4 Hz, 2H), 3.00 (d, J=16.2 Hz, 1H), 2.93 (t, J=5.8 Hz, 2H), 2.83-2.62 (m, 3H), 2.09-2.02 (m, 1H), 1.80-1.66 (m, 2H), 1.60 (d, J=13.1 Hz, 2H), 1.15 (dq, J=4.0, 12.1 Hz, 2H). LC/MS (Table 1, Method A) R$_t$=3.08 min; MS m/z: 491 [M+H]$^+$.

Example #20. 2-[(3-Morpholinobenzoyl)amino]-4-tetralin-2-yl-thiophene-3-carboxylic acid (Compound #70)

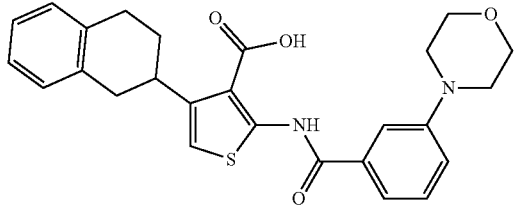 [SMILES: O=C(Nc1scc(C2CCc3ccccc3C2)c1C(=O)O)c1cccc(N2CCOCC2)c1]

To a stirred solution of 3-morpholinobenzoic acid (CAS: 215309-00-5, 500 mg, 2.41 mmol) in DCM (10.0 ml) at 0° C. was added DMF (10 μl, 0.12 mmol) and oxalyl chloride (CAS: 79-37-8, 0.21 ml, 2.46 mmol). The reaction mixture was warmed to RT and stirred at RT overnight. The solvent was removed under reduced pressure to afford 3-morpholinobenzoyl chloride as a yellow oil (337 mg, yield 62%). The residue (337 mg, 1.49 mmol) was then added to a stirred solution of ethyl 2-amino-4-(1,2,3,4-tetrahydronaphthalen-2-yl)thiophene-3-carboxylate (Preparation #1, 300 mg, 1.00 mmol) and DIPEA (CAS: 7087-68-5, 0.52 ml, 2.99 mmol) in DCM (10.0 ml). The reaction mixture was stirred at RT overnight. The reaction was diluted with DCM and the organic phase was sequentially washed with 1N aqueous HCl solution and brine. The organic phase was dried over MgSO$_4$ and the solvent was removed under reduced pressure. Purification by flash chromatography on silica gel (eluting with 0-50% EtOAc in isohexane) afforded ethyl 2-(3-morpholinobenzamido)-4-(1,2,3,4-tetrahydronaphthalen-2-yl)thiophene-3-carboxylate as a yellow oil (328 mg, yield 67%). Ethyl 2-(3-morpholinobenzamido)-4-(1,2,3,4-tetrahydronaphthalen-2-yl)thiophene-3-carboxylate (320 mg, 0.65 mmol) was dissolved in THF (6.0 ml) and MeOH (6.0 ml) and water (6.0 ml). Lithium hydroxide monohydrate (CAS: 1310-66-3, 137 mg, 3.26 mmol) was added. The reaction mixture was stirred at 40° C. overnight. The mixture was allowed to cool to RT and then diluted with EtOAc. The reaction was sequentially washed with 1N aqueous HCl solution and brine. The organic phase was dried over MgSO$_4$ and the solvent was removed under reduced pressure. Trituration with MeOH afforded 2-[(3-morpholinobenzoyl)amino]-4-tetralin-2-yl-thiophene-3-carboxylic acid as an off-white solid (220 mg, yield 73%). $^1$H NMR (DMSO-d$_6$, 400 MHz): δ=13.69 (br s, 1H), 12.54 (s, 1H), 7.56-7.48 (m, 2H), 7.41-7.32 (m, 2H), 7.18-7.14 (m, 4H), 6.87 (s, 1H), 3.85-3.80 (m, 4H), 3.66 (dd, J=10.4, 10.4 Hz, 1H), 3.29-3.24 (m, 4H), 3.12 (dd, J=3.0, 16.0 Hz, 1H), 2.95-2.77 (m, 3H), 2.19 (d, J=11.6 Hz, 1H), 1.90-1.79 (m, 1H). LC/MS (Table 1, Method A) R$_t$=3.07 min; MS m/z: 463 [M+H]$^+$.

Example #21. 2-[(4-Methyl-2,3-dihydro-1,4-benzoxazine-7-carbonyl)amino]-4-tetralin-2-yl-thiophene-3-carboxylic acid (Compound #86)

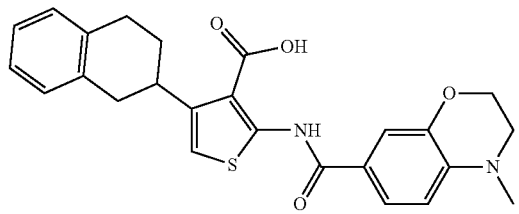 [SMILES: CN1CCOc2cc(C(=O)Nc3scc(C4CCc5ccccc5C4)c3C(=O)O)ccc21]

The title compound was synthesized according to the procedure described in Example #20, using 4-methyl-3,4-dihydro-2H-1,4-benzoxazine-7-carboxylic acid (CAS: 532391-89-2) and ethyl 2-amino-4-(1,2,3,4-tetrahydronaphthalen-2-yl)thiophene-3-carboxylate (Preparation #1) as starting materials (pale yellow solid, yield 19%). $^1$H NMR (DMSO-d$_6$, 400 MHz): δ=13.52 (br s, 1H), 12.39 (s, 1H), 7.46 (d, J=8.6 Hz, 1H), 7.25 (s, 1H), 7.14 (br s, 4H), 6.89 (d, J=8.3 Hz, 1H), 6.78 (s, 1H), 4.30 (s, 2H), 3.64 (dd, J=9.7, 9.7 Hz, 1H), 3.45 (s, 2H), 3.13 (d, J=17.0 Hz, 1H), 3.03 (s, 3H), 2.95-2.75 (m, 3H), 2.19 (d, J=11.2 Hz, 1H), 1.88-1.76 (m, 1H). LC/MS (Table 1, Method B) R$_t$=3.83 min; MS m/z: 449 [M+H]$^+$.

Example #22. 2-[(2-Morpholinopyrimidine-5-carbonyl)amino]-4-tetralin-2-yl-thiophene-3-carboxylic acid (Compound #89)

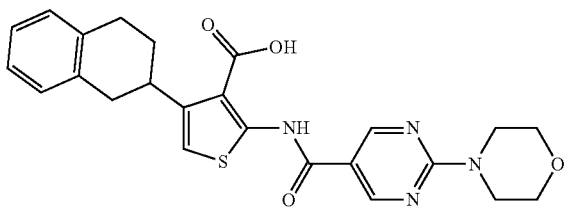 [SMILES: O=C(Nc1scc(C2CCc3ccccc3C2)c1C(=O)O)c1cnc(N2CCOCC2)nc1]

The title compound was synthesized according to the procedure described in Example #20, using 2-morpholinopyrimidine-5-carboxylic acid (CAS: 253315-C$_5$-8) and ethyl 2-amino-4-(1,2,3,4-tetrahydronaphthalen-2-yl)thiophene-3-carboxylate (Preparation #1) as starting materials (pale yellow solid, yield 12%). ¹H NMR (DMSO-d₆, 400 MHz): δ=12.75 (br s, 1H), 8.89 (s, 2H), 7.17-7.11 (m, 4H), 6.80 (s, 1H), 3.94-3.87 (m, 4H), 3.77-3.66 (m, 5H), 3.11 (dd, J=3.3, 16.1 Hz, 1H), 2.95-2.75 (m, 3H), 2.20-2.13 (m, 1H), 1.88-1.76 (m, 1H), one exchangeable proton not observed. LC/MS (Table 1, Method B) R$_t$=3.77 min; MS m/z: 465 [M+H]⁺.

Example #23. 2-[[3-(3-Methoxyazetidin-1-yl)benzoyl]amino]-4-tetralin-2-yl-thiophene-3-carboxylic acid (Compound #93)

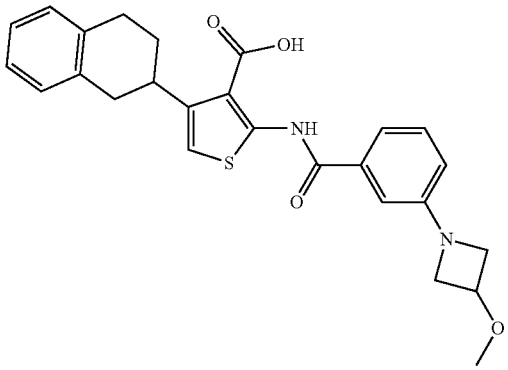 [SMILES: COC1CN(c2cccc(C(=O)Nc3scc(C4CCc5ccccc5C4)c3C(=O)O)c2)C1]

The title compound was synthesized according to the procedure described in Example #11, using ethyl 2-amino-4-(1,2,3,4-tetrahydronaphthalen-2-yl)thiophene-3-carboxylate (Preparation #1), 3-bromobenzoyl chloride (CAS: 1711-09-7) and 3-methoxyazetidine hydrochloride (CAS: 148644-09-1) as starting materials (yellow solid, yield 7%). ¹H NMR (DMSO-d₆, 400 MHz): δ=14.00 (br s, 1H), 7.38 (t, J=7.8 Hz, 1H), 7.27-7.18 (m, 2H), 7.13-7.06 (m, 4H), 6.98 (t, J=1.9 Hz, 1H), 6.72-6.67 (m, 2H), 4.40-4.33 (m, 1H), 4.15-4.11 (m, 2H), 3.84-3.75 (m, 1H), 3.69 (dd, J=4.2, 8.2 Hz, 2H), 3.27 (s, 3H), 3.10 (dd, J=3.7, 16.2 Hz, 1H), 2.90-2.69 (m, 3H), 2.17-2.09 (m, 1H), 1.84-1.72 (m, 1H). LC/MS (Table 1, Method A) R$_t$=2.99 min; MS m/z: 463 [M+H]⁺.

Example #24. 2-[[3-(2-Methoxyethylamino)benzoyl]amino]-4-tetralin-2-yl-thiophene-3-carboxylic acid (Compound #94)

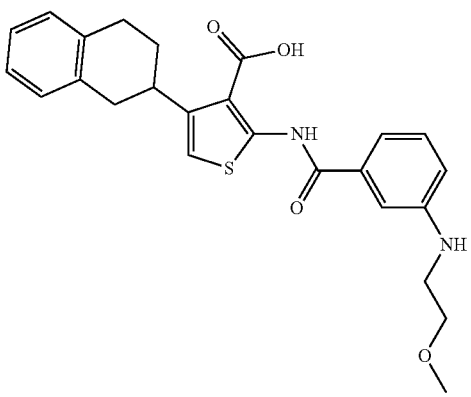 [SMILES: COCCNc1cccc(C(=O)Nc2scc(C3CCc4ccccc4C3)c2C(=O)O)c1]

The title compound was synthesized according to the procedure described in Example #11, using ethyl 2-amino-4-(1,2,3,4-tetrahydronaphthalen-2-yl)thiophene-3-carboxylate (Preparation #1), 3-bromobenzoyl chloride (CAS: 1711-09-7) and 2-methoxyethanamine (CAS: 109-85-3) as starting materials (yellow solid, yield 8%). ¹H NMR (DMSO-d₆, 400 MHz): δ=13.67 (br s, 1H), 7.31-7.06 (m, 8H), 6.87 (dd, J=2.0, 8.1 Hz, 1H), 6.69 (s, 1H), 6.05 (s, 1H), 3.77 (dd, J=9.5, 9.5 Hz, 1H), 3.53 (t, J=5.7 Hz, 2H), 3.31 (s, 3H), 3.26 (t, J=5.7 Hz, 2H), 3.09 (dd, J=3.9, 16.4 Hz, 1H), 2.93-2.69 (m, 3H), 2.17-2.09 (m, 1H), 1.85-1.72 (m, 1H). LC/MS (Table 1, Method A) R$_t$=2.97 min; MS m/z: 451 [M+H]⁺.

Example #25. 2-[[4-(2-methoxyethoxy)benzoyl]amino]-4-tetralin-2-yl-thiophene-3-carboxylic acid (Compound #101)

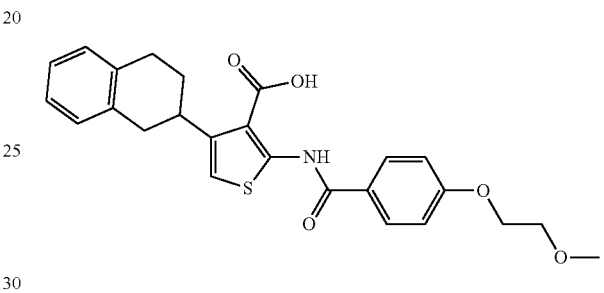

The title compound was synthesized according to the procedure described in Example #20, using 4-(2-methoxyethoxy)benzoic acid (CAS: 27890-92-2) and ethyl 2-amino-4-(1,2,3,4-tetrahydronaphthalen-2-yl)thiophene-3-carboxylate (Preparation #1) as starting materials (white solid, yield 10%). ¹H NMR (DMSO-d₆, 400 MHz): δ=13.60 (br s, 1H), 12.60 (s, 1H), 7.93 (d, J=8.6 Hz, 2H), 7.22 (d, J=8.7 Hz, 2H), 7.19-7.12 (m, 4H), 6.83 (s, 1H), 4.29-4.24 (m, 2H), 3.78-3.61 (m, 3H), 3.37 (s, 3H), 3.12 (dd, J=3.0, 16.0 Hz, 1H), 2.99-2.77 (m, 3H), 2.23-2.13 (m, 1H), 1.90-1.76 (m, 1H). LC/MS (Table 1, Method B) R$_t$=3.81 min; MS m/z: 452 [M+H]⁺.

Example #26. 2-Benzamido-4-(6,7,8,9-tetrahydro-5H-benzo[7]annulen-7-yl)thiophene-3-carboxylic acid (Compound #122)

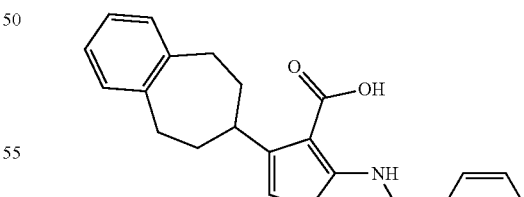

The title compound was synthesized according to the procedure described in Example #4 using ethyl 2-amino-4-(6,7,8,9-tetrahydro-5H-benzo[7]annulen-7-yl)thiophene-3-carboxylate (Preparation #3) and benzoyl chloride (CAS: 98-88-4) as starting materials (pale yellow solid, yield 56%). ¹H NMR (DMSO-d₆, 400 MHz): δ=13.53 (br s, 1H), 12.49 (br s, 1H), 7.82 (d, J=7.3 Hz, 2H), 7.61-7.48 (m, 3H), 7.06-6.96 (m, 4H), 6.58 (s, 1H), 3.58 (t, J=11.4 Hz, 1H), 2.83-2.67 (m, 4H), 2.07 (t, J=10.7 Hz, 2H), 1.25 (dd, J=12.7, 24.2 Hz, 2H). LC/MS (Table 1, Method D) $R_t$=3.91 min; MS m/z: 392 [M+H]$^+$.

Example #27. 2-Benzamido-4-tetralin-6-yl-thiophene-3-carboxylic acid (Compound #123)

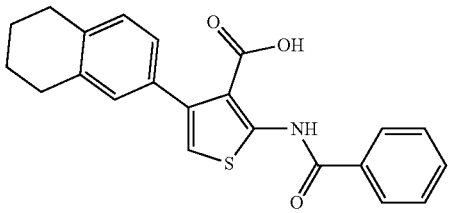 [SMILES: O=C(Nc1scc(-c2ccc3c(c2)CCCC3)c1C(=O)O)c1ccccc1]

The title compound was synthesized according to the procedure described in Example #1 using 1-(1,2,3,4-tetrahydronaphthalen-1-yl)ethan-1-one (CAS: 7369-63-3) as a starting material (off-white solid, yield 7%). $^1$H NMR (DMSO-d$_6$, 400 MHz): δ=8.09-8.04 (m, 1H), 7.74-7.68 (m, 1H), 7.52-7.43 (m, 2H), 7.17-7.10 (m, 4H), 6.79-6.75 (m, 1H), 3.83-3.75 (m, 1H), 3.16-3.10 (m, 2H), 2.94-2.89 (m, 2H), 2.82-2.73 (m, 1H), 2.19-2.11 (m, 1H), 1.88-1.80 (m, 1H), two exchangeable protons not observed. LC/MS (Table 1, Method C) $R_t$=5.92 min; MS m/z: 378 [M+H]$^+$.

Example #28. 2-Benzamido-4-tetralin-1-yl-thiophene-3-carboxylic acid (Compound #124)

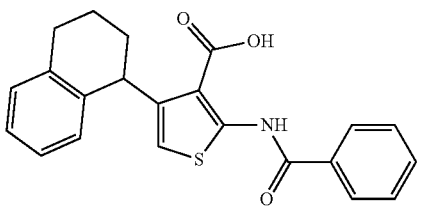 [SMILES: O=C(Nc1scc(C2CCCc3ccccc32)c1C(=O)O)c1ccccc1]

The title compound was synthesized according to the procedure described in Example #4 using ethyl 2-amino-4-(1,2,3,4-tetrahydronaphthalen-1-yl)thiophene-3-carboxylate (Preparation #4) as a starting material (pale yellow solid, yield 38%). $^1$H NMR (DMSO-d$_6$, 400 MHz): δ=13.92 (br s, 1H), 8.01 (d, J=6.8 Hz, 2H), 7.72-7.62 (m, 3H), 7.26 (br s, 1H), 7.18-7.07 (m, 3H), 6.96 (d, J=7.3 Hz, 1H), 5.96 (s, 1H), 5.12-5.06 (m, 1H), 2.92-2.73 (m, 2H), 2.05-1.98 (m, 2H), 1.79-1.68 (m, 2H). LC/MS (Table 1, Method D) $R_t$=4.00 min; MS m/z: 378 [M+H]$^+$.

Example #29. 2-[(4-Fluorobenzoyl)amino]-4-tetralin-6-yl-thiophene-3-carboxylic acid (Compound #125)

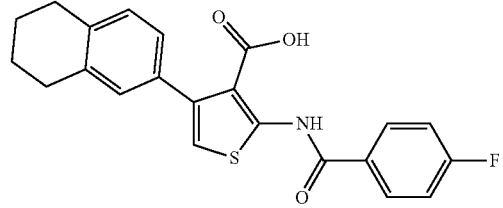 [SMILES: O=C(Nc1scc(-c2ccc3c(c2)CCCC3)c1C(=O)O)c1ccc(F)cc1]

The title compound was synthesized according to the procedure described in Example #1 using 1-(1,2,3,4-tetrahydronaphthalen-1-yl)ethan-1-one (CAS: 7369-63-3) and 4-fluorobenzoyl chloride (CAS: 403-43-0) as starting materials (pale yellow solid, yield 4%). $^1$H NMR (DMSO-d$_6$, 400 MHz): δ=13.45 (br s, 1H), 8.05 (dd, J=5.6, 8.6 Hz, 2H), 7.49 (t, J=8.8 Hz, 2H), 7.11-7.00 (m, 3H), 6.82 (s, 1H), 2.76-2.73 (m, 4H), 1.79 (s, 4H), one exchangeable proton not observed. LC/MS (Table 1, Method C) $R_t$=5.97 min; MS m/z: 396 [M+H]$^+$.

Example #30. 2-[(4-Fluorobenzoyl)amino]-4-tetralin-1-yl-thiophene-3-carboxylic acid (Compound #126)

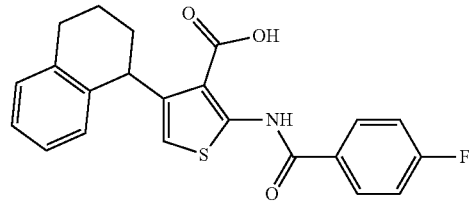 [SMILES: O=C(Nc1scc(C2CCCc3ccccc32)c1C(=O)O)c1ccc(F)cc1]

The title compound was synthesized according to the procedure described in Example #4 using ethyl 2-amino-4-(1,2,3,4-tetrahydronaphthalen-1-yl)thiophene-3-carboxylate (Preparation #4) and 4-fluorobenzoyl chloride (CAS: 403-43-0) as starting materials (off-white solid, yield 11%). $^1$H NMR (DMSO-d$_6$, 400 MHz): δ=13.70 (br s, 1H), 12.60 (br s, 1H), 8.03 (dd, J=5.4, 8.7 Hz, 2H), 7.52 (t, J=8.7 Hz, 2H), 7.17-7.09 (m, 3H), 6.94 (d, J=7.5 Hz, 1H), 6.05 (s, 1H), 4.90 (t, J=4.8 Hz, 1H), 2.89-2.70 (m, 2H), 2.05-1.95 (m, 2H), 1.80-1.67 (m, 2H). LC/MS (Table 1, Method C) $R_t$=5.98 min; MS m/z: 396 [M+H]$^+$.

Example #31. 2-[[3-Methoxy-4-(tetrahydropyran-4-ylmethylamino)benzoyl]amino]-4-tetralin-2-yl-thiophene-3-carboxylic acid (Compound #127)

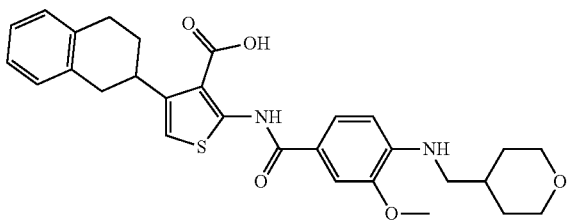 [SMILES: COc1cc(C(=O)Nc2scc(C3CCc4ccccc4C3)c2C(=O)O)ccc1NCC1CCOCC1]

Ethyl 2-amino-4-(1,2,3,4-tetrahydronaphthalen-2-yl)thiophene-3-carboxylate (Preparation #1, 250 mg, 0.83 mmol), 4-bromo-3-methoxybenzoic acid (CAS: 56256-14-5, 287 mg, 1.24 mmol), 2-chloro-1-methylpyridinium iodide (CAS: 14338-32-0, 339 mg, 1.33 mmol) and 4-(dimethylamino)pyridine (CAS: 1122-58-3, 30 mg, 0.24 mmol) were suspended in MeCN (10 nil). Triethylamine (CAS: 121-44-8, 0.23 ml, 1.66 mmol) was added and the reaction mixture was heated at 60° C. for 20 hours. The reaction mixture was allowed to cool to RT and next diluted with diluted with DCM and 1N aqueous HCl solution. The two phases were separated. The aqueous phase was further extracted with DCM (×2). The combined organic phases were washed with brine and passed through a phase separator. The solvent was removed under reduced pressure and the residue was purified by flash chromatography on silica gel (eluting with 0-25% EtOAc in cyclohexane) to afford ethyl 2-(4-bromo-3-methoxybenzamido)-4-(1,2,3,4-tetrahydronaphthalen-2-yl)thiophene-3-carboxylate as a yellow solid (380 mg, yield 89%). The title compound was then synthesized according to the procedure described in Example #9 using ethyl 2-(4-bromo-3-methoxybenzamido)-4-(1,2,3,4-tetrahydronaphthalen-2-yl)thiophene-3-carboxylate and tetrahydropyran-4-ylmethanamine (CAS: 130290-79-8) as starting materials (yellow solid, yield 26%). $^1$H NMR (DMSO-$d_6$, 400 MHz): δ=13.54 (br s, 1H), 12.47 (br s, 1H), 7.46 (d, J=8.0 Hz, 1H), 7.38 (s, 1H), 7.18-7.12 (m, 4H), 6.79-6.74 (m, 2H), 5.97 (t, J=5.8 Hz, 1H), 3.95 (s, 3H), 3.90 (d, J=11.5 Hz, 2H), 3.68-3.62 (m, 1H), 3.31 (t, J=11.5 Hz, 2H, partially obscured by the water peak), 3.18-3.08 (m, 3H), 2.94-2.78 (m, 3H), 2.18 (d, J=10.9 Hz, 1H), 1.97-1.77 (m, 2H), 1.67 (d, J=12.8 Hz, 2H), 1.31-1.21 (m, 2H). LC/MS (Table 1, Method D) $R_t$=3.94 min; MS m/z: 521 [M+H]$^+$.

Example #32. 2-[[4-(Cyclohexylmethylamino)benzoyl]amino]-4-tetralin-2-yl-thiophene-3-carboxylic acid (Compound #128)

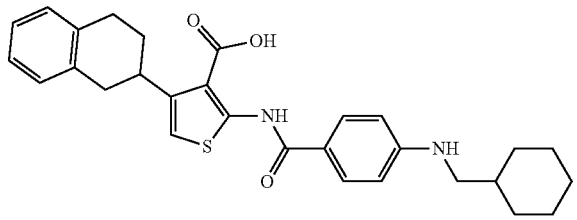 [SMILES: O=C(Nc1scc(C2CCc3ccccc3C2)c1C(=O)O)c1ccc(NCC2CCCCC2)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and cyclohexanemethylamine (CAS: 3218-02-8) as starting materials (yellow solid, yield 31%). $^1$H NMR (DMSO-$d_6$, 400 MHz): δ=7.71 (d, J=8.7 Hz, 2H), 7.17-7.11 (m, 4H), 6.73 (d, J=8.6 Hz, 2H), 6.70-6.62 (m, 2H), 3.77-3.70 (m, 1H), 3.15-3.10 (m, 1H), 3.00 (t, J=5.7 Hz, 2H), 2.94-2.88 (m, 2H), 2.82-2.73 (m, 1H), 2.17 (d, J=12.6 Hz, 1H), 1.87-1.59 (m, 7H), 1.29-1.19 (m, 3H), 1.05-0.95 (m, 2H), two exchangeable protons not observed. LC/MS (Table 1, Method D) $R_t$=4.47 min; MS m/z: 489 [M+H]$^+$.

Example #33. 2-[(2-Morpholinobenzoyl)amino]-4-tetralin-2-yl-thiophene-3-carboxylic acid (Compound #129)

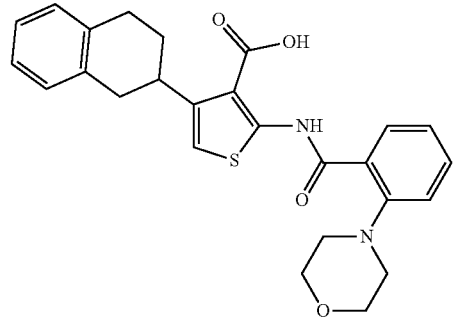 [SMILES: O=C(Nc1scc(C2CCc3ccccc3C2)c1C(=O)O)c1ccccc1N1CCOCC1]

The title compound was synthesized according to the procedure described in Example #20 using ethyl 2-amino-4-(1,2,3,4-tetrahydronaphthalen-2-yl)thiophene-3-carboxylate (Preparation #1) and 2-(morpholin-4-yl)benzoic acid (CAS: 42106-48-9) as starting materials (white solid, yield 10%). $^1$H NMR (DMSO-$d_6$, 400 MHz): δ=13.38 (br s, 1H), 13.12 (br s, 1H), 7.83 (d, J=7.6 Hz, 1H), 7.61 (t, J=7.3 Hz, 1H), 7.32 (d, J=7.6 Hz, 1H), 7.26 (t, J=7.3 Hz, 1H), 7.16-7.11 (m, 4H), 6.83 (s, 1H), 3.82 (br s, 4H), 3.70-3.64 (m, 1H), 3.14-3.07 (m, 1H), 3.00 (br s, 4H), 2.91-2.86 (m, 2H), 2.82-2.75 (m, 1H), 2.17-2.13 (m, 1H), 1.88-1.78 (m, 1H). LC/MS (Table 1, Method D) $R_t$=3.62 min; MS m/z: 463 [M+H]$^+$.

Example #34. 2-[[2-(Morpholinomethyl)benzoyl]amino]-4-tetralin-2-yl-thiophene-3-carboxylic acid (Compound #130)

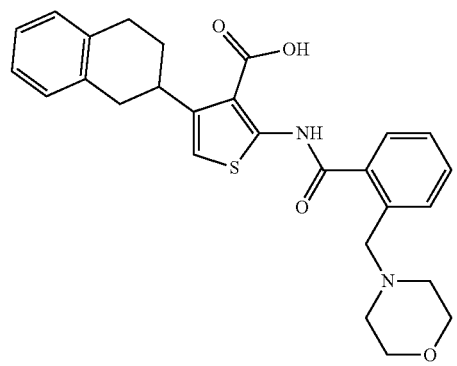 [SMILES: O=C(Nc1scc(C2CCc3ccccc3C2)c1C(=O)O)c1ccccc1CN1CCOCC1]

The title compound was synthesized according to the procedure described in Example #20 using ethyl 2-amino-4-(1,2,3,4-tetrahydronaphthalen-2-yl)thiophene-3-carboxylate (Preparation #1) and 2-[(morpholin-4-yl)methyl]benzoic acid (CAS: 868543-19-5) as starting materials (white solid, yield 80%). $^1$H NMR (DMSO-$d_6$, 400 MHz): δ=12.44 (br s, 2H), 7.70-7.62 (m, 1H), 7.60-7.45 (m, 3H), 7.12-7.07 (4H, m), 6.81 (s, 1H), 3.78 (br s, 2H), 3.66-3.55 (m, 1H), 3.42 (br s, 4H), 3.11-3.01 (m, 1H), 2.90-2.82 (m, 2H), 2.81-2.71 (m, 1H), 2.43 (br s, 4H), 2.16-2.05 (m, 1H), 1.86-1.70 (m, 1H). LC/MS (Table 1, Method E) $R_t$=3.67 min; MS m/z: 475 [M−H]$^−$.

Example #35. 2-[[4-[(2-Hydroxy-1-tetrahydropyran-4-yl-ethyl)amino]benzoyl]amino]-4-tetralin-2-yl-thiophene-3-carboxylic acid (Compound #131)

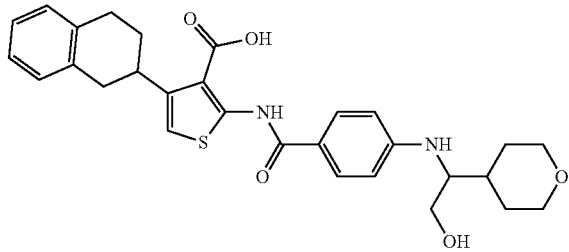 [SMILES: O=C(Nc1scc(C2CCc3ccccc3C2)c1C(=O)O)c1ccc(NC(CO)C2CCOCC2)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 2-amino-2-(oxan-4-yl)ethan-1-ol (CAS: 889949-63-7) as starting materials (white solid, yield 5%). $^{1}$H NMR (DMSO-$d_6$, 400 MHz): δ=13.20 (br s, 1H), 7.69 (d, J=8.5 Hz, 2H), 7.17-7.11 (m, 4H), 6.80 (d, J=8.6 Hz, 2H), 6.69 (s, 1H), 6.34 (d, J=8.2 Hz, 1H), 4.71 (s, 1H), 3.96-3.88 (m, 2H), 3.77-3.70 (m, 1H), 3.58-3.51 (m, 2H), 3.34-3.26 (m, 3H), 3.13 (dd, J=3.2, 16.3 Hz, 1H), 2.94-2.89 (m, 2H), 2.82-2.72 (m, 1H), 2.17 (d, J=11.2 Hz, 1H), 1.92-1.77 (m, 2H), 1.67 (t, J=13.2 Hz, 2H), 1.45-1.34 (m, 2H), one exchangeable proton not observed. LC/MS (Table 1, Method C) $R_t$=5.18 min; MS m/z: 521 [M+H]$^+$.

Example #36. 2-[[4-[Methyl(tetrahydropyran-4-ylmethyl)amino]benzoyl]amino]-4-tetralin-2-yl-thiophene-3-carboxylic acid (Compound #132)

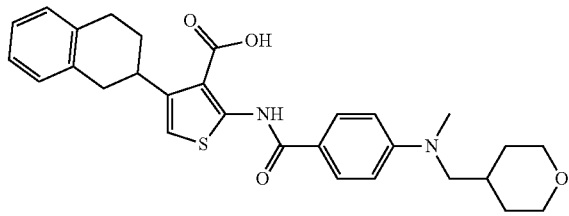 [SMILES: CN(CC1CCOCC1)c1ccc(C(=O)Nc2scc(C3CCc4ccccc4C3)c2C(=O)O)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and methyl[(oxan-4-yl)methyl]amine (CAS: 439081-52-4) as starting materials (pale yellow solid, yield 24%). $^{1}$H NMR (DMSO-$d_6$, 400 MHz): δ=13.47 (br s, 1H), 7.80 (d, J=8.9 Hz, 2H), 7.17-7.11 (m, 5H), 6.88 (d, J=9.1 Hz, 2H), 6.69 (s, 1H), 3.93-3.88 (m, 2H), 3.80-3.74 (m, 1H), 3.36-3.28 (m, 4H, partially obscured by the water peak), 3.16-3.09 (m, 4H), 2.94-2.88 (m, 2H), 2.83-2.72 (m, 1H), 2.19-2.14 (m, 1H), 2.06-1.97 (m, 1H), 1.87-1.77 (m, 1H), 1.57 (d, J=12.3 Hz, 2H), 1.38-1.27 (m, 2H). LC/MS (Table 1, Method C) $R_t$=6.00 min; MS m/z: 505 [M+H]$^+$.

Example #37. 2-[[4-(4-Hydroxybutylamino)benzoyl]amino]-4-tetralin-2-yl-thiophene-3-carboxylic acid (Compound #133)

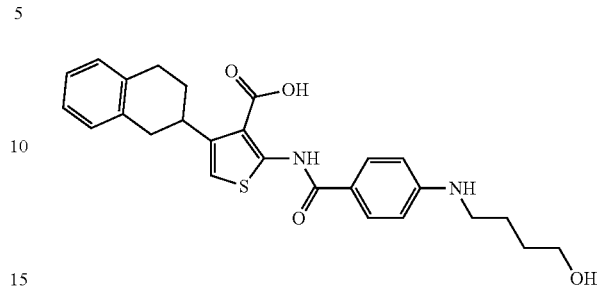

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 4-aminobutan-1-ol (CAS: 13325-10-5) as starting materials (white solid, yield 14%). $^{1}$H NMR (DMSO-$d_6$, 400 MHz): δ=13.45 (br s, 1H), 12.41 (s, 1H), 7.68 (d, J=8.8 Hz, 2H), 7.12-7.10 (m, 4H), 6.72-6.68 (m, 3H), 6.63 (t, J=5.2 Hz, 1H), 4.46 (s, 1H), 3.66-3.56 (m, 1H), 3.45 (t, J=6.1 Hz, 2H), 3.16-3.04 (m, 3H), 2.91-2.84 (m, 2H), 2.77 (dd, J=11.3, 16.0 Hz, 1H), 2.18-2.09 (m, 1H), 1.84-1.74 (m, 1H), 1.65-1.49 (m, 4H). LC/MS (Table 1, Method D) $R_t$=3.60 min; MS m/z: 465 [M+H]$^+$.

Example #38. 2-[[3-Hydroxy-4-(tetrahydropyran-4-ylmethylamino)benzoyl]amino]-4-tetralin-2-yl-thiophene-3-carboxylic acid (Compound #134)

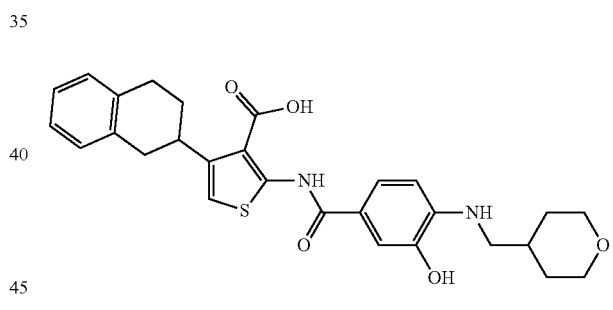

To a stirred solution of 2-[[3-methoxy-4-(tetrahydropyran-4-ylmethylamino)benzoyl]amino]-4-tetralin-2-yl-thiophene-3-carboxylic acid (Example #31, 100 mg, 0.19 mmol) in DCM (3.0 ml) at 0° C. was added a solution of boron tribromide in DCM (CAS: 10294-33-4, 1.0 M, 0.58 ml, 0.58 mmol). The reaction mixture was stirred at 0° C. for 15 minutes, allowed to warm to RT and stirred at RT for 20 hours. The reaction was quenched by the addition of MeOH (5.0 ml) and water (5.0 ml) at 0° C. and the reaction was allowed to warm to RT. The reaction was partitioned between DCM and a 1N aqueous HCl solution. The two phases were separated and the aqueous phase was extracted with DCM/MeOH (9:1) (×3). The combined organic phases were passed through a phase separator and the solvent was removed under reduced pressure. Purification by RP-HPLC (Table 2, Method B) afforded 2-[[3-hydroxy-4-(tetrahydropyran-4-ylmethylamino)benzoyl]amino]-4-tetralin-2-yl-thiophene-3-carboxylic acid as a yellow solid (30 mg, yield 31%). $^{1}$H NMR (DMSO-$d_6$, 400 MHz): δ=12.77 (br s, 1H), 9.49 (s, 1H), 7.38 (d, J=1.4 Hz, 1H), 7.33 (d, J=8.5 Hz, 1H), 7.16-7.13 (m, 4H), 6.72 (s, 1H), 6.67 (d, J=8.5 Hz, 1H), 4.55-4.46 (m, 1H), 3.73-3.63 (m, 2H), 3.57-3.50 (m, 4H), 3.21-3.09 (m, 2H), 2.93-2.75 (m, 3H), 2.34-2.06 (m, 3H), 1.87-1.77 (m, 1H), 1.67-1.54 (m, 3H), one exchangeable proton not observed. LC/MS (Table 1, Method C) $R_f$=4.97 min; MS m/z: 507 [M+H]$^+$.

Example #39. 2-[[4-(4-Methoxybutylamino)benzoyl]amino]-4-tetralin-2-yl-thiophene-3-carboxylic acid (Compound #135)

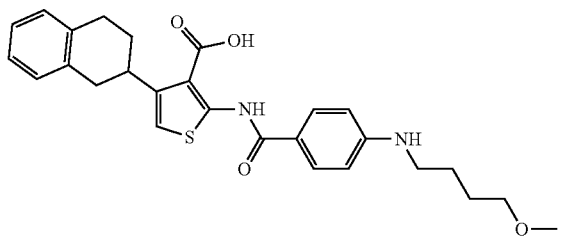 [SMILES: COCCCCNc1ccc(C(=O)Nc2scc(C3CCc4ccccc4C3)c2C(=O)O)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 4-methoxybutan-1-amine (CAS: 34039-36-6) as starting materials (off-white solid, yield 30%). $^1$H NMR (DMSO-d$_6$, 400 MHz): δ=13.45 (br s, 1H), 12.40 (s, 1H), 7.72 (d, J=8.6 Hz, 2H), 7.18-7.11 (m, 4H), 6.77-6.71 (m, 3H), 6.69-6.62 (m, 1H), 3.63 (dd, J=9.9, 9.9 Hz, 1H), 3.42-3.39 (m, 2H, partially obscured by the water peak), 3.29 (s, 3H), 3.21-3.07 (m, 3H), 2.95-2.76 (m, 3H), 2.17 (d, J=11.8 Hz, 1H), 1.87-1.76 (m, 1H), 1.69-1.61 (m, 4H). LC/MS (Table 1, Method C) $R_f$=5.93 min; MS m/z: 479 [M+H]$^+$.

Example #40. 2-[[4-[(4-Hydroxytetrahydropyran-4-yl)methylamino]benzoyl]amino]-4-tetralin-2-yl-thiophene-3-carboxylic acid (Compound #136)

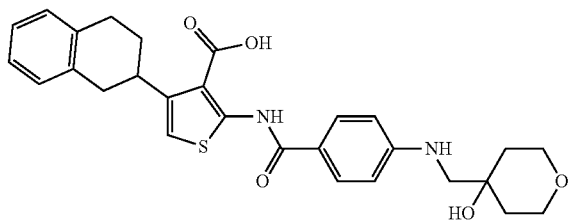 [SMILES: O=C(Nc1scc(C2CCc3ccccc3C2)c1C(=O)O)c1ccc(NCC2(O)CCOCC2)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 4-(aminomethyl)oxan-4-ol (CAS: 783303-73-1) as starting materials (white solid, yield 29%). $^1$H NMR (DMSO-d$_6$, 400 MHz): δ=13.47 (br s, 1H), 12.39 (s, 1H), 7.70 (d, J=8.4 Hz, 2H), 7.18-7.12 (m, 4H), 6.87 (d, J=8.8 Hz, 2H), 6.76 (s, 1H), 6.51-6.45 (m, 1H), 4.63 (s, 1H), 3.72-3.62 (m, 5H), 3.20-3.08 (m, 3H), 2.95-2.72 (m, 3H), 2.18 (d, J=12.1 Hz, 1H), 1.87-1.76 (m, 1H), 1.72-1.62 (m, 2H), 1.54 (d, J=13.6 Hz, 2H). LC/MS (Table 1, Method C) $R_f$=5.26 min; MS m/z: 507 [M+H]$^+$.

Example #41. 2-[[3,5-Dimethoxy-4-(tetrahydropyran-4-ylmethylamino)benzoyl]amino]-4-tetralin-2-yl-thiophene-3-carboxylic acid (Compound #137)

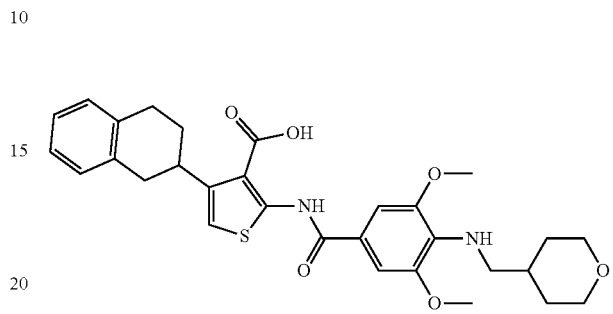

The title compound was synthesized according to the procedure described in Example #31 using ethyl 2-amino-4-(1,2,3,4-tetrahydronaphthalen-2-yl)thiophene-3-carboxylate (Preparation #1), 4-bromo-3,5-dimethoxybenzoic acid (CAS: 56518-42-4) and tetrahydropyran-4-ylmethanamine (CAS: 130290-79-8) as starting materials (white solid, yield 53%). $^1$H NMR (DMSO-d$_6$, 400 MHz): δ=13.79 (br s, 1H), 12.70 (br s, 1H), 7.34 (s, 2H), 7.31-7.24 (m, 4H), 6.92 (s, 1H), 5.22 (br s, 1H), 4.05 (s, 6H), 4.02-3.96 (m, 2H), 3.81-3.76 (m, 1H), 3.49-3.46 (m, 2H, partially obscured by the water peak), 3.40 (t, J=11.7 Hz, 2H), 3.28-3.22 (m, 1H), 3.07-2.89 (m, 3H), 2.30 (d, J=10.9 Hz, 1H), 2.01-1.81 (m, 2H), 1.72 (d, J=12.9 Hz, 2H), 1.40-1.28 (m, 2H). LC/MS (Table 1, Method D) $R_f$=4.03 min; MS m/z: 551 [M+H]$^+$.

Example #42. 2-[[4-[(1,1-Dioxothian-4-yl)methylamino]benzoyl]amino]-4-tetralin-2-yl-thiophene-3-carboxylic acid (Compound #138)

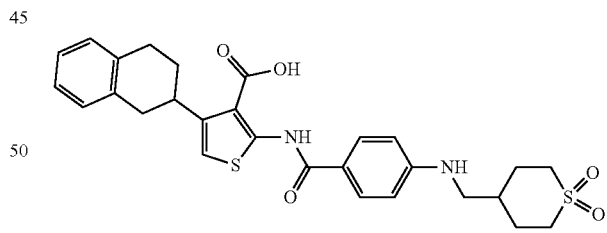

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 4-(aminomethyl)-1lambda6-thiane-1,1-dione (CAS: 476660-77-2) as starting materials (off-white solid, yield 15%). $^1$H NMR (DMSO-d$_6$, 400 MHz): δ=7.70 (d, J=8.8 Hz, 2H), 7.16-7.06 (m, 5H), 6.71 (d, J=8.9 Hz, 2H), 6.66-6.62 (m, 1H), 6.51 (s, 1H), 3.89 (br s, 1H), 3.19-3.02 (m, 8H), 2.91-2.79 (m, 2H), 2.72-2.65 (m, 1H), 2.15-2.07 (m, 3H), 1.95-1.86 (m, 1H), 1.81-1.65 (m, 3H). LC/MS (Table 1, Method D) $R_f$=3.69 min; MS m/z: 539 [M+H]$^+$.

Example #43. 2-[[4-(6-Oxa-3-azabicyclo[3.1.1]heptan-3-yl)benzoyl]amino]-4-tetralin-2-yl-thiophene-3-carboxylic acid (Compound #139)

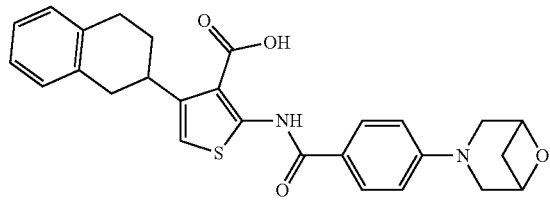 [SMILES: O=C(Nc1scc(C2CCc3ccccc3C2)c1C(=O)O)c1ccc(N2CC3CC(C2)O3)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 6-oxa-3-azabicyclo[3.1.1]heptane (CAS: 112461-31-1) as starting materials (yellow solid, yield 43%). $^1$H NMR (DMSO-$d_6$, 400 MHz): δ=13.53 (br s, 1H), 12.50 (br s, 1H), 7.87 (d, J=8.9 Hz, 2H), 7.15 (dd, J=3.9, 5.5 Hz, 4H), 6.97 (d, J=8.9 Hz, 2H), 6.78 (s, 1H), 4.80 (d, J=6.1 Hz, 2H), 3.72-3.56 (m, 5H), 3.21 (dd, J=6.7, 14.3 Hz, 1H), 3.14-3.09 (m, 1H), 2.95-2.77 (m, 3H), 2.20-2.16 (m, 1H), 1.95 (d, J=8.7 Hz, 1H), 1.88-1.77 (m, 1H). LC/MS (Table 1, Method C) $R_t$=5.62 min; MS m/z: 475 [M+H]$^+$.

Example #44. 2-[[4-[(1S,4S)-2-Oxa-5-azabicyclo[2.2.1]heptan-5-yl]benzoyl]amino]-4-tetralin-2-yl-thiophene-3-carboxylic acid (Compound #140)

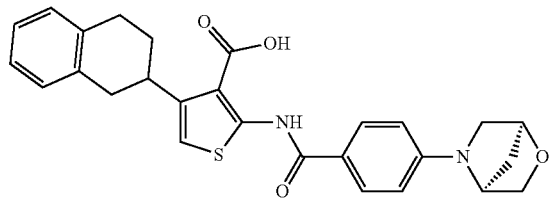 [SMILES: O=C(Nc1scc(C2CCc3ccccc3C2)c1C(=O)O)c1ccc(N2C[C@@H]3C[C@H]2CO3)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and (1S,4S)-2-oxa-5-azabicyclo[2.2.1]heptane hydrochloride (CAS: 31560-06-2) as starting materials (off-white solid, yield 64%). $^1$H NMR (DMSO-$d_6$, 400 MHz): δ=13.61 (br s, 1H), 12.79 (br s, 1H), 7.80 (d, J=8.7 Hz, 2H), 7.18-7.11 (m, 4H), 6.83 (d, J=8.9 Hz, 2H), 6.74 (s, 1H), 4.76 (d, J=22.5 Hz, 2H), 3.84 (d, J=7.1 Hz, 1H), 3.74-3.67 (m, 2H), 3.58 (d, J=9.7 Hz, 1H), 3.19-3.08 (m, 2H), 2.95-2.75 (m, 3H), 2.18 (d, J=11.6 Hz, 1H), 1.99 (dd, J=9.7, 24.3 Hz, 2H), 1.88-1.80 (m, 1H). LC/MS (Table 1, Method C) $R_t$=5.67 min; MS m/z: 475 [M+H]$^+$.

Example #45. 2-[[4-[(1R,4R)-2-Oxa-5-azabicyclo[2.2.1]heptan-5-yl]benzoyl]amino]-4-tetralin-2-yl-thiophene-3-carboxylic acid (Compound #141)

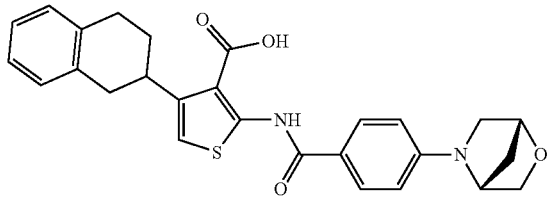 [SMILES: O=C(Nc1scc(C2CCc3ccccc3C2)c1C(=O)O)c1ccc(N2C[C@H]3C[C@@H]2CO3)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and (1R,4R)-2-oxa-5-azabicyclo[2.2.1]heptane hydrochloride (CAS: δ01515-79-1) as starting materials (off-white solid, yield 61%). $^1$H NMR (DMSO-$d_6$, 400 MHz): δ=13.12 (br s, 1H), 7.77 (d, J=8.7 Hz, 2H), 7.13-7.08 (m, 4H), 6.78 (d, J=8.7 Hz, 2H), 6.67 (s, 1H), 4.72 (d, J=21.1 Hz, 2H), 3.79 (d, J=7.3 Hz, 1H), 3.74-3.66 (m, 2H), 3.53 (d, J=9.8 Hz, 1H), 3.14-3.05 (m, 2H), 2.89-2.71 (m, 3H), 2.14 (d, J=11.9 Hz, 1H), 1.93 (dd, J=9.6, 24.5 Hz, 2H), 1.83-1.72 (m, 1H), one exchangeable proton not observed. LC/MS (Table 1, Method C) $R_t$=5.67 min; MS m/z: 475 [M+H]$^+$.

Example #46. 2-[[4-(8-Oxa-3-azabicyclo[3.2.1]octan-3-yl)benzoyl]amino]-4-tetralin-2-yl-thiophene-3-carboxylic acid (Compound #142)

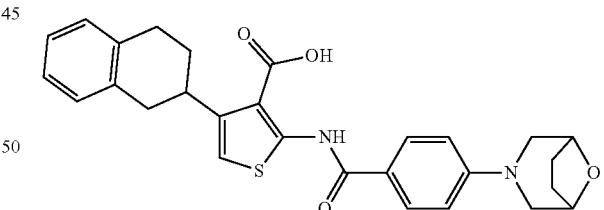

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 8-oxa-3-azabicyclo[3.2.1]octane hydrochloride (CAS: 54745-74-3) as starting materials (off-white solid, yield 25%). $^1$H NMR (DMSO-$d_6$, 400 MHz): δ=13.12 (br s, 1H), 7.83 (d, J=8.9 Hz, 2H), 7.17-7.11 (m, 4H), 7.04 (d, J=8.7 Hz, 2H), 6.73 (s, 1H), 4.50 (s, 2H), 3.76-3.71 (m, 1H), 3.62 (d, J=11.4 Hz, 2H), 3.17-3.09 (m, 1H), 2.99 (d, J=9.9 Hz, 2H), 2.95-2.88 (m, 2H), 2.84-2.75 (m, 1H), 2.20-2.16 (m, 1H), 1.94-1.78 (m, 5H), one exchangeable proton not observed. LC/MS (Table 1, Method D) $R_t$=3.85 min; MS m/z: 489 [M+H]$^+$.

Example #47. 2-[[4-[(2S)-2-Methylmorpholin-4-yl]benzoyl]amino]-4-tetralin-2-yl-thiophene-3-carboxylic acid (Compound #143)

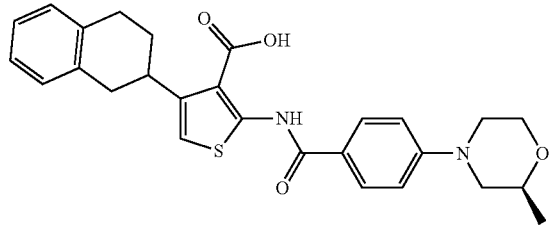

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and (2S)-2-methylmorpholine (CAS: 74572-13-7) as starting materials (white solid, yield 38%). $^1$H NMR (DMSO-$d_6$, 400 MHz): δ=13.55 (br s, 1H), 12.49 (br s, 1H), 7.83 (d, J=8.8 Hz, 2H), 7.20-7.12 (m, 6H), 6.80 (s, 1H), 3.99 (d, J=9.7 Hz, 1H), 3.88 (d, J=12.4 Hz, 1H), 3.78 (d, J=12.1 Hz, 1H), 3.72-3.62 (m, 3H), 3.15-3.08 (m, 1H), 2.95-2.77 (m, 4H), 2.56-2.52 (m, 1H, partially obscured by the DMSO peak), 2.17 (d, J=11.2 Hz, 1H), 1.88-1.77 (m, 1H), 1.23 (d, J=6.2 Hz, 3H). LC/MS (Table 1, Method C) $R_t$=5.96 min; MS m/z: 477 [M+H]$^+$.

Example #48. 2-[[4-(3-Oxa-8-azabicyclo[3.2.1]octan-8-yl)benzoyl]amino]-4-tetralin-2-yl-thiophene-3-carboxylic acid (Compound #144)

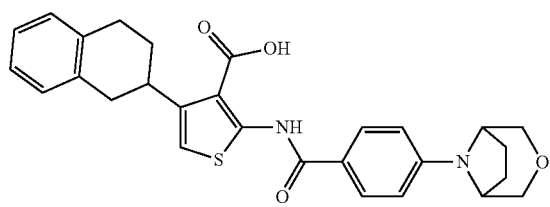 [SMILES: O=C(Nc1scc(C2CCc3ccccc3C2)c1C(=O)O)c1ccc(N2C3CCC2COC3)cc1]

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 3-oxa-8-azabicyclo[3.2.1]octane hydrochloride (CAS: 904316-92-3) as starting materials (off-white solid, yield 14%). $^1$H NMR (DMSO-$d_6$, 400 MHz): δ=13.50 (br s, 1H), 7.82 (d, J=9.0 Hz, 2H), 7.17-7.10 (m, 5H), 7.05 (d, J=8.8 Hz, 2H), 6.68 (s, 1H), 4.39 (s, 2H), 3.82-3.70 (m, 3H), 3.52 (d, J=10.7 Hz, 2H), 3.14 (dd, J=3.5, 16.5 Hz, 1H), 2.93-2.72 (m, 3H), 2.19-2.15 (m, 1H), 2.07-1.97 (m, 4H), 1.84-1.76 (m, 1H). LC/MS (Table 1, Method C) $R_t$=5.92 min; MS m/z: 489 [M+H]$^+$.

Example #49. 2-[[4-[(3R)-3-Methylmorpholin-4-yl]benzoyl]amino]-4-tetralin-2-yl-thiophene-3-carboxylic acid (Compound #145)

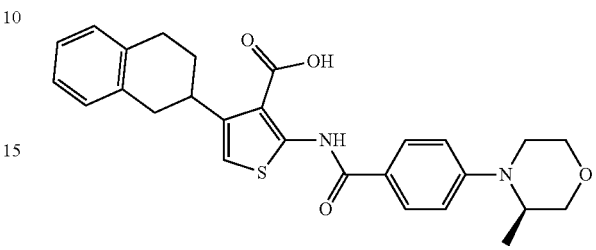

The title compound was synthesized according to the procedure described in Example #9 using ethyl 2-(4-bromobenzamido)-4-(1,2,3,4-tetrahydronaphthalen-2-yl)thiophene-3-carboxylate (Preparation #4) and (3R)-3-methylmorpholine (CAS: 74572-04-6) as starting materials (off-white solid, yield 37%). $^1$H NMR (DMSO-$d_6$, 400 MHz): δ=13.54 (br s, 1H), 12.69 (br s, 1H), 7.84 (d, J=8.7 Hz, 2H), 7.17-7.12 (m, 4H), 7.10 (d, J=8.7 Hz, 2H), 6.77 (s, 1H), 4.15-4.11 (m, 1H), 4.01 (dd, J=2.7, 10.9 Hz, 1H), 3.82-3.51 (m, 5H), 3.19-3.09 (m, 2H), 2.94-2.72 (m, 3H), 2.21-2.15 (m, 1H), 1.88-1.77 (m, 1H), 1.15 (d, J=6.3 Hz, 3H). LC/MS (Table 1, Method C) $R_t$=5.92 min; MS m/z: 477 [M+H]$^+$.

Example #50. 2-[[4-[(3S)-3-Methylmorpholin-4-yl]benzoyl]amino]-4-tetralin-2-yl-thiophene-3-carboxylic acid (Compound #146)

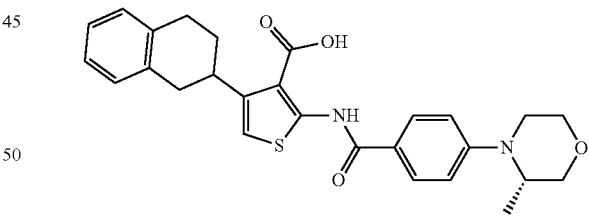

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and (3S)-3-methylmorpholine (CAS: 350595-57-2) as starting materials (off-white solid, yield 37%). $^1$H NMR (DMSO-$d_6$, 400 MHz): δ=12.83 (br s, 1H), 7.72 (d, J=8.8 Hz, 2H), 7.05-6.99 (m, 5H), 6.96 (d, J=9.0 Hz, 2H), 6.62 (s, 1H), 4.04-3.98 (m, 1H), 3.89 (dd, J=3.2, 11.1 Hz, 1H), 3.70-3.56 (m, 3H), 3.50-3.36 (m, 2H), 3.06-2.99 (m, 2H), 2.82-2.63 (m, 3H), 2.06 (d, J=12.0 Hz, 1H), 1.75-1.64 (m, 1H), 1.02 (d, J=6.4 Hz, 3H). LC/MS (Table 1, Method C) $R_t$=5.92 min; MS m/z: 477 [M+H]$^+$.

Example #51. 2-[[4-[(2R)-2-Methylmorpholin-4-yl]benzoyl]amino]-4-tetralin-2-yl-thiophene-3-carboxylic acid (Compound #147)

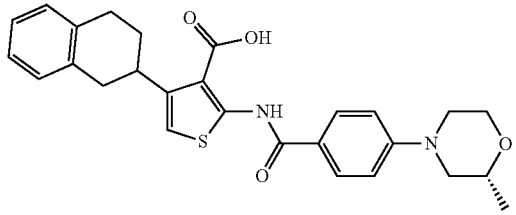

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and (2R)-2-methylmorpholine (CAS: 790184-33-7) as starting materials (off-white solid, yield 50%). $^1$H NMR (DMSO-$d_6$, 400 MHz): δ=13.53 (br s, 1H), 12.48 (br s, 1H), 7.83 (d, J=8.9 Hz, 2H), 7.19-7.13 (m, 6H), 6.80 (s, 1H), 3.99 (dd, J=2.4, 11.6 Hz, 1H), 3.89 (d, J=12.2 Hz, 1H), 3.78 (d, J=13.3 Hz, 1H), 3.72-3.62 (m, 3H), 3.12 (dd, J=2.8, 16.4 Hz, 1H), 2.95-2.80 (m, 4H), 2.21-2.16 (m, 1H), 1.89-1.78 (m, 1H), 1.23 (d, J=6.1 Hz, 3H), one proton obscured by the DMSO peak. LC/MS (Table 1, Method D) $R_t$=3.87 min; MS m/z: 477 [M+H]$^+$.

Example #52. 2-[[4-[(2R,6S)-2,6-Dimethylmorpholin-4-yl]benzoyl]amino]-4-tetralin-2-yl-thiophene-3-carboxylic acid (Compound #148)

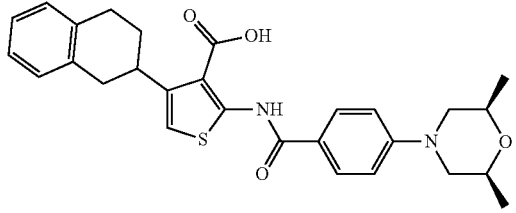

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and cis-(2R,6S)-2,6-dimethylmorpholine (CAS: δ485-55-8) as starting materials (yellow solid, yield 19%). $^1$H NMR (DMSO-$d_6$, 400 MHz): δ=13.56 (br s, 1H), 12.50 (br s, 1H), 7.83 (d, J=9.0 Hz, 2H), 7.19-7.14 (m, 6H), 6.80 (s, 1H), 3.88 (d, J=11.8 Hz, 2H), 3.77-3.62 (m, 3H), 3.12 (dd, J=3.1, 16.1 Hz, 1H), 2.95-2.77 (m, 3H), 2.47 (dd, J=10.9, 12.2 Hz, 2H), 2.21-2.15 (m, 1H), 1.89-1.77 (m, 1H), 1.23 (d, J=6.2 Hz, 6H). LC/MS (Table 1, Method C) $R_t$=6.22 min; MS m/z: 491 [M+H]$^+$.

Example #53. 2-[[4-[(3S,5R)-3,5-Dimethylmorpholin-4-yl]benzoyl]amino]-4-tetralin-2-yl-thiophene-3-carboxylic acid (Compound #149)

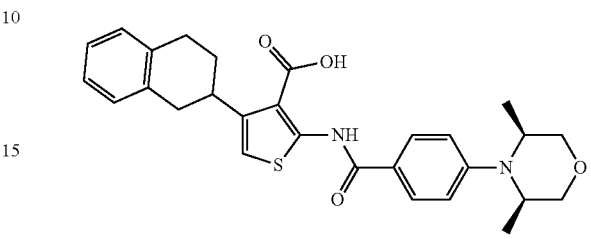

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and cis-(3R,5S)-3,5-dimethylmorpholine hydrochloride (CAS: 154596-17-5) as starting materials (yellow solid, yield 58%). $^1$H NMR (DMSO-$d_6$, 400 MHz): δ=13.56 (br s, 1H), 12.49 (br s, 1H), 7.83 (d, J=9.0 Hz, 2H), 7.19-7.12 (m, 6H), 6.80 (s, 1H), 3.89 (d, J=11.6 Hz, 2H), 3.78-3.61 (m, 3H), 3.15-3.08 (m, 1H), 2.94-2.77 (m, 3H), 2.47 (dd, J=10.8, 12.2 Hz, 2H), 2.21-2.14 (m, 1H), 1.88-1.77 (m, 1H), 1.23 (d, J=6.2 Hz, 6H). LC/MS (Table 1, Method C) $R_t$=6.18 min; MS m/z: 491 [M+H]$^+$.

Example #54. 2-[[4-(3-Oxa-6-azabicyclo[3.1.1]heptan-6-yl)benzoyl]amino]-4-tetralin-2-yl-thiophene-3-carboxylic acid (Compound #150)

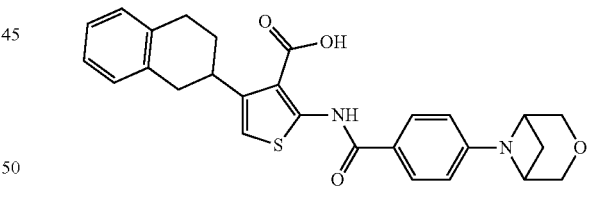

The title compound was synthesized according to the procedure described in Example #9 using ethyl 2-(4-bromobenzamido)-4-(1,2,3,4-tetrahydronaphthalen-2-yl)thiophene-3-carboxylate (Preparation #2) and 3-oxa-6-azabicyclo[3.1.1]heptane hydrochloride (CAS: 1860028-23-4) as starting materials (white solid, yield 32%). $^1$H NMR (DMSO-$d_6$, 400 MHz): δ=13.03 (br s, 1H), 7.71 (d, J=8.7 Hz, 2H), 7.10-6.99 (m, 5H), 6.67 (d, J=8.7 Hz, 2H), 6.60 (s, 1H), 4.30 (d, J=6.1 Hz, 2H), 4.07 (d, J=10.8 Hz, 2H), 3.68-3.57 (m, 3H), 3.01 (dd, J=3.4, 16.2 Hz, 1H), 2.82-2.60 (m, 4H), 2.09-2.02 (m, 1H), 1.79 (d, J=8.1 Hz, 1H), 1.75-1.63 (m, 1H). LC/MS (Table 1, Method C) $R_t$=5.65 min; MS m/z: 475 [M+H]$^+$.

Example #55. 2-[(4-Fluorobenzoyl)amino]-4-tetralin-2-yl-thiophene-3-carboxylic acid (Compound #151)

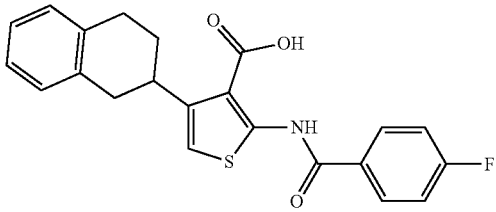 [SMILES: O=C(Nc1scc(C2CCc3ccccc3C2)c1C(=O)O)c1ccc(F)cc1]

The title compound was then synthesized according to the procedure described in Example #4 using ethyl 2-amino-4-(1,2,3,4-tetrahydronaphthalen-2-yl)thiophene-3-carboxylate (Preparation #1) and 4-fluorobenzoyl chloride (CAS: 403-43-0) as starting materials (off-white solid, yield 38%). $^1$H NMR (DMSO-d$_6$, 400 MHz): δ=13.64 (br s, 1H), 12.57 (s, 1H), 8.05 (dd, J=5.3, 8.6 Hz, 2H), 7.53 (t, J=8.7 Hz, 2H), 7.18-7.12 (m, 4H), 6.88 (s, 1H), 3.70-3.64 (m, 1H), 3.16-3.08 (m, 1H), 2.95-2.78 (m, 3H), 2.17-2.20 (m, 1H), 1.90-1.78 (m, 1H). LC/MS (Table 1, Method C) R$_t$=6.02 min, MS m/z: 396 [M+H]$^+$.

Example #56. 2-[[4-(Difluoromethoxy)benzoyl]amino]-4-tetralin-2-yl-thiophene-3-carboxylic acid (Compound #152)

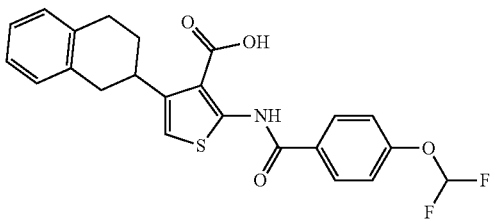 [SMILES: O=C(Nc1scc(C2CCc3ccccc3C2)c1C(=O)O)c1ccc(OC(F)F)cc1]

The title compound was then synthesized according to the procedure described in Example #4 using ethyl 2-amino-4-(1,2,3,4-tetrahydronaphthalen-2-yl)thiophene-3-carboxylate (Preparation #1) and 4-(difluoromethoxy)benzoyl chloride (CAS: 57320-63-5) as starting materials (pale yellow solid, yield 47%). $^1$H NMR (DMSO-d$_6$, 400 MHz): δ=13.65 (br s, 1H), 12.60 (br s, 1H), 8.07-8.02 (m, 2H), 7.48 (d, J=8.0 Hz, 2H), 7.48 (t, J=73.2 Hz, 1H), 7.18-7.12 (m, 4H), 6.88 (s, 1H), 3.67 (dd, J=10.4, 10.4 Hz, 1H), 3.11 (dd, J=3.1, 16.0 Hz, 1H), 2.92-2.78 (m, 3H), 2.20-2.14 (m, 1H), 1.89-1.78 (m, 1H). LC/MS (Table 1, Method D) R$_t$=3.99 min, MS m/z: 444 [M+H]$^+$.

Example #57. 4-Tetralin-2-yl-2-[[4-(trifluoromethoxy)benzoyl]amino]thiophene-3-carboxylic acid (Compound #153)

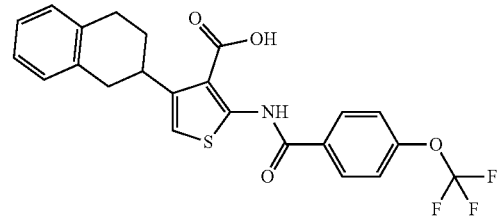 [SMILES: O=C(Nc1scc(C2CCc3ccccc3C2)c1C(=O)O)c1ccc(OC(F)(F)F)cc1]

The title compound was then synthesized according to the procedure described in Example #4 using ethyl 2-amino-4-(1,2,3,4-tetrahydronaphthalen-2-yl)thiophene-3-carboxylate (Preparation #1) and 4-(trifluoromethoxy)benzoyl chloride (CAS: 36823-88-8) as starting materials (off-white solid, yield 9%). $^1$H NMR (DMSO-d$_6$, 400 MHz): δ=13.14 (br s, 1H), 8.11 (d, J=8.5 Hz, 2H), 7.68 (d, J=8.1 Hz, 2H), 7.16-7.14 (m, 4H), 6.87-6.84 (m, 1H), 3.74-3.68 (m, 1H), 3.13 (dd, J=3.0, 16.2 Hz, 1H), 2.92-2.77 (m, 3H), 2.18 (d, J=12.1 Hz, 1H), 1.89-1.78 (m, 1H), one exchangeable proton not observed. LC/MS (Table 1, Method C) R$_t$=6.28 min, MS m/z: 460 [M−H]$^-$.

Example #58. 2-[(4-Methoxybenzoyl)amino]-4-tetralin-2-yl-thiophene-3-carboxylic acid (Compound #154)

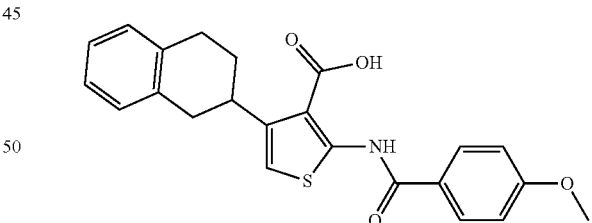

The title compound was then synthesized according to the procedure described in Example #4 using ethyl 2-amino-4-(1,2,3,4-tetrahydronaphthalen-2-yl)thiophene-3-carboxylate (Preparation #1) and 4-methoxybenzoyl chloride (CAS: 100-07-2) as starting materials (white solid, yield 65%). $^1$H NMR (DMSO-d$_6$, 400 MHz): δ=13.61 (br s, 1H), 12.60 (br s, 1H), 7.95 (d, J=8.6 Hz, 2H), 7.22 (d, J=8.6 Hz, 2H), 7.18-7.12 (m, 4H), 6.83 (s, 1H), 3.92 (s, 3H), 3.69-3.63 (m, 1H), 3.13 (d, J=15.4 Hz, 1H), 2.92-2.78 (m, 3H), 2.22-2.16 (m, 1H), 1.88-1.78 (m, 1H). LC/MS (Table 1, Method D) R$_t$=3.78 min, MS m/z: 408 [M+H]$^+$.

Example #59. 2-[(3,4-Dimethoxybenzoyl)amino]-4-tetralin-2-yl-thiophene-3-carboxylic acid (Compound #155)

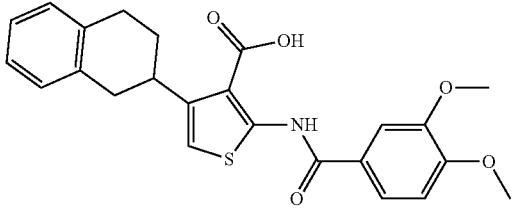 [SMILES: COc1ccc(C(=O)Nc2scc(C3CCc4ccccc4C3)c2C(=O)O)cc1OC]

The title compound was then synthesized according to the procedure described in Example #4 using ethyl 2-amino-4-(1,2,3,4-tetrahydronaphthalen-2-yl)thiophene-3-carboxylate (Preparation #1) and 3,4-dimethoxybenzoyl chloride (CAS: 3535-37-3) as starting materials (white solid, yield 59%). $^1$H NMR (DMSO-$d_6$, 400 MHz): δ=13.65 (br s, 1H), 12.60 (br s, 1H), 7.58-7.53 (m, 2H), 7.26 (d, J=9.9 Hz, 1H), 7.15 (br s, 4H), 6.84 (s, 1H), 3.94-3.92 (m, 6H), 3.70-3.63 (m, 1H), 3.12 (dd, J=3.0, 15.4 Hz, 1H), 2.91-2.77 (m, 3H), 2.20-2.16 (m, 1H), 1.89-1.78 (m, 1H). LC/MS (Table 1, Method C) $R_t$=5.72 min, MS m/z: 438 [M+H]$^+$.

Example #60. 2-Benzamido-4-tetralin-2-yl-thiophene-3-carboxylic acid, enantiomer 1 (Compound #156)

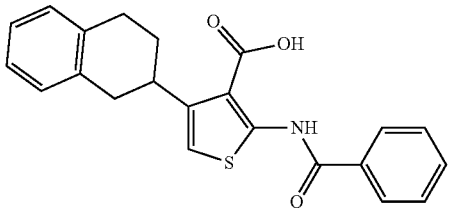 [SMILES: O=C(Nc1scc(C2CCc3ccccc3C2)c1C(=O)O)c1ccccc1]

Ethyl 2-benzamido-4-(1,2,3,4-tetrahydronaphthalen-2-yl)thiophene-3-carboxylate (prepared as described in Example #4, 161 mg, 0.40 mmol) was purified by chiral SFC (Table 3, Method A) to give ethyl 2-benzamido-4-(1,2,3,4-tetrahydronaphthalen-2-yl)thiophene-3-carboxylate, enantiomer 1 as a yellow solid (58 mg, yield 36%) and ethyl 2-benzamido-4-(1,2,3,4-tetrahydronaphthalen-2-yl)thiophene-3-carboxylate, enantiomer 2 as a yellow solid (70 mg, yield 44%). Chiral SFC (Table 1, Method F) $R_t$=2.37 min; e.e. 98.5%, first eluting enantiomer and $R_t$=3.35 min; e.e. 94.7%, second eluting enantiomer. To a stirred solution of ethyl 2-benzamido-4-(1,2,3,4-tetrahydronaphthalen-2-yl)thiophene-3-carboxylate (Enantiomer 1, 58 mg, 0.14 mmol) in THF (1.2 ml) and MeOH (1.2 ml) was added LiOH aq. (1 M, 30 mg, 0.71 mmol). The reaction mixture was stirred at 50° C. for 16 hours. The mixture was cooled to RT and then partitioned between DCM and 1N aqueous HCl solution. The two phases were separated and the aqueous phase was extracted with DCM (×2). The combined organic phases were passed through a phase separator and the solvent was removed under reduced pressure. Purification by RP-HPLC (Table 2, Method A) afforded 2-benzamido-4-tetralin-2-yl-thiophene-3-carboxylic acid, enantiomer 1 as a white solid (31 mg, yield 57%). $^1$H NMR (DMSO-$d_6$, 400 MHz): δ=13.65 (br s, 1H), 12.59 (br s, 1H), 7.99 (d, J=7.5 Hz, 2H), 7.79-7.66 (m, 3H), 7.18-7.12 (m, 4H), 6.88 (s, 1H), 3.71-3.62 (m, 1H), 3.12 (dd, J=3.4, 16.2 Hz, 1H), 2.96-2.78 (m, 3H), 2.22-2.14 (m, 1H), 1.90-1.78 (m, 1H). LC/MS (Table 1, Method C) $R_t$=5.91 min; MS m/z: 378 [M+H]$^+$. Chiral SFC (Table 1, Method G) $R_t$=3.6 min; e.e. 100%, first eluting enantiomer.

Example #61. 2-Benzamido-4-tetralin-2-yl-thiophene-3-carboxylic acid, enantiomer 2 (Compound #157)

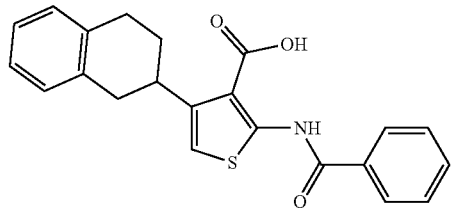 [SMILES: O=C(Nc1scc(C2CCc3ccccc3C2)c1C(=O)O)c1ccccc1]

The title compound was then synthesized according to the procedure described in Example #60 using ethyl 2-benzamido-4-(1,2,3,4-tetrahydronaphthalen-2-yl)thiophene-3-carboxylate, enantiomer 2 (prepared as described in Example #60) as a starting material (white solid, yield 38%). $^1$H NMR (DMSO-$d_6$, 400 MHz): δ=13.65 (br s, 1H), 12.59 (br s, 1H), 7.99 (d, J=7.5 Hz, 2H), 7.79-7.66 (m, 3H), 7.18-7.12 (m, 4H), 6.88 (s, 1H), 3.71-3.62 (m, 1H), 3.12 (dd, J=3.4, 16.2 Hz, 1H), 2.96-2.78 (m, 3H), 2.22-2.14 (m, 1H), 1.90-1.78 (m, 1H). LC/MS (Table 1, Method C) $R_t$=5.86 min; MS m/z: 378 [M+H]$^+$. Chiral SFC (Table 1, Method G) $R_t$=3.92 min; e.e. 100%, second eluting enantiomer.

Example #62. 4-Tetralin-2-yl-2-[[4-(trifluoromethyl)benzoyl]amino]thiophene-3-carboxylic acid (Compound #158)

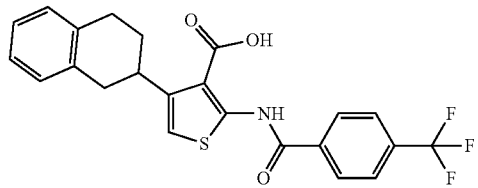 [SMILES: O=C(Nc1scc(C2CCc3ccccc3C2)c1C(=O)O)c1ccc(C(F)(F)F)cc1]

The title compound was then synthesized according to the procedure described in Example #4 using ethyl 2-amino-4-(1,2,3,4-tetrahydronaphthalen-2-yl)thiophene-3-carboxylate (Preparation #1) and 4-(trifluoromethyl)benzoyl chloride (CAS: 329-15-7) as starting materials (off-white solid, yield 22%). $^1$H NMR (DMSO-$d_6$, 400 MHz): δ=13.70 (br s, 1H), 12.81 (br s, 1H), 8.15 (d, J=8.1 Hz, 2H), 8.03 (d, J=8.2 Hz, 2H), 7.13-7.09 (m, 4H), 6.87 (s, 1H), 3.69-3.60 (m, 1H), 3.13-3.06 (m, 1H), 2.91-2.75 (m, 3H), 2.16-2.09 (m, 1H), 1.86-1.74 (m, 1H). LC/MS (Table 1, Method D) $R_t$=4.20 min, MS m/z: 446 [M+H]$^+$.

Example #63. 2-[(2-Methoxybenzoyl)amino]-4-tetralin-2-yl-thiophene-3-carboxylic acid (Compound #159)

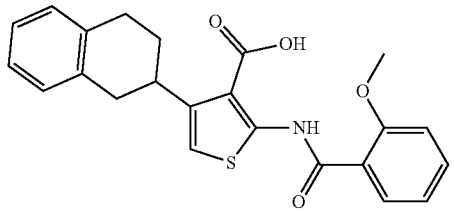 [SMILES: COc1ccccc1C(=O)Nc1scc(C2CCc3ccccc3C2)c1C(=O)O]

The title compound was then synthesized according to the procedure described in Example #4 using ethyl 2-amino-4-(1,2,3,4-tetrahydronaphthalen-2-yl)thiophene-3-carboxylate (Preparation #1) and 2-methoxybenzoyl chloride (CAS: 21615-34-9) as starting materials (off-white solid, yield 40%). $^1$H NMR (DMSO-$d_6$, 400 MHz): δ=13.43 (br s, 1H), 13.20 (br s, 1H), 8.13 (dd, J=1.8, 7.8 Hz, 1H), 7.68-7.63 (m, 1H), 7.32-7.29 (m, 1H), 7.21-7.09 (m, 5H), 6.79 (s, 1H), 4.10 (s, 3H), 3.71-3.65 (m, 1H), 3.08 (dd, J=3.0, 16.2 Hz, 1H), 2.91-2.85 (m, 2H), 2.76 (dd, J=11.3, 16.0 Hz, 1H), 2.12 (dd, J=2.0, 11.8 Hz, 1H), 1.85-1.74 (m, 1H). LC/MS (Table 1, Method C) $R_t$=5.89 min, MS m/z: 408 [M+H]$^+$.

Example #64. 2-[(2-Hydroxybenzoyl)amino]-4-tetralin-2-yl-thiophene-3-carboxylic acid (Compound #160)

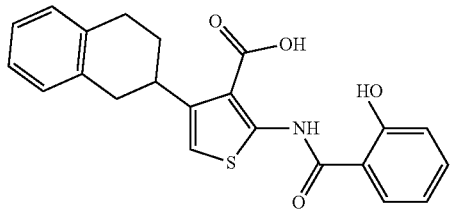 [SMILES: O=C(Nc1scc(C2CCc3ccccc3C2)c1C(=O)O)c1ccccc1O]

The title compound was synthesized according to the procedure described in Example #38 using 2-[(2-methoxybenzoyl)amino]-4-tetralin-2-yl-thiophene-3-carboxylic acid (Example #63) as a starting material (off-white solid, yield 55%). $^1$H NMR (DMSO-$d_6$, 400 MHz): δ=13.20 (br s, 2H), 11.66 (br s, 1H), 8.01 (dd, J=1.8, 7.9 Hz, 1H), 7.49-7.44 (m, 1H), 7.13-6.98 (m, 6H), 6.78 (s, 1H), 3.68-3.61 (m, 1H), 3.11-3.05 (m, 1H), 2.91-2.73 (m, 3H), 2.15-2.10 (m, 1H), 1.85-1.73 (m, 1H). LC/MS (Table 1, Method C) $R_t$=5.79 min, MS m/z: 394 [M+H]$^+$.

Example #65. 2-[(4-Chlorobenzoyl)amino]-4-tetralin-2-yl-thiophene-3-carboxylic acid (Compound #161)

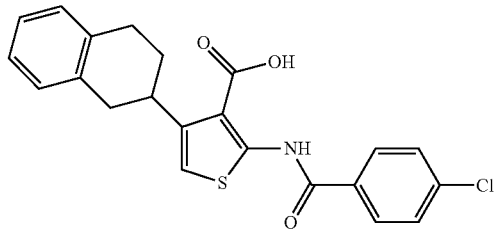 [SMILES: O=C(Nc1scc(C2CCc3ccccc3C2)c1C(=O)O)c1ccc(Cl)cc1]

The title compound was then synthesized according to the procedure described in Example #4 using ethyl 2-amino-4-(1,2,3,4-tetrahydronaphthalen-2-yl)thiophene-3-carboxylate (Preparation #1) and 4-chlorobenzoyl chloride (CAS: 122-01-0) as starting materials (off-white solid, yield 22%). $^1$H NMR (DMSO-$d_6$, 400 MHz): δ=13.64 (br s, 1H), 12.77 (br s, 1H), 7.98-7.93 (m, 2H), 7.75-7.70 (m, 2H), 7.12-7.10 (m, 4H), 6.84 (s, 1H), 3.69-3.60 (m, 1H), 3.11-3.06 (m, 1H), 2.91-2.74 (m, 3H), 2.18-2.09 (m, 1H), 1.85-1.73 (m, 1H). LC/MS (Table 1, Method C) $R_t$=6.24 min, MS m/z: 410 [M−H]$^-$.

Example #66. 2-[(3-Fluoro-4-methoxy-benzoyl)amino]-4-tetralin-2-yl-thiophene-3-carboxylic acid (Compound #162)

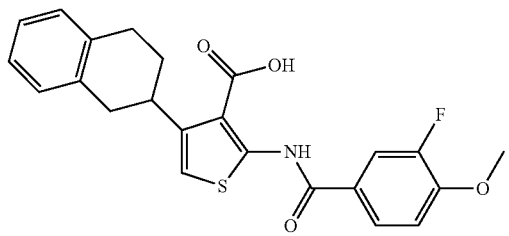 [SMILES: COc1ccc(C(=O)Nc2scc(C3CCc4ccccc4C3)c2C(=O)O)cc1F]

The title compound was then synthesized according to the procedure described in Example #4 using ethyl 2-amino-4-(1,2,3,4-tetrahydronaphthalen-2-yl)thiophene-3-carboxylate (Preparation #1) and 3-fluoro-4-methoxybenzoyl chloride (CAS: 3907-15-1) as starting materials (off-white solid, yield 43%). $^1$H NMR (DMSO-$d_6$, 400 MHz): δ=13.65 (br s, 1H), 12.95 (br s, 1H), 7.77-7.70 (m, 2H), 7.43 (t, J=8.5 Hz, 1H), 7.13-7.09 (m, 4H), 6.78 (s, 1H), 3.96 (s, 3H), 3.70-3.73 (m, 1H), 3.11-3.06 (m, 1H), 2.91-2.72 (m, 3H), 2.16-2.09 (m, 1H), 1.85-1.73 (m, 1H). LC/MS (Table 1, Method C) $R_t$=5.89 min, MS m/z: 426 [M+H]$^+$.

Example #67. 2-[(2-Fluorobenzoyl)amino]-4-tetralin-2-yl-thiophene-3-carboxylic acid (Compound #163)

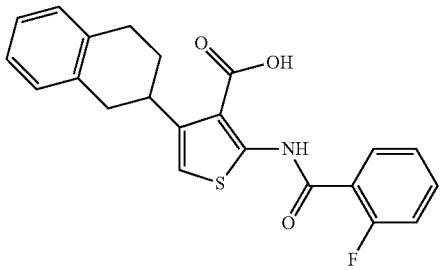 [SMILES: O=C(Nc1scc(C2CCc3ccccc3C2)c1C(=O)O)c1ccccc1F]

The title compound was then synthesized according to the procedure described in Example #4 using ethyl 2-amino-4-(1,2,3,4-tetrahydronaphthalen-2-yl)thiophene-3-carboxylate (Preparation #1) and 2-fluorobenzoyl chloride (CAS: 393-52-2) as starting materials (pale yellow solid, yield 30%). $^1$H NMR (DMSO-d$_6$, 400 MHz): δ=8.09-8.04 (m, 1H), 7.74-7.68 (m, 1H), 7.52-7.43 (m, 2H), 7.17-7.10 (m, 4H), 6.77 (s, 1H), 3.83-3.75 (m, 1H), 3.16-3.10 (m, 1H), 2.94-2.89 (m, 2H), 2.82-2.73 (m, 1H), 2.19-2.11 (m, 1H), 1.88-1.80 (m, 1H), two exchangeable protons not observed. LC/MS (Table 1, Method C) R$_t$=5.93 min, MS m/z: 396 [M+H]$^+$.

Example #68. 2-[(4-Fluoro-3-methoxy-benzoyl)amino]-4-tetralin-2-yl-thiophene-3-carboxylic acid (Compound #164)

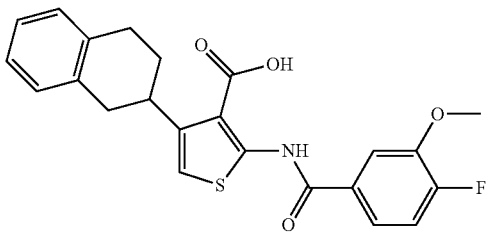 [SMILES: COc1cc(C(=O)Nc2scc(C3CCc4ccccc4C3)c2C(=O)O)ccc1F]

The title compound was then synthesized according to the procedure described in Example #4 using ethyl 2-amino-4-(1,2,3,4-tetrahydronaphthalen-2-yl)thiophene-3-carboxylate (Preparation #1) and 4-fluoro-3-methoxybenzoyl chloride (CAS: 82846-19-3) as starting materials (off-white solid, yield 8%). $^1$H NMR (DMSO-d$_6$, 400 MHz): δ=13.64 (br s, 1H), 12.90 (br s, 1H), 7.76-7.71 (m, 1H), 7.55-7.48 (m, 2H), 7.16-7.10 (m, 4H), 6.85-6.82 (m, 1H), 3.99 (s, 3H), 3.71-3.66 (m, 1H), 3.11 (dd, J=3.0, 16.2 Hz, 1H), 2.91-2.71 (m, 3H), 2.17 (d, J=12.0 Hz, 1H), 1.88-1.77 (m, 1H). LC/MS (Table 1, Method C) R$_t$=5.96 min, MS m/z: 426 [M+H]$^+$.

Example #69. 2-[(4-Methylsulfonylbenzoyl)amino]-4-tetralin-2-yl-thiophene-3-carboxylic acid (Compound #165)

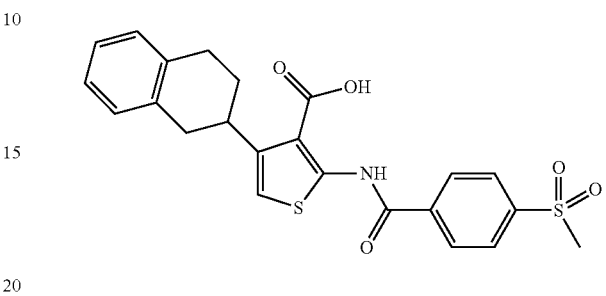

The title compound was then synthesized according to the procedure described in Example #4 using ethyl 2-amino-4-(1,2,3,4-tetrahydronaphthalen-2-yl)thiophene-3-carboxylate (Preparation #1) and 4-(methanesulfonyl)benzoyl chloride (CAS: 40913-92-6) as starting materials (off-white solid, yield 28%). $^1$H NMR (DMSO-d$_6$, 400 MHz): δ=8.17-8.12 (m, 4H), 7.13-7.09 (m, 5H), 6.75 (s, 1H), 3.81-3.74 (m, 1H), 3.26 (s, 3H), 3.15-3.06 (m, 1H), 2.92-2.81 (m, 3H), 2.22-2.16 (m, 1H), 1.90-1.79 (m, 1H), one exchangeable proton not observed. LC/MS (Table 1, Method C) R$_t$=5.39 min, MS m/z: 456 [M+H]$^+$.

Example #70. 2-[(4-Methylbenzoyl)amino]-4-tetralin-2-yl-thiophene-3-carboxylic acid (Compound #166)

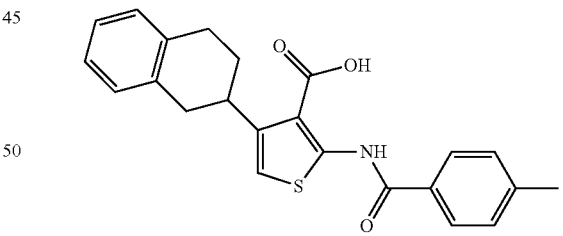

The title compound was then synthesized according to the procedure described in Example #4 using ethyl 2-amino-4-(1,2,3,4-tetrahydronaphthalen-2-yl)thiophene-3-carboxylate (Preparation #1) and 4-methylbenzoyl chloride (CAS: 874-60-2) as starting materials (off-white solid, yield 31%). $^1$H NMR (DMSO-d$_6$, 400 MHz): δ=13.66 (br s, 1H), 12.71 (br s, 1H), 7.89 (d, J=8.3 Hz, 2H), 7.49 (d, J=8.1 Hz, 2H), 7.18-7.11 (m, 4H), 6.85 (s, 1H), 3.71-3.65 (m, 1H), 3.13 (dd, J=2.8, 15.9 Hz, 1H), 2.92-2.77 (m, 3H), 2.47 (s, 3H), 2.20-2.12 (m, 1H), 1.90-1.78 (m, 1H). LC/MS (Table 1, Method C) R$_t$=6.10 min, MS m/z: 392 [M+H]$^+$.

Example #71. 2-[(3-Chlorobenzoyl)amino]-4-tetralin-2-yl-thiophene-3-carboxylic acid (Compound #167)

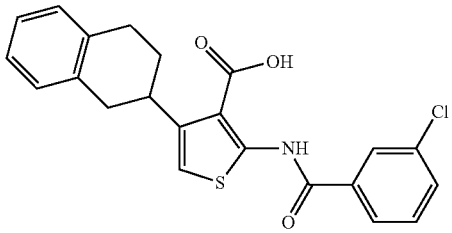 [SMILES: O=C(Nc1scc(C2CCc3ccccc3C2)c1C(=O)O)c1cccc(Cl)c1]

The title compound was then synthesized according to the procedure described in Example #4 using ethyl 2-amino-4-(1,2,3,4-tetrahydronaphthalen-2-yl)thiophene-3-carboxylate (Preparation #1) and 3-chlorobenzoyl chloride (CAS: 618-46-2) as starting materials (pale yellow solid, yield 33%). $^1$H NMR (DMSO-$d_6$, 400 MHz): δ=13.70 (br s, 1H), 12.79 (br s, 1H), 7.98 (s, 1H), 7.94 (d, J=8.0 Hz, 1H), 7.82 (d, J=8.0 Hz, 1H), 7.72 (dd, J=7.9, 7.9 Hz, 1H), 7.16-7.14 (m, 4H), 6.88 (s, 1H), 3.71-3.74 (m, 1H), 3.12 (dd, J=3.2, 16.0 Hz, 1H), 2.92-2.77 (m, 3H), 2.22-2.12 (m, 1H), 1.90-1.78 (m, 1H). LC/MS (Table 1, Method C) $R_t$=6.29 min, MS m/z: 412 [M+H]$^+$.

Example #72. 2-[[4-(2-Oxopyrrolidin-1-yl)benzoyl]amino]-4-tetralin-2-yl-thiophene-3-carboxylic acid (Compound #168)

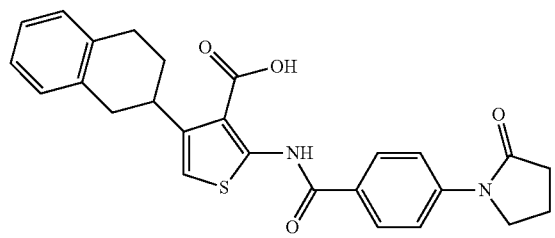 [SMILES: O=C(Nc1scc(C2CCc3ccccc3C2)c1C(=O)O)c1ccc(N2CCCC2=O)cc1]

To a stirred solution of ethyl 2-(4-bromobenzamido)-4-(1,2,3,4-tetrahydronaphthalen-2-yl)thiophene-3-carboxylate (Preparation #2, 150 mg, 0.31 mmol) in dioxane (5.0 ml) was added pyrrolidin-2-one (CAS: 616-45-5, 33 mg, 0.38 mmol), Xantphos (CAS: 161265-03-8, 179 mg, 0.31 mmol), Cs$_2$CO$_3$ (CAS: 534-17-8, 168 mg, 0.52 mmol) and tris(dibenzylideneacetone)dipalladium(0) (CAS: 51364-51-3, 12 mg, 0.013 mmol). The reaction mixture was sealed under nitrogen and heated at 80° C. for 3 hours. The reaction mixture was next cooled to RT and the solvent removed under reduced pressure. Water was added and the mixture was extracted with ethyl acetate (×3). The combined organic phases were concentrated under reduced pressure. Purification by flash chromatography on silica gel (eluting with 0-100% EtOAc in isohexane) afforded ethyl 2-(4-(2-oxopyrrolidin-1-yl)benzamido)-4-(1,2,3,4-tetrahydronaphthalen-2-yl)thiophene-3-carboxylate (80 mg, yield 63%), which was dissolved in a mixture of THF (3 ml), EtOH (3 ml) and water (1 ml). To the reaction was added lithium hydroxide monohydrate (CAS: 1310-66-3, 33 mg, 1.38 mmol) and the reaction was stirred at RT for 20 hours. The solvents were removed under reduced pressure, water was added and the mixture was acidified to pH 3 using 2N aqueous HCl solution. The precipitate formed was filtered, washed with water and dried in vacuo to afford 2-[[4-(2-oxopyrrolidin-1-yl)benzoyl]amino]-4-tetralin-2-yl-thiophene-3-carboxylic acid as an off-white solid (42 mg, yield 55%). $^1$H NMR (DMSO-$d_6$, 400 MHz): δ=13.66 (br s, 1H), 12.72 (br s, 1H), 8.02-7.94 (m, 4H), 7.18-7.12 (m, 4H), 6.84 (s, 1H), 3.96 (t, J=7.0 Hz, 2H), 3.73-3.63 (m, 1H), 3.13 (dd, J=3.0, 16.3 Hz, 1H), 2.95-2.79 (m, 3H), 2.62 (t, J=8.0 Hz, 2H), 2.22-2.10 (m, 3H), 1.90-1.77 (m, 1H). LC/MS (Table 1, Method C) $R_t$=5.55 min; MS m/z: 461 [M+H]$^+$.

Example #73. 2-[(3-Fluorobenzoyl)amino]-4-tetralin-2-yl-thiophene-3-carboxylic acid (Compound #169)

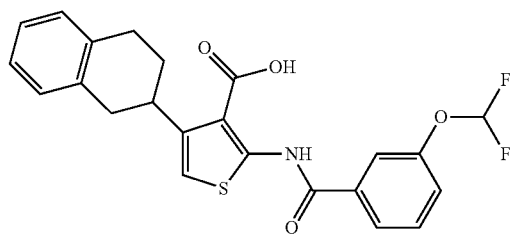 [SMILES: O=C(Nc1scc(C2CCc3ccccc3C2)c1C(=O)O)c1cccc(OC(F)F)c1]

The title compound was then synthesized according to the procedure described in Example #4 using ethyl 2-amino-4-(1,2,3,4-tetrahydronaphthalen-2-yl)thiophene-3-carboxylate (Preparation #1) and 3-fluorobenzoyl chloride (CAS: 1711-07-5) as starting materials (pale yellow solid, yield 22%). $^1$H NMR (DMSO-$d_6$, 400 MHz): δ=13.62 (br s, 1H), 13.22 (br s, 1H), 7.80-7.67 (m, 3H), 7.58-7.53 (m, 1H), 7.13-7.09 (m, 4H), 6.81 (s, 1H), 3.70-3.65 (m, 1H), 3.12-3.05 (m, 1H), 2.91-2.73 (m, 3H), 2.16-2.09 (m, 1H), 1.85-1.73 (m, 1H). LC/MS (Table 1, Method C) $R_t$=6.01 min, MS m/z: 396 [M+H]$^+$.

Example #74. 2-[[3-(Difluoromethoxy)benzoyl]amino]-4-tetralin-2-yl-thiophene-3-carboxylic acid (Compound #170)

To a solution of ethyl 2-amino-4-(1,2,3,4-tetrahydronaphthalen-2-yl)thiophene-3-carboxylate (Preparation #1, 125 mg, 0.41 mmol) in DMF (3.0 ml) was added 3-(difluoromethoxy)benzoic acid (CAS: 4837-19-8, 117 mg, 0.62 mmol), 2-chloro-1-methylpyridinium iodide (CAS: 14338-32-0, 170 mg, 0.66 mmol), triethylamine (CAS: 121-44-8, 0.12 ml, 0.82 mmol) and DMAP (CAS: 1122-58-3, 915 mg, 0.12 mmol). The reaction mixture was heated to 70° C. for 4 hours. The solvent was removed under reduced pressure and the residue was purified by flash chromatography on silica gel (eluting with 0-100% EtOAc in isohexane) to afford ethyl 2-(3-(difluoromethoxy)benzamido)-4-(1,2,3,4-tetrahydronaphthalen-2-yl)thiophene-3-carboxylate (130 mg, yield 66%), which was dissolved in a mixture of THF (3 ml), EtOH (3 ml) and water (1 ml). To this solution was added lithium hydroxide monohydrate (CAS: 1310-66-3, 33 mg, 1.38 mmol) and the reaction mixture was stirred at RT for 20 hours. The solvents were removed under reduced pressure. Water was added and the mixture was acidified to pH 3 using 2N aqueous HCl solution. The precipitate formed was filtered, washed with water and dried in vacuo to afford 2-[[3-(difluoromethoxy)benzoyl]amino]-4-tetralin-2-yl-thiophene-3-carboxylic acid as an off-white solid (30 mg, yield 24%). $^1$H NMR (DMSO-d$_6$, 400 MHz): δ=13.69 (br s, 1H), 12.79 (br s, 1H), 7.81 (d, J=7.8 Hz, 1H), 7.75-7.69 (m, 2H), 7.52 (dd, J=1.9, 8.1 Hz, 1H), 7.40 (t, J=73.5 Hz, 1H), 7.14-7.09 (m, 4H), 6.85 (s, 1H), 3.67-3.61 (m, 1H), 3.08 (dd, J=3.4, 16.4 Hz, 1H), 2.88-2.74 (m, 3H), 2.14 (d, J=11.9 Hz, 1H), 1.86-1.74 (m, 1H). LC/MS (Table 1, Method D) R$_t$=4.09 min, MS m/z: 444 [M+H]$^+$.

Example #75. 2-[(4-Fluorobenzoyl)amino]-4-tetralin-2-yl-thiophene-3-carboxylic acid, enantiomer 1 (Compound #171)

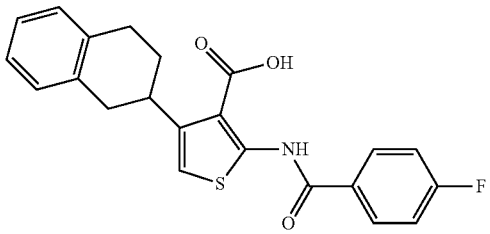 [SMILES: O=C(Nc1scc(C2CCc3ccccc3C2)c1C(=O)O)c1ccc(F)cc1]

The title compound was then synthesized according to the procedure described in Example #60 using ethyl 2-(4-fluorobenzamido)-4-(1,2,3,4-tetrahydronaphthalen-2-yl)thiophene-3-carboxylate (prepared as described in Example #55) as a starting material (off-white solid, yield 6%). $^1$H NMR (DMSO-d$_6$, 400 MHz): δ=14.62 (br s, 1H), 8.05-7.99 (m, 2H), 7.43 (dd, J=8.9, 8.9 Hz, 2H), 7.12-7.08 (m, 4H), 6.66 (s, 1H), 3.81-3.78 (m, 1H), 3.10 (dd, J=3.4, 16.2 Hz, 1H), 2.92-2.84 (m, 2H), 2.73 (dd, J=11.3, 16.1 Hz, 1H), 2.17-2.11 (m, 1H), 1.84-1.71 (m, 1H), one exchangeable proton not observed. LC/MS (Table 1, Method C) R$_t$=5.95 min; MS m/z: 396 [M+H]$^+$. Chiral SFC (Table 1, Method H) R$_t$=5.69 min; e.e. 98.8%, first eluting enantiomer.

Example #76. 2-[(4-Fluorobenzoyl)amino]-4-tetralin-2-yl-thiophene-3-carboxylic acid, enantiomer 2 (Compound #172)

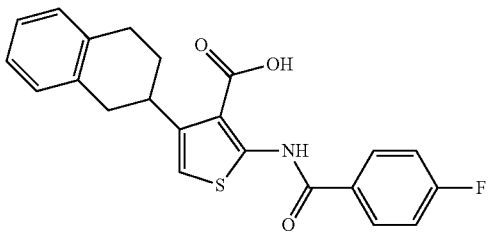 [SMILES: O=C(Nc1scc(C2CCc3ccccc3C2)c1C(=O)O)c1ccc(F)cc1]

The title compound was then synthesized according to the procedure described in Example #61 using ethyl 2-(4-fluorobenzamido)-4-(1,2,3,4-tetrahydronaphthalen-2-yl)thiophene-3-carboxylate (prepared as described in Example #55) as a starting material (off-white solid, yield 47%). $^1$H NMR (DMSO-d$_6$, 400 MHz): δ=13.64 (br s, 1H), 12.62 (br s, 1H), 8.04-8.00 (m, 2H), 7.49 (dd, J=8.8, 8.8 Hz, 2H), 7.11-7.09 (m, 4H), 6.83 (s, 1H), 3.84-3.77 (m, 1H), 3.08 (dd, J=3.2, 16.2 Hz, 1H), 2.93-2.82 (m, 2H), 2.73 (dd, J=11.4, 16.0 Hz, 1H), 2.16-2.10 (m, 1H), 1.86-1.73 (m, 1H). LC/MS (Table 1, Method C) R$_t$=5.95 min; MS m/z: 396 [M+H]$^+$. Chiral SFC (Table 1, Method H) R$_t$=7.59 min; e.e. 98.6%, second eluting enantiomer.

Example #77. 2-[[4-(Difluoromethoxy)benzoyl]amino]-4-tetralin-2-yl-thiophene-3-carboxylic acid, enantiomer 2 (Compound #174)

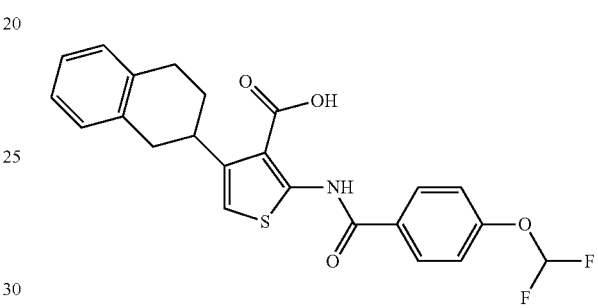

The title compound was then synthesized according to the procedure described in Example #61 using ethyl 2-(4-(difluoromethoxy)benzamido)-4-(1,2,3,4-tetrahydronaphthalen-2-yl)thiophene-3-carboxylate (prepared as described in Example #56) as a starting material (off-white solid, yield 55%). $^1$H NMR (DMSO-d$_6$, 400 MHz): δ=13.67 (br s, 1H), 13.02 (br s, 1H), 8.05 (d, J=8.6 Hz, 2H), 7.46 (t, J=73.5 Hz, 1H), 7.46 (d, J=8.3 Hz, 2H), 7.17-7.12 (m, 4H), 6.84 (s, 1H), 3.74-3.66 (m, 1H), 3.13 (dd, J=3.4, 16.2 Hz, 1H), 2.95-2.89 (m, 2H), 2.82 (dd, J=11.5, 16.2 Hz, 1H), 2.22-2.16 (m, 1H), 1.89-1.77 (m, 1H). LC/MS (Table 1, Method C) R$_t$=5.99 min, MS m/z: 442 [M−H]$^−$. Chiral SFC (Table 1, Method H) R$_t$=3.4 min, MS m/z 442 [M−H]$^−$, second eluting enantiomer.

Example #78. 2-[[4-(Difluoromethoxy)benzoyl]amino]-4-tetralin-2-yl-thiophene-3-carboxylic acid, enantiomer 1 (Compound #175)

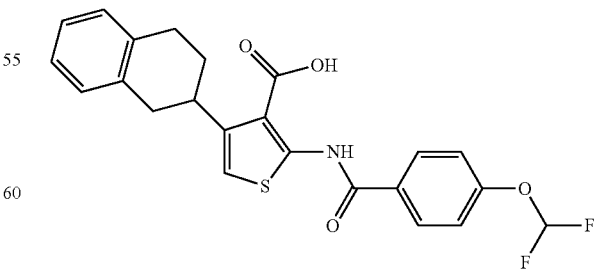

The title compound was then synthesized according to the procedure described in Example #60 using ethyl 2-(4-(difluoromethoxy)benzamido)-4-(1,2,3,4-tetrahydronaphthalen-2-yl)thiophene-3-carboxylate (prepared as described in Example #56) as a starting material (off-white solid, yield 42%). ¹H NMR (DMSO-d₆, 400 MHz): δ=13.39 (br s, 1H), 8.05 (d, J=8.5 Hz, 2H), 7.46 (t, J=73.5 Hz, 1H), 7.45 (d, J=8.5 Hz, 2H), 7.17-7.11 (m, 4H), 6.81 (s, 1H), 3.77-3.69 (m, 1H), 3.13 (dd, J=3.7, 16.0 Hz, 1H), 2.95-2.87 (m, 2H), 2.80 (dd, J=11.6, 15.9 Hz, 1H), 2.22-2.12 (m, 1H), 1.89-1.77 (m, 1H), one exchangeable proton not observed. LC/MS (Table 1, Method C) R$_t$=5.95 min, MS m/z: 442 [M−H]⁻. Chiral SFC (Table 1, Method H) R$_t$=2.6 min, MS m/z 442 [M−H]⁻, first eluting enantiomer.

Example #79. 2-(2,3-Dihydro-1,4-benzodioxine-6-carbonylamino)-4-tetralin-2-yl-thiophene-3-carboxylic acid (Compound #176)

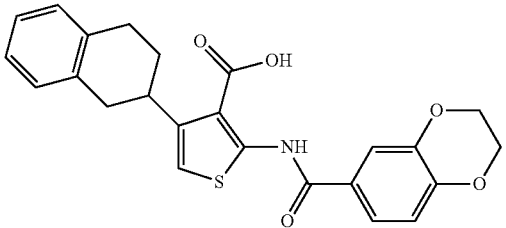 [SMILES: O=C(Nc1scc(C2CCc3ccccc3C2)c1C(=O)O)c1ccc2c(c1)OCCO2]

The title compound was synthesized according to the procedure described in Example #20 using ethyl 2-amino-4-(1,2,3,4-tetrahydronaphthalen-2-yl)thiophene-3-carboxylate (Preparation #1), thionyl chloride (CAS: 7719-09-7) and 2,3-dihydro-1,4-benzodioxine-6-carboxylic acid (CAS: 4442-54-0) as starting materials (off-white solid, yield 78%). ¹H NMR (DMSO-d₆, 400 MHz): δ=12.88 (br s, 1H), 7.46-7.40 (m, 2H), 7.13-7.07 (m, 5H), 6.76 (s, 1H), 4.38-4.31 (m, 4H), 3.69-3.64 (m, 1H), 3.13-3.00 (m, 1H), 2.91-2.71 (m, 3H), 2.17-2.08 (m, 1H), 1.85-1.72 (m, 1H), one exchangeable proton not observed. LC/MS (Table 1, Method C) R$_t$=5.85 min, MS m/z: 436 [M+H]⁺.

Example #80. 2-(2,3-Dihydrobenzofuran-5-carbonylamino)-4-tetralin-2-yl-thiophene-3-carboxylic acid (Compound #177)

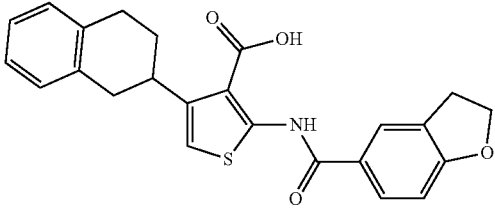 [SMILES: O=C(Nc1scc(C2CCc3ccccc3C2)c1C(=O)O)c1ccc2c(c1)CCO2]

The title compound was synthesized according to the procedure described in Example #74 using ethyl 2-amino-4-(1,2,3,4-tetrahydronaphthalen-2-yl)thiophene-3-carboxylate (Preparation #1) and 2,3-dihydrobenzofuran-5-carboxylic acid (CAS: 76429-73-7) as starting materials (off-white solid, yield 65%). ¹H NMR (DMSO-d₆, 400 MHz): δ=12.57 (s, 1H), 7.86 (s, 1H), 7.77 (d, J=8.3 Hz, 1H), 7.15-7.13 (m, 4H), 7.01 (d, J=8.3 Hz, 1H), 6.80 (s, 1H), 4.68 (t, J=8.7 Hz, 2H), 3.39-3.25 (m, 3H), 3.11 (dd, J=3.3, 16.2 Hz, 1H), 2.91-2.74 (m, 3H), 2.21-2.13 (m, 1H), 1.89-1.75 (m, 1H), one exchangeable proton not observed. LC/MS (Table 1, Method D) R$_t$=3.80 min, MS m/z: 420 [M+H]⁺.

Example #81. 2-[[4-(Cyclobutoxy)benzoyl]amino]-4-tetralin-2-yl-thiophene-3-carboxylic acid (Compound #178)

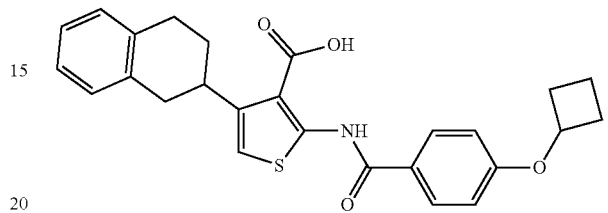

The title compound was synthesized according to the procedure described in Example #20 using ethyl 2-amino-4-(1,2,3,4-tetrahydronaphthalen-2-yl)thiophene-3-carboxylate (Preparation #1), thionyl chloride (CAS: 7719-09-7) and 4-cyclobutoxybenzoic acid (CAS: δ2577-95-1) as starting materials (off-white solid, yield 94%). ¹H NMR (DMSO-d₆, 400 MHz): δ=13.70 (br s, 1H), 13.06 (br s, 1H), 7.89 (d, J=8.7 Hz, 2H), 7.13-7.04 (m, 6H), 6.74 (s, 1H), 4.85-4.76 (m, 1H), 3.74-3.66 (m, 1H), 3.09 (dd, J=3.7, 16.2 Hz, 1H), 2.91-2.72 (m, 3H), 2.50-2.44 (m, 2H, partially obscured by the DMSO peak), 2.17-2.02 (m, 3H), 1.88-1.61 (m, 3H). LC/MS (Table 1, Method C) R$_t$=6.42 min, MS m/z: 448 [M+H]⁺.

Example #82. 2-[(2,2-Dimethyl-3H-benzofuran-5-carbonyl)amino]-4-tetralin-2-yl-thiophene-3-carboxylic acid (Compound #179)

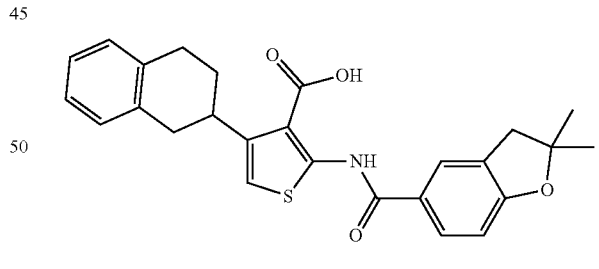

The title compound was synthesized according to the procedure described in Example #20 using ethyl 2-amino-4-(1,2,3,4-tetrahydronaphthalen-2-yl)thiophene-3-carboxylate (Preparation #1), thionyl chloride (CAS: 7719-09-7) and 2,2-dimethyl-2,3-dihydro-1-benzofuran-5-carboxylic acid (CAS: 123656-34-8) as starting materials (pale yellow solid, yield 96%). ¹H NMR (DMSO-d₆, 400 MHz): δ=13.97 (br s, 1H), 12.69 (br s, 1H), 7.79-7.72 (m, 2H), 7.13-7.08 (m, 4H), 6.94-6.91 (m, 1H), 6.76 (s, 1H), 3.67-3.62 (m, 1H), 3.14-3.12 (m, 3H), 2.88-2.73 (m, 3H), 2.14 (d, J=12.0 Hz, 1H), 1.85-1.73 (m, 1H), 1.48-1.46 (m, 6H). LC/MS (Table 1, Method C) R$_t$=6.25 min, MS m/z: 448 [M+H]⁺.

Example #83. 2-[(4-Isopropoxybenzoyl)amino]-4-tetralin-2-yl-thiophene-3-carboxylic acid (Compound #180)

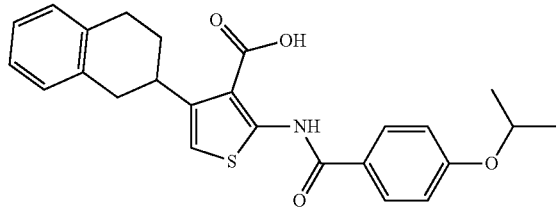

The title compound was synthesized according to the procedure described in Example #20 using ethyl 2-amino-4-(1,2,3,4-tetrahydronaphthalen-2-yl)thiophene-3-carboxylate (Preparation #1) and 4-(propan-2-yloxy)benzoic acid (CAS: 13205-46-4) as starting materials (pale yellow solid, yield 82%). $^1$H NMR (DMSO-$d_6$, 400 MHz): δ=13.16 (br s, 1H), 7.92-7.86 (m, 2H), 7.14-7.08 (m, 6H), 6.73 (s, 1H), 4.81-4.70 (m, 1H), 3.76-3.66 (m, 1H), 3.12-3.05 (m, 1H), 2.90-2.72 (m, 3H), 2.18-2.10 (m, 1H), 1.84-1.72 (m, 1H), 1.32 (s, 3H), 1.31 (s, 3H), one exchangeable proton not observed. LC/MS (Table 1, Method D) $R_t$=4.04 min, MS m/z: 436 [M+H]$^-$.

Example #84. 2-(Chromane-6-carbonylamino)-4-tetralin-2-yl-thiophene-3-carboxylic acid (Compound #181)

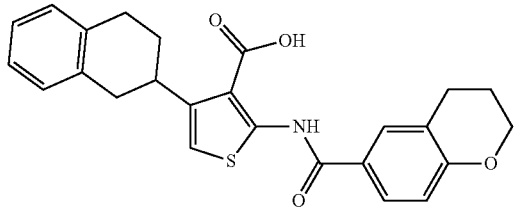

The title compound was synthesized according to the procedure described in Example #20 using ethyl 2-amino-4-(1,2,3,4-tetrahydronaphthalen-2-yl)thiophene-3-carboxylate (Preparation #1), thionyl chloride (CAS: 7719-09-7) and 3,4-dihydro-2H-chromene-6-carboxylic acid (CAS: 103203-84-5) as starting materials (off-white solid, yield 94%). $^1$H NMR (DMSO-$d_6$, 400 MHz): δ=12.89 (br s, 1H), 7.70-7.64 (m, 2H), 7.13-7.08 (m, 4H), 6.94 (d, J=8.4 Hz, 1H), 6.74 (s, 1H), 4.24 (dd, J=5.0, 5.0 Hz, 2H), 3.70-3.62 (m, 1H), 3.09 (dd, J=3.4, 16.1 Hz, 1H), 2.91-2.74 (m, 5H), 2.17-2.10 (m, 1H), 2.00-1.92 (m, 2H), 1.85-1.72 (m, 1H), one exchangeable proton not visible. LC/MS (Table 1, Method C) $R_t$=6.08 min, MS m/z: 434 [M+H]$^+$.

Example #85. 2-[(4-Tetrahydropyran-4-yloxybenzoyl)amino]-4-tetralin-2-yl-thiophene-3-carboxylic acid (Compound #182)

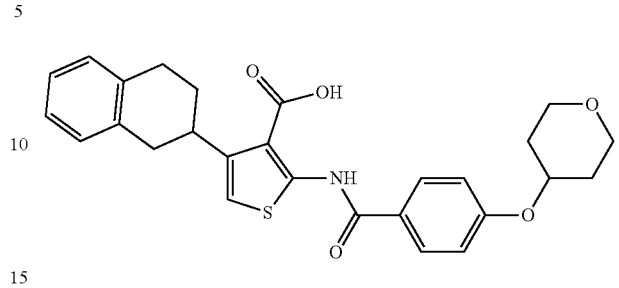

The title compound was synthesized according to the procedure described in Example 20 using ethyl 2-amino-4-(1,2,3,4-tetrahydronaphthalen-2-yl)thiophene-3-carboxylate (Preparation #1), thionyl chloride (CAS: 7719-09-7) and 4-(oxan-4-yloxy)benzoic acid (CAS: 851048-51-6) as starting materials (off-white solid, yield 90%). $^1$H NMR (DMSO-$d_6$, 400 MHz): δ=13.68 (br s, 1H), 7.93-7.87 (m, 2H), 7.22-7.16 (m, 2H), 7.12-7.08 (m, 4H), 6.69 (s, 1H), 4.78-4.70 (m, 1H), 3.92-3.84 (m, 2H), 3.77-3.72 (m, 1H), 3.57-3.48 (m, 2H), 3.09 (dd, J=3.4, 16.1 Hz, 1H), 2.91-2.84 (m, 2H), 2.79-2.67 (m, 1H), 2.13 (dd, J=2.3, 11.8 Hz, 1H), 2.06-1.99 (m, 2H), 1.84-1.58 (m, 3H), one exchangeable proton not observed. LC/MS (Table 1, Method C) $R_t$=5.96 min, MS m/z: 478 [M+H]$^+$.

Example #86. 2-[(4-Cyanobenzoyl)amino]-4-tetralin-2-yl-thiophene-3-carboxylic acid (Compound #183)

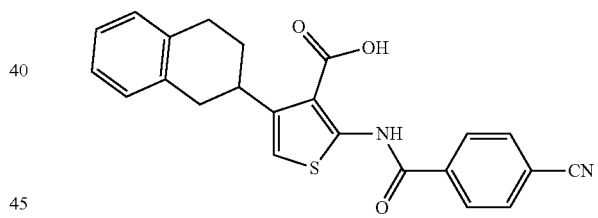

To a stirred solution of ethyl 2-(4-bromobenzamido)-4-(1,2,3,4-tetrahydronaphthalen-2-yl)thiophene-3-carboxylate (Preparation #2, 150 mg, 0.31 mmol) in DMF (3.0 ml) under nitrogen was added zinc cyanide (CAS: 557-21-1, 181 mg, 1.54 mmol) and Pd(PPh$_3$)$_4$ (CAS: 14221-01-3, 537 mg, 0.46 mmol). The reaction was heated to 140° C. for 18 hours. The solvent was removed under reduced pressure. Purification by flash chromatography on silica gel (eluting with 0-100% EtOAc in isohexane) afforded 2-(4-cyanobenzamido)-4-(1,2,3,4-tetrahydronaphthalen-2-yl)thiophene-3-carboxylic acid (90 mg, 21%), which was dissolved in THF (3.0 ml), EtOH (3.0 ml) and H$_2$O (1.0 ml). To this solution was added lithium hydroxide monohydrate (CAS: 1310-66-3, 18 mg, 0.74 mmol). The reaction mixture was stirred at RT for 18 hours. The solvents were removed under reduced pressure. The residue was diluted with water (3 ml) and acidified to pH 3 using 2N aqueous HCl solution. The mixture was extracted with EtOAc (×2) and the combined organic phases were dried over MgSO$_4$. The solvent was removed under reduced pressure.

Purification by reverse phase chromatography on a KP-C18-HS snap cartridge (eluting with 0-100% MeCN in water (0.1% ammonium bicarbonate), flow rate: 50 ml/min) afforded 2-[(4-cyanobenzoyl)amino]-4-tetralin-2-yl-thiophene-3-carboxylic acid as a pale yellow solid (20 mg, yield 23%). $^1$H NMR (DMSO-$d_6$, 400 MHz): δ=13.68 (br s, 1H), 12.70 (br s, 1H), 8.15-8.08 (m, 4H), 7.13-7.10 (m, 4H), 6.88 (s, 1H), 3.68-3.61 (m, 1H), 3.08 (dd, J=3.1, 16.3 Hz, 1H), 2.91-2.74 (m, 3H), 2.16-2.12 (m, 1H), 1.86-1.75 (m, 1H). LC/MS (Table 1, Method D) $R_t$=3.91 min, MS m/z: 401 [M–H]$^-$.

Example #87. 2-[[4-(1,1-Dioxo-1,2-thiazolidin-2-yl)benzoyl]amino]-4-tetralin-2-yl-thiophene-3-carboxylic acid (Compound #184)

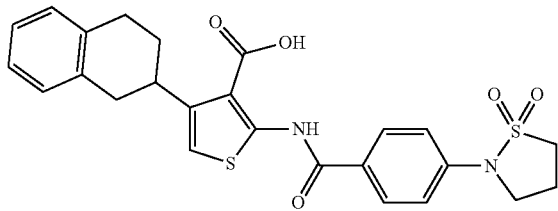 [SMILES: O=C(Nc1scc(C2CCc3ccccc3C2)c1C(=O)O)c1ccc(N2CCCS2(=O)=O)cc1]

The title compound was synthesized according to the procedure described in Example #72 using ethyl 2-(4-bromobenzamido)-4-(1,2,3,4-tetrahydronaphthalen-2-yl)thiophene-3-carboxylate (Preparation #2) and isothiazolidine-1,1-dioxide (CAS: 5908-62-3) as starting materials (off-white solid, yield 51%). $^1$H NMR (DMSO-$d_6$, 400 MHz): δ=13.61 (br s, 1H), 12.52 (br s, 1H), 7.95 (d, J=7.8 Hz, 2H), 7.40 (d, J=7.8 Hz, 2H), 7.13-7.09 (m, 4H), 6.82 (s, 1H), 3.87 (t, J=6.5 Hz, 2H), 3.67-3.60 (m, 3H), 3.08 (dd, J=3.1, 16.2 Hz, 1H), 2.88-2.68 (m, 3H), 2.49-2.43 (m, 2H), 2.16-2.12 (m, 1H), 1.85-1.74 (m, 1H). LC/MS (Table 1, Method D) $R_t$=3.74 min, MS m/z: 495 [M–H]$^-$.

Example #88. 2-Benzamido-4-(3,4-dihydronaphthalen-2-yl)thiophene-3-carboxylic acid (Compound #185)

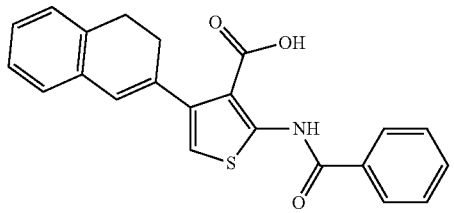 [SMILES: O=C(Nc1scc(C2=Cc3ccccc3CC2)c1C(=O)O)c1ccccc1]

The title compound was synthesized according to the procedure described in Example #4 using methyl 2-amino-4-(3,4-dihydronaphthalen-2-yl)thiophene-3-carboxylate (Preparation #5) and benzoyl chloride (CAS: 98-88-4) as starting materials (off-white solid, yield 18%). $^1$H NMR (DMSO-$d_6$, 400 MHz): δ=13.62 (br s, 1H), 13.06 (br s, 1H), 8.03-7.99 (m, 2H), 7.77-7.66 (m, 3H), 7.24-7.13 (m, 4H), 6.91 (s, 1H), 6.50 (s, 1H), 2.91 (t, J=7.9 Hz, 2H), 2.56-2.53 (m, 2H, partially obscured by the DMSO peak). LC/MS (Table 1, Method C) $R_t$=5.74 min; MS m/z: 376 [M+H]$^+$.

Example #89. 2-(Pyridine-2-carbonylamino)-4-tetralin-2-yl-thiophene-3-carboxylic acid (Compound #186)

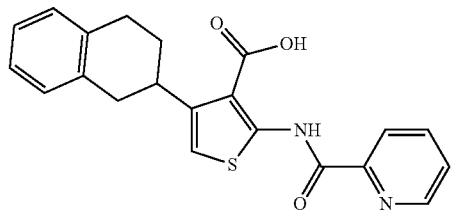

The title compound was synthesized according to the procedure described in Example #74 using ethyl 2-amino-4-(1,2,3,4-tetrahydronaphthalen-2-yl)thiophene-3-carboxylate (Preparation #1) and pyridine-2-carboxylic acid (CAS: 98-98-6) as starting materials (off-white solid, yield 14%). $^1$H NMR (DMSO-$d_6$, 400 MHz): δ=13.33 (br s, 1H), 13.01 (br s, 1H), 8.65 (d, J=4.8 Hz, 1H), 8.09 (d, J=7.9 Hz, 1H), 8.00 (dt, J=1.6, 7.7 Hz, 1H), 7.61 (ddd, J=1.2, 4.8, 7.6 Hz, 1H), 6.99-6.97 (m, 4H), 6.74 (s, 1H), 3.57-3.48 (m, 1H), 2.98-2.91 (m, 1H), 2.78-2.72 (m, 2H), 2.65 (dd, J=11.1, 16.3 Hz, 1H), 2.04-1.97 (m, 1H), 1.72-1.61 (m, 1H). LC/MS (Table 1, Method C) $R_t$=5.63 min; MS m/z: 379 [M+H]$^+$.

Example #90. 2-[(5-Methoxypyridine-2-carbonyl)amino]-4-tetralin-2-yl-thiophene-3-carboxylic acid (Compound #187)

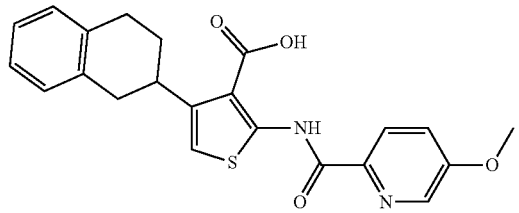 [SMILES: COc1ccc(C(=O)Nc2scc(C3CCc4ccccc4C3)c2C(=O)O)nc1]

The title compound was synthesized according to the procedure described in Example #74 using ethyl 2-amino-4-(1,2,3,4-tetrahydronaphthalen-2-yl)thiophene-3-carboxylate (Preparation #1) and 5-methoxypyridine-2-carboxylic acid (CAS: 29082-92-6) as starting materials (white solid, yield 48%). $^1$H NMR (DMSO-$d_6$, 400 MHz): δ=13.44 (br s, 1H), 13.05 (br s, 1H), 8.51 (d, J=2.6 Hz, 1H), 8.23 (d, J=8.8 Hz, 1H), 7.71 (dd, J=2.8, 8.9 Hz, 1H), 7.18-7.13 (m, 4H), 6.89 (s, 1H), 4.02 (s, 3H), 3.73-3.65 (m, 1H), 3.16-3.10 (m, 1H), 2.94-2.89 (m, 2H), 2.83 (dd, J=11.2, 16.3 Hz, 1H), 2.21-2.15 (m, 1H), 1.90-1.78 (m, 1H). LC/MS (Table 1, Method C) $R_t$=5.71 min; MS m/z: 409 [M+H]$^+$.

121

Example #91. 2-[(4-tert-Butoxybenzoyl)amino]-4-tetralin-2-yl-thiophene-3-carboxylic acid (Compound #188)

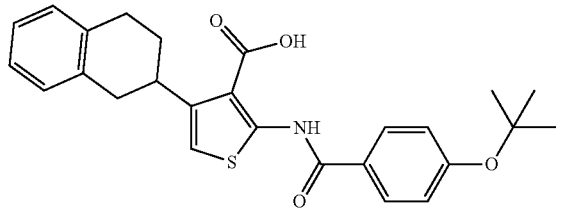 [SMILES: CC(C)(C)Oc1ccc(C(=O)Nc2scc(C3CCc4ccccc4C3)c2C(=O)O)cc1]

The title compound was synthesized according to the procedure described in Example #74 using ethyl 2-amino-4-(1,2,3,4-tetrahydronaphthalen-2-yl)thiophene-3-carboxylate (Preparation #1) and 4-(tert-butoxy)benzoic acid (CAS: 13205-47-5) as starting materials (off-white solid, yield 54%). $^1$H NMR (DMSO-$d_6$, 400 MHz): δ=13.59 (br s, 1H), 12.61 (br s, 1H), 7.90-7.85 (m, 2H), 7.22 (d, J=9.1 Hz, 2H), 7.12-7.10 (m, 4H), 6.80 (s, 1H), 3.67-3.60 (m, 1H), 3.08 (dd, J=3.0, 16.1 Hz, 1H), 2.88-2.73 (m, 3H), 2.16-2.12 (m, 1H), 1.85-1.73 (m, 1H), 1.42 (s, 9H). LC/MS (Table 1, Method C) $R_t$=6.44 min, MS m/z: 450 [M+H]$^+$.

Example #92. 2-Benzamido-4-(7-fluorotetralin-2-yl)thiophene-3-carboxylic acid (Compound #189)

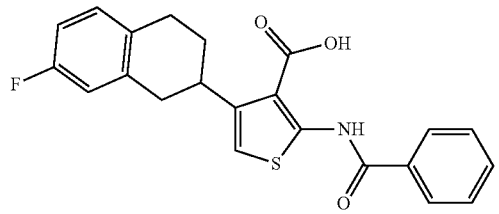 [SMILES: O=C(Nc1scc(C2CCc3ccc(F)cc3C2)c1C(=O)O)c1ccccc1]

The title compound was synthesized according to the procedure described in Example #4 using 7-fluoro-1,2,3,4-tetrahydronaphthalene-2-carboxylic acid (CAS: 1314902-19-6, prepared according to Compound #1.10 in WO201608411) as a starting material (white solid, yield 24%). $^1$H NMR (DMSO-$d_6$, 400 MHz): δ=12.69 (s, 1H), 7.95 (d, J=7.2 Hz, 2H), 7.72-7.61 (m, 3H), 7.15 (dd, J=5.9, 9.3 Hz, 1H), 6.98-6.91 (m, 2H), 6.82 (s, 1H), 3.66-3.58 (m, 1H), 3.10 (dd, J=3.5, 16.3 Hz, 1H), 2.88-2.72 (m, 3H), 2.13 (d, J=12.2 Hz, 1H), 1.86-1.72 (m, 1H), one exchangeable proton not observed. LC/MS (Table 1, Method C) $R_t$=5.88 min, MS m/z: 396 [M+H]$^+$.

122

Example #93. 2-Benzamido-4-(5-fluorotetralin-2-yl)thiophene-3-carboxylic acid (Compound #190)

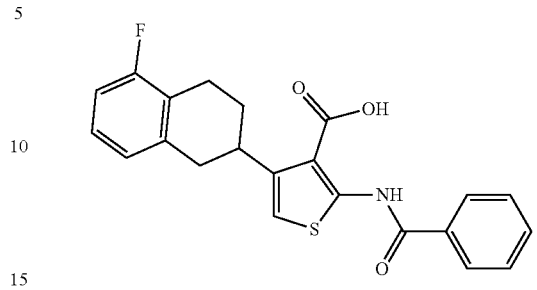

The title compound was synthesized according to the procedure described in Example #92 using 5-fluoro-3,4-dihydronaphthalen-1(2H)-one (CAS: 93742-85-9) as the starting material (off-white solid, yield 58%). $^1$H NMR (DMSO-$d_6$, 400 MHz): δ=13.68 (s, 1H), 12.57 (s, 1H), 8.00-7.98 (m, 2H), 7.78-7.67 (m, 3H), 7.21 (dd, J=7.7, 14.1 Hz, 1H), 7.04-6.99 (m, 2H), 6.89 (s, 1H), 3.67-3.61 (m, 1H), 3.16 (dd, J=3.7, 17.0 Hz, 1H), 2.98-2.71 (m, 3H), 2.26-2.21 (m, 1H), 1.88-1.78 (m, 1H). LC/MS (Table 1, Method C) $R_t$=5.87 min, MS m/z: 396 [M+H]$^+$.

Example #94. 2-Benzamido-4-(6-fluorotetralin-2-yl)thiophene-3-carboxylic acid (Compound #191)

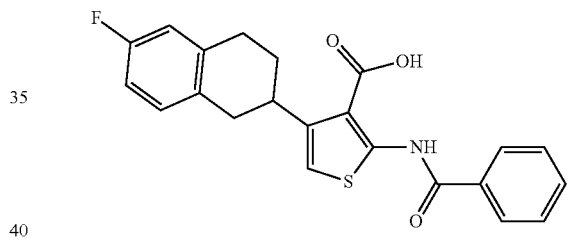

The title compound was synthesized according to the procedure described in Example #92 using 6-fluoro-1,2,3,4-tetrahydronaphthalen-1-one (CAS: 703-67-3) as the starting material (off-white solid, yield 12%). $^1$H NMR (DMSO-$d_6$, 400 MHz): δ=13.63 (s, 1H), 12.56 (s, 1H), 7.97-7.94 (m, 2H), 7.74-7.69 (m, 1H), 7.68-7.63 (m, 2H), 7.17-7.11 (m, 1H), 6.99-6.91 (m, 2H), 6.84 (s, 1H), 3.64-3.59 (m, 1H), 3.07 (dd, J=3.6, 16.1 Hz, 1H), 2.91-2.85 (m, 2H), 2.78-2.68 (m, 1H), 2.13 (d, J=12.3 Hz, 1H), 1.84-1.72 (m, 1H). LC/MS (Table 1, Method C) $R_t$=5.87 min, MS m/z: 396 [M+H]$^+$.

Example #95. 2-(Bicyclo[1.1.1]pentane-3-carbonylamino)-4-tetralin-2-yl-thiophene-3-carboxylic acid (Compound #192)

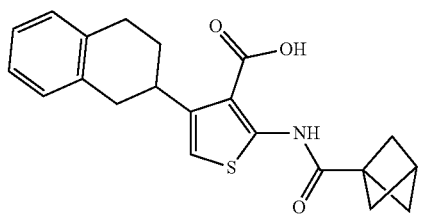 [SMILES: O=C(O)c1c(C2CCc3ccccc3C2)csc1NC(=O)C12CC(C1)C2]

The title compound was synthesized according to the procedure described in Example #20 using bicyclo[1.1.1]pentane-1-carboxylic acid (CAS: 22287-28-1) and ethyl 2-amino-4-(1,2,3,4-tetrahydronaphthalen-2-yl)thiophene-3-carboxylate (Preparation #1) as starting materials (white solid, yield 11%). $^1$H NMR (DMSO-d$_6$, 400 MHz): δ=12.14 (s, 1H), 7.15-7.11 (m, 4H), 6.75 (s, 1H), 3.72-3.66 (m, 1H), 3.12-3.06 (m, 1H), 2.96-2.85 (m, 2H), 2.77 (dd, J=11.4, 16.0 Hz, 1H), 2.59 (s, 1H), 2.16-2.11 (m, 7H), 1.84-1.74 (m, 1H), one exchangeable proton not observed. LC/MS (Table 1, Method C) R$_t$=5.66 min, MS m/z: 368 [M+H]$^+$.

Example #96. 2-[(3-Fluorobicyclo[1.1.1]pentane-1-carbonyl)amino]-4-tetralin-2-yl-thiophene-3-carboxylic acid (Compound #193)

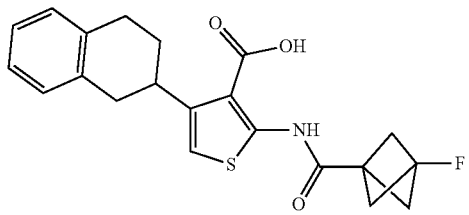 [SMILES: O=C(O)c1c(C2CCc3ccccc3C2)csc1NC(=O)C12CC(F)(C1)C2]

The title compound was synthesized according to the procedure described in Example #20 using 3-fluorobicyclo[1.1.1]pentane-1-carboxylic acid (CAS: 146038-53-1) and ethyl 2-amino-4-(1,2,3,4-tetrahydronaphthalen-2-yl)thiophene-3-carboxylate (Preparation #1) as starting materials (off-white solid, yield 5%). $^1$H NMR (DMSO-d$_6$, 400 MHz): δ=13.63 (s, 1H), 11.93 (s, 1H), 7.16-7.12 (m, 4H), 6.82 (s, 1H), 3.67-3.60 (m, 1H), 3.11-3.06 (m, 1H), 2.91-2.87 (m, 2H), 2.79 (dd, J=11.2, 16.2 Hz, 1H), 2.51 (d, J=2.6 Hz, 6H), 2.17-2.12 (m, 1H), 1.85-1.75 (m, 1H). LC/MS (Table 1, Method D) R$_t$=3.68 min, MS m/z: 386 [M+H]$^+$.

Example #97. 2-Benzamido-4-tetralin-5-yl-thiophene-3-carboxylic acid (Compound #194)

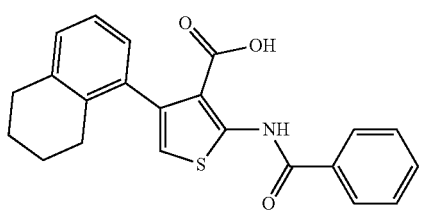 [SMILES: O=C(Nc1scc(-c2cccc3c2CCCC3)c1C(=O)O)c1ccccc1]

The title compound was synthesized according to the procedure described in Example #4 using benzoyl chloride (CAS: 98-88-4) and 5,6,7,8-tetrahydronaphthalene-1-carboxylic acid (CAS: 4242-18-6) as starting materials (off white solid, yield 22%). $^1$H NMR (DMSO-d$_6$, 400 MHz): δ=13.12 (br s, 1H), 7.98-7.94 (m, 2H), 7.70-7.66 (m, 1H), 7.64-7.59 (m, 2H), 7.12 (br s, 1H), 7.08-6.99 (m, 2H), 6.91-6.89 (m, 1H), 6.71 (s, 1H), 2.79-2.72 (m, 2H), 2.44-2.33 (m, 2H), 1.74-1.59 (m, 4H). LC/MS (Table 1, Method C) R$_t$=5.81 min, MS m/z: 376 [M–H]$^-$.

Preparation #1. Ethyl 2-amino-4-(1,2,3,4-tetrahydronaphthalen-2-yl)thiophene-3-carboxylate

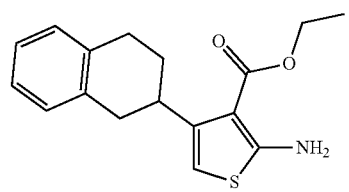 [SMILES: CCOC(=O)c1c(C2CCc3ccccc3C2)csc1N]

Step A. N-Methoxy-N-methyl-1,2,3,4-tetrahydronaphthalene-2-carboxamide

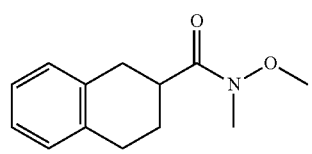 [SMILES: CON(C)C(=O)C1CCc2ccccc2C1]

A solution of tetralin-2-carboxylic acid (2.00 g, 11.35 mmol) was dissolved in DMF (18 ml) was treated with DIPEA (CAS: CAS: 7087-68-5, 5.9 ml, 34.05 mmol), HATU (CAS: 148893-10-1, 6.47 g, 17.02 mmol) and N,O-dimethylhydroxylamine hydrochloride (CAS: δ638-79-5, 1.44 g, 14.75 mmol). The reaction mixture was stirred at RT for 24 hours. The reaction mixture was diluted with EtOAc and brine and the two phases were separated. The organic phase was washed with brine (×3), dried over MgSO$_4$ and the solvent was removed under reduced pressure. Purification by flash chromatography on silica gel (eluting with 0-20% EtOAc in isohexane) afforded N-methoxy-N-methyl-1,2,3,4-tetrahydronaphthalene-2-carboxamide as an oil (2.50 g, yield quant.). $^1$H NMR (CDCl$_3$, 400 MHz): δ=7.11 (s, 4H), 3.71 (s, 3H), 3.24 (s, 3H), 3.16-2.99 (m, 2H), 2.93-2.85 (m, 3H), 2.11-2.04 (m, 1H), 1.96-1.84 ppm (m, 1H).

Step B. Ethyl 2-amino-4-(1,2,3,4-tetrahydronaphthalen-2-yl)thiophene-3-carboxylate

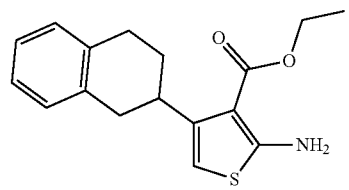 [SMILES: CCOC(=O)c1c(C2CCc3ccccc3C2)csc1N]

To a stirred solution of N-methoxy-N-methyl-1,2,3,4-tetrahydronaphthalene-2-carboxamide (Preparation #1, 2.50 g, 11.40 mmol) in diethyl ether (30 ml) was added a solution of methylmagnesium bromide in Et₂O (CAS: 75-16-1, 3.0 M, 9.5 ml, 28.5 mmol) and the reaction mixture was stirred at RT for 1.5 hours. The reaction was quenched with a saturated aqueous NH₄Cl solution and the two phases were separated. The aqueous phase was extracted with diethyl ether. The combined organic phases were dried over MgSO₄ and the solvent was removed under reduced pressure. The residue (2.45 g, 14.06 mmol) was dissolved in ethanol (15 ml) and then ethyl cyanoacetate (CAS: 105-56-6, 1.5 ml, 14.06 mmol), sulfur (CAS: 7704-34-9, 451 mg, 14.06 mmol) and morpholine (CAS: 110-91-8, 3.7 ml, 42.18 mmol) were added. The reaction mixture was heated at 80° C. for 16 hours and then it was allowed to cool to RT. The volatiles were removed under reduced pressure and the residue was partitioned between EtOAc and brine and the two phases were separated. The organic phase was washed with brine, dried over MgSO₄ and the solvent was removed under reduced pressure. Purification by flash chromatography on silica gel (eluting with 0-20% EtOAc in isohexane) afforded ethyl 2-amino-4-(1,2,3,4-tetrahydronaphthalen-2-yl)thiophene-3-carboxylate as a white solid (1.56 g, yield 37%). ¹H NMR (CDCl₃, 400 MHz): δ=7.14-7.06 (m, 4H), 6.11 (br s, 2H), 5.93 (s, 1H), 4.29 (q, J=7.1 Hz, 2H), 3.56-3.49 (m, 1H), 3.15-2.77 (m, 4H), 2.23-2.15 (m, 1H), 1.79-1.69 (m, 1H), 1.29 (t, J=7.1 Hz, 3H).

Preparation #2. Ethyl 2-(4-bromobenzamido)-4-(1,2,3,4-tetrahydronaphthalen-2-yl)thiophene-3-carboxylate

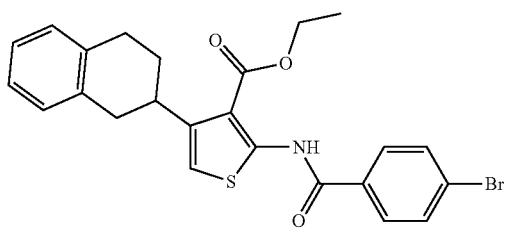 [SMILES: CCOC(=O)c1c(C2CCc3ccccc3C2)csc1NC(=O)c1ccc(Br)cc1]

To a solution of ethyl 2-amino-4-(1,2,3,4-tetrahydronaphthalen-2-yl)thiophene-3-carboxylate (Preparation #1, 1.20 g, 3.98 mmol) in DCM (50 ml) was added DIPEA (CAS: 7087-68-5, 1.7 ml, 9.95 mmol) and 4-bromobenzoyl chloride (CAS: 586-75-4, 1.09 g, 4.98 mmol). The reaction mixture was stirred at RT for 20 hours. The resulting mixture was partitioned between DCM and saturated aqueous NaHCO₃ solution. The two phases were separated. The aqueous phase was extracted with DCM (×3). The combined organic phases were dried over MgSO₄ and the solvent was removed under reduced pressure. Purification by flash chromatography on silica gel (eluting with 0-20% EtOAc in isohexane) afforded ethyl 2-(4-bromobenzamido)-4-(1,2,3,4-tetrahydronaphthalen-2-yl)thiophene-3-carboxylate as a yellow solid (1.15 g, yield 60%). ¹H NMR (CDCl₃, 400 MHz): δ=12.55 (s, 1H), 7.90 (d, J=8.6 Hz, 2H), 7.67 (d, J=8.4 Hz, 2H), 7.16-7.10 (m, 4H), 6.57 (s, 1H), 4.45-4.38 (m, 2H), 3.68-3.61 (m, 1H), 3.17-3.10 (m, 1H), 2.99-2.85 (m, 3H), 2.25-2.19 (m, 1H), 1.88-1.76 (m, 1H), 1.36 (t, J=7.1 Hz, 3H).

Preparation #3. Ethyl 2-amino-4-(6,7,8,9-tetrahydro-5H-benzo[7]annulen-7-yl)thiophene-3-carboxylate

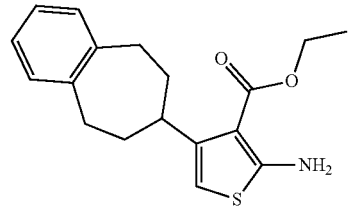 [SMILES: CCOC(=O)c1c(C2CCc3ccccc3CC2)csc1N]

The title compound was synthesized according to the procedure described in Preparation #1, using 6,7,8,9-tetrahydro-5H-benzo[7]annulene-7-carboxylic acid (CAS: 1400229-72-2) as a starting material (3.0 g, yield 72%). ¹H NMR (CDCl₃, 400 MHz): δ=7.15-7.09 (m, 4H), 6.05 (br s, 2H), 5.76 (s, 1H), 4.35 (q, J=7.0 Hz, 2H), 3.52 (t, J=11.7 Hz, 1H), 2.99-2.79 (m, 5H), 2.27-2.07 (m, 3H), 1.42 (t, J=6.9 Hz, 3H).

Preparation #4. Ethyl 2-amino-4-(1,2,3,4-tetrahydronaphthalen-1-yl)thiophene-3-carboxylate

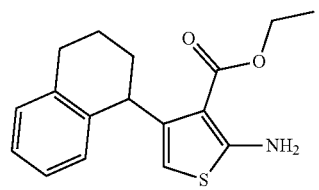 [SMILES: CCOC(=O)c1c(C2CCCc3ccccc32)csc1N]

To a stirred solution of N-methoxy-N-methyl-1,2,3,4-tetrahydronaphthalene-1-carboxamide (4.8 g, 21.9 mmol, prepared as described in Preparation #1, Step A starting with 1,2,3,4-tetrahydronaphthalene-1-carboxylic acid, CAS: 1914-65-4) in Et₂O (50 ml) at 0° C. was slowly added a solution of methylmagnesium bromide in Et₂O (CAS: 75-16-1, 3.0 M, 14.6 ml, 43.8 mmol). The reaction mixture was stirred at 0° C. for 20 minutes, allowed to warm to RT and stirred at RT for 1.5 hours. The reaction was again cooled to 0° C. and additional methylmagnesium bromide in Et₂O (3.0 M, 6.5 ml, 18.0 mmol) was added. The reaction was allowed to warm to RT and stirred for an additional 3 hours. The reaction mixture was cooled to 0° C. and quenched with saturated aqueous NH₄Cl solution. The two phases were separated and the aqueous phase was extracted with Et₂O (×3). The combined organic phases were dried over MgSO₄ and the solvent was removed under reduced pressure to afford 1-(1,2,3,4-tetrahydronaphthalen-1-yl)ethan-1-one as a yellow oil (2.8 g, yield 73%). 1-(1,2,3,4-Tetrahydronaphthalen-1-yl)ethan-1-one (1.0 g, 5.74 mmol) was dissolved in toluene (20 ml). Ethyl cyanoacetate (CAS: 105-56-6, 0.61 ml, 5.74 mmol), ammonium acetate (CAS: δ31-61-8, 310 mg, 4.02 mmol) and acetic acid (0.5 ml) were added. The reaction mixture was heated at reflux for 20 hours, allowed to cool to RT and the partitioned between EtOAc and brine. The two phases were separated and the aqueous phase was extracted with EtOAc. The organic solvent was removed under reduced pressure and the residue was purified by flash chromatography on silica gel (eluting with 0-25% EtOAc in cyclohexane) to afford ethyl 2-cyano-3-(1,2,3,4-tetrahydronaphthalen-1-yl)but-2-enoate as a colorless oil (1.02 g, yield 66%). The residue was dissolved in ethanol (20 ml) and then morpholine (CAS: 110-91-8, 0.75 ml, 8.61 mmol) and sulfur (CAS: 7704-34-9, 202 mg, 6.31 mmol) were added. The reaction mixture was heated at 80° C. for 24 hours, followed by the addition of another aliquot of sulfur (150 mg, 4.73 mmol). The reaction mixture was heated at 80° C. for an additional 24 hours, cooled to RT and the solvent was removed under reduced pressure. Purification by flash chromatography on silica gel (eluting with 0-30% EtOAc in cyclohexane) afforded ethyl 2-amino-4-(1,2,3,4-tetrahydronaphthalen-1-yl)thiophene-3-carboxylate as a yellow oil (466 mg, yield 27%). $^1$H NMR (CDCl$_3$, 400 MHz): δ=7.16-7.03 (m, 4H), 6.06 (s, 2H), 5.25 (s, 1H), 4.75-4.70 (m, 1H), 4.38-4.24 (m, 2H), 2.84-2.75 (m, 2H), 1.99-1.92 (m, 2H), 1.78-1.63 (m, 2H), 1.33 (t, J=7.1 Hz, 3H).

Preparation #5. Methyl 2-amino-4-(3,4-dihydronaphthalen-2-yl)thiophene-3-carboxylate

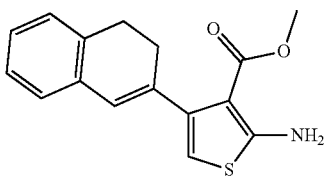 [SMILES: COC(=O)c1c(C2=Cc3ccccc3CC2)csc1N]

Step A. 2-(3,4-Dihydronaphthalen-2-yl)-4,4,5,5-tetramethyl-1,3,2-dioxaborolane

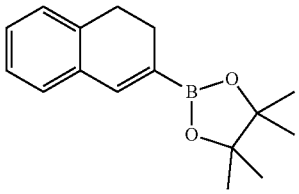 [SMILES: CC1(C)OB(C2=Cc3ccccc3CC2)OC1(C)C]

To a stirred solution of diisopropylamine (CAS: 108-18-9, 0.64 ml, 4.54 mmol) in THF (8.0 ml) under nitrogen at −78° C. was slowly added a solution of n-BuLi in hexanes (CAS: 109-72-8, 2.5 M, 1.8 ml, 4.54 mmol) and the reaction mixture was stirred at −78° C. for 30 minutes. A solution of β-tetralone (CAS: 530-93-8, 0.5 ml, 3.78 mmol) in THF (7.0 ml) was added slowly maintaining an internal temperature during the addition <−60° C. The reaction mixture was stirred at −78° C. for 1 hour. A solution of N-phenyl-bis(trifluoromethanesulfonimide (CAS: 37595-74-7, 1.62 g, 4.54 mmol) in THF (7.0 ml) was added slowly maintaining an internal temperature during the addition <−60° C. The reaction mixture was stirred at −78° C. for 2 hours and then allowed to warm to RT overnight. The resulting mixture was quenched with EtOAc and water and the two phases were separated. The aqueous phase was extracted with EtOAc (×2) and the combined organic phases were dried over MgSO$_4$. The solvent was removed under reduced pressure. Purification by flash chromatography on silica gel (eluting with 0-3% EtOAc in cyclohexane) afforded 3,4-dihydronaphthalen-2-yl trifluoromethanesulfonate as a colorless oil (859 mg, yield 82%). To 3,4-dihydronaphthalen-2-yl trifluoromethanesulfonate (859 mg, 3.09 mmol), bis(pinacolato)diboron (CAS: 73183-34-3, 1.18 g, 4.63 mmol), Pd(dppf)Cl$_2$ (CAS: 72287-26-4, 23 mg, 0.03 mmol) and potassium acetate (CAS: 127-08-2, 606 mg, 6.17 mmol) under nitrogen was added THF (20 ml) and the resulting mixture was heated at 80° C. for 20 hours. The reaction mixture was cooled to RT, diluted with DCM and filtered through a pad of Celite®. The solvents were removed under reduced pressure and the residue was purified by flash chromatography on silica gel (eluting with 0-5% EtOAc in cyclohexane) to afford the 2-(3,4-dihydronaphthalen-2-yl)-4,4,5,5-tetramethyl-1,3,2-dioxaborolane as a colorless oil (470 mg, yield 59%). $^1$H NMR (CDCl$_3$, 400 MHz): δ=7.21-7.19 (m, 1H), 7.17-7.08 (m, 4H), 2.75 (t, J=8.1 Hz, 2H), 2.42-2.36 (m, 2H), 1.31 (s, 12H).

Step B. Methyl 2-((((9H-fluoren-9-yl)methoxy)carbonyl)amino)-4-(((trifluoromethyl)sulfonyl)oxy) thiophene-3-carboxylate

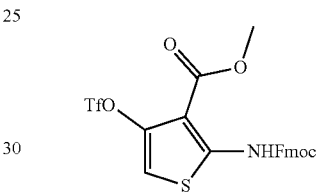

To a stirred suspension of sodium hydride (60% in mineral oil, CAS: 7646-69-7, 530 mg, 13.3 mmol) in 1,2-dimethoxyethane (50 ml) at 0° C. under nitrogen was added ethyl 4-chloroacetoacetate (CAS: δ38-07-3, 1.6 ml, 13.3 mmol). The reaction mixture was warmed at RT and stirred at this temperature for 30 minutes. The resulting mixture was cooled to 0° C. and then Fmoc isothiocyanate (CAS: 199915-38-3, 3.74 g, 13.3 mmol) was added. The reaction mixture was allowed to warm to RT and stirred at RT for 5 hours. The mixture was quenched with water and then partitioned between DCM and brine. The two phases were separated and the aqueous phase was further extracted with DCM (×2). The combined organic phases were dried over MgSO$_4$ and the solvent was removed under reduced pressure. Purification by flash chromatography on silica gel (eluting with 0-70% EtOAc in isohexane) afforded methyl 2-((((9H-fluoren-9-yl)methoxy)carbonyl)amino)-4-oxo-4,5-dihydrothiophene-3-carboxylate as an orange solid (3.74 g, yield 71%). To a solution of methyl 2-((((9H-fluoren-9-yl)methoxy)carbonyl)amino)-4-oxo-4,5-dihydrothiophene-3-carboxylate (250 mg, 0.63 mmol) in DCM (3.0 ml) was added triethylamine (CAS: 121-44-8, 0.13 ml, 0.95 mmol) and, dropwise, trifluoromethanesulfonic anhydride (CAS: 358-23-6, 0.12 ml, 0.70 mmol). The reaction mixture was stirred at RT for 1 hour and then it was diluted with DCM and water. The two phases were separated. The organic phase was dried over MgSO$_4$ and the solvent was removed under reduced pressure to afford the methyl 2-((((9H-fluoren-9-yl)methoxy)carbonyl)amino)-4-(((trifluoromethyl)sulfonyl)oxy)thiophene-3-carboxylate as a brown solid (390 mg, yield quant.) which was used without further purifications. $^1$H NMR (CDCl$_3$, 400 MHz): δ=10.52 (s, 1H), 7.79 (d, J=7.6 Hz, 2H), 7.61 (d, J=7.3 Hz, 2H), 7.42 (dd, J=7.5, 7.5

Hz, 2H), 7.34 (dd, J=7.5, 7.5 Hz, 2H), 6.61 (s, 1H), 4.55 (d, J=7.1 Hz, 2H), 4.30 (dd, J=7.1, 7.1 Hz, 1H), 3.96 (s, 3H).

Step C. Methyl 2-amino-4-(3,4-dihydronaphthalen-2-yl)thiophene-3-carboxylate

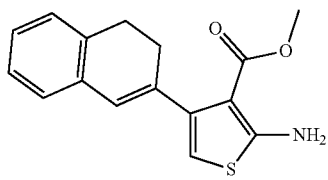 [SMILES: COC(=O)c1c(C2=Cc3ccccc3CC2)csc1N]

Methyl 2-((((9H-fluoren-9-yl)methoxy)carbonyl)amino)-4-(((trifluoromethyl)sulfonyl)oxy)thiophene-3-carboxylate (Preparation #5, Step B, 165 mg, 0.31 mmol), 2-(3,4-dihydronaphthalen-2-yl)-4,4,5,5-tetramethyl-1,3,2-dioxaborolane (Preparation #5, Step A, 96 mg, 0.37 mmol), Pd(dppf)Cl$_2$ (CAS: 72287-26-4, 11 mg, 0.016 mmol) and potassium phosphate tribasic (CAS: 7778-53-2, 199 mg, 0.94 mmol) were suspended in THF (2.0 ml) and water (0.2 ml). The reaction mixture was degassed, placed under nitrogen and then stirred at RT for 20 hours. The reaction mixture was diluted with DCM, filtered through a pad of Celite® and dried over MgSO$_4$. The solvent was removed under reduced pressure and the residue was purified by flash chromatography on silica gel (eluting with 0-20% EtOAc in cyclohexane) to afford methyl 2-((((9H-fluoren-9-yl)methoxy)carbonyl)amino)-4-(3,4-dihydronaphthalen-2-yl)thiophene-3-carboxylate as a white solid (104 mg, yield 65%). Methyl 2-((((9H-fluoren-9-yl)methoxy)carbonyl)amino)-4-(3,4-dihydronaphthalen-2-yl)thiophene-3-carboxylate (104 mg, 0.21 mmol) was dissolved in DCM (2.0 ml) and then morpholine (CAS: 110-91-8, 90 µl, 1.02 mmol) was added. The reaction mixture was stirred at RT for 72 hours and then the volatiles were removed under reduced pressure. Purification by flash chromatography on silica gel (eluting with 0-20% EtOAc in isohexane) afforded the methyl 2-amino-4-(3,4-dihydronaphthalen-2-yl)thiophene-3-carboxylate as a pink solid (50 mg, yield 86%). $^1$H NMR (CDCl$_3$, 400 MHz): δ=7.18-7.05 (m, 4H), 6.46 (s, 1H), 6.09-6.05 (m, 3H), 3.78 (s, 3H), 2.93-2.88 (m, 2H), 2.47 (dt, J=1.2, 7.9 Hz, 2H).

Example B—Biology

Example B1—Antiviral Effect

The antiviral effect of the compounds of the invention have been tested on A549 cell lines infected with H1N1 (influenza A/New Caledonia/20/99). IC50 are reported in the following Table 1. The results show that the compounds of the present invention present an antiviral effect.

TABLE 1

| Compound | IC50 (µM) | Compound | IC50 (µM) | Compound | IC50 (µM) |
|---|---|---|---|---|---|
| #16 | 0.0111 | #17 | 0.0383 | #19 | 0.067 |
| #7 | 0.1442 | #8 | 0.1867 | #3 | 0.28 |
| #49 | 0.13 | #51 | 0.052 | #52 | 0.0004 |
| #53 | 0.004 | #55 | 0.0338 | #56 | 0.11 |
| #57 | 0.076 | #58 | 0.1 | #64 | 0.0033 |
| #65 | 0.004 | #67 | 0.002 | #68 | 0.052 |
| #69 | 0.003 | #70 | 0.0075 | #86 | 0.002 |

TABLE 1-continued

| Compound | IC50 (µM) | Compound | IC50 (µM) | Compound | IC50 (µM) |
|---|---|---|---|---|---|
| #89 | 0.24 | #93 | 0.008 | #94 | 0.002 |
| #101 | 0.0446 | #122 | 0.744 | #123 | 0.133 |
| #124 | 0.237 | #125 | 0.237 | #126 | 0.237 |
| #127 | 0.0018 | #128 | 0.0008 | #129 | 0.460 |
| #130 | 0.560 | #131 | 0.110 | #132 | 0.002 |
| #133 | 0.050 | #134 | 0.024 | #135 | 0.003 |
| #136 | 0.030 | #137 | 0.0042 | #138 | 0.022 |
| #139 | 0.015 | #140 | 0.0035 | #141 | 0.0027 |
| #142 | 0.0003 | #143 | 0.004 | #144 | 0.004 |
| #145 | 0.032 | #146 | 0.0005 | #147 | 0.008 |
| #148 | 0.024 | #149 | 0.029 | #151 | 0.002 |
| #152 | 0.002 | #153 | 0.0004 | #154 | 0.0027 |
| #155 | 0.003 | #156 | 0.185 | #157 | 0.007 |
| #158 | 0.007 | #159 | 0.100 | #160 | 0.147 |
| #161 | 0.016 | #162 | 0.004 | #163 | 0.043 |
| #164 | 0.008 | #165 | 0.900 | #166 | 0.039 |
| #167 | 0.075 | #168 | 0.011 | #169 | 0.162 |
| #170 | 0.018 | #171 | 0.006 | #172 | 0.617 |
| #150 | 0.001 | #174 | 0.0003 | #175 | 0.014 |
| #176 | 0.076 | #179 | 0.029 | #178 | 0.122 |
| #177 | 0.035 | #180 | 0.0003 | #181 | 0.002 |
| #182 | 0.003 | #83 | 0.462 | #184 | 0.032 |
| #185 | 0.260 | #186 | 0.134 | #187 | 0.015 |
| #188 | 0.015 | #189 | 0.178 | #190 | 0.008 |
| #191 | 0.046 | #192 | 0.347 | #193 | 0.315 |

Materials & Methods

Human A549 cells (80,000 cells/well in a 96 well plate) were treated with a range of concentration of test compounds and immediately infected by H1N1 A/New Caledonia/20/99 virus (clinical isolate) at MOI of 0.1 in DMEM/1% Penicillin/streptomycin supplemented with 0.25 µg/ml TPCK trypsin (Sigma) and incubated at 37° C. in 5% CO$_2$. 48 h post-infection, supernatants (25 µl) were collected and transferred into a 96-well black flat-bottom plate, mixed with 25 µl PBS with Ca++/Mg++(Thermo Fisher) and 50 µl of 2'-(4-Methylumbelliferyl)-α-D-N-acetylneuraminic acid sodium salt hydrate stock-solution (20 µM, MUNANA, Sigma). Plates were incubated 1 h at 37° C. and reaction is stopped by adding 100 µl of Stop Solution (glycine 0.1 M pH10.7/25% ethanol). The amount of fluorescent product released by MUNANA hydrolysis (4-MU) was measured in a Tecan spectrophotometer with excitation and emission wavelengths of 365 and 450 nm respectively.

Example B2—Antitumoral Effect

Results

The cytotoxicity was tested for compounds of the invention on five different cell-lines, namely LXFL 1121, MAXF 401, MMXF L-636, PRXF PC-3M and UXF 1138 which are respectively lung large cell carcinoma, breast adeno carcinoma, multiple myeloma, prostate adeno carcinoma and uterine sarcoma.

The IC50 are provided in the following table 2

TABLE 2

| Absolute IC50 (µM) | Compound |
|---|---|
| Cell Line | #16 |
| LXFL 1121 | 0.878 |
| MAXF 401 | 0.507 |
| MMXF L-363 | 0.357 |
| PRXF PC-3M | 0.485 |
| UXF 1138 | 0.324 |

Therefore, the compounds have a cytotoxicity against tumor cells and can be used for treating cancer.

Materials and Methods

Compound Handling

A working stock solution of the test compounds was prepared in DMSO at a concentration of 33 mM or 8.25 mM, and small aliquots were stored at −20° C. On each day of an experiment, a frozen aliquot of the working stock solution was thawed and stored at room temperature prior to and during treatment.

All liquid handling steps were performed using the Tecan Freedom EVO 200 platform. First, serial 2-fold dilutions of the 33 mM DMSO working stock solution were done in DMSO. The DMSO dilutions were then diluted 1:22 into cell culture medium in an intermediate dilution plate. Finally, 10 µl taken from the intermediate dilution plate were transferred to 140 µl/well of the final assay plate. Thus, the DMSO serial dilutions were diluted 1:330 with cell culture medium, and the DMSO concentration in the assay was 0.3% v/v.

Tumor Cell Lines

The cell lines used in this study were derived from solid tumors as well as from hematological malignancies.

Cell lines were routinely passaged once or twice weekly and maintained in culture for up to 20 passages. Most cell lines were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.05 mg/mL gentamicin (Life Technologies, Karlsruhe, Germany).

Propidium Ioded-Based Monolayer Assay

A modified propidium iodide (PI) based monolayer assay was used to assess the anti-cancer activity of the compounds. Briefly, cells were harvested from exponential phase cultures, counted and plated in 96 well flat-bottom microtiter plates at a cell density of 4,000 to 40,000 cells/well dependent on the cell line's growth rate. The individual seeding density for each cell line ensure exponential growth conditions over the whole or at least the bigger part of the treatment period. After a 24 h recovery period, to allow the cells to resume exponential growth, 10 µl of culture medium (6 control wells/cell line/plate) or of culture medium with test compounds were added. Compounds were applied at ten concentrations in 2-fold increments in duplicates up to 25 µM or 100 µM and treatment continued for four days. After four days of treatment, cells were next washed with 200 µl PBS to remove dead cells and debris, then 200 µl of a solution containing 7 µg/ml propidium iodide (PI) and 0.1% (v/v) Triton X-100 was added. After an incubation period of 1-2 hours at room temperature, fluorescence (FU) was measured using the Enspire Multimode Plate Reader (excitation λ=530 nm, emission λ=620 nm) to quantify the amount of attached viable cells.

Data Evaluation

An assay was considered fully evaluable if the following quality control criteria were fulfilled:
Z'-factor calculated within the assay plate ≥0.5
control/background ratio >3.0
coefficient of variation in the growth control wells ≤30%

Drug effects were expressed in terms of the percentage of the fluorescence signal, obtained by comparison of the mean signal in the treated wells with the mean signal of the untreated controls (expressed by the test-versus-control value, T/C-value [%]):

$$\frac{T}{C}[\%] = \frac{\text{mean fluorescence } signal_{treated\ group}}{\text{mean fluorescence } signal_{control\ group}} \cdot 100$$

IC values reported reflect the concentration of the test compound that achieves T/C=50%. Calculation was done by 4 parameter non-linear curve fit.

Example B3—Modulators of NEET Proteins

The modulator effect on the NEET proteins encoded by human CISD1, CISD2, and CISD3 genes by the compounds of the invention has been tested and is reported below. Particularly, the biochemical function of the NEET proteins is measured by the stability of Fe—S cluster binding of the purified NEET proteins.

The Fe—S cluster binding capacity of NEET proteins is known to be coordinated by four amino-acids in a stretch of 16 (three Cysteine and one Histidine). As the lability of the Fe—S cluster of NEET proteins is sensitive to the environment, cluster stability measurements are one of the measures of interactions of NEET proteins with small molecules and compounds. NEET protein/2Fe-2S cluster stability can be assessed by monitoring the decay in absorbance of its characteristic 458-nm peak (characteristic of the oxidized 2Fe-2S cluster) over time. Each NEET protein (mitoNEET, NAF-1 and Miner 2) was tested for its Fe—S binding in the absence or presence of a compound according to the invention (see table 3 below). The rate of cluster release (time in minutes to achieve 50% loss of bound Fe—S cluster) was compared for each NEET protein in the presence of one of the compounds of the invention (in a 1:3 protein:compound molar ratio) relative to each protein alone.

At pH 6, all the three NEET proteins (mitoNEET, NAF-1 and Miner 2) have a characteristic rate of loss of the bound Fe—S cluster that can be measured by the decrease of absorbance at wavelength 458 nm over time, using a spectrophotometer. Thus, Bis-Tris buffer (100 mM Bis-Tris pH6, 100 mM Nacl) was used at pH 6 to dilute either DMSO (Blank sample: Bis-Tris Buffer pH 6, 66 µM DMSO), DMSO and one of the three NEET proteins (Control sample: Bis-Tris Buffer pH 6, 66 µM DMSO, 20 µM purified NEET protein) or DMSO, one of the three NEET proteins and a compound of the invention (Test sample: Bis-Tris Buffer pH 6, 66 µM DMSO, 20 µM purified NEET protein, 60 µM compound of the invention).

A reaction mix containing DMSO diluted in the Bis-Tris Buffer with or without a compound of the invention was prepared. The purified NEET protein was the last component added to the reaction mix which was then aliquoted into 4 replicates in 96 wells plates. The absorbance at wavelength 458 nm was taken at 5 minutes intervals at 37° C. with a spectrofluorimeter. The assay run time for CISD2 gene product (NAF-1) was 500 minutes and 180 minutes for both the CISD 1 gene product (mitoNEET) and the CISD3 gene product (Miner 2).

In addition to time monitoring, residual bound Fe—S cluster to NEET protein was measured at the final point of the spectrometry assay for each Test sample and compared to the Control sample data (in parenthesis table 3). This residual binding is measured by the differential percentage between the absorbance 458 nm at time zero and the absorbance 458 nm at the end of the experiment (i.e. respectively 500 or 180 minutes as described hereabove), showing the percentage of NEET protein still able to bind a Fe—S cluster.

TABLE 3

| Compound | Time (in minutes) to achieve 50% loss of bound cluster (Absorbance 458 nm), (Vehicle control data in parenthesis) | | | Residual cluster bound at end of experiment (Percentage Absorbance 458 nm at time zero) (Vehicle control data in parenthesis) | | |
|---|---|---|---|---|---|---|
| | CISD1 Gene Product (mitoNEET) | CISD2 Gene Product (NAF-1) | CISD3 Gene Product (Miner2) | CISD1 Gene Product (mitoNEET) | CISD2 Gene Product (NAF-1) | CISD3 Gene Product (DMSO 11%) |
| #16 | 35 (80) | 35 (310) | 35 (60) | 0% (16%) | 4% (3%) | 11% (11%) |

Analysis of the absorbance enables the time for which 50% loss of bound Fe—S cluster is reached (i.e. a 50% absorbance decrease at 458 nm) for each Test sample and each Control sample (in parenthesis table 3) to be determined. The data are then compared to determine whether the compound of the invention stabilizes or destabilizes the NEET protein/Fe—S cluster binding.

Destabilisers enhance the release of bound Fe—S cluster (i.e. decrease the time needed to reach 50% Fe—S cluster bound loss by more than 25% for the Test sample compared to the Control sample). As illustrated by table 3, at the concentrations tested, destabilisers of CISD1 Gene Product (mitoNEET), CISD2 Gene Product (NAF-1), CISD3 Gene Product (Miner2) is the compound #16.

Example B4—Compounds Inhibit NFkB Activation in Response to TNFa Stimulation Compounds of the present invention have been tested for their capacity to inhibit NFκB. The results are shown in the following table.

TABLE 4

| Compounds | NFκB EC50 (μM) |
|---|---|
| #16 | 0.08 |
| #17 | 0.18 |
| #57 | 0.08 |
| #19 | 0.20 |
| #124 | 0.91 |
| #86 | 0.04 |
| #140 | 0.04 |
| #180 | 0.05 |
| #94 | 0.09 |
| #151 | 0.09 |
| #152 | 0.16 |
| #162 | 0.2 |

Materials and Methods

Construction of a NFκB Reporter Cell Line

The NFκB reporter construct was made by cloning 5 NFκB responsive elements upstream of a NanoLuciferase reporter gene flanked by AAVS1 genomic sequences.

NFκB Responsive element fused with NanoLuciferase and SV40 late Poly(A) signal was amplified from pNL3.2-NFκB-Nluc (Promega) using NFKB-NLUC-F and NFKB-NLUC-R primers and inserted by Infusion (TaKaRa) in AAVS1 SA-2A-puro-pA donor plasmid (Hockemeyer et al, Nat Biotechnol. 2009, 27, 851-7) digested by SalI. pCRISPR AAVS1-T2 expressing a guide RNA (gRNA) to target human AAVS1 (T2 target sequence) was constructed by inserting AAVS1-T2A hybridized primers in pLentiCRISPR v2-blast (Sanjana et al, Nat Methods. 2014, 11, 783-4) digested by Bsmb1.

```
Oligonucleotide sequences
NFKB-NLUC-F:
                                         (SEQ ID NO: 1)
ggctctatggGTCGACGGCCTAACTGGCCGGTACC NFKB-NLUC-R:
                                         (SEQ ID NO: 2)
agcttagtactGTCGACGATCAGCGGAAGAGCGCCCA AAVS1-T2A-1
                                         (SEQ ID NO: 3)
CACCGGGGGCCACTAGGGACAGGAT AAVS1-T2A-2
                                         (SEQ ID NO: 4)
AAACATCCTGTCCCTAGTGGCCCCC
```

A549 cells were transfected by the plasmids and puromycine selected for 5 days (1 μg mL-1). Then clones were obtained by limiting dilution and selected to maximize TNFα dependent NFkB-NanoLuciferase induction.

NFκB Reporter Assay

The reporter cells were seeded on a 96-well plate for overnight with DMEM including 10% FBS. Test compounds were added at varying concentrations. The cells then were treated with 4 ng/ml TNFα (Peprotech, ref E251) in DMEM+10% FBS. NanoGlo luciferase assay (Promega) was carried out 6 hours later. Luminescence was measured using a Spark 20M spectrofluorimeter (Tecan). Values were normalized to the luminescence measured in untreated cells.

Example B5—Compounds of the Invention Decrease Glycemia in a Diabetic Mice Model Compound #16 has been tested on a diabetic mice model. As shown in FIG. 1, compound #16 is capable of reducing glycated hemoglobin, HbA1C, after one-month treatment. Therefore, this compound can be useful for treating diabetes.

Materials and Methods

Male db/db (BKS.Cg-m 1/1 Leprdb/J) mice aged 6 weeks at the time of arrival were obtained from Janvier (France) and acclimatized to their new environment. Animals were housed in groups of 2 in a light, temperature and humidity-controlled room (a 12-hour light/dark cycle, with lights off at 4 PM; 23+/−1° C.; 50% relative humidity). All animals had free access to standard Purina 5008 chow (LabDiet) and domestic-quality tap water.

The study was initiated in mice aged 8 weeks. Three days before first dosing, a blood sample was collected for determination of baseline blood glucose and hemoglobin A1c (HbA1c) levels. Based on these baseline HbA1c and fed blood glucose levels, mice were stratified into treatment groups (n=10) receiving vehicle (CMC (1.5% W/V) Sigma (ref.C9481), Tween 80 (0.25% V/V) Sigma (ref.59924) in water) or orally administered Compound #16 as follows:

7 mg/kg, PO BID (twice a day)
20 mg/kg, PO BID (twice a day)
40 mg/kg PO QD (Once a day)

Throughout the experimental period, body weight and food and water intake were measured daily in the morning.

Animals were terminated after a total of 28 days of dosing. Terminal blood samples were collected from the orbital plexus vein for measurements of blood HbA1c as previously described (Fosgerau et al. (2013) Diabetes Obes Metab 15:62-71).

The invention claimed is:

1. A compound of formula (I):

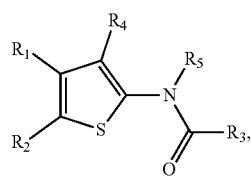

(I)

wherein:

$R_1$ represents:

a fused arylcycloalkyl selected from the group consisting of:

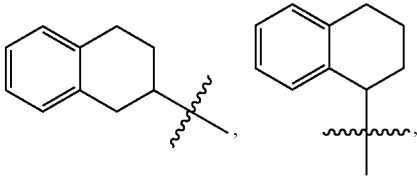

-continued

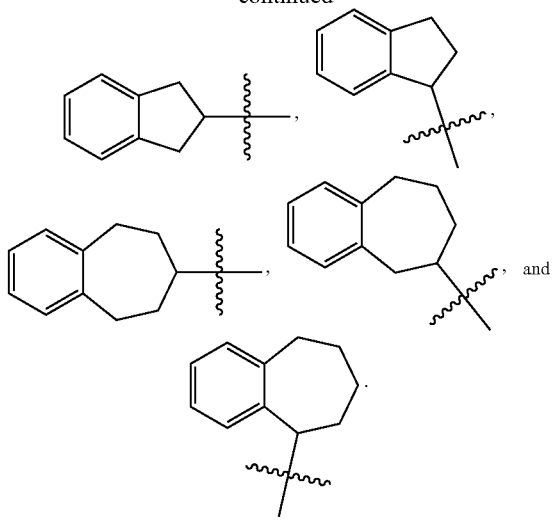

$R_2$ represents:
  a hydrogen,
  a halogen,
  a $(C_1-C_6)$alkyl optionally substituted by at least one halogen,
  an optionally substituted aryl, or
  an optionally substituted cycloalkyl;
$R_3$ represents:
  a 5-10 membered ring, saturated or unsaturated selected from the group consisting of:
    an aryl optionally fused to a heterocycloalkyl,
    a heteroaryl selected from the group consisting of a pyrimidinyl, a pyrazolyl, and a benzoisoxazolyl, and
    a 5-10 membered bridged carbocyclyl or heterocyclyl,
    said 5-10 membered ring is optionally substituted by at least one radical selected from the group consisting of:
      a halogen,
      a $(C_1-C_6)$alkyl optionally substituted by at least one halogen, or by an optionally bridged heterocycloalkyl optionally substituted by a $(C_1-C_6)$alkyl,
      a —NH—$(C_1-C_6)$alkyl or a —N—$((C_1-C_6)$alkyl$)_2$, optionally substituted by at least one radical selected from the group consisting of a heterocycloalkyl, a cycloalkyl, a hydroxyl, a thiacycloalkyl-1,1dioxide and a $(C_1-C_6)$alkyloxy,
      a —NH-heterocycloalkyl, a —NH-cycloalkyl, a —N($(C_1-C_6)$alkyl)-heterocycloalkyl, or a —NH($(C_1-C_6)$alkyl)-thiacycloalkyl-1,1dioxide, optionally substituted by a hydroxyl, a $(C_1-C_6)$alkyl, a $(C_1-C_6)$alkyloxy or a —CO—$R_6$ with $R_6$ being a hydrogen or a $(C_1-C_6)$alkyl,
      a hydroxy, a —CN, a —CO—$R_6$ or a —CO$_2R_6$ with $R_6$ being a hydrogen or a $(C_1-C_6)$alkyl,
      a $(C_1-C_6)$alkyloxy optionally substituted by at least one radical selected from the group consisting of a halogen, a hydroxy, a $(C_1-C_6)$alkyloxy, a —NR$_7$R$_8$ with $R_7$ and $R_8$ are independently a hydrogen or a $(C_1-C_6)$alkyl, a —NHCOR$_9$, a —NHCO$_2$R$_9$, with $R_9$ being a $(C_1-C_6)$alkyl, a —CO$_2$R$_6$ with $R_6$ being a hydrogen or a $(C_1-C_6)$alkyl, and a heterocycle,
      a —NHCOR$_9$, a —NHCO$_2$R$_9$, or a —SO$_2$R$_9$, with $R_9$ being a $(C_1-C_6)$alkyl, and
      a heterocycloalkyl, a bridged heterocycloalkyl, a heterocycloalkyloxy, a cycloalkyloxy, a thiaheterocycloalkyl-1,1-dioxide or a spiroheterocycloalkyl, optionally substituted by a $(C_1-C_6)$alkyl, a $(C_1-C_6)$alkyloxy, a hydroxy, a ketone, a halogen or a $(C_1-C_6)$alkyl optionally substituted by a $(C_1-C_6)$alkyloxy;
$R_4$ represents: a —CO$_2$R$_{10}$ with $R_{10}$ being a hydrogen; and
$R_5$ represents:
  a hydrogen, or
  a $(C_1-C_6)$alkyl optionally substituted by at least one halogen
and stereoisomers and pharmaceutical salts thereof.

2. The compound according to claim 1, wherein $R_1$ is

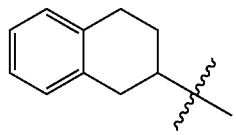

3. The compound according to claim 1, wherein:
$R_3$ represents an aryl optionally fused to a heterocycloalkyl, said aryl or fused aryl is optionally substituted by at least one radical selected from the group consisting of:
  a heterocycloalkyl or a bridged heterocycloalkyl, optionally substituted by a $(C_1-C_6)$alkyl, a $(C_1-C_6)$alkyloxy, or a ketone,
  a thiaheterocycloalkyl-1,1-dioxide, a heterocycloalkyloxy, or a cycloalkyloxy;
  a $(C_1-C_6)$alkyloxy or a $(C_1-C_6)$alkyl, optionally substituted by at least one halogen, or a $(C_1-C_6)$alkyloxy, halogen,
  a —NH—$(C_1-C_6)$alkyl or a —N—$((C_1-C_6)$alkyl$)_2$, optionally substituted by a heterocycloalkyl, a cycloalkyl, a hydroxyl, a thiacycloalkyl-1,1-dioxide or a $(C_1-C_6)$alkyloxy,
  a —NH-heterocycloalkyl, a —N($(C_1-C_6)$alkyl)-heterocycloalkyl, or a —NH($(C_1-C_6)$alkyl)-thiacycloalkyl-1,1-dioxide,
  a hydroxy,
  a —CN,
  a $(C_1-C_6)$alkyl substituted by an optionally bridged heterocycloalkyl or an optionally substituted heterocycloalkyl; and
  a —SO$_2$R$_9$, with $R_9$ being a $(C_1-C_6)$alkyl.

4. The compound according to claim 1, wherein:
$R_3$ represents:
  a phenyl optionally substituted by at least one radical selected from the group consisting of:
    a morpholinyl optionally substituted by at least one methyl,
    a —NH-tetrahydropyranyl,
    a —NH—$(C_1-C_6)$alkyl or a —N(CH$_3$)$(C_1-C_6)$alkyl), optionally substituted by a tetrahydropyranyl, a cyclohexyl, an optionally bridged morpholinyl optionally substituted by at least one methyl, a thiacycloalkyl-1,1-dioxide, a hydroxy, or a $(C_1-C_6)$alkyloxy,
    an azetidinyl optionally substituted by a $(C_1-C_6)$alkyloxy, a pyrrolidin-2-one,
a 6-oxa-3-azabicyclo[3.1.1]heptane, or a 8 oxa-3-azabicyclo[3.2.1]octane,
a ($C_1$-$C_6$)alkyloxy, optionally substituted by at least one halogen, or one ($C_1$-$C_6$)alkyloxy,
a halogen,
a hydroxy,
a —CN,
a —$SO_2$—$CH_3$,
a 1,1-dioxo-1,2-thiazolidin,
a cyclobutyloxy, or a tetrahydropyranyloxy,
a ($C_1$-$C_6$)alkyl optionally substituted by at least one halogen, and a ($C_1$-$C_6$)alkyl substituted by a morpholinyl optionally substituted by at least one methyl, a 6-oxa-3-azabicyclo[3.1.1]heptane, a 8 oxa-3-azabicyclo[3.2.1]octane or a tetrahydropyranyl.

5. The compound according to claim 1, wherein:
$R_2$ represents:
  a hydrogen,
  a halogen, or
  an optionally substituted ($C_3$-$C_6$)cycloalkyl.

6. The compound according to claim 1, wherein $R_2$ represents a hydrogen.

7. The compound of formula (I) according to claim 1, wherein said compound is selected from the group consisting of:

Compound #7
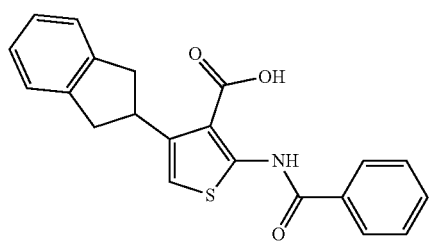

Compound #8
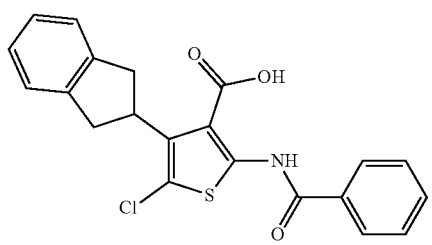

Compound #16
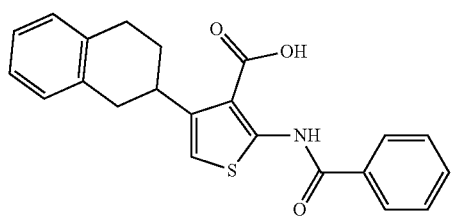

Compound #17
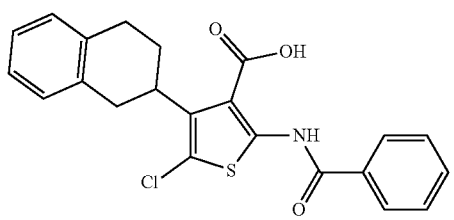

Compound #19
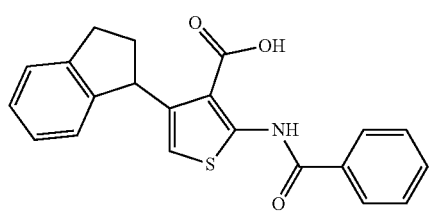

Compound #49
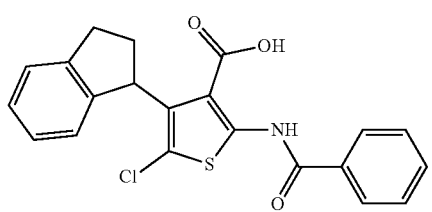

Compound #51
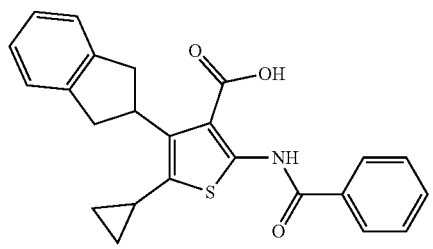

Compound #52
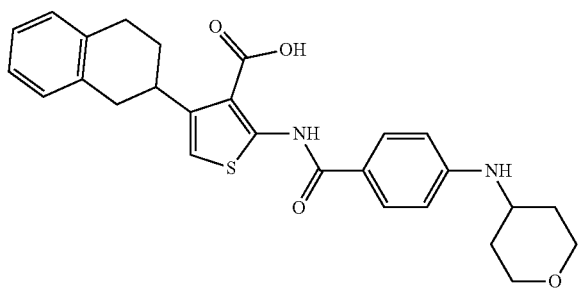

Compound #53
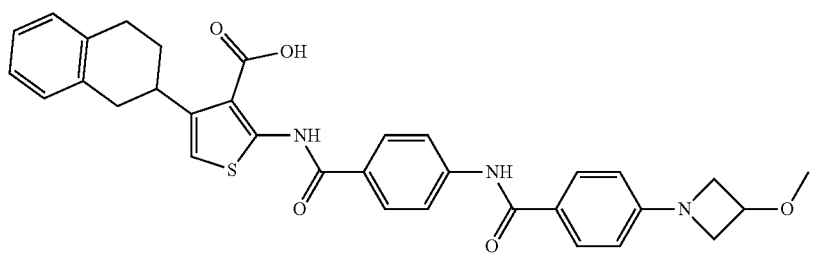

Compound #55
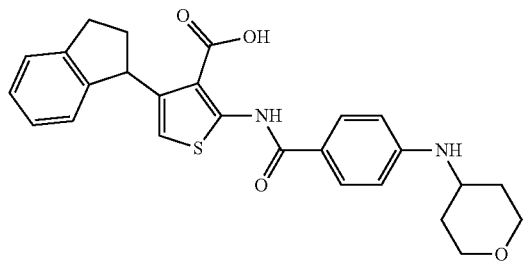
Compound #56
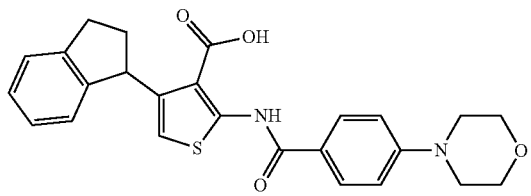
Compound #57
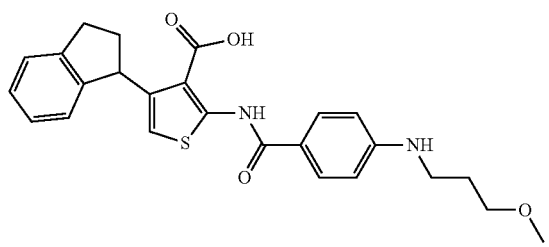
Compound #58
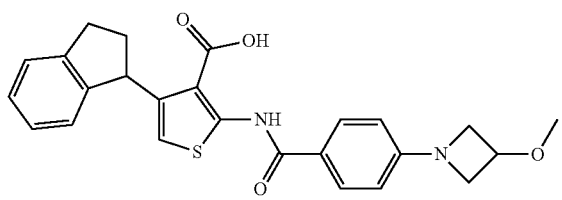
Compound #64
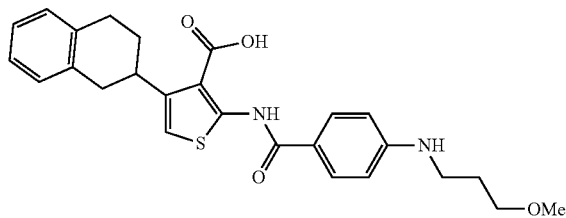
Compound #65
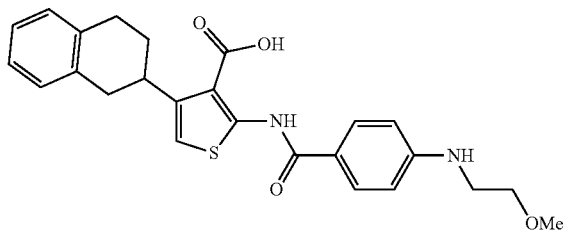
Compound #67
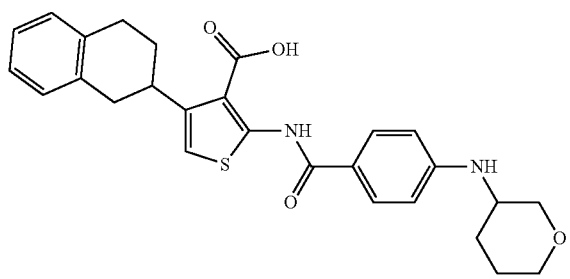
Compound #68
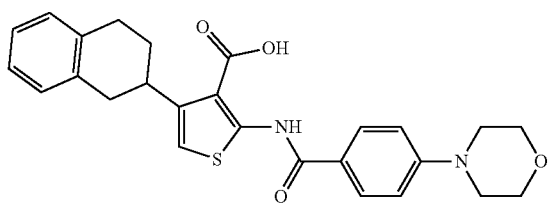
Compound #69
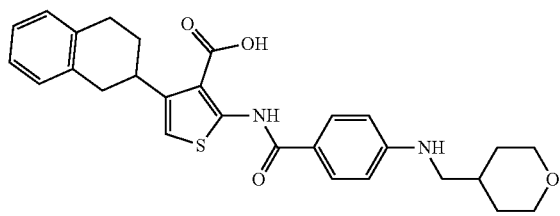
Compound #70
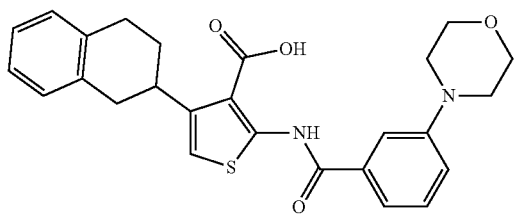
Compound #86
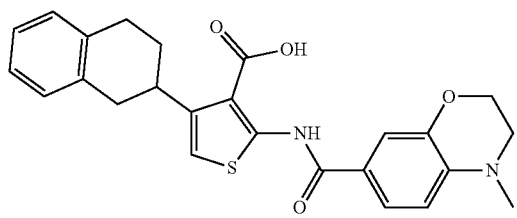
Compound #89
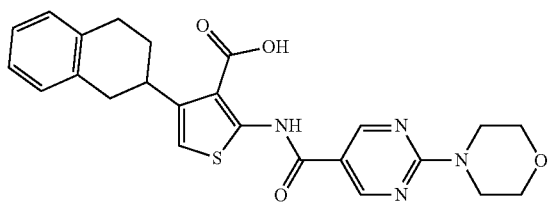

-continued
Compound #93
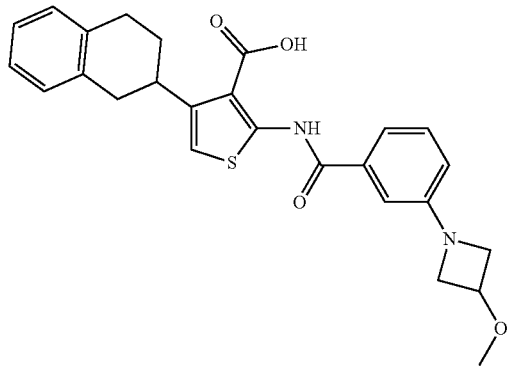
Compound #94
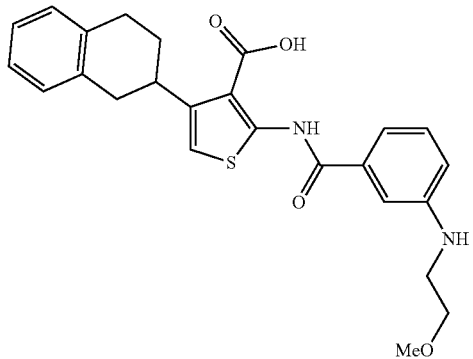
Compound #101
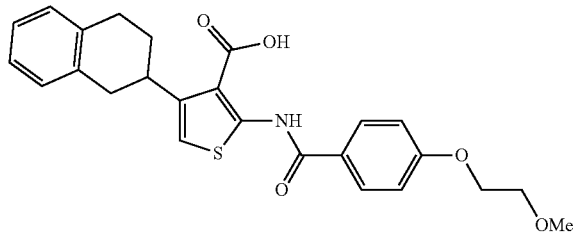
Compound #122
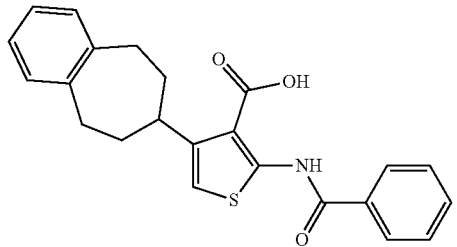
Compound #124
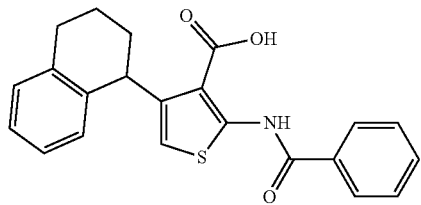
Compound #126
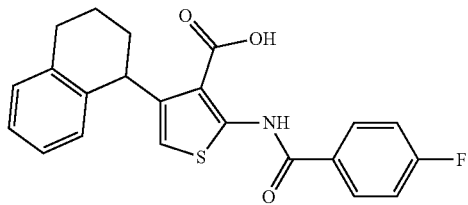
Compound #127
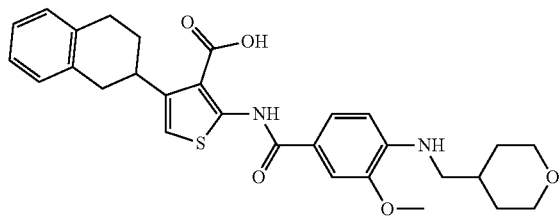
Compound #128
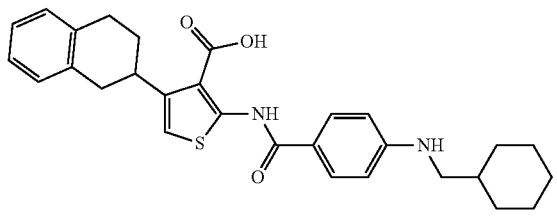
Compound #129
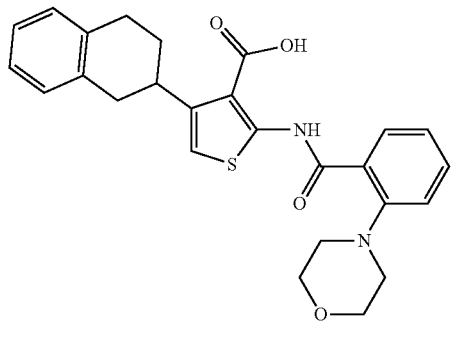
Compound #130
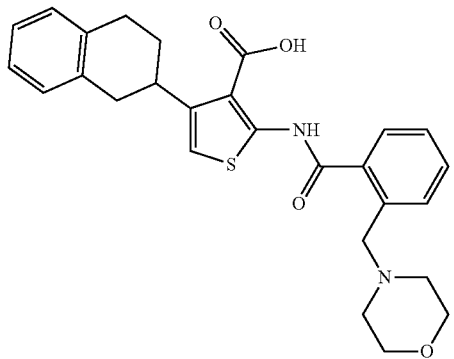

Compound #131
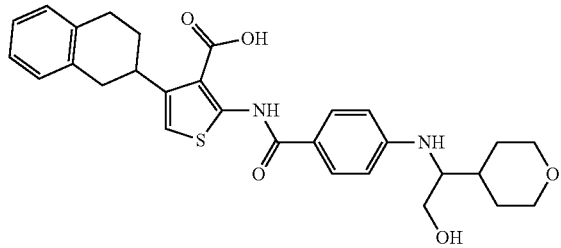
Compound #132
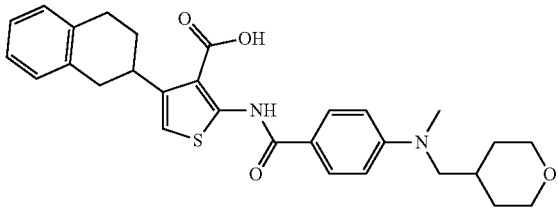
Compound #133
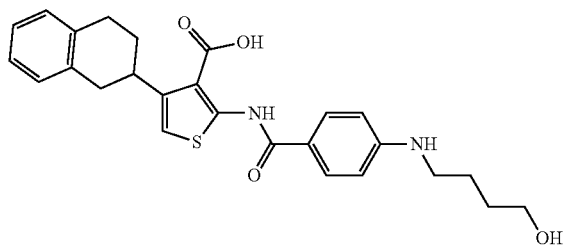
Compound #134
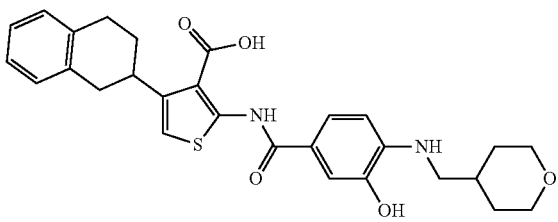
Compound #135
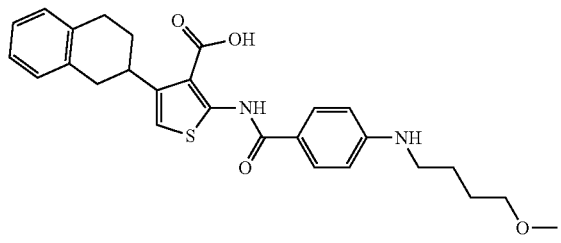
Compound #136
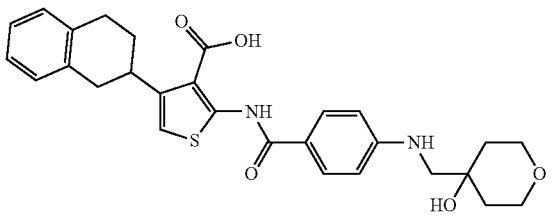
Compound #137
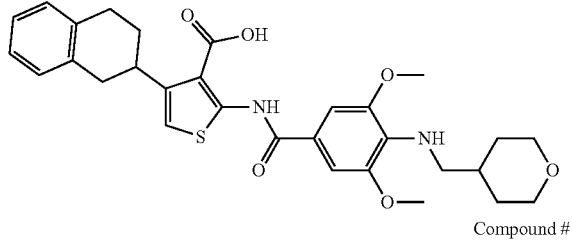
Compound #138
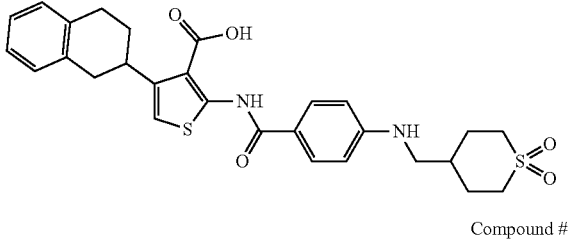
Compound #139
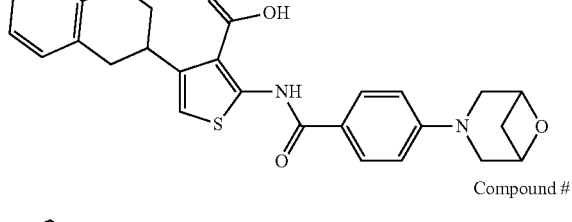
Compound #140
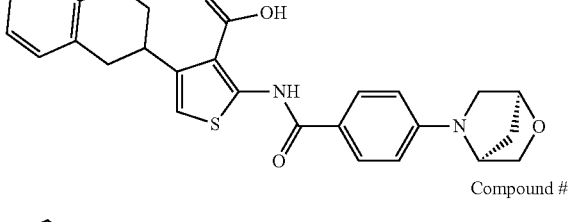
Compound #141
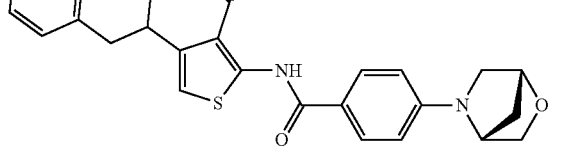
Compound #142
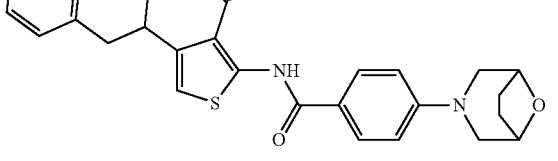

-continued
Compound #143
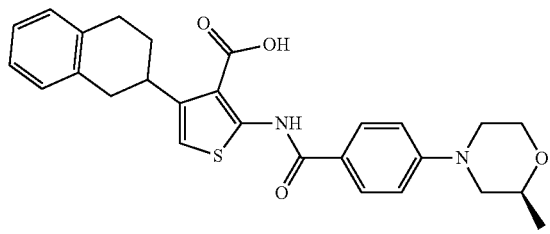
Compound #144
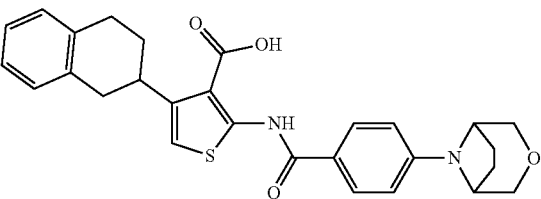
Compound #145
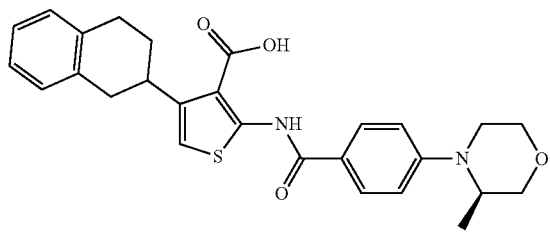
Compound #146
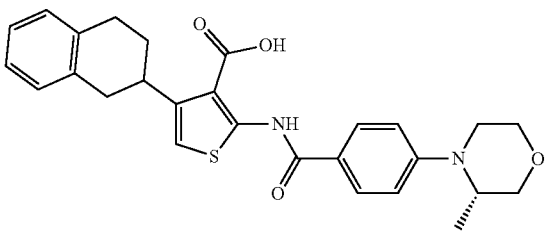
Compound #147
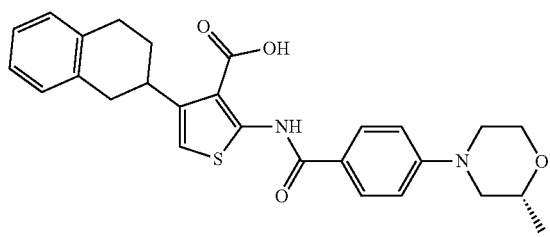
Compound #148
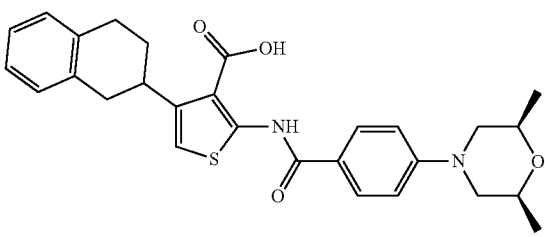
Compound #149
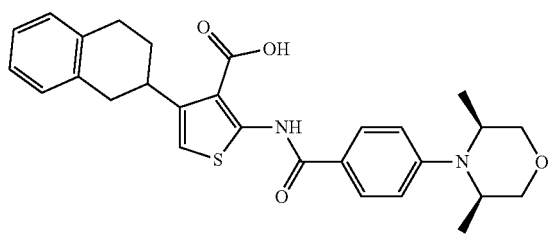
Compound #150
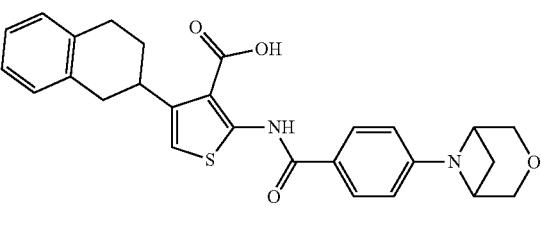
Compound #151
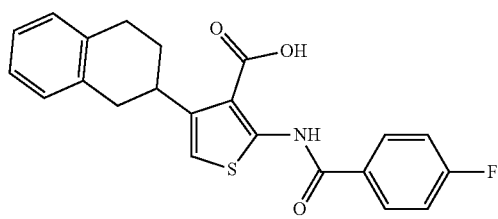
Compound #152
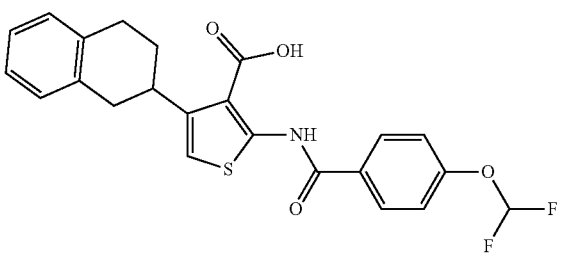
Compound #153
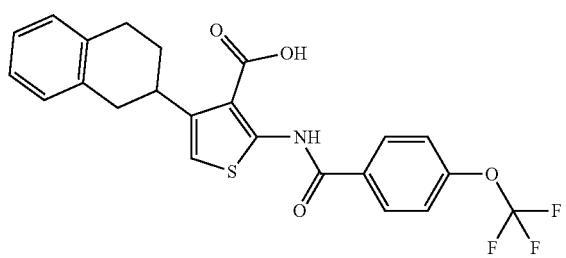
Compound #154

Compound #155
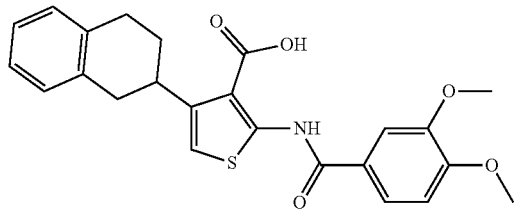
Compound #156
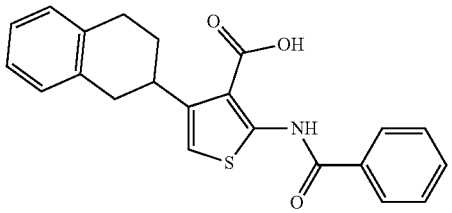
Compound #157
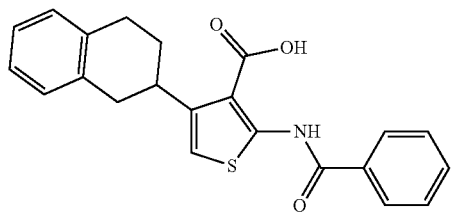
Compound #158
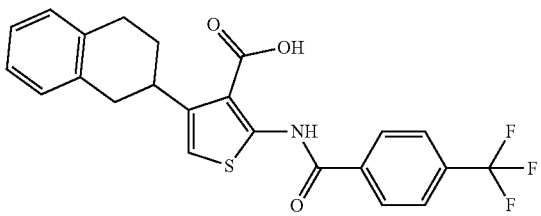
Compound #159
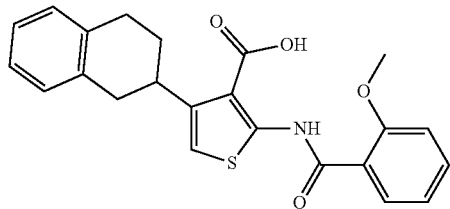
Compound #160
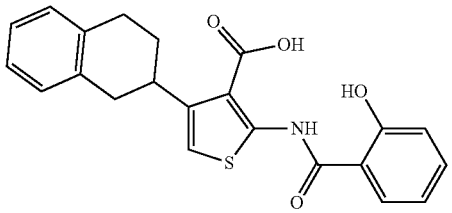
Compound #161
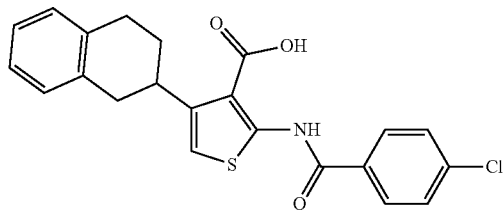
Compound #162
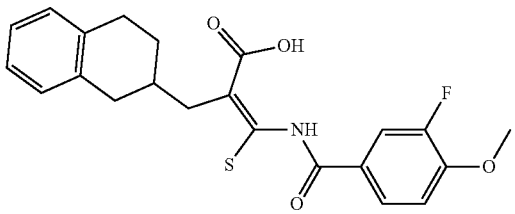
Compound #163
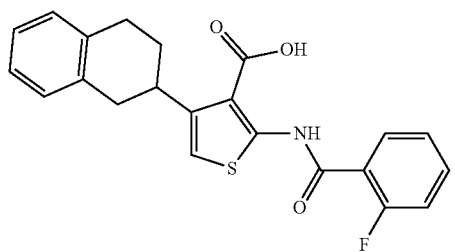
Compound #164
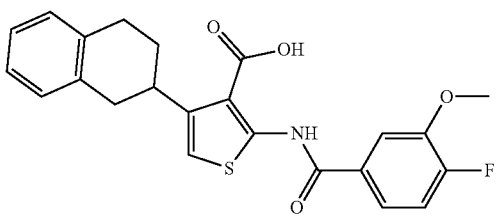
Compound #165
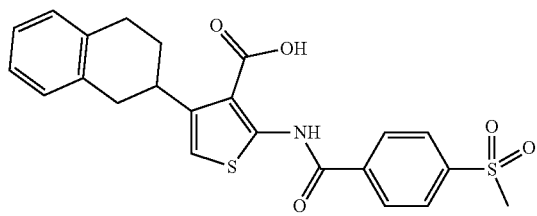
Compound #166
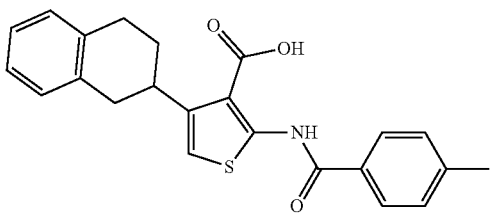

Compound #167
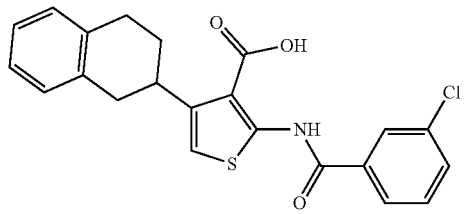
Compound #168
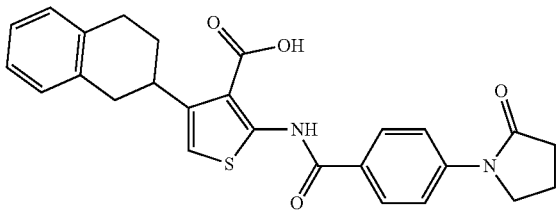
Compound #169
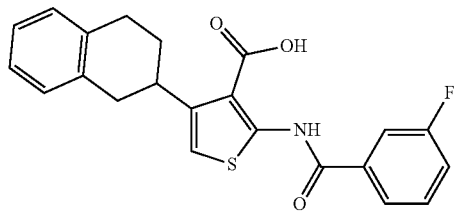
Compound #170
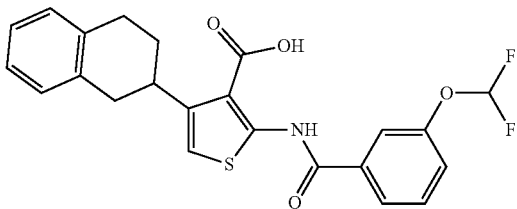
Compound #171
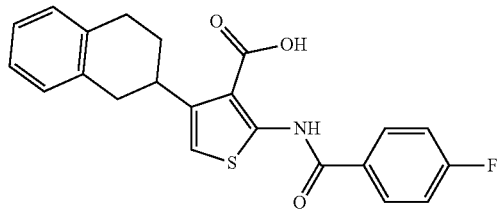
Compound #172
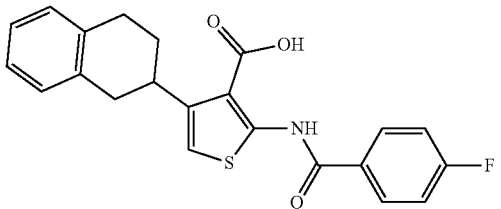
Compound #174
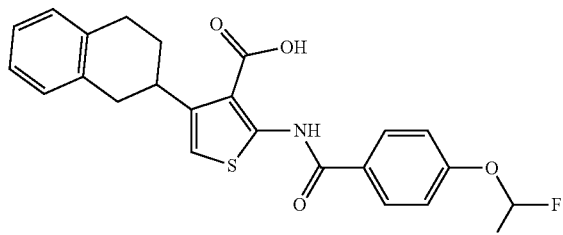
Compound #175
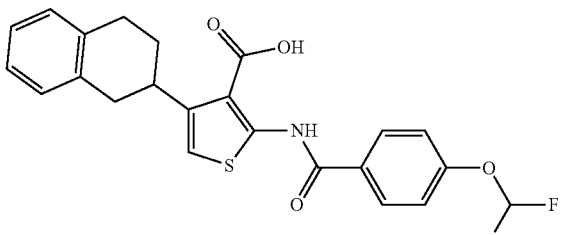
Compound #176
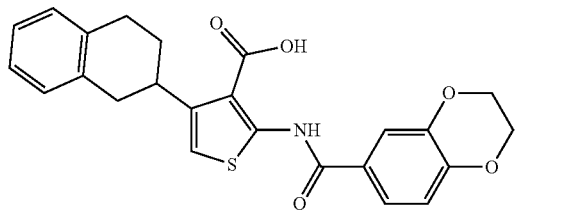
Compound #177
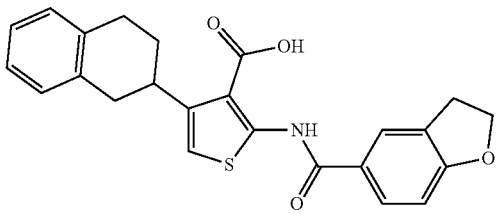
Compound #178
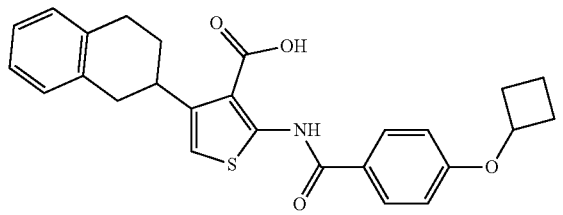
Compound #179
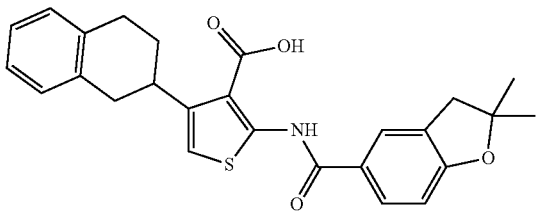

-continued
Compound #180
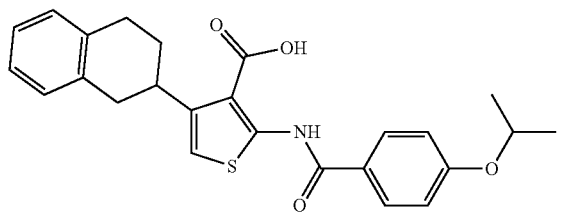
Compound #181
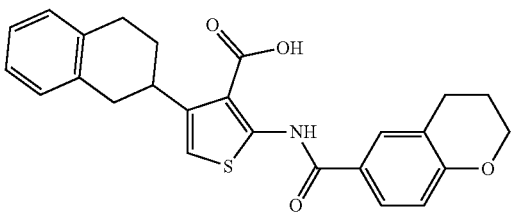
Compound #182
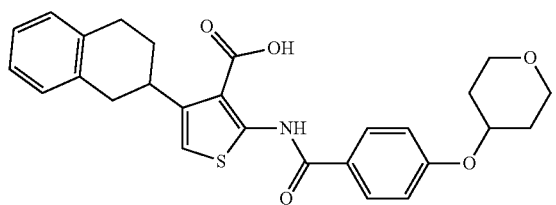
Compound #183
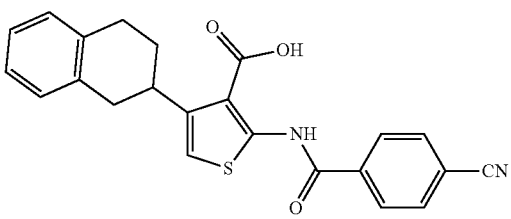
Compound #184
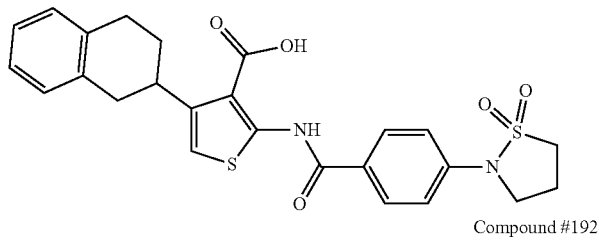
Compound #188
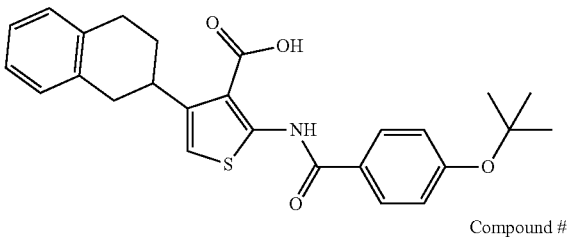
Compound #192
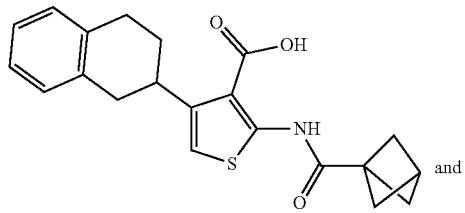
Compound #193
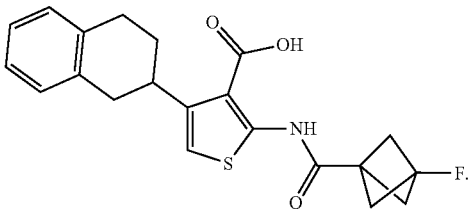
8. A pharmaceutical composition comprising a compound as defined in claim 1, and an acceptable pharmaceutical excipient.
9. A pharmaceutical composition comprising a compound according to claim 7 and an acceptable pharmaceutical excipient.
* * * * *

UNITED STATES PATENT AND TRADEMARK OFFICE
CERTIFICATE OF CORRECTION

PATENT NO. : 11,767,316 B2
APPLICATION NO. : 16/967744
DATED : September 26, 2023
INVENTOR(S) : Eric Meldrum et al.

Page 1 of 1

It is certified that error appears in the above-identified patent and that said Letters Patent is hereby corrected as shown below:

In the Specification

Column 101,
Line 60, "(CAS: δ485-55-8)" should read --(CAS: 6485-55-8)--.

Column 111,
Line 49, "(CAS: δ16-45-5," should read --(CAS: 616-45-5,--.

Column 116,
Line 27, "(CAS: δ2577-95-1)" should read --(CAS: 62577-95-1)--.

Column 128,
Line 37, "(CAS: δ38-07-3," should read --(CAS: 638-07-3,--.

In the Claims

Column 150,

Lines 36-46, Compound #162, in Claim 7, " 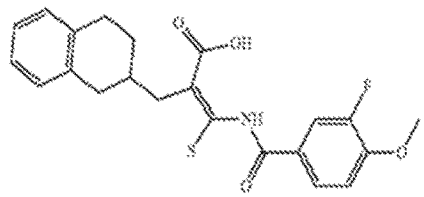 " should read
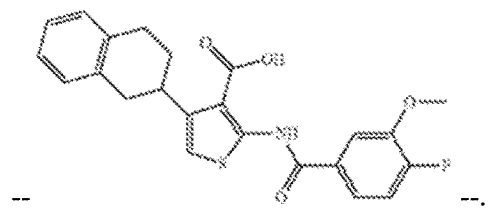
--  --.

Signed and Sealed this
Thirteenth Day of February, 2024

Katherine Kelly Vidal
*Director of the United States Patent and Trademark Office*